US011365407B2

(12) United States Patent
Baltes

(10) Patent No.: US 11,365,407 B2
(45) Date of Patent: *Jun. 21, 2022

(54) METHODS FOR TARGETED INSERTION OF DNA IN GENES

(71) Applicant: BLUEALLELE CORPORATION, Oakdale, MN (US)

(72) Inventor: Nicholas J. Baltes, Oakdale, MN (US)

(73) Assignee: BLUEALLELE CORPORATION, Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/590,613

(22) Filed: Feb. 1, 2022

(65) Prior Publication Data

US 2022/0154168 A1     May 19, 2022

Related U.S. Application Data

(63) Continuation of application No. 17/366,290, filed on Jul. 2, 2021, now Pat. No. 11,254,930, which is a continuation of application No. 16/800,444, filed on Feb. 25, 2020, now Pat. No. 11,091,756, which is a continuation of application No. 16/601,144, filed on Oct. 14, 2019, now abandoned.

(60) Provisional application No. 62/864,432, filed on Jun. 20, 2019, provisional application No. 62/830,654, filed on Apr. 8, 2019, provisional application No. 62/746,497, filed on Oct. 16, 2018.

(51) Int. Cl.
     *C12N 15/10*      (2006.01)
     *C12N 15/90*      (2006.01)

(52) U.S. Cl.
     CPC ......... *C12N 15/102* (2013.01); *C12N 15/907* (2013.01); *C12N 2310/20* (2017.05); *C12N 2800/80* (2013.01)

(58) Field of Classification Search
     CPC .................................................. C12N 15/102
     See application file for complete search history.

(56) References Cited

U.S. PATENT DOCUMENTS

| | | | |
|---|---|---|---|
| 6,228,639 B1 | 5/2001 | Gaitanaris | |
| 6,740,503 B1 | 5/2004 | Harrington et al. | |
| 7,005,299 B1 | 2/2006 | Smith et al. | |
| 9,255,250 B2 | 2/2016 | Gregory et al. | |
| 9,677,070 B2 | 6/2017 | Allison et al. | |
| 9,765,404 B2 | 9/2017 | Sastry-Dent et al. | |
| 10,240,115 B2 | 3/2019 | Tang | |
| 11,254,930 B2 * | 2/2022 | Baltes ................... | C12N 15/907 |
| 2004/0106566 A1 | 6/2004 | Lin et al. | |
| 2005/0064474 A1 | 3/2005 | Umov | |
| 2005/0208489 A1 | 9/2005 | Carroll | |
| 2013/0280222 A1 | 10/2013 | Kay et al. | |
| 2014/0130205 A1 | 5/2014 | Bhyri | |
| 2016/0040155 A1 | 2/2016 | Maizels et al. | |
| 2016/0102322 A1 | 4/2016 | Ravinder et al. | |
| 2016/0281111 A1 | 9/2016 | Cotta-Ramusino et al. | |
| 2017/0073664 A1 | 3/2017 | Mccafferty et al. | |
| 2018/0023075 A1 | 1/2018 | Liang et al. | |
| 2018/0110877 A1 | 4/2018 | Wilson et al. | |
| 2018/0112213 A1 | 4/2018 | Welstead et al. | |
| 2018/0119123 A1 | 5/2018 | Gori et al. | |
| 2018/0273932 A1 | 9/2018 | Bothmer et al. | |
| 2018/0296603 A1 | 10/2018 | Gori et al. | |
| 2018/0362590 A1 | 12/2018 | Monds et al. | |
| 2019/0032089 A1 | 1/2019 | Townes et al. | |
| 2019/0032092 A1 | 1/2019 | Gong et al. | |
| 2019/0032156 A1 | 1/2019 | Gong et al. | |
| 2019/0093114 A1 | 3/2019 | Bower et al. | |
| 2019/0134221 A1 | 5/2019 | Bumcrot et al. | |
| 2019/0136210 A1 | 5/2019 | Cotta-Ramusino et al. | |
| 2019/0276850 A1 | 9/2019 | Brinkmann et al. | |
| 2019/0330603 A1 | 10/2019 | Ahlfors et al. | |
| 2019/0390189 A1 | 12/2019 | Lee et al. | |
| 2020/0040362 A1 | 2/2020 | Carlo et al. | |
| 2020/0231974 A1 | 7/2020 | Jarvis et al. | |

FOREIGN PATENT DOCUMENTS

| | | |
|---|---|---|
| BR | 102014027 448 A2 | 9/2015 |
| CA | 2906747 A1 | 9/2014 |
| EP | 2893025 B1 | 7/2015 |
| EP | 3114227 A1 | 1/2017 |
| EP | 3122880 A2 | 2/2017 |
| EP | 3344771 A1 | 7/2018 |
| EP | 3375877 A1 | 9/2018 |
| EP | 3426784 A1 | 1/2019 |
| EP | 3556858 A2 | 10/2019 |
| EP | 3592140 A1 | 1/2020 |
| ES | 2653212 T3 | 2/2018 |
| ES | 2699848 T3 | 2/2019 |

(Continued)

OTHER PUBLICATIONS

Yew et al. (Human Gene Therapy 8:575-584 (Mar. 20, 1997)). (Year: 1997).*
Blueallele, LLC in connection with PCT/US2019/058857 filed Oct. 30, 2019, "The International Search Report and the Written Opinion of the International Searching Authority, or the Declaration", 19 pages, dated Jun. 23, 2020.
Robert, Francois, "Bidirectional terminators: an underestimated aspect of gene regulation", Curr Genet, vol. 64, pp. 389-391, 2018.
Ouyang et al., "CRISPR/Cas9-Targeted Deletion of Polyglutamine in Spinocerebellar Ataxia Type 3-Derived Induced Pluripotent Stem Cells", vol. 27, No. 11, pp. 756-770, 2018.
Blueallele, LLC in connection with PCTUS2019/056083 filed Oct. 14, 2019, "The International Search Report and the Written Opinion of the International Searching Authority, or the Declaration", 21 pages, dated Dec. 19, 2019.

(Continued)

*Primary Examiner* — Scott Long
(74) *Attorney, Agent, or Firm* — Arrigo, Lee, Guttman & Mouta-Bellum LLP; Carla Mouta-Bellum

(57) ABSTRACT

Methods and compositions for modifying the coding sequence of endogenous genes using rare-cutting endonucleases and transposases. The methods and compositions described herein can be used to modify the coding sequence of endogenous genes.

22 Claims, 8 Drawing Sheets
Specification includes a Sequence Listing.

(56) References Cited

FOREIGN PATENT DOCUMENTS

| | | | |
|---|---|---|---|
| ES | 2730378 | T3 | 11/2019 |
| WO | 2013075008 | A1 | 5/2013 |
| WO | 2013169802 | A1 | 11/2013 |
| WO | 2015017866 | A1 | 2/2015 |
| WO | 2015089351 | A1 | 6/2015 |
| WO | 2015153780 | A1 | 10/2015 |
| WO | 2015173436 | A1 | 11/2015 |
| WO | 2016073990 | A2 | 5/2016 |
| WO | 2016109840 | A2 | 7/2016 |
| WO | 2016161380 | A1 | 10/2016 |
| WO | 2016172727 | A1 | 10/2016 |
| WO | 2016182959 | A8 | 11/2016 |
| WO | 2017048995 | A1 | 3/2017 |
| WO | 2017155408 | A1 | 9/2017 |
| WO | 2018009534 | A1 | 1/2018 |
| WO | 2018009562 | A1 | 1/2018 |
| WO | 2018195555 | A1 | 10/2018 |
| WO | 2018197020 | A1 | 11/2018 |
| WO | 2019005851 | A1 | 1/2019 |
| WO | 2019092505 | A1 | 5/2019 |
| WO | 2019113149 | A1 | 6/2019 |
| WO | 2019118875 | A1 | 6/2019 |
| WO | 2019157326 | A1 | 8/2019 |
| WO | 2019157326 | A2 | 9/2019 |
| WO | 2019183123 | A1 | 9/2019 |
| WO | 2019210216 | A2 | 10/2019 |
| WO | 020082042 | A2 | 4/2020 |
| WO | 2020082041 | A1 | 4/2020 |
| WO | 2020082046 | A2 | 4/2020 |
| WO | 2020082047 | A1 | 4/2020 |

OTHER PUBLICATIONS

Friedel et al., "Gene targeting using a promoterless gene trap vector ("targeted trapping") is an efficient method to mutate a large fraction of genes", PNAS, vol. 102, No. 37, pp. 13188-13193, Sep. 13, 2005.

Gilles et al., "Efficient CRISPR-mediated gene targeting and transgene replacement in the beetle Tribolium castaneum", The Company of Biologists, vol. 142, pp. 2832-2839, Jun. 29, 2015.

Hahm et al., "Construction of retroviral vectors with enhanced efficiency of transgene expression", Journal of Virological Methods, vol. 121, pp. 127-136, May 27, 2004.

Hildinger et al., "Design of 5' Untranslated Sequences in Retroviral Vectors Developed for Medical Use", Journal of Virology, vol. 73, No. 5, pp. 4083-4089, May 1999.

Intellia Therapeutics, "Q3 2018 Earnings and Corporate Development", Powerpoint, 23 pages, presented Oct. 31, 2018.

Ruan et al., "Highly efficient CRISPR/Cas9-mediated transgene knockin at the H11 locus in pigs", Scientific Reports, 10 pages, Sep. 18, 2015.

Suzuki et al., "In vivo genome editing via CRISPR/Cas9 mediated homology-independent targeted integration", Nature, vol. 540, 24 pages, Dec. 1, 2016.

Uno et al., "CRISPR/Cas9-induced transgene insertion and telomere-associated truncation of a single human chromosome for chromosome engineering in CHO and A9 cells", Scientific Reports, 10 pages, Oct. 6, 2017.

Yao et al., "Homology-mediated end joining-based targeted integration using CRISPR/Cas9", Cell Research, vol. 27, pp. 801-814, Apr. 6, 2017.

Sheng et al. Canadian Journal of Microbiology, 445-454 (Year: 2014).

Ryu et al. Plant Molecular Biology 54: 489-502 (Year: 2004).

Senis et al. Nucleic acid Res. , 45(1), e3 (Year: 2016).

Kaiser Science, 317, 580 (Year: 2007).

Frank et al N. Engl. J Med. Jul. 9;361 (2): 161-9 (Year: 2009).

Edelstein Journal Gene Med., 597-602 (Year: 2004).

High Nature, 435, 577- 579 (Year: 2005).

Ramirez Nature Methods, 5(5): 374-375 (Year: 2008).

Li Nature, Jul. 14,, 475, 7355, 217-221 (Year: 2011).

Christian Genetics, 757-761 (Year: 2010).

Hauschild PNAS, 108( 29), 12013-12017 (Year: 2011).

Hsu et al. Nat Biotechnology. Sep. 31 (9):827-32 (Year: 2013).

Lee et al., (Drug Discovery Today: Disease Models, vol. 20, 13-20 (Year: 2016).

Kosicki et al. Nature Biotechnology, 36, 765-771 (Year: 2018).

Robert et al Curr Genetics, 64(2):389-391 (Year: 2018).

Cox et al , Nature Medicine 21 (2), 121-13 (Year: 2015).

Kuscu et al Nature biotechnology, 32(7), 677 (Year: 2014).

Kleinstiver Nature, 523, 481-485 (Year: 2015).

Pluta et al. (Acta Biochimica Polonica. Nov. 23, 2009. 54(4): 531-595) (Year: 2009).

Kurosaki et al. (Journal of Human Genetics (2011) 56, 727-733). (Year: 2011).

\* cited by examiner

SEQUENCE LISTING

<160> NUMBER OF SEQ ID NOS: 51

<210> SEQ ID NO 1
<211> LENGTH: 3527
<212> TYPE: DNA
<213> ORGANISM: Artificial Sequence
<220> FEATURE:
<223> OTHER INFORMATION: Construct

<400> SEQUENCE: 1

| | | | | | |
|---|---|---|---|---|---|
| gtgcggctgc | aagtgacccc | aggctgggct | cggccgggag | gcggggagga | gagaagggga | 60 |
| taccccatcc | aacagccact | ctaggcaaag | gtccccggat | cccggctgtg | accacctccc | 120 |
| atcctgcccc | caagccaccg | gggtgcccgg | cggccggagc | ggacacggat | ccccaccaca | 180 |
| ccagctgcct | atgctgtccc | cccagccccc | ttgcccaccc | gccgccccct | cccgccgcc | 240 |
| cgcagctgct | tgctcctcgg | ttgtggatca | tatttgagtt | ctgggccgtg | ccgcccgacc | 300 |
| tttcactttc | ctttaacccg | gcttctgttt | ttgtttcaat | tatgatttct | gtcctctgga | 360 |
| cgcctgtgag | taattttttga | aacttctgct | atttttaacc | ccgaaactta | caaaactcca | 420 |
| tttctcattt | ctcttttcac | tttgttgtgt | tggttttcga | ctcctcccct | ccctgtctca | 480 |
| ctccccctcc | tcccctccct | cctccctgtg | gctgttgctt | ttttccattc | aatgtcctgt | 540 |
| gtcccccctc | tcctcctcct | cctcctcctc | cccctccccc | tcctccctct | cctcccggcc | 600 |
| cctctccctt | cgctcccctc | tcttcctccc | aatcccgtgt | ctccctttgat | tttgttgtat | 660 |
| cttttttttt | gatttccttt | gtttcaattt | tcgtgtaggg | cagtagttcc | gtaagtggaa | 720 |
| gcccagcccc | ctcaacatct | ggtaccagca | ctccgcggcg | gggccgccgc | cagctccccc | 780 |
| agacccccctc | cacccccccgg | ccacacgtgt | cctattcccc | tgtgatccgt | aaggccggcg | 840 |
| gctcggggcc | cccgcagcag | cagcagcagc | agcagcagca | gcagcagcag | caggcggtgg | 900 |
| ccaggccggg | ccgggcggcc | accagcggcc | ctcggaggta | cccaggcccc | acggccgagc | 960 |
| ctctggccgg | agatcggccg | cccacggggg | gccacagcag | cggccgctcg | cccaggatgg | 1020 |
| agaggcgggt | cccaggcccg | gcccggagcg | agtcccccag | ggcctgtcga | cacgcgggg | 1080 |
| cccggtggcc | ggcatctggc | ccgcacgtgt | ccgaggggcc | cccgggtccc | cggcaccatg | 1140 |
| gctactaccg | gggctccgac | tacgacgagg | ccgatggccc | gggcagcggg | ggcggcgagg | 1200 |
| aggccatggc | cggggcctac | gacgcgccac | ccccccgtacg | acacgcgtcc | tcgggcgcca | 1260 |
| ccgggcgctc | gcccaggact | ccccgggcct | cgggccccggc | ctgcgcctcg | ccttctcggc | 1320 |
| acggccggcg | actccccaac | ggctactacc | cggcgcacgg | actggccagg | cccgcgggc | 1380 |
| cgggctccag | gaagggcctg | cacgaaccct | acagcgagag | tgacgatgat | tggtgctaaa | 1440 |
| acttgtttat | tgcagcttat | aatggttaca | aataaagcaa | tagcatcaca | aatttcacaa | 1500 |
| ataaagcatt | tttttcactg | cattctagtt | gtggtttgtc | caaactcatc | aatgtatctt | 1560 |
| atcatgtctg | gatctcccca | gcatgcctgc | tattctcttc | ccaatcctcc | cccttgctgt | 1620 |
| cctgccccac | cccacccccc | agaatagaat | gacacctact | cagacaatgc | gatgcaattt | 1680 |
| cctcattttta | ttaggaaagg | acagtgggag | tggcaccttc | cagggtcaag | gaaggcacgg | 1740 |
| gggaggggca | acaacagat | ggctggcaac | tagaaggcac | agtcagcacc | agtcgtcgtc | 1800 |
| ggattcgctg | tagggttcat | ggagacccct | ccgagaccca | ggtcctcttg | gccgggccaa | 1860 |
| gccgtgtgca | gggtaatatc | cattgggag | cctccggcca | tgccgagaag | gtgaagcgca | 1920 |
| cgctggtcct | gacgccgggg | gggtgcgagg | agacctccct | gtcgcccggg | aagacgcatg | 1980 |
| cctaacggga | ggcggagcat | cataagcacc | agccatcgct | tcctcgccac | caccactgcc | 2040 |

```
gggcccgtca gcttcgtcat agtcagaacc ccgataatat ccgtgatggc gaggccctgg   2100
aggtccttcg ctaacgtgtg gcccagaagc aggccaccgc gcacctccat ggcgacatgc   2160
tctaggactc tcgcttcttg caggtccagg aacccgccgc tccattgcgg ggcttcgccc   2220
actactgtgt ccacctgtcg gagggcggtc tccggcaagg ggttcagcgg ttgggcctgg   2280
atagcgccgc ggaccggagg tagcagcccg accgggtcgt gctaccgctt gctgttgctg   2340
ttgttgctgt tgctgctgtt gttgttgggg tggcccgcta cctcccgctt ttctaataac   2400
tggtgaataa ctcacatgtg ggcgcggagt ggatggtgtc tgagggagtt gccttctccc   2460
tcggcggggt gtagacgtac cagatgttga aggcgccggg ctcccgctta ctgaactact   2520
gtaaatgaat gagaaaaccg gtttagaaag tgcacagctg tcagggaagt caacacttca   2580
gtgagcatgt gaccatgtgg agtcagcttc ctgtttcgtg ctgcaatcgc ccgggcgagg   2640
tggcgcccgc ccggcccccc acgcaccccca cgcacacacc ccacccgagg agccgcgcag   2700
aggccgcggg ggcccagcac agagggcccg ggagagggcc agccgggaga ccccagactc   2760
tggagaggcc agggctgggc cacaagggtg tcccgcagag accctcggcc aaaagagacc   2820
ctcctgggca gccacggcgc cccccaacca gccccgatcc ccccacccac gacagggggct   2880 ctcgggtggg aggcagggag cagacaaacc acacagccaa gggatttgaa ttaactcagc   2940 cattttttgga gaactttggg gaacatgaaa aaaaaaaaa aaaaaaaaa aaaaaacatt   3000 tttaaaagaa aaaacgggga gaaaaaaata gcttctattg atgagtttta tcatctcaat   3060
tgaatctttc ctttccctga tgaagacagc tggtggccga gtgcggcaaa gaagccagaa   3120
ggaaccagaa tcccagtgcc ctacacccac caccagacac actcacaccc acacgttc   3180 tcagacacac acaagagtgc ttgccggtta taccaaaccc tactattact gcctgcagaa   3240
atcaatttaa aaaataata ataacaataa acaattttaa aaaggacaaa aaaattaatg   3300
attgagaaaa gaggcatttt ttctgacat ttggtcctgc ttgaaacaac aaaagaagaa   3360
gaaaaaccca ccatcaccac cgattccttt gcttcttttt tcctttttttc ctaccttgtt   3420 tgaaaaccgt gggcttggga ctgtgaatta ttgcatgaca ttcaaaaaga aaaaaaaaat   3480 aaaaaaagt tgaatcaaat ttctgtcctc tggacgcctg tgagtaa   3527

<210> SEQ ID NO 2
<211> LENGTH: 703
<212> TYPE: DNA
<213> ORGANISM: Artificial Sequence
<220> FEATURE:
<223> OTHER INFORMATION: Construct

<400> SEQUENCE: 2
gtgcggctgc aagtgacccc aggctgggct cggccgggag gcggggagga gagaagggga    60 tacccccatcc aacagccact ctaggcaaag gtccccggat cccggctgtg accacctccc   120
atcctgcccc caagccaccg gggtgccggg cggccgagc ggacacggat ccccaccaca   180
ccagctgcct atgctgtccc cccagccccc ttgcccaccc gccgccccct cccgccgcc   240 cgcagctgct tgctcctcgg ttgtggatca tatttgagtt ctgggccgtg ccgcccgacc   300
tttcactttc ctttaacccg gcttctgttt ttgtttcaat tatgattcct gtcctctgga   360
cgcctgtgag taattttttga aacttctgct attttttaacc ccgaaactta caaaactcca   420
tttctcattt ctcttttcac tttgttgtgt tggttttcga ctcctcccct ccctgtctca   480 ctcccccctcc tccccctccct cctccctgtg gctgttgctt ttttccattc aatgtcctgt   540
```

```
gtcccccctc tcctcctcct cctcctcctc ccctcccc tcctccctct cctcccggcc    600
cctctccctt cgctccctc tcttcctccc aatcccgtgt ctcctttgat tttgttgtat    660 ctttttttt gatttccttt gtttcaattt tcgtgtaggg cag                     703
```

```
<210> SEQ ID NO 3
<211> LENGTH: 736
<212> TYPE: DNA
<213> ORGANISM: Artificial Sequence
<220> FEATURE:
<223> OTHER INFORMATION: Construct

<400> SEQUENCE: 3
tagttccgta agtggaagcc cagccccctc aacatctggt accagcactc cgcggcgggg    60
ccgccgccag ctcccccaga cccctccac cccccggcca cacgtgtcct attcccctgt    120
gatccgtaag gccggcggct cggggccccc gcagcagcag cagcagcagc agcagcagca    180
gcagcagcag gcggtggcca ggccgggccg ggcggccacc agcggccctc ggaggtaccc    240
aggccccacg gccgagcctc tggccggaga tcggccgccc acgggggcc acagcagcgg    300 ccgctcgccc aggatggaga ggcgggtccc aggcccggcc cggagcgagt ccccagggc    360 ctgtcgacac ggcgggccc ggtggccggc atctggcccg cacgtgtccg aggggccccc    420
gggtccccgg caccatggct actaccgggg ctccgactac gacgaggccg atggcccggg    480 cagcggggc ggcgaggagg ccatggccgg ggcctacgac gcgccacccc ccgtacgaca    540
cgcgtcctcg ggcgccaccg ggcgctcgcc caggactccc cgggcctcgg gcccggcctg    600
cgcctcgcct tctcggcacg gccggcgact ccccaacggc tactaccgg cgcacggact    660 ggccaggccc cgcgggccgg gctccaggaa gggcctgcac gaaccctaca gcgagagtga    720
cgatgattgg tgctaa                                                   736
```

```
<210> SEQ ID NO 4
<211> LENGTH: 135
<212> TYPE: DNA
<213> ORGANISM: Artificial Sequence
<220> FEATURE:
<223> OTHER INFORMATION: Construct

<400> SEQUENCE: 4
aacttgttta ttgcagctta taatggttac aaataaagca atagcatcac aaatttcaca    60
aataaagcat ttttttcact gcattctagt tgtggtttgt ccaaactcat caatgtatct    120
tatcatgtct ggatc                                                    135
```

```
<210> SEQ ID NO 5
<211> LENGTH: 208
<212> TYPE: DNA
<213> ORGANISM: Artificial Sequence
<220> FEATURE:
<223> OTHER INFORMATION: Construct

<400> SEQUENCE: 5
tccccagcat gcctgctatt ctcttcccaa tcctccccct tgctgtcctg ccccacccca    60
ccccccagaa tagaatgaca cctactcaga caatgcgatg caatttcctc attttattag    120
gaaaggacag tgggagtggc accttccagg gtcaaggaag gcacggggga ggggcaaaca    180
acagatggct ggcaactaga aggcacag                                      208
```

```
<210> SEQ ID NO 6
<211> LENGTH: 736
```

<212> TYPE: DNA
<213> ORGANISM: Artificial Sequence
<220> FEATURE:
<223> OTHER INFORMATION: Construct

<400> SEQUENCE: 6

```
tcagcaccag tcgtcgtcgg attcgctgta gggttcatgg agacccttcc gagacccagg      60
tcctcttggc cgggccaagc cgtgtgcagg gtaatatcca ttggggagcc tccggccatg     120
ccgagaaggt gaagcgcacg ctggtcctga cgcccggggg gtgcgaggag acctccctgt     180
cgccccggaa gacgcatgcc taacgggagg cggagcatca taagcaccag ccatcgcttc     240
ctcgccacca ccactgccgg gcccgtcagc ttcgtcatag tcagaacccc gataatatcc     300
gtgatggcga ggccctggag gtccttcgct aacgtgtggc ccagaagcag gccaccgcgc     360
acctccatgg cgacatgctc taggactctc gcttcttgca ggtccaggaa cccgccgctc     420
cattcgcggg cttcgcccac tactgtgtcc acctgtcgga gggcggtctc cggcaagggg     480
ttcagcggtt gggcctggat agcgccgcgg accggaggta gcagcccgac cgggtcgtgc     540
taccgcttgc tgttgctgtt gttgctgttg ctgctgttgt tgttggggtg cccgctacc      600
tcccgctttt ctaataactg gtgaataact cacatgtggg cgcggagtgg atggtgtctg     660
agggagttgc cttctccctc ggcggggtgt agacgtacca gatgttgaag gcgccgggct     720
cccgcttact gaacta                                                    736
```

<210> SEQ ID NO 7
<211> LENGTH: 110
<212> TYPE: DNA
<213> ORGANISM: Artificial Sequence
<220> FEATURE:
<223> OTHER INFORMATION: Construct

<400> SEQUENCE: 7

```
ctgtaaatga atgagaaaac cggtttagaa agtgcacagc tgtcagggaa gtcaacactt      60
cagtgagcat gtgaccatgt ggagtcagct tcctgtttcg tgctgcaatc                 110
```

<210> SEQ ID NO 8
<211> LENGTH: 446
<212> TYPE: DNA
<213> ORGANISM: Artificial Sequence
<220> FEATURE:
<223> OTHER INFORMATION: Construct

<400> SEQUENCE: 8

```
gcccgggcga ggtggcgccc gcccggcccc ccacgcaccc cacgcacaca ccccacccga      60
ggagccgcgc agaggccgcg ggggcccagc acagagggcc cgggagaggg ccagccggga     120
gaccccagac tctggagagg ccaggctgg gccacaaggg tgtcccgcag agaccctcgg     180
ccaaaagaga ccctcctggg cagccacggc gccccccaac cagccccgat ccccccaccc     240
acgacaggg ctctcgggtg ggaggcaggg agcagacaaa ccacacagcc aagggatttg     300
aattaactca gccattttg gagaactttg gggaacatga aaaaaaaaa aaaaaaaaa       360
aaaaaaaaca tttttaaaag aaaaacggg gagaaaaaaa tagcttctat tgatgagttt     420
tatcatctca attgaatctt tcctttt                                         446
```

<210> SEQ ID NO 9
<211> LENGTH: 24
<212> TYPE: DNA
<213> ORGANISM: Artificial Sequence
<220> FEATURE:

<223> OTHER INFORMATION: Target site

<400> SEQUENCE: 9
tttctgtcct ctggacgcct gtga                                          24

<210> SEQ ID NO 10
<211> LENGTH: 2288
<212> TYPE: DNA
<213> ORGANISM: Artificial Sequence
<220> FEATURE:
<223> OTHER INFORMATION: Construct

<400> SEQUENCE: 10
atttcattta tcaggtgttc agtgaatgct tactatgtaa cagcacagtt atcagcactg     60
gggaaataga tgagtaagat aagatttgca ctttcattag cttacatgcc ataaagaggg    120
aaataaagag aacaccagat gatgataagt ttatgctgag aattaaaatg aagtgatgaa    180
ataatgggaa tgtcaggtgg ctacttttgg tgggatggtc aggaaaggca tctctgggga    240
gataaatttt aagctcagac ctgagtgaaa agaatgagcc agccatggaa acattatgtt    300
aactcacatg gtagtttgaa atgctttatc tgatcaaagg tacttatttt tggtgacttt    360
caacaatatt aagggtctat aaaccaacac tcatttgcat aagaataact accagtgaat    420
ctttttgtat gataggtttt ttgtttgttg ttttttgag acagagtctc gctctgtcgc    480
ccaggctgga gtgcagtggc gcgatcttgg ctcactgcaa cctctacctc cccggttcaa    540
gtgattctcc tgcctcagcc tcccaaagta gctgggatta caggtgcctg ccaccacgcc    600
tggctaattt ttgtattttt agtagagatg gggtttcacc gtgttgtcca ggctcgtgtc    660
aaacttctga cctcaagcca tccacccgcc tcggcctccc aaagtgctgg gattacaggt    720
gtgagccacc actcctggcc atgataggtt attttgtgat gaaataccct acctcttaat    780
ttgtctgata aatttaaatt ttatgtctag atttcctaag atcagcactt ccatatttta    840
aagtaatctg tatcagacta actgctcttg cattctttta ataccagtga ctactttgat    900
tcgtgaaaca atgtattttc cttatgaata gttttctca tggtgtattt attcttttaa    960
gttttgttt ttaaatatac ttcacttttg aatgtttcag acagcagcaa aagcagcaac   1020
agcagcagca gcagcagcag caggggggacc tatcaggaca gagttcacat ccatgtgaaa   1080
ggccagccac cagttcagga gcacttggga gtgatctagg tgatgctatg agtgaagaag   1140
acatgcttca ggcagctgtg accatgtctt tagaaactgt cagaaatgat tgaaaacag    1200
aaggaaaaaa ataaaacttg tttattgcag cttataatgg ttacaaataa agcaatagca   1260
tcacaaattt cacaaataaa gcatttttt cactgcattc tagttgtggt ttgtccaaac   1320
tcatcaatgt atcttatcat gtctggatct ccccagcatg cctgctattc tcttcccaat   1380
cctccccctt gctgtcctgc cccaccccac ccccagaat agaatgacac ctactcagac   1440
aatgcgatgc aatttcctca ttttattagg aaaggacagt gggagtggca ccttccaggg   1500
tcaaggaagg cacggggag gggcaaacaa cagatggctg gcaactagaa ggcacagcta   1560
cttcttgccc tcggtcttca ggtcgttgcg cacggtctcc aggctcatgg tcacggcggc   1620
ctgcagcatg tcctcctcgc tcatggcgtc gcccaggtcg ctgcccaggg cgccgctgct   1680
ggtggcgggg cgctcgcagg ggtggctgct ctggccgctc aggtcgccct gctgctgctg   1740
ctgctgctgc tgctgctgct tctgctgctg tctgtaaatg aatgagaaaa ccggtttaga   1800
aagtgcacag ctgtcaggga agtcaacact tcagtgagca tgtgaccatg tggagtcagc   1860
ttcctgtttc gtgctgcaat cgtaaggcct gctcaccatt catcatgttc gctaccttca   1920

```
cactttatct gacatacgag ctccatgtga tttttgcttt acattattct tcattccctc    1980
tttaatcata ttaagaatct taagtaaatt tgtaatctac taaatttccc tggattaagg    2040
agcagttacc aaaagaaaaa aaaaaaaaaa agctagatgt ggtggctcac atctgtaatc    2100
ccagcacttt gggaaaccaa ggcaggagag gattgctaga acatttaatg aatactttaa    2160
cataataatt taaacttcac agtaatttgt acagtctcca aaaattcctt agacatcatg    2220
gatatttttc tttttttgag atggagtctt gctctgtcac tttgagacag agtctcgctc    2280
tgtcgccc                                                             2288

<210> SEQ ID NO 11
<211> LENGTH: 24
<212> TYPE: DNA
<213> ORGANISM: Artificial Sequence
<220> FEATURE:
<223> OTHER INFORMATION: Target site

<400> SEQUENCE: 11
tttgagacag agtctcgctc tgtc                                            24

<210> SEQ ID NO 12
<211> LENGTH: 60
<212> TYPE: DNA
<213> ORGANISM: Artificial Sequence
<220> FEATURE:
<223> OTHER INFORMATION: gRNA
<220> FEATURE:
<221> NAME/KEY: misc_feature
<222> LOCATION: (9)..(40)
<223> OTHER INFORMATION: n is a, c, g, or t

<400> SEQUENCE: 12
ctgataacnn nnnnnnnnnn nnnnnnnnnn nnnnnnnnnn gtgaactgcc gagtaggtag     60

<210> SEQ ID NO 13
<211> LENGTH: 47
<212> TYPE: DNA
<213> ORGANISM: Vibrio cholerae

<400> SEQUENCE: 13
aattatcaat ttatgggtgt aattatcatt ttatggttgt atcaaca                   47

<210> SEQ ID NO 14
<211> LENGTH: 258
<212> TYPE: DNA
<213> ORGANISM: Artificial Sequence
<220> FEATURE:
<223> OTHER INFORMATION: gRNA
<220> FEATURE:
<221> NAME/KEY: misc_feature
<222> LOCATION: (236)..(258)
<223> OTHER INFORMATION: n is a, c, g, or t

<400> SEQUENCE: 14
tattaatagc gccgcaattc atgctgcttg cagcctctga attttgttaa atgagggtta     60
gtttgactgt ataaatacag tcttgctttc tgaccctggt agctgctcac cctgatgctg    120
ctgtcaatag acaggatagg tgcgctccca gcaataaggg cgcggatgta ctgctgtagt    180
ggctactgaa tcaccccccga tcaaggggga accctccaaa aggtgggttg aaagtnnnnn    240
nnnnnnnnnn nnnnnnnn                                                  258

<210> SEQ ID NO 15
```

```
<211> LENGTH: 20
<212> TYPE: DNA
<213> ORGANISM: Artificial Sequence
<220> FEATURE:
<223> OTHER INFORMATION: Target site

<400> SEQUENCE: 15
ccgcccgacc tttcactttc                                                 20

<210> SEQ ID NO 16
<211> LENGTH: 20
<212> TYPE: DNA
<213> ORGANISM: Artificial Sequence
<220> FEATURE:
<223> OTHER INFORMATION: Target site

<400> SEQUENCE: 16
cccggatccc ggctgtgacc                                                 20

<210> SEQ ID NO 17
<211> LENGTH: 2391
<212> TYPE: DNA
<213> ORGANISM: Artificial Sequence
<220> FEATURE:
<223> OTHER INFORMATION: Construct

<400> SEQUENCE: 17
atttcattta tcaggtgttc agtgaatgct tactatgtaa cagcacagtt atcagcactg     60
gggaaataga tgagtaagat aagatttgca ctttcattag cttacatgcc ataaagaggg    120
aaataaagag aacaccagat gatgataagt ttatgctgag aattaaaatg aagtgatgaa    180
ataatgggaa tgtcaggtgg ctacttttgg tgggatggtc aggaaaggca tctctgggga    240
gataaatttt aagctcagac ctgagtgaaa agaatgagcc agccatggaa acattatgtt    300
aactcacatg gtagtttgaa atgctttatc tgatcaaagg tacttatttt tggtgacttt    360
caacaatatt aagggtctat aaaccaacac tcatttgcat aagaataact accagtgaat    420 cttttttgtat gataggtttt ttgtttgttg ttttttttgag acagagtctc gctctgtcgc    480
ccaggctgga gtgcagtggc gcgatcttgg ctcactgcaa cctctacctc cccggttcaa    540
gtgattctcc tgcctcagcc tcccaaagta gctgggatta caggtgcctg ccaccacgcc    600
tggctaattt ttgtattttt agtagagatg gggtttcacc gtgttgtcca ggctcgtgtc    660
aaacttctga cctcaagcca tccacccgcc tcggcctccc aaagtgctgg gattacaggt    720
gtgagccacc actcctggcc atgataggtt attttgtgat gaaatacct acctcttaat    780 ttgtctgata aatttaaatt ttatgtctag atttcctaag atcagcactt ccatatttta    840
aagtaatctg tatcagacta actgctcttg cattctttta ataccagtga ctactttgat    900
tcgtgaaaca atgtattttc cttatgaata gttttttctca tggtgtattt attcttttaa    960
gttttgtttt ttaaatatac ttcacttttg aatgtttcag acagcagcaa aagcagcaac   1020
agcagcagca gcagcagcag cagggggacc tatcaggaca gagttcacat ccatgtgaaa   1080
ggccagccac cagttcagga gcacttggga gtgatctagg tgatgctatg agtgaagaag   1140
acatgcttca ggcagctgtg accatgtctt tagaaactgt cagaaatgat ttgaaaacag   1200
aaggaaaaaa ataaaacttg tttattgcag cttataatgg ttacaaataa agcaatagca   1260
tcacaaattt cacaaataaa gcattttttt cactgcattc tagttgtggt tgtccaaac    1320 tcatcaatgt atcttatcat gtctggatct ccccagcatg cctgctattc tcttcccaat   1380 cctcccccctt gctgtcctgc cccaccccac cccccagaat agaatgacac ctactcagac   1440
```

```
aatgcgatgc aatttcctca ttttattagg aaaggacagt gggagtggca ccttccaggg    1500
tcaaggaagg cacggggag gggcaaacaa cagatggctg caactagaa ggcacagcta      1560 cttcttgccc tcggtcttca ggtcgttgcg cacggtctcc aggctcatgg tcacggcggc    1620
ctgcagcatg tcctcctcgc tcatggcgtc gcccaggtcg ctgcccaggg cgccgctgct    1680
ggtggcgggg cgctcgcagg ggtggctgct ctggccgctc aggtcgccct gctgctgctg    1740
ctgctgctgc tgctgctgct tctgctgctg tctgtaaatg aatgagaaaa ccggtttaga    1800
aagtgcacag ctgtcaggga agtcaacact tcagtgagca tgtgaccatg tggagtcagc    1860
ttcctgtttc gtgctgcaat cgtaaggcct gctcaccatt catcatgttc gctaccttca    1920
cactttatct gacatacgag ctccatgtga tttttgcttt acattattct tcattccctc    1980
tttaatcata ttaagaatct taagtaaatt tgtaatctac taaatttccc tggattaagg    2040
agcagttacc aaaagaaaaa aaaaaaaaaa agctagatgt ggtggctcac atctgtaatc    2100
ccagcacttt gggaaaccaa ggcaggagag gattgctaga acatttaatg aatactttaa    2160
cataataatt taaacttcac agtaatttgt acagtctcca aaaattcctt agacatcatg    2220 gatattttc ttttttttgag atggagtctt gctcttttaa gctcagacct gagtgaaaag    2280
aatttgagac agagtctcgc tctgtcgcct ttcctaagat cagcacttcc atatttggtg    2340
actttcaaca atattaaggg tctataaacc aacactcatt tgcataagaa t             2391

<210> SEQ ID NO 18
<211> LENGTH: 20
<212> TYPE: DNA
<213> ORGANISM: Artificial Sequence
<220> FEATURE:
<223> OTHER INFORMATION: Target site

<400> SEQUENCE: 18
aatatggaag tgctgatctt                                                  20

<210> SEQ ID NO 19
<211> LENGTH: 1205
<212> TYPE: DNA
<213> ORGANISM: Artificial Sequence
<220> FEATURE:
<223> OTHER INFORMATION: Construct

<400> SEQUENCE: 19
tttaagctca gacctgagtg aaaagaattt gagacagagt ctcgctctgt cgcctttcct     60
aagatcagca cttccatatt ttaaagtaat ctgtatcaga ctaactgctc ttgcattctt    120
ttaataccag tgactacttt gattcgtgaa acaatgtatt ttccttatga atagttttc     180 tcatggtgta tttattcttt taagttttgt tttttaaata tacttcactt ttgaatgttt    240
cagacagcag caaaagcagc aacagcagca gcagcagcag cagcagggg acctatcagg     300 acagagttca catccatgtg aaaggccagc caccagttca ggagcacttg ggagtgatct    360
aggtgatgct atgagtgaag aagacatgct tcaggcagct gtgaccatgt ctttagaaac    420
tgtcagaaat gatttgaaaa cagaaggaaa aaaataaaac ttgtttattg cagcttataa    480
tggttacaaa taaagcaata gcatcacaaa tttcacaaat aaagcatttt tttcactgca    540
ttctagttgt ggtttgtcca aactcatcaa tgtatcttat catgtctgga tctccccagc    600
atgcctgcta ttctcttccc aatcctcccc cttgctgtcc tgccccaccc cacccccag    660 aatagaatga cacctactca gacaatgcga tgcaatttcc tcatttttatt aggaaaggac    720
```

-continued

| | |
|---|---|
| agtgggagtg gcaccttcca gggtcaagga aggcacgggg gaggggcaaa caacagatgg | 780 |
| ctggcaacta gaaggcacag ctacttcttg ccctcggtct tcaggtcgtt gcgcacggtc | 840 |
| tccaggctca tggtcacggc ggcctgcagc atgtcctcct cgctcatggc gtcgcccagg | 900 |
| tcgctgccca gggcgccgct gctggtggcg gggcgctcgc aggggtggct gctctggccg | 960 |
| ctcaggtcgc cctgctgctg ctgctgctgc tgctgctgct gcttctgctg ctgtctgtaa | 1020 |
| atgaatgaga aaaccggttt agaaagtgca cagctgtcag ggaagtcaac acttcagtga | 1080 |
| gcatgtgacc atgtggagtc agcttcctgt ttcgtgctgc aatctttaag ctcagacctg | 1140 |
| agtgaaaaga atttgagaca gagtctcgct ctgtcgcctt tcctaagatc agcacttcca | 1200 |
| tattt | 1205 |

<210> SEQ ID NO 20
<211> LENGTH: 1723
<212> TYPE: DNA
<213> ORGANISM: Artificial Sequence
<220> FEATURE:
<223> OTHER INFORMATION: Construct

<400> SEQUENCE: 20

| | |
|---|---|
| atttcattta tcaggtgttc agtgaatgct tactatgtaa cagcacagtt atcagcactg | 60 |
| gggaaataga tgagtaagat aagatttgca ctttcattag cttacatgcc ataaagaggg | 120 |
| aaataaagag aacaccagat gatgataagt ttatgctgag aattaaaatg aagtgatgaa | 180 |
| ataatgggaa tgtcaggtgg ctacttttgg tgggatggtc aggaaaggca tctctgggga | 240 |
| gataaatttt aagctcagac ctgagtgaaa agaatgagcc agccatggaa acattatgtt | 300 |
| aactcacatg gtagtttgaa atgctttatc tgatcaaagg tacttatttt tggtgacttt | 360 |
| caacaatatt aagggtctat aaaccaacac tcatttgcat aagaataact accagtgaat | 420 |
| cttttttgtat gataggtttt ttgtttgttg ttttttttgag acagagtctc gctctgtcgc | 480 |
| ccaggctgga gtgcagtggc gcgatcttgg ctcactgcaa cctctacctc cccggttcaa | 540 |
| gtgattctcc tgcctcagcc tcccaaagta gctgggatta caggtgcctg ccaccacgcc | 600 |
| tggctaattt ttgtattttt agtagagatg gggtttcacc gtgttgtcca ggctcgtgtc | 660 |
| aaacttctga cctcaagcca tccacccgcc tcggcctccc aaagtgctgg gattacaggt | 720 |
| gtgagccacc actcctggcc atgataggtt attttgtgat gaaatacct acctcttaat | 780 |
| ttgtctgata aatttaaatt ttatgtctag aaatcctaag atcagcactt ccatatttta | 840 |
| aagtaatctg tatcagacta actgctcttg cattcttttta ataccagtga ctactttgat | 900 |
| tcgtgaaaca atgtattttc cttatgaata gttttctca tggtgtattt attctttta | 960 |
| gttttgttt ttaaatatac ttcacttttg aatgtttcag acagcagcaa aagcagcaac | 1020 |
| agcagcagca gcagcagcag caggggggacc tatcaggaca gagttcacat ccatgtgaaa | 1080 |
| ggccagccac cagttcagga gcacttggga gtgatctagg tgatgctatg agtgaagaag | 1140 |
| acatgcttca ggcagctgtg accatgtctt tagaaactgt cagaaatgat ttgaaaacag | 1200 |
| aaggaaaaaa ataaaacttg tttattgcag cttataatgg ttacaaataa agcaatagca | 1260 |
| tcacaaattt cacaaataaa gcattttttt cactgcattc tagttgtggt ttgtccaaac | 1320 |
| tcatcaatgt atcttatcat gtctggatcg taaggcctgc tcaccattca tcatgttcgc | 1380 |
| taccttcaca ctttatctga catacgagct ccatgtgatt tttgctttac attattcttc | 1440 |
| attccctctt taatcatatt aagaatctta agtaaatttg taatctacta aatttccctg | 1500 |
| gattaaggag cagttaccaa aagaaaaaaa aaaaaaaaag ctagatgtgg tggctcacat | 1560 |

-continued

```
ctgtaatccc agcactttgg gaaaccaagg caggagagga ttgctagaac atttaatgaa    1620
tactttaaca taataattta aacttcacag taatttgtac agtctccaaa aattccttag    1680
acatcatgga tattttctt tttttgagat ggagtcttgc tct                       1723
```

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21

```
caaaggtgcc cttgaggtt                                                   19
```

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22

```
aggagaagtc tgccgttact                                                  20
```

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23

```
ggacaaaacca caactagaat gc                                              22
```

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24

```
taggaaagga cagtgggagt                                                  20
```

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25

```
ccattatgtc tcagttgttc agtg                                             24
```

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26

```
ccagaccatc tcagacacc                                                   19
```

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
ggctgggctt ccacttac                                                    18

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gtggtttgtc caaactcatc aa                                               22

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
agtaactctg cacttcccat tg                                               22

<210> SEQ ID NO 30
<211> LENGTH: 639
<212> TYPE: PRT
<213> ORGANISM: Scytonema hoffmanni

<400> SEQUENCE: 30

Met Ser Gln Ile Thr Ile Gln Ala Arg Leu Ile Ser Phe Glu Ser Asn
1               5                   10                  15

Arg Gln Gln Leu Trp Lys Leu Met Ala Asp Leu Asn Thr Pro Leu Ile
            20                  25                  30

Asn Glu Leu Leu Cys Gln Leu Gly Gln His Pro Asp Phe Glu Lys Trp
        35                  40                  45

Gln Gln Lys Gly Lys Leu Pro Ser Thr Val Val Ser Gln Leu Cys Gln
    50                  55                  60

Pro Leu Lys Thr Asp Pro Arg Phe Ala Gly Gln Pro Ser Arg Leu Tyr
65                  70                  75                  80

Met Ser Ala Ile His Ile Val Asp Tyr Ile Tyr Lys Ser Trp Leu Ala
                85                  90                  95

Ile Gln Lys Arg Leu Gln Gln Leu Asp Gly Lys Thr Arg Trp Leu
            100                 105                 110

Glu Met Leu Asn Ser Asp Ala Glu Leu Val Glu Leu Ser Gly Asp Thr
        115                 120                 125

Leu Glu Ala Ile Arg Val Lys Ala Ala Glu Ile Leu Ala Ile Ala Met
    130                 135                 140

Pro Ala Ser Glu Ser Asp Ser Ala Ser Pro Lys Gly Lys Lys Gly Lys
145                 150                 155                 160

Lys Glu Lys Lys Pro Ser Ser Ser Pro Arg Ser Leu Ser Lys
                165                 170                 175

Thr Leu Phe Asp Ala Tyr Gln Glu Thr Glu Asp Ile Lys Ser Arg Ser
        180                 185                 190

```
Ala Ile Ser Tyr Leu Leu Lys Asn Gly Cys Lys Leu Thr Asp Lys Glu
        195                 200                 205

Glu Asp Ser Glu Lys Phe Ala Lys Arg Arg Gln Val Glu Ile Gln
    210                 215                 220

Ile Gln Arg Leu Thr Glu Lys Leu Ile Ser Arg Met Pro Lys Gly Arg
225                 230                 235                 240

Asp Leu Thr Asn Ala Lys Trp Leu Glu Thr Leu Thr Ala Thr Thr
            245                 250                 255

Thr Val Ala Glu Asp Asn Ala Gln Ala Lys Arg Trp Gln Asp Ile Leu
        260                 265                 270

Leu Thr Arg Ser Ser Leu Pro Phe Pro Leu Val Phe Glu Thr Asn
        275                 280                 285

Glu Asp Met Val Trp Ser Lys Asn Gln Lys Gly Arg Leu Cys Val His
        290                 295                 300

Phe Asn Gly Leu Ser Asp Leu Ile Phe Glu Val Tyr Cys Gly Asn Arg
305                 310                 315                 320

Gln Leu His Trp Phe Gln Arg Phe Leu Glu Asp Gln Thr Lys Arg
                325                 330                 335

Lys Ser Lys Asn Gln His Ser Ser Gly Leu Phe Thr Leu Arg Asn Gly
            340                 345                 350

His Leu Val Trp Leu Glu Gly Glu Lys Gly Glu Pro Trp Asn Leu
        355                 360                 365

His His Leu Thr Leu Tyr Cys Cys Val Asp Asn Arg Leu Trp Thr Glu
        370                 375                 380

Glu Gly Thr Glu Ile Val Arg Gln Glu Lys Ala Asp Glu Ile Thr Lys
385                 390                 395                 400

Phe Ile Thr Asn Met Lys Lys Ser Asp Leu Ser Asp Thr Gln Gln
                405                 410                 415

Ala Leu Ile Gln Arg Lys Gln Ser Thr Leu Thr Arg Ile Asn Asn Ser
            420                 425                 430

Phe Glu Arg Pro Ser Gln Pro Leu Tyr Gln Gly Gln Ser His Ile Leu
        435                 440                 445

Val Gly Val Ser Leu Gly Leu Glu Lys Pro Ala Thr Val Ala Val Val
        450                 455                 460

Asp Ala Ile Ala Asn Lys Val Leu Ala Tyr Arg Ser Ile Lys Gln Leu
465                 470                 475                 480

Leu Gly Asp Asn Tyr Glu Leu Leu Asn Arg Gln Arg Gln Gln Gln
                485                 490                 495

Tyr Leu Ser His Glu Arg His Lys Ala Gln Lys Asn Phe Ser Pro Asn
            500                 505                 510

Gln Phe Gly Ala Ser Glu Leu Gly Gln His Ile Asp Arg Leu Leu Ala
        515                 520                 525

Lys Ala Ile Val Ala Leu Ala Arg Thr Tyr Lys Ala Gly Ser Ile Val
        530                 535                 540

Leu Pro Lys Leu Gly Asp Met Arg Glu Val Val Gln Ser Glu Ile Gln
545                 550                 555                 560

Ala Ile Ala Glu Gln Lys Phe Pro Gly Tyr Ile Glu Gly Gln Lys
                565                 570                 575

Tyr Ala Lys Gln Tyr Arg Val Asn Val His Arg Trp Ser Tyr Gly Arg
            580                 585                 590

Leu Ile Gln Ser Ile Gln Ser Lys Ala Ala Gln Thr Gly Ile Val Ile
        595                 600                 605
```

Glu Gly Lys Gln Pro Ile Arg Gly Ser Pro His Asp Lys Ala Lys
610                 615                 620

Glu Leu Ala Leu Ser Ala Tyr Asn Leu Arg Leu Thr Arg Arg Ser
625                 630                 635

<210> SEQ ID NO 31
<211> LENGTH: 642
<212> TYPE: PRT
<213> ORGANISM: Anabaena cylindrica

<400> SEQUENCE: 31

Met Ser Val Ile Thr Ile Gln Cys Arg Leu Val Ala Glu Glu Asp Ser
1               5                   10                  15

Leu Arg Gln Leu Trp Glu Leu Met Ser Glu Lys Asn Thr Pro Phe Ile
                20                  25                  30

Asn Glu Ile Leu Leu Gln Ile Gly Lys His Pro Glu Phe Glu Thr Trp
            35                  40                  45

Leu Glu Lys Gly Arg Ile Pro Ala Glu Leu Leu Lys Thr Leu Gly Asn
        50                  55                  60

Ser Leu Lys Thr Gln Glu Pro Phe Thr Gly Gln Pro Gly Arg Phe Tyr
65                  70                  75                  80

Thr Ser Ala Ile Thr Leu Val Asp Tyr Leu Tyr Lys Ser Trp Phe Ala
                85                  90                  95

Leu Gln Lys Arg Arg Lys Gln Gln Ile Glu Gly Lys Gln Arg Trp Leu
            100                 105                 110

Lys Met Leu Lys Ser Asp Gln Glu Leu Glu Gln Glu Ser Gln Ser Ser
        115                 120                 125

Leu Glu Val Ile Arg Asn Lys Ala Thr Glu Leu Phe Ser Lys Phe Thr
130                 135                 140

Pro Gln Ser Asp Ser Glu Ala Leu Arg Arg Asn Gln Asn Asp Lys Gln
145                 150                 155                 160

Lys Lys Val Lys Lys Thr Lys Lys Ser Thr Lys Pro Lys Thr Ser Ser
                165                 170                 175

Ile Phe Lys Ile Phe Leu Ser Thr Tyr Glu Glu Ala Glu Glu Pro Leu
            180                 185                 190

Thr Arg Cys Ala Leu Ala Tyr Leu Leu Lys Asn Asn Cys Gln Ile Ser
        195                 200                 205

Glu Leu Asp Glu Asn Pro Glu Glu Phe Thr Arg Asn Lys Arg Arg Lys
210                 215                 220

Glu Ile Glu Ile Glu Arg Leu Lys Asp Gln Leu Gln Ser Arg Ile Pro
225                 230                 235                 240

Lys Gly Arg Asp Leu Thr Gly Glu Glu Trp Leu Glu Thr Leu Glu Ile
                245                 250                 255

Ala Thr Phe Asn Val Pro Gln Asn Glu Asn Glu Ala Lys Ala Trp Gln
            260                 265                 270

Ala Ala Leu Leu Arg Lys Thr Ala Asn Val Pro Phe Pro Val Ala Tyr
        275                 280                 285

Glu Ser Asn Glu Asp Met Thr Trp Leu Lys Asn Asp Lys Asn Arg Leu
290                 295                 300

Phe Val Arg Phe Asn Gly Leu Gly Lys Leu Thr Phe Glu Ile Tyr Cys
305                 310                 315                 320

Asp Lys Arg His Leu His Tyr Phe Gln Arg Phe Leu Glu Asp Gln Glu
                325                 330                 335

Ile Leu Arg Asn Ser Lys Arg Gln His Ser Ser Ser Leu Phe Thr Leu
            340                 345                 350

```
                                       -continued

Arg Ser Gly Arg Ile Ala Trp Leu Pro Gly Glu Glu Lys Gly Glu His
            355                 360                 365

Trp Lys Val Asn Gln Leu Asn Phe Tyr Cys Ser Leu Asp Thr Arg Met
    370                 375                 380

Leu Thr Thr Glu Gly Thr Gln Gln Val Glu Glu Lys Val Thr Ala
385                 390                 395                 400

Ile Thr Glu Ile Leu Asn Lys Thr Lys Gln Lys Asp Asp Leu Asn Asp
                405                 410                 415

Lys Gln Gln Ala Phe Ile Thr Arg Gln Gln Ser Thr Leu Ala Arg Ile
            420                 425                 430

Asn Asn Pro Phe Pro Arg Pro Ser Lys Pro Asn Tyr Gln Gly Lys Ser
            435                 440                 445

Ser Ile Leu Ile Gly Val Ser Phe Gly Leu Glu Lys Pro Val Thr Val
        450                 455                 460

Ala Val Val Asp Val Val Lys Asn Lys Val Ile Ala Tyr Arg Ser Val
465                 470                 475                 480

Lys Gln Leu Leu Gly Glu Asn Tyr Asn Leu Leu Asn Arg Gln Arg Gln
                485                 490                 495

Gln Gln Gln Arg Leu Ser His Glu Arg His Lys Ala Gln Lys Gln Asn
            500                 505                 510

Ala Pro Asn Ser Phe Gly Glu Ser Glu Leu Gly Gln Tyr Val Asp Arg
            515                 520                 525

Leu Leu Ala Asp Ala Ile Ile Ala Ile Ala Lys Lys Tyr Gln Ala Gly
        530                 535                 540

Ser Ile Val Leu Pro Lys Leu Arg Asp Met Arg Glu Gln Ile Ser Ser
545                 550                 555                 560

Glu Ile Gln Ser Arg Ala Glu Asn Gln Cys Pro Gly Tyr Lys Glu Gly
                565                 570                 575

Gln Gln Lys Tyr Ala Lys Glu Tyr Arg Ile Asn Val His Arg Trp Ser
            580                 585                 590

Tyr Gly Arg Leu Ile Glu Ser Ile Lys Ser Gln Ala Ala Gln Ala Gly
        595                 600                 605

Ile Ala Ile Glu Thr Gly Lys Gln Ser Ile Arg Gly Ser Pro Gln Glu
    610                 615                 620

Lys Ala Arg Asp Leu Ala Val Phe Thr Tyr Gln Glu Arg Gln Ala Ala
625                 630                 635                 640

Leu Ile

<210> SEQ ID NO 32
<211> LENGTH: 208
<212> TYPE: DNA
<213> ORGANISM: Artificial Sequence
<220> FEATURE:
<223> OTHER INFORMATION: Transposon left end

<400> SEQUENCE: 32
tacagtgaca aattatctgt cgtcggtgac agattaatgt cattgtgact atttaattgt    60
cgtcgtgacc catcagcgtt gcttaattaa ttgatgacaa attaaatgtc atcaatataa   120
tatgctctgc aattattata caaagcaatt aaaacaagcg gataaaagga cttgctttca   180
acccacccct aagtttaata gttactga                                      208

<210> SEQ ID NO 33
<211> LENGTH: 219
<212> TYPE: DNA
```

<213> ORGANISM: Artificial Sequence
<220> FEATURE:
<223> OTHER INFORMATION: Transposon right end

<400> SEQUENCE: 33

```
cgacagtcaa tttgtcatta tgaaaataca caaaagcttt ttcctatctt gcaaagcgac    60
agctaatttg tcacaatcac ggacaacgac atctattttg tcactgcaaa gaggttatgc   120
taaaactgcc aaagcgctat aatctatact gtataaggat tttactgatg acaataattt   180
gtcacaacga catataatta gtcactgtac acgtagaga                          219
```

<210> SEQ ID NO 34
<211> LENGTH: 394
<212> TYPE: PRT
<213> ORGANISM: Vibrio cholerae

<400> SEQUENCE: 34

```
Met Phe Leu Gln Arg Pro Lys Pro Tyr Ser Asp Glu Ser Leu Glu Ser
1               5                   10                  15

Phe Phe Ile Arg Val Ala Asn Lys Asn Gly Tyr Gly Asp Val His Arg
            20                  25                  30

Phe Leu Glu Ala Thr Lys Arg Phe Leu Gln Asp Ile Asp His Asn Gly
        35                  40                  45

Tyr Gln Thr Phe Pro Thr Asp Ile Thr Arg Ile Asn Pro Tyr Ser Ala
    50                  55                  60

Lys Asn Ser Ser Ser Ala Arg Thr Ala Ser Phe Leu Lys Leu Ala Gln
65                  70                  75                  80

Leu Thr Phe Asn Glu Pro Pro Glu Leu Leu Gly Leu Ala Ile Asn Arg
                85                  90                  95

Thr Asn Met Lys Tyr Ser Pro Ser Thr Ser Ala Val Val Arg Gly Ala
            100                 105                 110

Glu Val Phe Pro Arg Ser Leu Leu Arg Thr His Ser Ile Pro Cys Cys
        115                 120                 125

Pro Leu Cys Leu Arg Glu Asn Gly Tyr Ala Ser Tyr Leu Trp His Phe
    130                 135                 140

Gln Gly Tyr Glu Tyr Cys His Ser His Asn Val Pro Leu Ile Thr Thr
145                 150                 155                 160

Cys Ser Cys Gly Lys Glu Phe Asp Tyr Arg Val Ser Gly Leu Lys Gly
                165                 170                 175

Ile Cys Cys Lys Cys Lys Glu Pro Ile Thr Leu Thr Ser Arg Glu Asn
            180                 185                 190

Gly His Glu Ala Ala Cys Thr Val Ser Asn Trp Leu Ala Gly His Glu
        195                 200                 205

Ser Lys Pro Leu Pro Asn Leu Pro Lys Ser Tyr Arg Trp Gly Leu Val
    210                 215                 220

His Trp Trp Met Gly Ile Lys Asp Ser Glu Phe Asp His Phe Ser Phe
225                 230                 235                 240

Val Gln Phe Phe Ser Asn Trp Pro Arg Ser Phe His Ser Ile Ile Glu
                245                 250                 255

Asp Glu Val Glu Phe Asn Leu Glu His Ala Val Val Ser Thr Ser Glu
            260                 265                 270

Leu Arg Leu Lys Asp Leu Leu Gly Arg Leu Phe Phe Gly Ser Ile Arg
        275                 280                 285

Leu Pro Glu Arg Asn Leu Gln His Asn Ile Ile Leu Gly Glu Leu Leu
    290                 295                 300
```

```
Cys Tyr Leu Glu Asn Arg Leu Trp Gln Asp Lys Gly Leu Ile Ala Asn
305                 310                 315                 320

Leu Lys Met Asn Ala Leu Glu Ala Thr Val Met Leu Asn Cys Ser Leu
            325                 330                 335

Asp Gln Ile Ala Ser Met Val Glu Gln Arg Ile Leu Lys Pro Asn Arg
        340                 345                 350

Lys Ser Lys Pro Asn Ser Pro Leu Asp Val Thr Asp Tyr Leu Phe His
    355                 360                 365

Phe Gly Asp Ile Phe Cys Leu Trp Leu Ala Glu Phe Gln Ser Asp Glu
370                 375                 380

Phe Asn Arg Ser Phe Tyr Val Ser Arg Trp
385                 390

<210> SEQ ID NO 35
<211> LENGTH: 640
<212> TYPE: PRT
<213> ORGANISM: Vibrio cholerae

<400> SEQUENCE: 35

Met Gln Thr Leu Lys Glu Leu Ile Ala Ser Asn Pro Asp Asp Leu Thr
1               5                   10                  15

Thr Glu Leu Lys Arg Ala Phe Arg Pro Leu Thr Pro His Ile Ala Ile
            20                  25                  30

Asp Gly Asn Glu Leu Asp Ala Leu Thr Ile Leu Val Asn Leu Thr Asp
        35                  40                  45

Lys Thr Asp Asp Gln Lys Asp Leu Leu Asp Arg Ala Lys Cys Lys Gln
    50                  55                  60

Lys Leu Arg Asp Glu Lys Trp Trp Ala Ser Cys Ile Asn Cys Val Asn
65                  70                  75                  80

Tyr Arg Gln Ser His Asn Pro Lys Phe Pro Asp Ile Arg Ser Glu Gly
                85                  90                  95

Val Ile Arg Thr Gln Ala Leu Gly Glu Leu Pro Ser Phe Leu Leu Ser
            100                 105                 110

Ser Ser Lys Ile Pro Pro Tyr His Trp Ser Tyr Ser His Asp Ser Lys
        115                 120                 125

Tyr Val Asn Lys Ser Ala Phe Leu Thr Asn Glu Phe Cys Trp Asp Gly
    130                 135                 140

Glu Ile Ser Cys Leu Gly Glu Leu Leu Lys Asp Ala Asp His Pro Leu
145                 150                 155                 160

Trp Asn Thr Leu Lys Lys Leu Gly Cys Ser Gln Lys Thr Cys Lys Ala
                165                 170                 175

Met Ala Lys Gln Leu Ala Asp Ile Thr Leu Thr Thr Ile Asn Val Thr
            180                 185                 190

Leu Ala Pro Asn Tyr Leu Thr Gln Ile Ser Leu Pro Asp Ser Asp Thr
        195                 200                 205

Ser Tyr Ile Ser Leu Ser Pro Val Ala Ser Leu Ser Met Gln Ser His
    210                 215                 220

Phe His Gln Arg Leu Gln Asp Glu Asn Arg His Ser Ala Ile Thr Arg
225                 230                 235                 240

Phe Ser Arg Thr Thr Asn Met Gly Val Thr Ala Met Thr Cys Gly Gly
                245                 250                 255

Ala Phe Arg Met Leu Lys Ser Gly Ala Lys Phe Ser Ser Pro Pro His
            260                 265                 270

His Arg Leu Asn Ser Lys Arg Ser Trp Leu Thr Ser Glu His Val Gln
        275                 280                 285
```

Ser Leu Lys Gln Tyr Gln Arg Leu Asn Lys Ser Leu Ile Pro Glu Asn
    290                 295                 300

Ser Arg Ile Ala Leu Arg Arg Lys Tyr Lys Ile Glu Leu Gln Asn Met
305                 310                 315                 320

Val Arg Ser Trp Phe Ala Met Gln Asp His Thr Leu Asp Ser Asn Ile
            325                 330                 335

Leu Ile Gln His Leu Asn His Asp Leu Ser Tyr Leu Gly Ala Thr Lys
        340                 345                 350

Arg Phe Ala Tyr Asp Pro Ala Met Thr Lys Leu Phe Thr Glu Leu Leu
    355                 360                 365

Lys Arg Glu Leu Ser Asn Ser Ile Asn Asn Gly Glu Gln His Thr Asn
370                 375                 380

Gly Ser Phe Leu Val Leu Pro Asn Ile Arg Val Cys Gly Ala Thr Ala
385                 390                 395                 400

Leu Ser Ser Pro Val Thr Val Gly Ile Pro Ser Leu Thr Ala Phe Phe
            405                 410                 415

Gly Phe Val His Ala Phe Glu Arg Asn Ile Asn Arg Thr Thr Ser Ser
        420                 425                 430

Phe Arg Val Glu Ser Phe Ala Ile Cys Val His Gln Leu His Val Glu
    435                 440                 445

Lys Arg Gly Leu Thr Ala Glu Phe Val Glu Lys Gly Asp Gly Thr Ile
450                 455                 460

Ser Ala Pro Ala Thr Arg Asp Asp Trp Gln Cys Asp Val Val Phe Ser
465                 470                 475                 480

Leu Ile Leu Asn Thr Asn Phe Ala Gln His Ile Asp Gln Asp Thr Leu
            485                 490                 495

Val Thr Ser Leu Pro Lys Arg Leu Ala Arg Gly Ser Ala Lys Ile Ala
        500                 505                 510

Ile Asp Asp Phe Lys His Ile Asn Ser Phe Ser Thr Leu Glu Thr Ala
    515                 520                 525

Ile Glu Ser Leu Pro Ile Glu Ala Gly Arg Trp Leu Ser Leu Tyr Ala
530                 535                 540

Gln Ser Asn Asn Asn Leu Ser Asp Leu Leu Ala Ala Met Thr Glu Asp
545                 550                 555                 560

His Gln Leu Met Ala Ser Cys Val Gly Tyr His Leu Leu Glu Glu Pro
            565                 570                 575

Lys Asp Lys Pro Asn Ser Leu Arg Gly Tyr Lys His Ala Ile Ala Glu
        580                 585                 590

Cys Ile Ile Gly Leu Ile Asn Ser Ile Thr Phe Ser Ser Glu Thr Asp
    595                 600                 605

Pro Asn Thr Ile Phe Trp Ser Leu Lys Asn Tyr Gln Asn Tyr Leu Val
610                 615                 620

Val Gln Pro Arg Ser Ile Asn Asp Glu Thr Thr Asp Lys Ser Ser Leu
625                 630                 635                 640

<210> SEQ ID NO 36
<211> LENGTH: 352
<212> TYPE: PRT
<213> ORGANISM: Vibrio cholerae

<400> SEQUENCE: 36

Met Lys Leu Pro Thr Asn Leu Ala Tyr Glu Arg Ser Ile Asp Pro Ser
1               5                   10                  15

Asp Val Cys Phe Phe Val Val Trp Pro Asp Asp Arg Lys Thr Pro Leu

```
            20                  25                  30
Thr Tyr Asn Ser Arg Thr Leu Leu Gly Gln Met Glu Ala Ala Ser Leu
             35                  40                  45

Ala Tyr Asp Val Ser Gly Gln Pro Ile Lys Ser Ala Thr Ala Glu Ala
 50                  55                  60

Leu Ala Gln Gly Asn Pro His Gln Val Asp Phe Cys His Val Pro Tyr
 65                  70                  75                  80

Gly Ala Ser His Ile Glu Cys Ser Phe Ser Val Ser Phe Ser Ser Glu
                 85                  90                  95

Leu Arg Gln Pro Tyr Lys Cys Asn Ser Ser Lys Val Lys Gln Thr Leu
            100                 105                 110

Val Gln Leu Val Glu Leu Tyr Glu Thr Lys Ile Gly Trp Thr Glu Leu
            115                 120                 125

Ala Thr Arg Tyr Leu Met Asn Ile Cys Asn Gly Lys Trp Leu Trp Lys
            130                 135                 140

Asn Thr Arg Lys Ala Tyr Cys Trp Asn Ile Val Leu Thr Pro Trp Pro
145                 150                 155                 160

Trp Asn Gly Glu Lys Val Gly Phe Glu Asp Ile Arg Thr Asn Tyr Thr
                165                 170                 175

Ser Arg Gln Asp Phe Lys Asn Asn Lys Asn Trp Ser Ala Ile Val Glu
            180                 185                 190

Met Ile Lys Thr Ala Phe Ser Ser Thr Asp Gly Leu Ala Ile Phe Glu
            195                 200                 205

Val Arg Ala Thr Leu His Leu Pro Thr Asn Ala Met Val Arg Pro Ser
            210                 215                 220

Gln Val Phe Thr Glu Lys Glu Ser Gly Ser Lys Ser Lys Ser Lys Thr
225                 230                 235                 240

Gln Asn Ser Arg Val Phe Gln Ser Thr Thr Ile Asp Gly Glu Arg Ser
                245                 250                 255

Pro Ile Leu Gly Ala Phe Lys Thr Gly Ala Ala Ile Ala Thr Ile Asp
            260                 265                 270

Asp Trp Tyr Pro Glu Ala Thr Glu Pro Leu Arg Val Gly Arg Phe Gly
            275                 280                 285

Val His Arg Glu Asp Val Thr Cys Tyr Arg His Pro Ser Thr Gly Lys
            290                 295                 300

Asp Phe Phe Ser Ile Leu Gln Gln Ala Glu His Tyr Ile Glu Val Leu
305                 310                 315                 320

Ser Ala Asn Lys Thr Pro Ala Gln Glu Thr Ile Asn Asp Met His Phe
                325                 330                 335

Leu Met Ala Asn Leu Ile Lys Gly Gly Met Phe Gln His Lys Gly Asp
            340                 345                 350

<210> SEQ ID NO 37
<211> LENGTH: 199
<212> TYPE: PRT
<213> ORGANISM: Vibrio cholerae

<400> SEQUENCE: 37

Met Lys Trp Tyr Tyr Lys Thr Ile Thr Phe Leu Pro Glu Leu Cys Asn
 1               5                  10                  15

Asn Glu Ser Leu Ala Ala Lys Cys Leu Arg Val Leu His Gly Phe Asn
             20                  25                  30

Tyr Gln Tyr Glu Thr Arg Asn Ile Gly Val Ser Phe Pro Leu Trp Cys
             35                  40                  45
```

Asp Ala Thr Val Gly Lys Lys Ile Ser Phe Val Ser Lys Asn Lys Ile
            50                  55                  60

Glu Leu Asp Leu Leu Lys Gln His Tyr Phe Val Gln Met Glu Gln
65                  70                  75                  80

Leu Gln Tyr Phe His Ile Ser Asn Thr Val Leu Val Pro Glu Asp Cys
                        85                  90                  95

Thr Tyr Val Ser Phe Arg Arg Cys Gln Ser Ile Asp Lys Leu Thr Ala
                100                 105                 110

Ala Gly Leu Ala Arg Lys Ile Arg Arg Leu Glu Lys Arg Ala Leu Ser
            115                 120                 125

Arg Gly Glu Gln Phe Asp Pro Ser Ser Phe Ala Gln Lys Glu His Thr
130                 135                 140

Ala Ile Ala His Tyr His Ser Leu Gly Glu Ser Ser Lys Gln Thr Asn
145                 150                 155                 160

Arg Asn Phe Arg Leu Asn Ile Arg Met Leu Ser Glu Gln Pro Arg Glu
                    165                 170                 175

Gly Asn Ser Ile Phe Ser Ser Tyr Gly Leu Ser Asn Ser Glu Asn Ser
                180                 185                 190

Phe Gln Pro Val Pro Leu Ile
        195

<210> SEQ ID NO 38
<211> LENGTH: 230
<212> TYPE: PRT
<213> ORGANISM: Vibrio cholerae

<400> SEQUENCE: 38

Met Ala Thr Ser Leu Pro Thr Pro Ser Ala Ile Thr Thr Ser Ala Leu
1               5                   10                  15

Glu Tyr Ala Phe His Thr Pro Ala Arg Asn Leu Thr Lys Ser Arg Gly
            20                  25                  30

Lys Asn Ile His Arg Tyr Val Ser Val Lys Met Ser Lys Arg Ile Thr
            35                  40                  45

Val Glu Ser Thr Leu Glu Cys Asp Ala Cys Tyr His Phe Asp Phe Glu
50                  55                  60

Pro Ser Ile Val Arg Phe Cys Ala Gln Pro Ile Arg Phe Leu Tyr Tyr
65                  70                  75                  80

Leu Asn Gly Gln Ser His Ser Tyr Val Pro Asp Phe Leu Val Gln Phe
                    85                  90                  95

Asp Thr Asn Glu Phe Val Leu Tyr Glu Val Lys Ser Ala Tyr Ala Lys
                100                 105                 110

Asn Lys Pro Asp Phe Asp Val Glu Trp Glu Ala Lys Val Lys Ala Ala
            115                 120                 125

Thr Glu Leu Gly Leu Glu Leu Glu Leu Val Glu Ser Asp Ile Arg
            130                 135                 140

Asp Thr Val Val Leu Asn Asn Leu Lys Arg Met His Arg Tyr Ala Ser
145                 150                 155                 160

Lys Asp Glu Leu Asn Asn Val His Asn Ser Leu Leu Lys Ile Ile Lys
                    165                 170                 175

Tyr Asn Gly Ala Gln Ser Ala Arg Cys Leu Gly Glu Gln Leu Gly Leu
                180                 185                 190

Lys Gly Arg Thr Val Leu Pro Ile Leu Cys Asp Leu Leu Ser Arg Cys
            195                 200                 205

Leu Leu Asp Thr Arg Leu Asp Lys Pro Leu Ser Leu Glu Ser Arg Phe
210                 215                 220

```
Glu Leu Ala Ser Tyr Gly
225                 230

<210> SEQ ID NO 39
<211> LENGTH: 603
<212> TYPE: PRT
<213> ORGANISM: Vibrio cholerae

<400> SEQUENCE: 39

Met Ala Lys Lys Gly Phe Ser Ser Phe His Arg Lys Ala Val Ser Ser
1               5                   10                  15

Gln Asp Thr Leu Glu Ser Ile Glu Leu Val Ser Ser Ala Asn Cys Leu
            20                  25                  30

Glu Ser Val Thr Tyr Gln Asp Ile Ser Ala Phe Pro Glu Thr Ile Ala
        35                  40                  45

Val Glu Ile Asn Phe Arg Leu Ser Ile Leu Arg Phe Leu Ala Arg Lys
    50                  55                  60

Cys Glu Thr Ile Val Ala Lys Ser Ile Glu Pro His Arg Val Glu Leu
65                  70                  75                  80

Gln Gln Asn Tyr Ser Arg Lys Ile Pro Ser Ala Ile Thr Ile Tyr Arg
                85                  90                  95

Trp Trp Leu Ala Phe Arg Lys Ser Asp Tyr Asn Pro Ile Ser Leu Ala
            100                 105                 110

Pro Asn Ile Lys Asp Arg Gly Asn Arg Glu Thr Lys Val Ser Thr Val
        115                 120                 125

Val Asp Ser Ile Met Glu Gln Ala Val Glu Arg Val Ile Ser Gly Arg
    130                 135                 140

Lys Val Asn Val Ser Ser Ala Tyr Lys Arg Val Arg Arg Lys Val Arg
145                 150                 155                 160

Gln Tyr Asn Leu Thr His Gly Thr Lys Tyr Thr Tyr Pro Lys Tyr Glu
                165                 170                 175

Ser Val Arg Lys Arg Val Lys Lys Thr Pro Phe Glu Leu Leu Ala
            180                 185                 190

Ala Gly Lys Gly Glu Arg Val Ala Lys Arg Glu Phe Arg Arg Met Gly
        195                 200                 205

Lys Lys Ile Leu Thr Ser Ser Val Leu Glu Arg Val Glu Ile Asp His
    210                 215                 220

Thr Val Val Asp Leu Phe Ala Val His Glu Glu Tyr Arg Ile Pro Leu
225                 230                 235                 240

Gly Arg Pro Trp Leu Thr Gln Leu Val Asp Cys Tyr Ser Lys Ala Val
                245                 250                 255

Ile Gly Phe Tyr Leu Gly Phe Glu Pro Pro Ser Tyr Val Ser Val Ser
            260                 265                 270

Leu Ala Leu Lys Asn Ala Ile Gln Arg Lys Asp Asp Leu Ile Ser Ser
        275                 280                 285

Tyr Glu Ser Ile Glu Asn Glu Trp Leu Cys Tyr Gly Ile Pro Asp Leu
    290                 295                 300

Leu Val Thr Asp Asn Gly Lys Glu Phe Leu Ser Lys Ala Phe Asp Gln
305                 310                 315                 320

Ala Cys Glu Ser Leu Leu Ile Asn Val His Gln Asn Lys Val Glu Thr
                325                 330                 335

Pro Asp Asn Lys Pro His Val Glu Arg Asn Tyr Gly Thr Ile Asn Thr
            340                 345                 350

Ser Leu Leu Asp Asp Leu Pro Gly Lys Ser Phe Ser Gln Tyr Leu Gln
```

355                 360                 365
Arg Glu Gly Tyr Asp Ser Val Gly Glu Ala Thr Leu Thr Leu Asn Glu
    370                 375                 380

Ile Arg Glu Ile Tyr Leu Ile Trp Leu Val Asp Ile Tyr His Lys Lys
385                 390                 395                 400

Pro Asn Gln Arg Gly Thr Asn Cys Pro Asn Val Ala Trp Lys Lys Gly
                405                 410                 415

Cys Gln Glu Trp Glu Pro Glu Phe Ser Gly Ser Lys Asp Glu Leu
                420                 425                 430

Asp Phe Lys Phe Ala Ile Val Asp Tyr Lys Gln Leu Thr Lys Val Gly
            435                 440                 445

Ile Thr Val Tyr Lys Glu Leu Ser Tyr Ser Asn Asp Arg Leu Ala Glu
    450                 455                 460

Tyr Arg Gly Lys Lys Gly Asn His Lys Val Gln Phe Lys Tyr Asn Pro
465                 470                 475                 480

Glu Cys Met Ala Val Ile Trp Val Leu Asp Glu Asp Met Asn Glu Tyr
                485                 490                 495

Phe Thr Val Asn Ala Ile Asp Tyr Glu Tyr Ala Ser Arg Val Ser Leu
            500                 505                 510

Trp Gln His Lys Tyr Asn Met Lys Tyr Gln Ala Glu Leu Asn Ser Ala
    515                 520                 525

Glu Tyr Asp Glu Asp Lys Glu Ile Asp Ala Glu Ile Lys Ile Glu Glu
530                 535                 540

Ile Ala Asp Arg Ser Ile Val Lys Thr Asn Lys Ile Arg Ala Arg Arg
545                 550                 555                 560

Arg Gly Ala Arg His Gln Glu Asn Ser Ala Arg Ala Lys Ser Ile Ser
                565                 570                 575

Asn Ala Asn Pro Ala Ser Ile Gln Lys His Glu Asp Glu Ile Val Ser
            580                 585                 590

Ala Asp Asn Asp Asp Trp Asp Ile Asp Tyr Val
        595                 600

<210> SEQ ID NO 40
<211> LENGTH: 330
<212> TYPE: PRT
<213> ORGANISM: Vibrio cholerae

<400> SEQUENCE: 40

Met Ser Glu Thr Arg Glu Ala Arg Ile Ser Arg Ala Lys Arg Ala Phe
1               5                   10                  15

Val Ser Thr Pro Ser Val Arg Lys Ile Leu Ser Tyr Met Asp Arg Cys
                20                  25                  30

Arg Asp Leu Ser Asp Leu Glu Ser Glu Pro Thr Cys Met Met Val Tyr
            35                  40                  45

Gly Ala Ser Gly Val Gly Lys Thr Thr Val Ile Lys Lys Tyr Leu Asn
    50                  55                  60

Gln Asn Arg Arg Glu Ser Glu Ala Gly Gly Asp Ile Ile Pro Val Leu
65                  70                  75                  80

His Ile Glu Leu Pro Asp Asn Ala Lys Pro Val Asp Ala Ala Arg Glu
                85                  90                  95

Leu Leu Val Glu Met Gly Asp Pro Leu Ala Leu Tyr Glu Thr Asp Leu
            100                 105                 110

Ala Arg Leu Thr Lys Arg Leu Thr Glu Leu Ile Pro Ala Val Gly Val
        115                 120                 125

```
Lys Leu Ile Ile Ile Asp Glu Phe Gln His Leu Val Glu Glu Arg Ser
    130                 135                 140

Asn Arg Val Leu Thr Gln Val Gly Asn Trp Leu Lys Met Ile Leu Asn
145                 150                 155                 160

Lys Thr Lys Cys Pro Ile Val Ile Phe Gly Met Pro Tyr Ser Lys Val
                165                 170                 175

Val Leu Gln Ala Asn Ser Gln Leu His Gly Arg Phe Ser Ile Gln Val
            180                 185                 190

Glu Leu Arg Pro Phe Ser Tyr Gln Gly Gly Arg Gly Val Phe Lys Thr
        195                 200                 205

Phe Leu Glu Tyr Leu Asp Lys Ala Leu Pro Phe Glu Lys Gln Ala Gly
    210                 215                 220

Leu Ala Asn Glu Ser Leu Gln Lys Lys Leu Tyr Ala Phe Ser Gln Gly
225                 230                 235                 240

Asn Met Arg Ser Leu Arg Asn Leu Ile Tyr Gln Ala Ser Ile Glu Ala
                245                 250                 255

Ile Asp Asn Gln His Glu Thr Ile Thr Glu Asp Phe Val Phe Ala
            260                 265                 270

Ser Lys Leu Thr Ser Gly Asp Lys Pro Asn Ser Trp Lys Asn Pro Phe
        275                 280                 285

Glu Glu Gly Val Glu Val Thr Glu Asp Met Leu Arg Pro Pro Lys
    290                 295                 300

Asp Ile Gly Trp Glu Asp Tyr Leu Arg His Ser Thr Pro Arg Val Ser
305                 310                 315                 320

Lys Pro Gly Arg Asn Lys Asn Phe Phe Glu
                325                 330

<210> SEQ ID NO 41
<211> LENGTH: 105
<212> TYPE: DNA
<213> ORGANISM: Vibrio cholerae

<400> SEQUENCE: 41
tgttgatgca accataaagt gatatttaat aattatttat aatcagcaac ttaaccacaa      60
aacaaccata tattgatatc tcacaaaaca accataagtt gatat                    105

<210> SEQ ID NO 42
<211> LENGTH: 48031
<212> TYPE: DNA
<213> ORGANISM: Homo sapiens

<400> SEQUENCE: 42
gtgggggccg ttggctccag acaaataaac atggagtcca tcttccacga gaaagtgagt      60
gtccgcgttc ggtggggagc tgtctgccgc gcggtggcgg gcgtggagcg cggcatcacc     120
gcctctcgga gggctgggtg gggcccgagt cgcccccatg ccgatctcgc ccggcgaggg     180
gcgacgccgc agcctcccgc ctcctcggct cgaggagggg agcatcacct acgcccctac     240 ttccccgcg gcccccgccc tgggagccgg gagggagtat gggcggggcc ggggggcgtct     300 cgggacacgg gagtgggtg gcgcccagtg ggtttgcttc tgcctttctc cgtcactttc     360
catcgctttt cggaggattc cttcacccct ccccaatcct tccctctccc tagggtctag     420
ctagagtcat ctctgggaca cctccctcaa ccccctcctac cctaatcctg gcagaattaa     480
cttttcctcc tccggactgc tcaattctat attggagtct tccctacacg tagatctttg     540
gggtcttgtt cgtgtctttc ccctgcacta ggtccgcgag cctcccgagg gaggagacct     600
```

```
tggctcgccc actgtagggc ctgacattta ggaagtgaag taggaaaccc ggcgtgcccc      660
taaacaggga agtcgtcaca agagttttta ttacggatgt tttgggtttg gtttcttttg      720
gtactcccat ctttccggag caggcggcca gctttgtttt taggtattag gagtggactg      780
ggatgatttt gttgtagtct gcctagcctg ctgtcccttt aactcttccg tgaccatgca      840
cttgaagata ctgtttgtga tatgtaaaga aactcctcgt ttctctcata ctattatcca      900
gccatttgtg tgtgagtgaa gccttcccca ggacagcttt ggcacatggt atcatgtttc      960
ataatagttt cgtgtttgga aagagttgct ggtaaggctg ttatttaata ggaggagcaa     1020 agggttttg ttttattaaa tacttataaa tgatcattta tcccagacat ttaaaattca      1080
cacacacaca acaaataaag caaagacaaa agaatacatt taccaaatgt aaatctgtag     1140 cataaattt ttttaatttt tattttaaag atggggtctc attctgtcac ccaggcaggt      1200
gtgcaatgga gagatcatgg ctcactgcag ccttgatctc ctaggcacaa gcgatcctcc     1260
cgcctctgcc tccagagtag ctgggactac aggtgcatat cgccagggcc aggtaatgtt     1320
tttgggagag acgggtctc gctgtgttgc ccaggctggt ctcgaactcc tggactcagg      1380
tgattctccc acctcggcct ctcgaagtgc tgtgattaca ggcgtgagcc actgtgcctg     1440
gaacaaattg ttaagtacaa tgcttttcat tgtagaaaac atctcggaaa cttttgaaat     1500
aggctgatgt tcagtggggg aggaaggact cagtcgtata gttgtcacta atttttgac      1560 ttgattgaca tgactcgtaa atcatagaca atagagattt ggttgcttgg ctgagtagag     1620
tgcgtgaaaa atacacacgt actttttttt tttttttttt gagatggagt ttggctcttg     1680
tcacccaggc tggagtgcaa tggcgccatc atggctcact gcaacctccg cctccccgtt     1740
caagcgattc tcctgcctca gtctccccag tagctgagat tacaggcgcc cgccaccacg     1800
cccagctaat ttttgtattt ttagtagaga cagggttca ccatgttggc caggctggtc      1860
tccaactcct gacaggtggt ccgcccgcct cggcctccca aagtgctggg attacaggcg     1920
tgagccaccg cacccggcca tattttgtt attaattttc aaaggctttg gtgtgggacc      1980
acatttcaac atggaaggcc ttaaacatgt tccacactac ttcctgagaa ttagacaaga     2040 ttttaacaa tattgttacc tagttgggac acatttgtac tgacccatgg gatgaaaaaa      2100
agctgagtgc tagcctagtg aaaatctact tacccgaaag aaatccctct tagtctgggt     2160
gcagtggctc acaccagtgc tttgggaggc cagacgggc ggatcatgag gtcagtagtt      2220
tgagaccagc ctggccaaca tggtgaaacc ccgtctctac taaaaataca aaaaattagc     2280
caggtgtggt ggcaggcgcc tgtaatccca ggtactctgg aggctgaggc aggagaattg     2340
cttgaacccg agaggcagag gttgcagtga gccgagaccg tgccactgca cttcagcctg     2400
ggcaacagag cgagactccg tctcaaaaaa aagaaaagga aaaagagtc cctcttaatt      2460 atcagcatgt gtataggcct acagatactt caggaatacc tttaccatta tcatcaactt     2520
gtatctacat agcatgtgaa gattcaacaa tttagttttt tgggcgtcct caagagtacg     2580
cacctataac catatggccc aattgttaat ctcctataca gtccattctg ggaatgtttg     2640
ggcttactgt gccatttttc cgttcactgc cttcccctct gcaatatacc tttaacccctt    2700 gctaggtcct gggtttggag agccagagaa ccaactttgg ccctaaagaa gctgtgtagg     2760
tagcaatatc tgcctacgaa gggccttgca accatttcct cttggaacct tggtttcctc     2820
tttctgagta gtcactttga gtaccctta ttaagttaga atgtaaaaac agtttctcac      2880
tgatatatct gcagtgcctg agagagggcc tggcacagag taagtactca ataaatattt     2940
gaatggggcc gggcgtggtg agacctgtct ctacaagaat gaacaaaatt agctgggcgt     3000
```

```
gttagcacat gcctgtagac ttgggaggct gaggtgggag gattgcatga gtctgggagg    3060
tcgaggctgt agtgagccat gatcgcacca ctgcactcca gcctagggga cagagcaaga    3120
tcctgtctca aaagaaaaaa atgtatatat ttgaatggat aaagagatgg ctttgagttt    3180
ctgagatata tatggtgctg tttatctaaa gtaaacaagt tttctgtaaa tattttaagg    3240
ctttgcaggc cagctgtagt ctctgtcaca cattcttatt tgtgcatgtt tttcccaacc    3300
atgtaaaaat gtaaagtgca ttcttagcta ctggggcagg ttgaatttgg cccatgggct    3360
agagtttgcc aaccctaac ttaaaccttt gtactaactt tatgaccact actggatttt    3420
tgttgttgtt tgttttagtt ctggtgcctg ctttgttttt ttttttttt ttaatcctct    3480 tgctgatgtt tcttggtgca gttactgtgc catttgtatt ggtgcttta atgtaatgca    3540 aactggtaat aatatctaaa cttgctgggg ttgtacataa aattattgaa aagattgaaa    3600
agatgctgag cattgactct gtggcattca ttatgcccct ttgtgattgc tggattttag    3660
ccatctttag gacatttgag ctttaggaga agccaaattc tgtataaatg acttgaagtg    3720
ctaatagcac aggttttgaa acctctgcct gggtttgagt ctcagctctg ccttttacta    3780
cctgtgtgat cctgagcaag ttacttagta tccctgtcct ctagtttcct cctctgtagt    3840
gtggggataa taacatagac ataacctgag agttagagtg tagagaaggc tccctggcag    3900
atagtgctgt agaagtactg gccattgcca ttactcaggt gcttgtgttt gctgaacctc    3960
atagtaaggg ctcggagagc actaagagga ggtgagaaat gctgctagat tgacagcttg    4020
tccccagata gcccattccc gagagcacct taggtttata cctgatttgt gttgtagtta    4080
gtagtgtctc tggtaatttg aactagtttc aggttggtct tgaaaacctg gggaggttgg    4140
gggtaaatga tttggtagca gttctctttt gtgatttat acattatctt tgtagaactg    4200
cagtttgcta attctctgag cccaacacaa tgaagtctgg gcctaaaatc atagaatttc    4260
ttttattttt tttttgttt ttaatttatt tattccctcc ctccctcctt tcttcctttc    4320
ttccttttct ttctttcttt ccttccttcc ttccttcttt cttttctttc tttcttttct    4380
ttctttggag tctcactctg tcaccaggct ggagtgcagt ggcacgaact tcttcagag    4440 tctcactttg tcaccaggct ggagtgcagt ggcgcgaact cagctcactg caacctccgt    4500
ctcctgagtt caagagattc tcctgcctca gcctcccgag tagctgggac tataggcatg    4560
tgccaccatg cccagctaat tttcttattt ttagtagaga cgaggtttca ccatgttggc    4620
caggatggtc ttgatctctt gacctcgtga tccacctgcc tcagcctccc aaagtgcggg    4680
gattacaggc gtgagctacc acgcccagcc tattttttat tttttgaggc agagtctcac    4740
tctgtcaccc aggctggagt gcagtggtgc aatctcagct cactgcaacc tccgcctcct    4800
gggttcaggt gattctcctg ccttagcctc ctgagcacct gggactacag gcgcctgcca    4860
ccacacctgg ctaattctta tattttagt agaggcgggg tttcaccatg ttggccaggc    4920
tggtctcgaa ctcctgatct caagtgatca acctgcttg gcctcccaaa gtgctggaat    4980
tacagccatg agccaccatg cccagccaaa tcatgagatt caataccgc tgaactttga    5040 ttatggcaaa gtgaacttct gctttgatta aagcttgatg agagaggtgg ctggggatag    5100
tttgagataa gggcaaggca ggaaaatgca taatcttacg tgggctcatt gtcattgtac    5160
aattcttttg gtccatgtgg aatttgatcc gtcctatgac ttaagttatg tttattttg    5220 tttttatttt tatttatttt gtgtcttttt gagagacatg atgttgctct gtcacctggg    5280
ccagaataca gtggcacaat cttagctccg tgtagccttg aactcctggg ctcaagtgat    5340
```

```
cctcccacct cagcccctca aacagttgag attatagtat gaaccactgt gcctagcctt    5400
aagtgatttt taaatttgta ctgaacagtt tgtccttttcc ttccattaaa tcatattaga    5460
agtacagaac ttgatatttc ctgtagcaat acagtttttc tttgatgaag tttgatttca    5520
agtacttatt tttcataatt taaagctatt ttttatagag agaattttaa tcaaatattt    5580
ggatgtcact attgctatat atggtattaa gtatggtgac catagtttgt aaactccaaa    5640
ctgacagcaa gacaggaaat ttgtgttagc aaaggctttt ttcttactgt ttgaatttttt   5700 taaaaattag atacaataca gagaggagca cacaaatcat taagagtaca gctcagcgaa    5760
ttttcacaca gtgaacatgt gtaaacagca agtaacaaaa gatttacctg catcctataa    5820
cctcccatta ttcccttttc taggtactgt ctctccactg cattcccacc aaatataacc    5880
actatgctga attctgacat cataaatgag ttttgcctga ttttgagctt ttgtgactgg    5940
aagtgtacag tgtatatacc ctttcgattc tgtcctcttt agtttaccat tgtttgagaa    6000
atttatccat actgttccag aattaactac tgttaattat tgttaattaa ctactgttgt    6060
agttaattca tcctcattgt tatctagtat tcttttgtga gtaaacacaa tttccattct    6120
actgtgatcc cagctatcca tttgggtcgt ttccagtttg gggtccatta caaatagtaa    6180
tgctatctgt aatgctattt tgtattacta caaatagtaa tgctatttgt ggcacaaaaa    6240
tactgctttt gtgaacattc ttatacatgt cttttgatga atgtatgttt gcattgctgt    6300
tgtttacatt atgtacctag taatggaatt gctagatcat aggagatgta tatattaagc    6360
tttagtggat gcattacata attattagtt attattggtt ataccaattt atcctctcat    6420
cagtagtata caacagtttc tgtatctcta atctccaaca ttttagccat tttagagttt    6480
gtgtactaac acattgtggt tttaatttac atttccctga tgactaataa agttgagtac    6540
ctcttttgtg ttcttttatag ccatttgact gtcttgtgaa gtgcttgttt gtcttgccta    6600
ttttctcttt ctttctttct ttttcttcct tccttccttt cttctttct tctttcttc    6660 cttccttctt ttctttcttt ctgtcttttct ttcttgtctt tcttgtcttt ctgtcttttct   6720 tggtcttgcc ctgtcaccca tgctggagtg cagtggtgca gtctcagctt actgtagcct    6780
cgaccttttt ggggctcaag ttatcctcct ttctcagcct cccaagaagc tggactacaa    6840
gcacgcacca ccatgctcag ttaattttttt atttttgta gaaatggggt ttcaccatgt     6900
tgtccaggct ggtctcaaac ttctgggctc aagtaatcct cctgccttgg cctcccaaaa    6960
tgctgggatt acaggcatga gccaccgcag ccagccttgg ctattttca aaaggatata    7020 agtgaaacat ctgtatatcc cttcaattg catattattc agtaagagtt gcactctggt    7080
agtagaaata tataaggagg agaaagaagt ggaaacaaaa agtctattct catgagaaga    7140 cttggggggat agtgttctct ctagctccaa gctacttatt ccttacgaaa agttgaagat    7200
aaacttatct cagactgagg ctgtctcaat gttgtcttcc tattccatta tacacatata    7260 acccatatt tttcaccag ctgaattttg ctcctagaaa attgattcat caggaaaaat       7320
atccgtcttg caaggtggtt ctctttagag tctgctgtgt gacatagctc aggacaaatt    7380
gtgtgatgtc agataggttg ggttaaggaa tagaccttat tggggaaaga gagaacttgg    7440
agggccaagg ttagcaggag aaggaaatgt tctctcatct gccgtcaatt cagggagggg    7500
caaacctggt gtctgtgttc acagggaggg atccatccat ctgtgattct cccttcttat    7560
caggtagcat gggaaagcta cactgttgcg gggaggaggg tcacacgcag gctacttagt    7620
accaggcacc ctggacttgg attcaggttg ccagttgtgt gagaaactgc ccagcacctg    7680
aaggccctga acccatgaga agttgtacct acctcccatg aggaggaatc ctgtcatccc    7740
```

```
atgggagctg agcttgggtg cagtccctct tgctggcttg tccaggagtg agctccaggg    7800
ttgtttggga cagttctgct cattgcttta cactgtgtat acattatctg tagagttcca    7860
tgaagagaac ttcagcactg taactgcaag ttttaacatg aacagaatt tttctcacct     7920 gtattaattc ttaagatttg aagttctatc aacaagcatt tagattgtgt ggagattttt    7980 ttattttttat ttttggagac agagtcttgc tctgttaccc agactggagt ggcagtggca   8040
tggtcttggc tcactgcagg ctctacttcc tgggttcaag cgattctcat gcctcagtgt    8100
cctgattagc taggactaca ggtacacacc accatgctgg ctaattttg tattttttagt   8160 agagacgagg tttcaccgta ttggtcaggc tggtctcgaa ctcccagcct caagcagtcc   8220
acccacctcg gcctcccaaa ctgctgggat tacaggtgtg agccaccatg cttgactgac   8280
atcatcatgt taaaagaata aatgttctag ggagctgggc acagtgtcat gtttctgtag   8340
ttctagctgc tcgggaggct gaggcaggaa gatcccttga gccctggagt tcaagtccag   8400
cctgggcaac atagtgagat ctcttttttt aaataaataa ataactgttc tagggactaa   8460
aatttccttt caccattagt aatttactgt agaatctcca agaatgaact tattttaggt   8520
actgaaaatg agggagacta aatgttttat acagtagttt ttagtaaaat atgagatttg   8580
atgcatttga tagatgatgt ttgtttaaaa taattcttaa attttttgatc atgtaattat  8640 agtttcatta atggtagatt tgtaaaataa atgttaccaa atgaaaatgc atgtacctat   8700
gttaattatc cttatctaaa gctgaaagtt cagttcaact atgttaaaac atagtagggg   8760
cctggcaggg tggctcttgc ctgtaatccc agaacttagg gaggccaagg tgggcagatc   8820
acgaggtcag gagatcgaga ccatcctggc taacattgtg aaaccgtatc gctactaaaa   8880
atacaaaaaa ttagccgggc atggcggtgg gcacctgtag tcgcagctac ttggtaggct   8940
gaggcaggag aatggcgtga actcaggagg cagagcttac agtgagccga gatcatgcca   9000
ctgcactcca ggctgggtga cagagcaaga ctccatctca aaaaaaaaa aaaagttggc    9060 caggtgtggc ggctcacacc tgtaatccca gcacttttgg aggccgaggc aggcggatca   9120
caagatcagg agtttgagac cagcctggct aacagagtga acccctgtat atactaaaaa   9180
tacaaaaatt agccaggcat ggtggtgcat gcctgtagtc ccagctactt gagaggctga   9240
ggcaggagaa tcacttgaac ccgggaggcg gaggttgtgg taagctgaga ttgctccact   9300
gcactccagc ctgacaaaca gagcaagact ctgtctcaaa aaaaaaaaa attaatgatt    9360 aaattattta ggggagccgg gcgcagtggc tcacgcctgt aatcccagca ctttgggagg   9420
ccaaggcggg cggatcacga ggtcaggaga tcaagaccat cctggctaac acaggatgaa   9480
accccgtctc tactaaaaat acaaaaattt agccgggcgt ggtggcgggt gcctgtagta   9540
ccagctactc gggaggctga ggcaggagaa tggcatgaac ccgggtggcg gagcttgcag   9600
tgagccaaga tagcgccact gcactccggc ctgggtgaaa gagtgagact ccgtctcaaa   9660 aaaaaaaaa aattatttag gggaagatac tatacaattc tgtttaacaa gtcacatttt    9720
aattttttct tttggaaata ttagcaagaa ggctcacttt gtgctcaaca ttgcctgaat   9780
aacttattgc aaggagaata ttttagcccct gtggaattat cctcaattgc acatcagctg   9840
gatgaggagg agaggatgag aatgcagaa ggaggagtta ctagtgaaga ttatcgcacg     9900
tttttacagg tactgatttt aaactcacta agtcacattt ctttttttttt tttttttttg   9960 agacggagtc tcgccctgtt gcccatgctg gagtgcaatg gcgcgatctc ggctcactgc   10020
aacctctgcc tcccgggttc aagcgattct cctgcctcag cctcccaagt agctgggatt   10080
```

```
acaggcacac ggcactatgc ccggctaatt ttttgtatct tgttagaga tggggtttca    10140 ccatgttggt caggttggtc tcaaactcct gaccttatga tccacctgtc ttggcctccc    10200
aaagtgctgg gattataggt gtgagccacc acacccggct tacatttctt ttaaaaatgt    10260
ggataccatt tagaaaagga tgggccattc ttcctatagg gatctgactg gtgaattata    10320
actgtgctgt taactttgga aatgggaatg cacaagatat tgttttaaat atgcacgcta    10380
atgacagttt gtatccttct ttccccaccc ccacccttgc ttcaactacc tgtcaaaatt    10440
aacagcagcc ttctggaaat atggatgaca gtggtttttt ctctattcag gtaagtagtc    10500
acaagcatgt actatgtgtt gcttacatcc caggcaccgt ttcacagcct ttcaatagtc    10560
actgtaacaa ggcgaccttc ggaagttctt ctgtctacag agtatagatt atactctaga    10620
gtactagatt ttttttttct tgagacagag tctcgttctg tcacctaggc tggagtgcag    10680
tggcgtgatc ttggctcact gtagcctctg cctcccgggt tcaagcgatc ctcctgcctc    10740
agcctcccaa gtagctggga ttacaggcac ccgccaccac accagttaat atttgtattt    10800
ttagtagaga tagtggggtt tcaccgtgtt ggccagtctg gtctccaact cctgacctca    10860
gcctcccaaa gtgctgggat tacaggtgtg agccactgca cctggccaac tagagtacta    10920 gattttata tagataaaca tgaaaggatt gtagaatctt catattagag tggggcattt    10980
aaaaattcct tcttgagaaa gattaatttg catctggatg ctaataataa ccttaattct    11040
ggccgggcgc ggtggctcac acctgtaatc ccagcacttt ggggaggccg aggtgggcgg    11100
atcacgaggt caggagattg agaccatcct ggctaacatg gtgaaacccc gtctctacta    11160
aaaatacaaa aattagctgg acgtggtgac acgtgcctgt aatcccagct actcggggagg    11220 ctgaggcagg agaatcgctt gaaccaggga gtcgtaggtt gcagtgagcc aagatcgcgc    11280
cactgcactc tagcctggtg acagagcgag actccatctc aaagaaaaaa agaaatcctt    11340
aattctaata agtcacaatg tctcaaactt accatctgtt gggtaaattt gagaaaatgc    11400
aataccttgc taccatccett ttaaatcagc ctaccagact ggatttcctt attatggttt    11460
gtggcttttg attttttttt tttaatgtat agctctcttt gaattctttg gtggttatat    11520
atatatgtac tcgcaagatt cttttatctg tgggtctttc attcttttc taacactgtg    11580 agttgtatcc agagtacttt cggaacctct cctgagcgac ctatctctgc agatatcttt    11640
gtttatgttt cccttgtact gccctcctgg actcttcctc atccaccagc atttccatct    11700
agtgctttac cgtgccactg ctaacaggta atggctactg cagggctgaa atcagaggcc    11760
agagtaggcc cagcacttgg cgtttcctat ttgtgccttg ctgctcttgg tgcctgttca    11820
tgtgtgccca ctaccttgca ctcaatttct gtctttgctg gtacctggct cacttgcttc    11880
tttgttggct accttggagg gcagatagtg aattttcaga aatttcccctt tttttgtcag    11940 acagattgaa ataaacaggt ttgcattttg tttttttctac aagcggcaag cccatgaccc    12000
tagaagtctg acatctatgg aaccttcagt ttaaatgccc agggagaact tattttggta    12060
gatatgattt ctgacattgc aggtagcaag ttgaatataa ttttttctaaa gtagcaccca    12120 cagcagccaa attatcagat gtatatagta gactagtttt aagaaaagca cttatgggta    12180
gaatatacat ctgatttttt gaggcagttt tatttaggaa ttgtgtggtt ttctggaaca    12240
tctcagagac ctggtatgaa agcactctt ctaatatata tgtgttttttt tttatggatt    12300 tagtgatata tctatacaca cacactttt aaaacctata gccggctggg cgtggtggct    12360
catgcctgta atcccagtac tttgggaggc ccaggcgggt ggatcacaag gtcaggagat    12420
tgagaccagc ctggccaaca aggtgaaacc ctgtctctac taaaaataca aaaatagctg    12480
```

```
ggtgtggtgg cgtgtgcttg taatcccagc tactcgggag cctcaggagg agaatcgctt   12540
gaacctggga ggcggaggtt gcagcgagcc gagatcgtgc cactatactc cagcctgggc   12600
gacagagcaa gactctgtca caaaaaaaaa aaaaaaaacc tatagccttc tagagaaatt   12660
tatatatgaa gtacacaact aacatagcta cacttcctaa atttggaatg gagtggttta   12720
gcttatgaaa agttgctatt tttcttaaca ggttataagc aatgccttga aagtttgggg   12780
tttagaacta atcctgttca acagtccaga gtatcagagg ctcaggatcg atcctatgta   12840
agattctgtt ttgcatttca tacatttctt ttcccaaatt tgattttta agttgtaatt   12900 tcttaaagaa gagaaataca ttttgaatac ttttgttttg atgttccctg tttcattcac   12960
tcagactttc ctatttcacc tttgtgatgt ccatgagcat ctgcctgta gccttcctgg   13020 caccccagtg tctgtggcag cacagagctg accccataag tggtgcatga ggccatcttg   13080
tggcacagca tcactaagct gctgcagaga cgttcatatg gttgtgtgat cttttaaaaa   13140
catcagtgac acttaactat aaatataatc ttaaattatc acaaatttta tataatattt   13200
gccagtagac aacataaata tgaattcaat atttcaagtt aatattgtct gttttctttt   13260
ttagaaatga aagatcattt atatgcaatt ataaggaaca ctggtttaca gttagaaaat   13320
taggaaaaca ggtaacattt cttacccttc cttgtctttt tttcttatat tgtacccat    13380 ttaaaactaa aatgtgggcc aggtgtggtg gctcatgcca acagtttggg aggctgaggt   13440 gggggatca cttgaagcca ggagtttgag accagcctgg gcaacaaagg gaggtcctgt   13500
ctcttaaaaa aaaaataaaa ataaaaataa aaataaataa aaaaaaaaac aaagagccag   13560
gcatggtggc tcacatctgt aattccagct tacttggaag gctgagtcag aaggatcact   13620
tgagctcagg agtttgaggc tgcagtgaac tatgattttg tcactgtacc ccagcctggg   13680
tgacagagta agactgttct ataaaacata aaaataaaaa aatatatttt aaaaattaaa   13740 aaaaaaaag gattgctgac tttaaaatta ggaaactgac cagtaatgtg tgtgtgtgta   13800
gcatggttta tccttcttga tagatagaaa ttgtcatttt aaaagataat atcagttttc   13860
cttataaatt tatttgtgac aagtatatgc aatttaacta tatcataaga aaattctat    13920 attaaagata atacaaatgt ggttactttt aagtgggttt ttatgtgatg actatgttct   13980
gtcagttaat tattacattt atagatttgt atttagcata gtgctgtcac aaagcctgaa   14040
atagtgtcaa gcatgaataa agcattcaat tatgtttgct ttagtgtaag attattcatt   14100
atgattccaa aagccatgta atacgtacgt ctacagaaaa tcacttctat tttttaaata   14160
aaacatgaaa tatgtcttga gcaagctatt ttaagaaaca atcatttaac gtccttgtta   14220
ttagaatttt gaatctttga aagagggtta ttgaaaacca gctaggacag taaaaaagaa   14280
taaactagtg atacatgcag caatatggat gaatctcaaa ataattatgc tgaaagaata   14340
acccacaaac aaaatactac ctgctgtatg gtatcattta ttaaaagtct agaaaagtgc   14400
agattcatct gtagtgatgg aaagcagatt gaccagcggt tgcctgggga cgagaaggct   14460
atggaggagt gagaggggag ggttacagag aggcacggga aacatggcaa tgaggaatgt   14520
gttcactatc ttggttgtag taatggtttc atgggagtac agtatacaaa tgtgaaaaca   14580
tttcagaggc cagatgcagt ggctcatgcc tgtaatccca gcacttttgg aggccaaggc   14640
aggaggattg cttgagctca aggagttcag gaccagcctg ggcaatggca caagacccca   14700
tctctaaaaa aaaatgaaa gaaaaaaaa ttggctaggc gtggtgatgc atggccgtag   14760
tcccaggtgc tagggaggct gaggagggag cacagaggtc aagcctgcag tgaatcatga   14820
```

```
tcgtgctact gcactccagc ttgggtgaca gaaggagatc ctgtctcaaa aaaaaagttt   14880
caaattatac actttaaata tgtgcagttt attatatgtc acttataccc caataaatct   14940 gttttttta aaatgtaaat acaagccaaa aaggtataa gtcaagaaaa tatattgaat    15000
taaatctgta agagataatt caaaaacaaa aaccctattg ttatctttta agtcacccaa   15060
atcaaatttg ggaaaagtca cctacttagc ttcatcctaa gttggttctt tctttctttc   15120
tttccttctt ttgagacgga ttcttgctct atcgcccagg ctggattgca gtggcgggat   15180
cttggctccc tgcaacctcc gccacctggg ttcaagcaat tctcttgtct cagcctccca   15240
aatagctgtg tctacagcca cgcaccacca cacccagcta attttgtat ttttagtaga    15300 gacggggttt cgccatgttg gtcaggctgg tcttgaactc ctgacctcag gtgatccgtc   15360
cgtctctgcc tctcaaagtg ctgggggttac aggcgtgagc caccatgccg agccctaagt   15420
tggttctttc ttaaagttct tcctgaggag ccaagagcaa gttaaggaga tgtaacctag   15480
aagcttacag tggaggctag ctgggtgcag tggttcacgc ctgtaatccc agcactttag   15540
gaggctgagg cagggagatc actgaggcca ggagcttgag agcagcttgg cccaacacag   15600
tgacaccttg tctctacaaa aaaaaaaaaa aaaaaggca gcttacagca gtagaggctg   15660
atgcgagtgg gaatcacctc taggtaaaaa ccagtgtagc gtactgctga gattatttaa   15720
cctctgggtt ttatttatgt gttttttaaa attatgatcc agtatttttt acttttttt    15780 gtataaagta agcactgaat ttttaaggtt gtattaattt gcaaataaat gtctatctta   15840
ttattttgag agatttaaaa aattttagtt cttcaaaatt gcattttcac attttgaatt   15900
acgttatctt tgacaaatac agaagatgtc aaattttggt ttattttctt tggttctaat   15960 ttatatttt gtttaaaact atatttttca ctatagactc tttctgtctc tcgaggtccc    16020
tgtataatga aaagaaggc tggaaaaagt attaacattg tcaaaatcca ggaaaagtag     16080
ttggtcatga tattgatcgt taactttaga aactttttgt atcttgtggg ttaaattagg   16140
attactatgt ggtagtgata aatgatgtta attagggccg agtgcagtgg ctaacacctg   16200
taattccagc atgtagggag gctgaggtgg gaggatgtct tgaatccagg agtttgagac   16260
cagcctgtac aacatagtgt aagaccccctt ctccacacaa aaaaattaga aaatttgtca   16320
agcatcttgg tgcacacctg tagtcccagc tgcttgggag gatgaagcga gagaatcact   16380
taagcccagg tgttcgaggc tgcagtgagc tatgattgca ccactgcact ccagactaga   16440
tgaccatctc ttttaaaaaa atgtgtttat atgttatatg tgatagtgct ttttaaaaac   16500 attttttaaat tatagagaca gggtctcact atgttacagc ccaggctggt ctcaaattcc   16560
tgggctcaag caatcctccc accttagcta acctcccaaa gtgctcggat tataggcatg   16620
agctgcatgc ccagctaatt tagtgatttt taaaaactga gctggtaatt ataaattctc   16680
ttcctggaac ttctgacttt ctcacaattg gaatcttttg acaaaaatta tcagtaatgg   16740
gaaaactttg tgtagttgtc attttttcctc ccatcagtgt gatagatatg attggagtta   16800
tgttggactg atatttgaa aaaagattta attatagcta ttaataaaga catttaaact    16860
actgactatg catttttatt cttttgggag ggtttaatgt ttatagttta agcaaactg    16920 ttgttttttaa aaaagtatct aacagggccg ggcgcgtgg ctcacacctg taatcccagc    16980
actttgggag gccaggcgg gcggatcaca aggtcaagag atcaagacca tcctggctaa   17040
catggtgaaa ccctgtctct actaaaaata caaaaaaata gctgggtgtg gcggcgtgcg   17100
cctgtagtcc cagctactcg ggaggctgag gcaggaggat ggcatgaacc cgggaggcgg   17160
agcttgcagt gagccgagat cgcgccactg cactccagcc tgggcgacag agcaatactc   17220
```

```
tgtctaaaaa aaaaaaaaaa aaaaaaaaaa gagtatttag cagaggccag gtgcagtggc   17280
tcatgtttgt aatcccagaa ctttgggagg ctgaggcggg cggatcattt gaggtcagga   17340
gtttgagacc agcctggcca atgtggcaaa tgtgctgtct ctaactaaaa atacaaaaat   17400
tagctgggtg tggtggtgca gacctgtagt cccagctact tgggaggctg aggcaggaga   17460
atcacttgaa cctgggaggc agaggttgca gtgatccgag atcatgccac tgcactccag   17520
cctgggttac agagtgagac tcttctcaaa aaaaaaaaaa agtatttaat agtgataaat   17580
ctgcagtatt ctcttgtagt ttttaagatc atattattca gtcaaagaaa agagctcaac   17640
ttgaaatatt tccagagttt aaacaatctt actaagcttt gatgggttgt atctattctt   17700
aacatgtgaa acttccttat tacctataat atacactaac ttaaatattg acaattttt   17760 tccagtggtt taacttgaat tctctcttga cgggtccaga attaatatca gatacatatc   17820
ttgcactttt cttggctcaa ttacaacagg aaggtaagta acggctgaac attttgtaat   17880
gttacctttc gaagtagtta ataaccagg cacattagat gacagtgtga taaaactgtt   17940
tttctggcag tggcagtgaa acaatcttta gttttgacgt ggtgataggc tgtgatttgg   18000
gtgacgctgt tcagttagag ttctcactga cacctggccc ttcctcttct gaggatgctg   18060 cttttctttgc agcccttcta agtaatggct ttttcttta tacatcacat atcacacggc   18120
tgagaggagg gatagatgtt tttcttcttt gcctcttcta ggccactgtt cttccttata   18180
aactccagtt tctttgaaat acatgcccct aacggctggg cacggtggct cacgcctgta   18240
atcccagcac tttgggaggc tgaggcaggc ggatcacgat gtcaggagat cgagaccatc   18300
ctggctaaca cggtgaaatc ctgtctctac taaaaataac aaaaaattag ccgggtgtg   18360 gtggcggacg cctgtagtcc gagctactcg ggaggctgag gcaggagaat ggcgtgaacc   18420
caggaggcgg agcttgcagt gagctgagat cgcgccactg ccctccagcc tgggcgacag   18480
agcgagactc cgtctcaaaa aaaaaagaa aagaaaaaa aagaaatac atgcccctag   18540 attaaactat cccttgtcct tttgcactca tccacaagtc tcttttcatc agtgatttta   18600
ggatctgact cgttgtcttt ttctctactt caactacttt tatcattctt aattatttct   18660
gtatcgtcaa tcaatccagt acctgcctct tagtttcaaa atcacttact cttgcttagc   18720
tattaccagt aatcataacc actgtcaaat ctcaattgca agcatattac tctttaacta   18780
ccacctccta tctttaaacc atgttttgtc tgttttttta ttccagccat tctttaaacc   18840
ctactgtggg gcccaagcat ttcctttata cgcattcttc ctttcttcta ctgcttattt   18900
tctgtaatcc gtcatcataa tcactccatt gcattcttca acgtgtttcc cctctctccc   18960
tccatcatac ttgaatgaca aaaatctcaa ccctggttaa accacatctt ggccttgtcc   19020
attcctgtac cagagtagct ggacgtggct aaaaataac ataaaacatg atgattggtt   19080 ttacttttt cttaaatgat ctatccatcc attcacccat ccatctatca aagtgactag   19140
gcctatttct gaagcccagg ctggagtgca gcagcataat cacagctcat tgcagctcca   19200
aactcctggg ctcaagtgat tctcttgcct tagcctgttg agtagctggg actacaggct   19260
tgtgctacca cacctagcta aggttttact ttaaatttat tataatcaca aaattcagat   19320
gagcctttag tgctgtctga tatttctact atgttttctt agtgatgtac cacctccaa   19380 ggtgtttata aaaattatg taccactctc caagaagttt ataaaaaata atgtgccacc   19440
ctccaaggtg actaatttca cagcttatgt ctttaaacct ttaagcactt tcctctccct   19500
tacacacctt ccttgtggct ttccgttaca ttctgctgag aacatagaag caattaaaat   19560
```

-continued

```
tatgttcttt ctaccagcaa atttatcaat ttgcttatat cttcacctgt gctttgagcc    19620
tatttaaata gatgaatggt cccctacctc taaccaaaac cagtcccctca cttgtgggct    19680 ggatcccagc tcttctcacc tactcaagat gttcctgctt tcatctctcc actctcttat    19740
ataatcagtt ccccccccct tttttttgtaa tattcctata agcagtaaaa taagcttttt    19800
atttccattg attaaaaata aaaatcctct cttaattcca tgaaactcca gctgcctccc    19860 cattttatt ttttccttag gattgtctct agtgtgcctt ctccttttct tgaactctgc    19920
ctcctgggtt caagcgattc tcctgcctca acctcccgag tagctgggat tacaggcgtg    19980
caccaccatg accggctaat ttttttttt tttttttgag atggagtttc cctcttgttg    20040
ctccggctgg agtgcaatgg cgtgatctcg gctcaccgta acttctgcct cctgggttca    20100
agcgattttc ttgcctcagc ctcccgagta gctggattta caggcatgtg ccaccatgcc    20160
tggctaattt tgtattttag tagagatgga agggtttct ccatgtttgt taggctggtc    20220
tccaactcct gacctcaggt gagccgccca cctcggcccc ctaaagtgct gggattacag    20280
gcatgagcca ctgcgcctgg ccccggctaa attttttttt tttttttttg tattttagt    20340 agagacaggg tttcaccata ttggccaggt tggtctcgaa ttcctggcct cgagtgatcc    20400
acctgcctca gcctcccaaa gtgctgggat tacaggcgtg agtcaccttg cctagccatc    20460
ttttagtaat ggtatttgga gatcacaatt tgagtgctgg catgcttatt gctgctgggt    20520
ttgttatgta gttattgtga attcacattt aggaatatag ggttttaat tctttgattt    20580 tagatacttg tatctttttt cttttatatt taaaaccttg gttcctgatg atatcccttc    20640
ttagaaaccc tgtctacctt tggccttcag cccaccatgc tgtggtttc ctaacttgct    20700 gcctgcactt ttcagattcc tttcatggat cttaaatatc atctgtaaat aagatctatg    20760
tgtcaataat taccaaactt ttatctttag tcttgacatc taccctgaac acctagcttt    20820
gactaactcc tagctttggc atctccactt ggaaatccaa aaagtgtttc aaactgaaca    20880
tgtctatgaa agacttattt ttttctctct atccatgcta tccatcaggt tttccatttc    20940
cataagggtg actcttgtac tctggttcct atatattata ccgacagagc agcccagagt    21000
gcttcttaac cagtgtaagg cctgttatgt cccaccctca ctctttgtcc ttcagtggct    21060
tcccagcaca cttagaataa aatctgaagt cttaggccgg gcttggtggc tcatgcctgc    21120
aatcccagca ctttgggagg atgaggggc agatcacttg aggtcaggag ttgatgagac    21180
cagcctggcc aacatggtga aaccctgtct ctaccaaaaa atacaaaaat taactgggtg    21240
tggtgttgtg cacctgtagt cccagctact cgggaggctg agataggaga atcacttgaa    21300
cccgggaggc agaggttaca gcgagccaag atcataccac tgcactccag cctgggtgac    21360
agaacgagac tctcaaaaaa aaattaaaaa aaaaaatat gtgaagtctt gaataaaacc    21420
caagatcttt accatggccc ctgaacaggg cagagtatcc attcttcaga cactcttcat    21480
agaataccat ggtgagctgg catatttatt atacaataca gaaacaattt tactggcaga    21540
aaacacatta aaccgtctaa actctgaata cagttgtcct cataaaaaat gttcaacata    21600
ctattttgag gttttccatt aatagttctt ataatctttg tcccattatg tgttaatcca    21660
acaaaggata tccaataaca aacaccaaag tttaagaaaa atgtgctagg cgcggtggct    21720
cacacctgta atcccagcac tttgggaggc cgaggtgggc agatcacctg aggtcaggag    21780
ttcgagacca gccagccaa catggtgaaa ccctgcctct cctaaaaata caaacattaa    21840
ctgggtgtgg tggtgggtgc ctgtaatccc agctactcag gaggctgagg caggagaatc    21900
gcttgaacct cctgggaggc agaggttgca gtgagctaat attgcaccac tgcactccag    21960
```

```
cctgggtgac agagtgagac tccatctcaa attaaaaaaa aaaaaaaatt aatgatagag   22020
aaacttaaat cagttagatt gttttaggta tagcccatcc ttggtttttg tgtgtagcat   22080
ctagcttggg gaaaccctgg atttctggaa tcatatttag acacagtcac actagactaa   22140
tgtaattctt ttgggatgca aaccacacgt ttgacacctt aaatagcttt taggtatttg   22200
gcttcccagc ccctatttt agttacaagg ggtgtacatg tgtgggtcag ggtggggta    22260 gctctttccg cagatgatta gttttagcca tgttactagt tattgcacac attatctgtg   22320
tcctcacagc agccctgtga gtaagtgtat tagggttctc tagagggaca gaactaataa   22380
ggtagatgta tatatgaagg gtaatgtatt aaggagtatc gactcgtatg atcacaaggt   22440
gaagtcccac aataggctct ctgcaggctg aggaaccagg aagccagtcc aagtcccaaa   22500
acctcaaaag tagggaagct gacagtgcag ccttcagtct gtggcaaaag gcctgagagc   22560
ccctggcaaa ccactggtgt aagttcaaga gtccaaaaga tgaagaactt ggagtctgat   22620
gtttgagggc aggaagcatc cagcatggga gaaagatgaa ggctcagcaa gtctagtact   22680
tccacactct tatttctgcc tgctttattc tagctgagct ggcagctgat tagatggtga   22740
ccacccagtt tgagggtggg tctacctctc ccagttcact ggcttaaatg ttaatctcct   22800
ttggcaacac cctcgcagac acacccagaa acaataattt gtagccttca atccaatcaa   22860
gttgataata ttaaccatca caggaaggta ctagtatcat atgtttaaca gtagaaacca   22920
agacaaatgc agctaggaag tgggagaact gggatcagat gcaggcagtc tgattctaaa   22980
tcagttgctg ttacccactc tgacaacagt aagtgagtag cctgctcagt caagtactat   23040
attagtaggg ccctttacag acatatttat ttctcacagt cactcaatga gacggctctt   23100
ccagtcttac aatggagaaa gtgaggctca gagactttaa gtaacttacc ttagacgact   23160
ttactagtaa gtataagaat cattatttgg actaaagtct ttctgaatcc tcagcttgta   23220 ttttttttcca gtgttctgtg ctgccttttt atctactagt gttttacatc aattttgaat   23280
ctctttacta actggttagg ttgatttttg cctttttttt ttaggttatt ctatatttgt   23340
cgttaagggt gatctgccag attgcgaagc tgaccaactc ctgcagatga ttagggtcca   23400
acagatgcat cgaccaaaac ttattggaga agaattagca caactaaaag agcaaaggta   23460
aaaatgaggc ctgcagtatg gaatatatgg tagtatttca ttatgagaat taaattttca   23520
tgcttagatt gaatatgtgg tccttgtgtt gttggcgact ctattttgga ccttatattt   23580
tagtgaagtt tattagttta aacttgaatc aactctttga aatacttaaa tatattaact   23640
tagttagctg gtatggtata ttcctagcac ttcggggaggc tgaggcaggc tgattgcttc   23700
aacccaggag ttcgagacca gcctgggcaa catggcaaaa cctcatctct acaaatagta   23760
caaaaattag ccagatgtgg tggtgtatgc ctatagtccc agctacttgg gaggcagagg   23820
aagaaggatc acctgaaact ggggaggtag agactacagt gagccataat cacactaccg   23880
cactccagcc tggtcgagag agtcagaccc tgtctcaaaa aaaaaaaaa aaagaaacgg   23940 aaaaaaaaaa cttagttgga ttcaaattgc aacacaatca ttatattact agagcttatt   24000
tgccagaaaa cattttaagt tttgacttac ttaaagcctt tacattacaa atgcctttat   24060
gttatgtcta aaatagaaga ttggttgcag ttattaccag tgctttgtt ctttagagtc   24120 cataaaacag acctggaacg agtgttagaa gcaaatgatg gctcaggaat gttagacgaa   24180
gatgaggagg atttgcagag ggctctggca ctaagtcgcc aagaaattga catgaagat    24240 gaggaagcag atctccgcag ggctattcag ctaagtatgc aaggtaaaga cattctgatg   24300
```

```
tgtgttgtat tcattgctga agaattgatt ccaattattc ttagatttca tggaagttaa    24360
tgtactctta gaggtgtttt gacaattact gcagaagcaa tagctatata gtgggctttc    24420
cctttagatt tcttataatg gaaatcactt tttacaacct atattttatt aggagtagtt    24480
atatttttac tcctggttat tttatttggt ttcaacactg tactaacaca atagtaaatt    24540
gtggttttaa tctttgtggg tatcagttga cccttatcca aatcagctgt tacataaata    24600
tgtgccatta gacactatgg aagggcctgg acagggaata taaactgatt ttacaaaaac    24660
ccaacattta ttggctatgc aacttaaacc gtaagcccac tttggtgggc ccagtttttt    24720
agtgatataa actatcaata gagaaaagcg aaaacatatc ccctagacaa tctaggcaaa    24780
gaaaaatgtt aagacatagc tcaaagtagc ttaattaaaa gtttgaagtg gttttttgt     24840 tttattttt tctaactcat atgtatttgc ttctactttc taatgaaatt atttatcagt     24900
tgatttcctt agatatctaa ataaaattga aatttcatta atgggaagat tatttttatc    24960
ctgaactttt cttgcctcta tgcatgcctc tgagtactcc atatggtgtg caatcccatt    25020
tttgattaat agagtcctgc tggattagca gggacagaaa tcagctttag atttctttct    25080
tttttttttt tctttctttt tttttttttt ttttttgag tcagagtctc actgtcgccc     25140
agcctggagt gcagtgatct tggctcactg caacccctgc ctccgaggtt caagcgattc    25200
tcctgcctca gcctcctgag tagctgggac tacaggcgcc taccaccacg cccagctaat    25260 ttttttgtact tttagtagag atagggtttt gcccttttgg ccaggctggt cttgaactcc    25320
tgacctcagg tgatccacct gccttggcct cccaaagtgc tgggattaca tgtgtgagcc    25380
accacgccca gccagaagag tagaatattc ttaaagagaa aacgttttaa aggcttactc    25440
aaatgagtat aaacaaacat attgttgctt gaattggtaa atacagtgat tggtttttgt    25500
tgtgttgtgt tttgtttttca ggtagttcca gaaacatatc tcaagatatg acacagacat    25560
caggtacaaa tcttacttca gaagagcttc ggaagagacg agaagcctac tttgaaaagt    25620
aaagtagttg gtacaagtta aagtagcatg tttaatattt gctttggcta ttttgtctat    25680
ttgtaaatgg ttactgcctg aatcctgtga atatttgaat gtattttta aaaatttaca    25740 gcaaatagga cgggcacggt ggcttacgcc tgtgatgcta gcagtttggg aggccaaggc    25800
gggcagattg cctgaggtca ggagttcgag accagcctgg gcaacacagt gaaacccat     25860 ctctactaaa aatacaaaag aatcagctgg gcatggaagc gtgcgcctgt agtcccagct    25920
gcttgggagg ctgagccagg agaattgctt gaacccggga cgtggaggtt gcagtgagcc    25980
gagatcgcac cactgccctc cagactgggt gacagagtga gactccgtct ccaaaaatat    26040
atgtatatat atataaataa aaataaaaat ttacggcaaa taacatgaaa caaaaaaacc    26100
ttgccccaat actggataaa ttttttaaac tgagtgaagg aaaccttata aaatttcatt    26160
tattaaaaga aaaatgaaat taggacaaga caagaagaat gccaattgat cctttggatg    26220
tacttcttgc ttacctgatt aaccctgcaa aattcctcta ccaatcagta cgaaaaacag    26280 cttttggaggt atgggagcgc attcccaaat agacgtggta gttcatttag ctgctcatgg    26340
ccgcttcagg cagtcctgta agcctgttag catcagggga atggatgcaa accataaatc    26400
tggatcaact cctaaaaacct taccttgtgc ccagccttgt aagtgcttgc taaataggaa    26460
ttccaccata tgaaaataca ttcttttcaa gtaactatca ttcagacttt tgtccccac     26520 tttttttttt taagaaaaa taaaaggctg gcacggtgg cttacgtctg taatcccacc      26580
attttaggag gccaaggcag gtggatcacc tgaggtcagg aattcaagac cagcctgacc    26640
aacatggtga aaccctcatct ctactaaaaa tacaaaaatt agccgggcat ggtggtgggt    26700
```

```
gcctgtaatc ccagctactt gggaggctca gacaggagaa tcgcttgaat ctggggaggca   26760 gaagttgcag tgagctgaga taacgccatt gcactccagc ctgggggaca agagcgagac   26820
ttcgtctcaa aaaaaagag aaagaaaact tcatgttaaa gattacaaga taaataatca    26880
gacccactga tcctaggtca gaaaacagag tcatagctca atctgactta ctatttgctg   26940
tatttcatcc attctgagat gcacatagtt tcacatttca atgtctctga aattgagaag   27000
catcttacag tcataattga cagtatatta gcagcaccta taaatattgg ctcattttac   27060
atttgatggt ataatgaaga aaatatttac cttttttct gttttgtttt taagtcacaa    27120
ctcagaagta gatgaaggaa aattctgatc agctgacatc ctcttaatgt gagatatttc   27180
tagtctttat tcagtataga ttaatggcta attatatgtt aaatttcaaa gtagtgctta   27240
ttagtgcttt ttacttttaa gtttcaaaat taacttttt attataataa actccaaatt    27300
tatacaaaag tagaaaaact agcatactcc tgtttatgac ccagattcaa caaatactag   27360
cacacggcca atcttgcttt ttttttttt ttttttgag atggagtctt gctctgttgc     27420
ccaggctgga gtgcaatggc acaatttctg ctcactgcaa cctctgcctc ctgagttcaa   27480
gcgattctcc cacttcagcc tcccaagtag ctgggattac aggtacacac caccatgcct   27540
ggctaattct tgtattttta gtagacacgg gatttcacca tgtcgtccag gctggcctta   27600
aactcctgac ctcaagtgat ccacctgcct cggcctccca gagtgctggg attacaggca   27660
tgagccactg agcccggccc aatctcgttt tataatactc ccatctccca ttcttttccac  27720 tgtcccacct gcaagtttgg attattttgt aacaaatctc aatcatcata ttattctata   27780 accatttaa tatgtgtctc taaaatatat tagctttatt tttaacatag ttaaatgcta    27840
ttgtcataaa ataataatca taataattaa ttgtaattct atatcatcaa ttatctagtt   27900
aatgtaaaaa ataaatctaa ggccaggcgc ggtggctcac acctgtaatc ccagcacttt   27960
gggaggctga ggtgggcaga tcacctgaga tcaggagttc aagaccagcc tgaccaacat   28020
ggagaaaccc catctctact aaaaatacaa aaaattagcc aggcgtggtg gcgcatgctt   28080
gtaatcccag ctacttgaga ggctgaggca ggagaatcac ttgaacccgg gaggcgaggt   28140
tgcggtgagc cgagatcgtg ccattgcact ctagcctggg caaaaagagt gaaactccat   28200
ctcaaataaa taaataaata aataataaaa aataacttaa atctacttaa ttagaaaaac   28260
taacattcta aaaattttat tttaagaaat atcaaaattg gctgggcacg gtggctcacg   28320
cctctaatcc ctgcactttg gaaggctgag gtgggcggat cacctgaggt caggagggtc   28380
aggagtacaa gaccagcctg gccaacatgg cgaaaccctg tctccactaa aaatacaaaa   28440
attagccagg catgatgatg ggcacctgta atcccagcta ctcaggaggc tgagacagaa   28500
gaatcgcttg aacccaggag gtagaggttg cagtgagctg agatcacccc actgcactcc   28560
agcctgggtg acagagtgaa actccgcctc aaaaaaaaa aaaagagaaa agaaatatag   28620
aaattaaagc atacatggcc aggcgtagtg gctcatgtct gtaatcccag cactttggga   28680
ggctgaggca ggcagatcac ttgaggccat gagttcaaga ccaacctggc caacatggcg   28740
aaagcctgtc tctactaaaa atacaaaaaa attagttggg catggtggtg cacacctgta   28800
atcacagcta ctttggaggc tgaggcagga gaatcgtttg aacccagagg tggaggttgc   28860
agtgagccga gattgtgcca ctgcactcta tcctgggtga cagagcgaga tactgtctca   28920 aaagaaaaa aaaaaggctg ggcgcggtag ttcatgcctg caatcccagc actttgggag   28980
gccgaggcag gcagattacg aagtcaggag atggagacca tcctggctaa tacagtgaaa   29040
```

```
ccccgtctct actaaaaaat acacaaaaat tagctgggtg tggtggcagg cacctgtagt   29100
cccagctact ctggaggctg aggcaggaga atggcatgaa cccgggaggt ggagcttgca   29160
gtgagcagag atcacaccac tgcactccag tctgggcgac agagcgaggc tctgtctcaa   29220
aaaaaaaaaa gaaagcatac tctcacctcc ttcagtgact gatgttagta ttttggcaca   29280 ttcttttttct gtgacatata cacacttacc ttgtaagtgt tgtactcatt tcctatgaca   29340
gtaaatagtc tttgtaacag gctgcatgat atttcataaa atgaatggat gtggcataat   29400
ttatatgtga gccttttgaa ttctgctatt ataattaata ttgcaatgaa caattcttat   29460
attgcctcta cacctcaaat gtcttatcat ttcttctagt ttttctgagg atgtcagatt   29520
attgggttaa aggatatgaa catttttaag gccttggaac agatttctaa attgctttcc   29580
agaataattc ccatgtgata ctttcaccat gtttatttca gactttttttt ttttttttt   29640 tttgagacga atctcactc tgtcacccag gctggagtgt agtggcatga tctcggctca   29700
ctgcaacctc cgcctcctga gtttaagcga ttattctgcc tcagcctccc aagtagctgc   29760
ggttacaggc aagtgcctcc atgcctggct aattttttgtg tcttttgtag acatggggtt   29820
tcaccatgtt gcccaggctg gtttcgaact cctgagctca ggcaatctgc ctacctcggc   29880
ctcccaaagt tctgggatta caggcgtgca ccaccgcgcc cagccatcag agtctttttt   29940
gtcaaaataa aatggtctaa agacatacat catagagaaa ctataataca aaatttacag   30000
gtatatctaa gaaaagaaaa gtatatttaa agcataaaaa taaactgctc ttttacttaa   30060 aatttttttaa aaactggatt aaaaaatatga aacttccaac aaattgagct ttttttttt   30120 ttttttttctt ttttgagacg aggtctcgct tttgtcaccc agtctggagt gcagtggcgc   30180
gatctcggct cactgcaacc tccacctccc tggttcaagc aattcccctg cctcagcctc   30240
ccaagtagct gggattacag gcgcatgcca ccacgtcggg ctaattttttt tgtatttta   30300 gtagagaggg ggtttcacca tgttggccag actggtctcg aactcctgat ctcaggcaat   30360
ctgccagcct gggtctccca acatgctggg attacaggca tgagccactg cactcggcct   30420 gaactttttta tagtagtaac gataattcag taatgtccaa taatgactaa gtaagttata   30480
acaagtacaa tgtcagcaat aactagtgct ttttagtaaa cagggtcagg caaccttgta   30540
cccttttaaa aatgttcgaa tatcgatata cctccttcct acttggtgga ggattgattg   30600
aggaggaaag tgtgcagtga tggttaccag cttcagcctc ttggcttgac tttgcaaata   30660
ctggtgagaa tttggaaaga gcttgagaat atcttacata gtcacatgtt gctgagaaga   30720
gttaagaact aacttcttga tgttcatttt taacaatggc ttgcattcaa accttgtag   30780 agctcattag taggagctaa gaagctaata tttgccttc actaaaattc ctgattactt   30840
agcctaggta gttcgttgtc tctctaggtt ctgtctttgg gagcttgggt ctaaggttat   30900
caagctaact cttttcttccc tctcacccctt cccaaattga ccctggtgct gatttgttat   30960
tcatacgatt ttctagttttt tctttttccct ttttgagtat ttgaagcttc atactgaata   31020
tagtaatcat agtattcatg cataaagaaa atcataaagt aattgcataa atgcataaag   31080
taatcatagt tttcatgcat taaaaaaact agttttggct gggcgctatg gctcacgctt   31140
gtaatcccag cactttcgga ggccaaggca ggcgaatcat ctgaggtcag gagttcgaga   31200
ctagcctggc caacatggcg aaaacctcttc tctactaaaa atacaaaaaa attagccgag   31260
tatggtggcg ggcgcctgta atcctagcta tttggcaggc tgaggcagga gaatcacttg   31320
aacctgggag gcagaggttg cagtgagccg aggttgtgcc attgcactac agcctaggcg   31380
acaagagcaa gactccatct caaaaaaaaa aaaaaaaaa aaaaaactcc ctattacaga   31440
```

```
ttcataattt atgagtcatt aaataatatt ttcaagccat gacattttt ccagcagtag    31500 tctctaaatc tgttttacca tcataaaacc ccaagcaaaa ctctactaca tcagctgtgt    31560
cactgtaaaa cctgccttaa ctcacagaag catgaaatta agcaatgtgt gtgaaactat    31620
tttataaact gtaaagtatt ccatacatac atgttggcag ttattaatgt cttctctagg    31680
tgtggctttg aaatggatgc agatgctttc tgttacaaaa aacataagtt gcaaatgttc    31740
tataacaagg agagacacaa atatcttcat ggacatggat tgctatgagt gtttgattgc    31800
ctaatacttg agccaccact tcagtgatat ggtataattt atcaaacagt gttgagaaac    31860
agaaactact ggggatgttt taaagaggaa aatacttaat atagaaatta ggggtttaca    31920
taatcttaag aaaggatgaa ggtgcagctc ttagccaggc ctccacagta ccacaaacca    31980
acttgcagga agagctgtaa ccactgcccc agttgggaca atgggtaatg aggatattaa    32040
atttaagaac atactgctat agcaatgatc cttggcatag aaagctgcca ccacaattgc    32100
ctagagatgg gaacatgaag tctggccccc attgcaacag cagtgaagca gaattttggg    32160
actggcatct cccaaatggc tttgcttgcc accagagaac aaccaaagtg gagggagatg    32220
gctaggcctc atttctgcct atttatttt attttttgag acggagtctt gtctgtcgcc    32280
caggctggag tgcagtagtg tgatctcggc tcactgcagc ctccgcctcc cagcttcaaa    32340
caattctcct gcctcagcct cctgagtagc tgggattaca ggcacccgcc actgtgccca    32400 gccaatttc ttatttttag tagaggtggg gttttgccac gttggccagg ctggtcttga    32460
actcctgacc tcaggtgatc tgcccgcctc agcctcccaa agtgttgtga ttacaggtat    32520
gagccaccat gcctggccca tttctccctt ttttttttt ttttttttt gaggtggagt    32580 ctcactctgt tgcccagact ggagtgcagt ggtgcaatct tggcgcattg caacctctgc    32640
ctcccagttt caagcaattc ttctgcttca gcctcctgag tagctgggac tacaggtgtg    32700
tagcaccaca cctggctaat ttttgttttt gttttgtttt ttttgagaca gagtctcact    32760
ctgtcaccca ggctggagtg tagtggcatg atctgggctc actacaacct ccgcctcccg    32820
ggttcaagca attctcctgc ctcagcctcc agagtagctg ggattacagg tgtgcgccaa    32880
cacacctggc taattttttt gtattttaa tagagatggg gtttcaccat gttggccagg    32940
ctggtctcga actcctgacc tcgtgatccg cccgcctcgg cctcccaaag tgctgggatt    33000
acaggcatga gccaccgtgc ccagacaagg tttgtattt tagtagagac agttttgcca    33060
tgttggccag gctggtcttg aactcctcac ctcaggtgat ccgcctgcct tggcctccca    33120
aagtgctggg attacaggcg caagccactg tgcctgaccc gtttctgctt tttaaagctc    33180
atgtgagcac ttaatttgta accagaatcc tacttgtaaa ataatctaag acatgtagct    33240
tttagctttg taacctctat aatattgatg gcacagtggg agtggatgct gagtaccact    33300
tgaacatgtt ccacctcagt gtcttcacag ctggaaggtg tctacattgt ttcaaggtgg    33360
acaattgatt tacttctcat ttttcataaa ctaaaagtag aataaaggct attcctctaa    33420
aattgctatc tcacctgtca ctcccttgca ttctcacata ccttcttgag tggaggggca    33480
gagggcatgg agtgatagca gatgtgccag gaattctcca taactcagtc cgtccctctt    33540
gtgctatgtt gcagcatcag gatttgctaa tgggaggata ctgcccttac gtgcatcatt    33600
agccatgcac actaaggtct tacacctaca cacaggtcag tattctggct cagagaccaa    33660
cagggagaaa ttgcagttct cattagttga actttcttta ttgttcacag ttttaaaaca    33720
caaaattgag aggaactcta taaaaaatgt gccattctat taataattgt tgctggtaat    33780
```

```
ttaaaaatcc ttgttcctttt tcaaattctt atatacccttt ttttttttaaa cacttgatct    33840 tagccaaaag accgagaagc aatcttttttt tttttttttt ttttttttta cctatagctt    33900
ctcactgaga ttgtcagctg tttgtaagtt ttggtttttg gttttctgtg tttgtattta    33960
catatatgaa atacagattg agtatcccctt atccaaaatg cttaagactg aagtgttttt    34020
agatttgggg ttttttagga tttgtgaata tttgcactat acttaccagt taagcattcc    34080
aaatccaaaa tttcaaatct gaagtgttcc actgagcacc tcttttgagt atcatgttgg    34140
tgctcaaaaa gtttctgatt ttggagcatt tggatttctg attctcggat ttaggatgct    34200
tgacctgtaa tttcagattt acataaaagc agaaatagta cacagagctc cttatatcct    34260
tcacccagat tcccccaatta ttggcctttc tgaaccattt gggaataata tgcagatatg    34320
attttccatt atgtctcagt tgttcagtgt atattttcta agtacaagaa tatattccta    34380
catatttaca tgataaccgt catgtttaaa cattttaaaa tggggatttg tattacattg    34440
tttctctttt tgaaaaaatt acagaggagc ttaatgcaat cagtattact taaaatctga    34500
taatgtgtgt taaatagtag ttttcattta tttcatttat caggtgttca gtgaatgctt    34560
actatgtaac agcacagtta tcagcactgg ggaaatagat gagtaagata agatttgcac    34620
tttcattagc ttacatgcca taagagggga aataaagaga acaccagatg atgataagtt    34680
tatgctgaga attaaaatga agtgatgaaa taatgggaat gtcaggtggc tacttttggt    34740
gggatggtca ggaaaggcat ctctggggag ataaatttta agctcagacc tgagtgaaaa    34800
gaatgagcca gccatggaaa cattatgtta actcacatgg tagtttgaaa tgctttatct    34860
gatcaaaggt acttatttttt ggtgactttc aacaatatta agggtctata aaccaacact    34920
catttgcata agaataacta ccagtgaatc tttttgtatg ataggttttt tgtttgttgt    34980
ttttttgaga cagagtctcg ctctgtcgcc caggctggag tgcagtggcg cgatcttggc    35040
tcactgcaac ctctacctcc ccggttcaag tgattctcct gcctcagcct cccaaagtag    35100
ctgggattac aggtgcctgc caccacgcct ggctaatttt tgtatttttta gtagagatgg    35160 ggtttcaccg tgttgtccag gctcgtgtca aacttctgac ctcaagccat ccacccgcct    35220
cggcctccca aagtgctggg attacaggtg tgagccacca ctcctggcca tgataggtta    35280
ttttgtgatg aaaatacccta cctcttaatt tgtctgataa atttaaattt tatgtctaga    35340
tttcctaaga tcagcacttc catattttaa agtaatctgt atcagactaa ctgctcttgc    35400 attctttttaa taccagtgac tactttgatt cgtgaaacaa tgtattttcc ttatgaatag    35460
tttttctcat ggtgtattta ttcttttaag ttttgttttt taaatatact tcactttga    35520 atgtttcaga cagcagcaaa agcagcaaca gcagcagcag cagcagcagc agggggacct    35580
atcaggacag agttcacatc catgtgaaag gccagccacc agttcaggag cacttgggag    35640
tgatctaggt aaggcctgct caccattcat catgttcgct accttcacac tttatctgac    35700
atacgagctc catgtgattt ttgctttaca ttattcttca ttccctctttt aatcatatta    35760 agaatcttaa gtaaatttgt aatctactaa atttccctgg attaaggagc agttaccaaa    35820
agaaaaaaaa aaaaaaaagc tagatgtggt ggctcacatc tgtaatccca gcactttggg    35880
aaaccaaggc aggagaggat tgctagaaca tttaatgaat actttaacat aataatttaa    35940
acttcacagt aatttgtaca gtctccaaaa attccttaga catcatggat attttttcttt    36000 ttttgagatg gagtcttgct ctgtcaccca ggctggagtg cagtgtcgcg atctcggctc    36060
actgcaagct ctgcttcctg ggttcatggc attctcctgc ctcagcctcc tgagtagctg    36120
ggactacagg cgcccgccac atcgcctggc taatttttttg tatttttagt agagacaggg    36180
```

```
tttcaccatg ttagccagga tggtctcaat ctcctgacct catgatccgc ccgcctcggc   36240
ctcccaaagt gctgggatta caggcgtgag ccatcacgtc cggccagaaa tcatgaatat   36300
tagtaggtga aaataaaca cattttacca cctggaaaat gaaaatact tgagtataat   36360 ctaaataaca atgggaagtg cagagttact ttccaggtct cggtttaaat atgtcttaaa   36420
ctttggccaa ttagtagtag aagttgagag aaaaagtaac tatctgacaa agaaattata   36480
agcagaatat ataagaact cttaaaactg aataatcaga aaacaactca ataaaaaggt   36540
gaaggatttg aaaagatatt tcaccaaata agacataggg atgacaaata agcacatgaa   36600
aagactctca gcatcactag tcacagggaa atgcacgata aaaccacagt gagacaccat   36660
ggcacccctg taggtatggc tttaatgaag aaataaaact gacaatacca agtgttggca   36720
aggatccaag cagctgagac tcatatactg ttaatgggaa tgtaaaagtg tacagctttg   36780
gaaaacagtt tggcattttt ttgataaatg tatacttagc catgtgatcc agcagtccca   36840
atcatgtata tataaccaaa agaaaagaaa acttaggttc acataaaaac ttatatcaaa   36900
tgcttatagc tgaccaggca tggtggccca tgcctataat cccagcactt tgggaggccg   36960
aggttggcag atacctgaag tcaagtgttc gagaccagcc tggccaacat ggcaaaaccc   37020
tgtctctact taaaatacaa aaattagcca ggcgtgatgg caggcacctg tagtccagct   37080
attcaggagg ctgaggcagg agaatcacgt gaacccggga ggcagaggtt gcagtgagcc   37140
gagatcgtgc cactatactc cagcctgggt gacagagcaa aactctgtct caaaaaaaaa   37200
aaaaaaaaaa agggctggac acggtggctt acgcctgtta tcccggcact ttgggaggcc   37260
aaggctgatg gatcacctga ggtcaggagt tcaagaccag cctggccaac atggtgaaac   37320
cccatctcta ctaaaaatac aaaaatttgc tgggcatggt ggtgggcacc tgtaatccca   37380
ggaggctgag gcaggagaat cacttgaacc cgggaggcgg agattgcagt gagccaagat   37440
tgtgccattg aactccagcc tgggtgacaa gaccaaaact ccttctcaaa aaaaaaaag   37500 attatagcat ctttattcat cattgcccaa aattacaaac tgcctaaatg tagaccttca   37560
tttagttaat gaatgcacaa actgtggtat atccaaacaa ttgaataaaa aaaggaatga   37620
actggtactt ttttctattc ctcctgttta agtacagcca aaacacctca acatttgtat   37680
aaaacatgag ctgggctggg tgcggtggct cacacgtgta atcccagcac tttgggaggc   37740
tgaggcgggt ggatcaccta aggttgggag ttcaagaccg tctgaccaa catggagaaa   37800 ccctgtctca actaaaaata caagattagt cgggcatggt ggcgcatgcc tgtaatccca   37860
gcttcttggg aggctgaggc aggagaattg cttgatcccg ggaagcgaag gttgcagtaa   37920
gctgagattg caccattgca ctccagcctg gcaacaagaa gcaaaactct gtctcaaaaa   37980
gaaaaaaaaa accattcagc tgaatctcaa aggcagagag aagacagact ggctagggac   38040
cttggaacca gaggagcagt gtggtgggga gtggactgga ttttctttt gcctcattta   38100 tcctggactt ggtgctggag aagctatggg ttcagaccaa gagaaaccc catgaaaagc   38160 ctgctctctc tagccaaaag aggcaaccta gcaagataaa aacctttaga taataagcac   38220
ttgactccag tcaaacaaaa cagaataaac tggccccatt caccctgtc agcaaaggcc   38280 aagtgggagc caagatatgt acccaacct ggaagtcata aggtacactt ctccccttc    38340 ccagccaagg tggtgttaga gaaggctgac tggggagctg ggattctcat tcctccagg   38400 aggtgataac actcctttca catggtgtca gtggtcacag ggaggctgaa cttccaccca   38460
gtaatacata ggcatctctc tggctcctat atgggtgatg ttggagaaga ggccgagtag   38520
```

```
agaatccaga ctgttgctga cacccagcag taacaaggac acctccacaa tgtccgtgga    38580
ggccatgtgg agatcagtaa caaggcactg ctctccctcc cagtcagaga gatgtcagtg    38640
gaggactagg gggctagaac tcccatgtgc gttcagcagt aatccccatg accgccactc    38700
cttgacatca caggccttga agaaacctgg actttcactc ccctctggtt gtagcgaggt    38760
ggcactccct tttccctgtt gccagtgctg tgtcagtgga ggcttgctaa attggaagat    38820
gtaaataaga ttcacattct cataacataa taccccaaat tttcaggatt taattgaaaa    38880
tcactaagct gggcatggtg gctcacacct gtaatcccag cactttggga ggccaaggtg    38940
ggccaaacac ttaaggtcag gaattcaaga ccagcctggc cagcatggtg aaaccctgtc    39000
tctactaaaa atacaaaaat tagctgggcg tggtggcaca tgcctgtaat cccagctact    39060
gggaaggcta aggcaggaaa atcactggaa cctgggagac ggaggttgca gtgatccaag    39120
atcgcactag tgtactgcag cctgggcaac agagcaagac tccatctaaa tttgtgtcag    39180
gattcccaga aggagatgag aaagggtggg gctgaaaaaa attgaggaag aagtcatggc    39240
tgaaaatttc ccaaatttgg caaaagtcag aaacctacag attgaaaaag ctgaatgaag    39300
ctcaaatatg ataaactcaa agaagttcac acagagacac atcacagtca gatttctgaa    39360
cactgcagac aaaaaatgaa gatctcgaaa ttagcaagaa atgaccttac ctaagcaatt    39420
tgaatgacag cagatttccc atcagagatc ataaaggcca gaaggaaggg gtacatacaa    39480 catttttttct agtgctgaaa gacaaaaact ctaggctggg cacggtggca cacctgta    39540 atcccagcac ttttggaggc tgaggcaggc agatcacctg aagtcaggag ttcgagacca    39600
gcctggccaa catggggaaa ccctgtctct actaaaaata caaaaattag ccaggtgtgg    39660
tggcacgcac ctataatcct agctacttgg gaggctgagg caggggaatc gcttgaacct    39720
gggaggcgac ggttgcagtg agccaaggtc gcgccactgc actccagcct gggcagttga    39780
gcgagactcc atctcaaaaa aaaaaaaatt atccaggctt ggtggtgggc gcctatagtc    39840
ccagctactt gggaggctga ggcaagagaa ttggttgaac ccaggaggtg gaggttgcag    39900
tgagccaagc tcatgccact gtactccagc ctgggtgaca gagcgagacc ttgtctcaaa    39960
aaaaaaaaaa aaaaaaaaaa acaagaaaaa aactctaaac ccagagttac atatccagtg    40020
aaatatcctt caggagtgaa gggaaaatta acgatttgtc ttcaggagac ctaccctaaa    40080
agaatggcta aaggaatttc tctaaacaga aaagaaatga taaagaagt aattttggaa    40140 catcaggaag gaagaaagaa caataaaaag agtaaaatat gggtaaacac aatagacttt    40200
cccctccttt tgaattttct aaattgtatg atggttgaag caagaattat agcactgatt    40260
tggttttcag tatatatatt ggaaatattt aaggcattat gttacagatg aaggagggtc    40320
aaaggatata aagggaggta acctttctat atttcttttg tactgatgca ggcactttgg    40380
aaaataattt cactatttgt ttaaaaactg aacatacact gaccatatga catagcatct    40440
atactcctgg gcatttatcc cagagaaaca gaaatttatt tatttttttt ttagtattac    40500
actccgtaag tgctgtaata ctagcactta gggaggctga ggcaagcaga ttgcttgagc    40560
ccaggagttc aagaccagcc tggcaatgc tgcacagtca aaaagaaaa acaaacattt    40620 agaaaactat tttaaaagtc tttaattgct gaatgcctct ttggctaata tttgaagat    40680 cattattatt attttctttt ttaggcaga gtcttgctct gtcactgagg ctggagtgca    40740
gtggcgccat ctcggcttac tgcaacctct gcctcccggg ttcacgccat tctcctgcct    40800
cagcctcccg agtagctggg actacaggcg tgtgccacca tgcccggcta atttttttgtg    40860 ttttagtag agatgggggtt tcactatgtt agtcaggatg gtctccatct cctaacctcg    40920
```

```
tgatccgccc acctcggctt cccaaaatgc tgggattaca ggcgtgagcc actgtgccca   40980
gcctggaaga tcattattta gtcctacaac tgacacattg ttccactgac gcaattgccc   41040
aggctggtct tgaactcctg ggctcaagca atctgcctgc ctcggcctcc ctaagtgcta   41100
gtattacagg cttgagccac tgtgcccagc caaaaataga aatttatatt ctcacaaaaa   41160
catgtacatg aatgtttata gcagctttac ttgtcataat caaaaactgg aaacaaccaa   41220
aatgtcctac agtgaaacaa actgtagtac atccatagca tgtaatactc tactgtcagg   41280
attaaaaaga aacccactgt tggcacaggc agcaccgtgg ctggatctca ggggcattat   41340
gctgagtgca aaaagcctc aaagggtctt acactgtatg attccacttg ttcaactaaa   41400
aatgacagct gtatagagat agagaacata ttagtggttt ccactagtta gagaaagtgg   41460
gtaaaagata ggtgggtggg aatataaatc gatagcaggg agatctttgt ggtattataa   41520
cacttctatg tcttgattgt agtggtggtg gttacatgaa tacacgtgtg ataaaatgcc   41580
atgtagaact acatataacg ttgtgccaat gtcaatatct aggttttagt ttgatcttta   41640
gttacataag atgtaactat tgggtgaaat tgggcaaaag agtacacgaa acctctctta   41700
aatatcttta caacttcctt tgaattgaca gttttcaaa atagaaagtt gggttttgt    41760 aaatacatga attgttgata tacacaacaa atctcaaatg cattatgcta cgtgaaagaa   41820
gccatattca aaaggctaca tacctactga tgccttttat atgacgtgca ggaaaagata   41880
aaactgtagg acagagaata tactggtggc tatctgggat taggaaatgg ggatcgacca   41940
caaaggggca gcatgggga attttctggg gcaatgaat ggttgtgtat cttgatggtg    42000
tatttgtcaa aatatataga actataaaag taaattttgc tttatatgta ttaaatcaaa   42060
aaaagaaact cgtgctcaaa tagaaataca ttttctgaga acttgccttt tgatgacttt   42120
gagaattttc tggaaatttt aaagaaatgt ggttttgttt cccaacaggt gatgctatga   42180
gtgaagaaga catgcttcag gcagctgtga ccatgtcttt agaaactgtc agaaatgatt   42240
tgaaaacaga aggaaaaaaa taatacccttt aaaaaataat ttagatattc atactttcca   42300
acattatcct gtgtgattac agcataggg ccactttggt aatgtgtcaa agagatgagg    42360
aaataagact tttagcggtt tgcaaacaaa atgatgggaa agtggaacaa tgcgtcggtt   42420
gtaggactaa ataatgatct tccaaatatt agccaaagag gcattcagca attaaagaca   42480
tttaaaatag ttttctaaat gtttctttt ctttttgag tgtgcaatat gtaacatgtc     42540
taaagttagg gcattttct tggatctttt tgcagactag ctaattagct ctcgcctcag    42600 gcttttcca tatagtttgt tttctttttc tgtcttgtag gtaagttggc tcacatcatg    42660
taatagtggc tttcatttct tattaaccaa attaaccttt caggaaagta tctctacttt   42720
cctgatgttg ataatagtaa tggttctaga aggatgaaca gttctcccttt caactgtata  42780 ccgtgtgctc cagtgttttc ttgtgttgtt ttctctgatc acaacttttc tgctacctgg   42840
ttttcattat tttcccacaa ttcttttgaa agatggtaat cttttctgag gtttagcgtt   42900
ttaagcccta cgatgggatc attatttcat gactggtgcg ttcctaaact ctgaaatcag   42960
ccttgcacaa gtacttgaga ataaatgagc attttttaaa atgtgtgagc atgtgctttc   43020
ccagatgctt tatgaatgtc ttttcactta tatcaaaacc ttacagcttt gttgcaaccc   43080
cttcttcctg cgccttattt tttccttcct tctccaattg agaaaactag gagaagcata   43140
gtatgcaggc aagtctccct ctgttagaag actaaacata cgtacccacc atgaatgtat   43200
gatacatgaa atttggcctt caattttaat agcagtttta tttattttt tctcctatga    43260
```

```
ctggagcttt gtgttctctt tacagttgag tcatggaatg taggtgtctg cttcacatct   43320
tttagtaggt atagcttgtc aaagatggtg atctggaaca tgaaaataat ttactaatga   43380
aaatatgttt aaatttatac tgtgatttga cacttgcatc atgtttagat agcttaagaa   43440
caatggaagt cacagtactt agtggatcta taaataagaa agtccatagt tttgataaat   43500
attctcttta attgagatgt acagagagtt tcttgctggg tcaataggat agtatcattt   43560
tggtgaaaac catgtctctg aaattgatgt tttagtttca gtgttcccta tccctcattc   43620
tccatctcct tttgaagctc ttttgaatgt tgaattgttc ataagctaaa atccaagaaa   43680
tttcagctga caacttcgaa aattataata tggtatattg ccctcctggt gtgtggctgc   43740
acacatttta tcagggaaag ttttttgatc taggatttat tgctaactaa ctgaaaagag   43800
aagaaaaaat atcttttatt tatgattata aaatagcttt ttcttcgata taacagattt   43860
tttaagtcat tattttgtgc caatcagttt tctgaagttt cccttacaca aaggatagc   43920 tttattttaa aatctaaagt ttcttttaat agttaaaaat gtttcagaag aattataaaa   43980
ctttaaaact gcaagggatg ttggagttta gtactactcc ctcaagattt aaaaagctaa   44040
atattttaag actgaacatt tatgttaatt attaccagtg tgtttgtcat attttccatg   44100
gatatttgtt cattaccttt ttccattgaa aagttacatt aaacttttca tacacttgaa   44160
ttgatgagct acctaatata aaaatgagaa aaccaatatg cattttaaag ttttaacttt   44220
agagtttata aagttcatat ataccctagt taaagcactt aagaaaatat ggcatgtttg   44280
acttttagtt cctagagagt ttttgttttt gttttgtttt tttttgaga cggagtcttg   44340 ctatgtctcc caggctggag ggcagtggca tgatctcggc tcactacaac ttccacctcc   44400
cgggttcaag caattctcct gcctcagcct ccagagtagc tgggattaca ggcgcccacc   44460
accacacccg gcagattttt gtattttgg tagagacgcg gtttcatcat gtttggccag   44520
gctggtctcg aactcctgac ctcaggtgat ccgcctgcct tggcctccca aagtgttggg   44580
attacaggca tgagccactg cgcctggcca gctagagagt ttttaaagca gagctgagca   44640
cacactggat gcgtttgaat gtgtttgtgt agtttgttgt gaaattgtta catttagcag   44700
gcagatccag aagcactagt gaactgtcat cttggtgggg ttggcttaaa tttaattgac   44760
tgtttagatt ccatttctta attgattggc cagtatgaaa agatgccagt gcaagtaacc   44820
atagtatcaa aaaagttaaa aattattcaa agctatagtt tatacatcag gtactgccat   44880
ttactgtaaa ccacctgcaa gaaagtcagg aacaactaaa ttcacaagaa ctgtcctgct   44940
aagaagtgta ttaaagattt ccatttgtt ttactaattg ggaacatctt aatgtttaat   45000
atttaaacta ttggtatcat ttttctaatg tataatttgt attactggga tcaagtatgt   45060
acagtggtga tgctagtaga agtttaagcc ttggaaatac cactttcata ttttcagatg   45120
tcatggattt aatgagtaat ttatgttttt aaaattcaga atagttaatc tctgatctaa   45180
aaccatcaat ctatgttttt tacggtaatc atgtaaatat ttcagtaata taaactgttt   45240
gaaaaggctg ctgcaggtaa actctatact aggatcttgg ccaataatt tacaattcac   45300 agaatatttt atttaaggtg gtgcttttt ttttgtcct taaaacttga tttttcttaa   45360
ctttattcat gatgccaaag taaatgagga aaaaaactca aaaccagttg agtatcattg   45420
cagacaaaac taccagtagt ccatattgtt taatattaag ttgaataaaa taaattttat   45480
ttcagtcaga gcctaaatca catttttgatt gtctgaattt ttgatactat ttttaaaatc   45540
atgctagtgg cggctgggcg tggtagctca cgcctgtaat cccagcattt tgggaggccg   45600
aagtgggtgg atcacgaggt cgggagttcg agaccagctt ggccaaaatg gtgaaacccc   45660
```

```
atctgtacta aaaactacaa aaattagctg ggcgcggtgg caggtgcctg taatcccagc    45720
tacctgggag tctgaggcag gagaattgct tgaaccctgg cgacagagga tgcagtgagc    45780
caagatggtg ccactgtact ccagactggg cgacagagtg agactctgtc tcaaaaaaaa    45840
aaaaaaaatc atgctagtgc caagagctac taaattctta aaaccggccc attggacctg    45900
tacagataaa aaatagattc agtgcataat caaaatatga taattttaaa atcttaagta    45960
gaaaaataaa tcttgatgtt ttaaattctt acgaggattc aatagttaat attgatgatc    46020
tcccggctgg gtgcagtggc tcacgcctgt aatcccagca gttctggagg ctgaggtggg    46080
cgaatcactt caggccagga gttcaagacc agtctgggca acatggtgaa acctcgtttc    46140
tactaaaaat acaaaaatta gccgggcgtg gttgcacaca cttgtaatcc cagctactca    46200
ggaggctaag aatcgcatga gcctaggagg cagaggttgc agagtgccaa gggctcacca    46260
ctgcattcca gcctgcccaa cagagtgaga cactgtttct gaaaaaaaaa aatatatata    46320
tatatatata tatgtgtgta tatatatatg tatatatata tgacttccta ttaaaaactt    46380
tatcccagtc gggggcagtg gctcacgcct gtaatcccaa cactttggga ggctgaggca    46440
ggtggatcac ctgaagtccg gagtttgaga ccagcctggc caacatggtg aaaccccatc    46500
tctactaaaa atacaaaact taagccaggt atggtggcgg gcacctgtaa tcccagttac    46560
ttgggaggct gaggcaggag aatcgtttaa acccaggagg tggaggttgc agtgagctga    46620
gatcgtgcca ttgcactcta gcctgggcaa caagagtaaa actccatctt aaaggtttgt    46680
ttgttttttt ttaatccgga aacgaagagg cgttgggccg ctattttctt tttctttctt    46740
tctttctttc ttttttttt tttctgagac ggagtctagc tctgctgccc aggctggagt    46800
acaatgacac gatgttggct cactgcaacc tccacctcct gggttcaagc gattctcctg    46860
cctcagcctc ccaagtacct gggattacag gcacctgcca ctacacctgg cgaatatttg    46920 tttttttag tagagacggg cttttaccat gttaggctgg tctcaaactc ctgacctcag    46980
gtgatctgcc tgccttggcc tcccaaagtg ctgggattac aggtgcaggc caccacaccc    47040
ggccttgggc cactgttttc aaagtgaatt gtttgttgta tcgagtcctt aagtatggat    47100
atatatgtga ccctaattaa gaactaccag attggatcaa ctaatcatgt cagcaatgta    47160
aataacttta ttttcatat tcaaaataaa aactttcttt tatttctggc cccttatatta    47220 ccagcatctt tttgctttaa aaaatgacct ggctttgtat ttttttagtc ttaaacataa    47280
taaaaatatt tttgttctaa tttgctttca tgagtgaaga ttattgacat cgttggtaaa    47340
ttctagaatt ttgattttgt tttttaattt gaagaaaatc tttgctatta ttatttttc     47400 caagtggtct ggcattttaa gaattagtgc taataacgta acttctaaat ttgtcgtaat    47460
tggcatgttt aatagcatat caaaaaacat tttaagcctg tggattcata gacaaagcaa    47520
tgagaaacat tagtaaaata taaatggata ttcctgatgc atttaggaag ctctcaattg    47580
tctcttgcat agttcaagga atgttttctg aattttttta atgctttttt tttttttgaa    47640
agaggaaaac atacattttt aaatgtgatt atctaatttt tacaacactg ggctattagg    47700 aataacttttt taaaaattac tgttctgtat aaatatttga aattcaagta cagaaaatat    47760
ctgaaacaaa aagcattgtt gtttggccat gatacaagtg cactgtggca gtgccgcttg    47820
ctcaggaccc agccctgcag cccttctgtg tgtgctccct cgttaagttc atttgctgtt    47880
attacacaca caggccttcc tgtctggtcg ttagaaaagc cgggcttcca aagcactgtt    47940
gaacacagga ttctgttgtt agtgtggatg ttcaatgagt tgtattttaa atatcaaaga    48000
```
ttattaaata aagataatgt ttgcttttct a                                          48031

<210> SEQ ID NO 43
<211> LENGTH: 300019
<212> TYPE: DNA
<213> ORGANISM: Homo sapiens

<400> SEQUENCE: 43

| | | | | | |
|---|---|---|---|---|---|
| gatgtcccga | gctgctatcc | ccggctcggc | ccgggcagcc | gccttctgag | cccccgaccc | 60 |
| gaggcgccga | gccgccgccg | cccgatgggc | tgggccgtgg | agcgtctccg | cagtcgtagc | 120 |
| tccagccgcc | gcgctcccag | ccccggcagc | ctcagcatca | gcggcggcgg | cggcggcggc | 180 |
| ggcgtcttcc | gcatcgttcg | ccgcagcgta | acccggagcc | ctttgctctt | tgcagaatgg | 240 |
| cccgcttcgg | agacgagatg | ccggcccgct | acggggagg | aggctccggg | gcagccgccg | 300 |
| gggtggtcgt | gggcagcgga | ggcgggcgag | gagccggggg | cagccggcag | ggcgggcagc | 360 |
| ccggggcgca | aaggatgtac | aagcagtcaa | tggcgcagag | agcgcggacc | atggcactct | 420 |
| acaaccccat | ccccgtccga | cagaactgcc | tcacggttaa | ccggtctctc | ttcctcttca | 480 |
| gcgaagacaa | cgtggtgaga | aaatacgcca | aaaagatcac | cgaatggcca | tatcctttg | 540 |
| cccgaacccc | agcagcagct | gcgcctcccc | ctcctccctc | cgcctcccct | cttccaggct | 600 |
| gggagagaga | cccggggtt | gatgggaggt | ggggaggagg | ggggtcttcc | aggggctggg | 660 |
| agaggggca | ccgggaggag | tgtgaaagaa | tctctccacc | ccgagctggg | ttgagctacc | 720 |
| ctggaggctt | gggaatgggt | ttgtgggggg | ctgggggtg | ggcagcggag | agtggatcct | 780 |
| tcccaaggac | cgactctaga | atgagatctg | gggcctgggg | tcgtgcagga | gccttggtgg | 840 |
| gggctttcga | gccaagtccg | gagggtttgg | agttctacgg | agtgagcttg | gagcgggctc | 900 |
| gggcctgggc | gcttctggcc | agggcagggg | aactatgggg | gccttggttg | ggtttcttg | 960 |
| gccgtcgctc | actggagtcc | acgcagggga | agctggacag | cctctccact | actgctttcc | 1020 |
| ccaaggtggg | gggccgccgc | acttttaggg | cagggcgctt | gggggctccc | agggctaaga | 1080 |
| gcaagaggga | gtccatgtgg | ccttcacact | gagaagccag | cactggccga | agtgagtacc | 1140 |
| ccagggtggg | ccgctgttcc | tatctggaga | ggatagtgat | gggctggggg | gcgcttatgt | 1200 |
| ttccctcatg | tgtgcaggtc | ccattgcctt | taaccgctga | ttggggaacc | tcatcatctt | 1260 |
| tggggggtgtc | gagaaagaga | tcccacttgc | tttatctggg | ccctggcct | gggaagacct | 1320 |
| gatctggaca | ctttcagtaa | gaaagacagg | gcaacagcaa | atgaggtggt | gggtccattt | 1380 |
| tagagcacca | tgtccagctt | ttcctacccc | gagtagccga | gagggaacac | caggagaatc | 1440 |
| agcacccatg | tggacatctt | aggtaggtaa | atgcctttta | aattttttt | tttttaatca | 1500 |
| aagatccaga | ggaaaaaggt | gaagcccaca | ttttcttctg | tggagatgct | atcaaaatgc | 1560 |
| agatcttctg | tgtttctta | aatccctgcc | tgcttgaaat | aaaccttgag | gagggcttaa | 1620 |
| catctatcga | gatgtaggca | ggcaagggtg | ggtaattagt | cgggctttct | agcagttatc | 1680 |
| taagcatgac | ccagattcca | ggagggggga | cacaccctgc | tgcccaggct | ggctggccac | 1740 |
| tgtgccatgc | ccagatgtgc | cgcttctccg | cacagttcca | accagctgcc | ctctgtgtaa | 1800 |
| aaatgaacgg | gctggatggg | tccctgggc | tcagcgatga | gtcccctatc | ccttttgtat | 1860 |
| gtggttttgc | agttatagac | taaacggggc | tgggccctgt | gtggtctccg | ggggttgctg | 1920 |
| tttgaggagc | atggcgggtg | gtagagggac | tcacttcagg | ggggttcaaa | atcgagcctg | 1980 |
| gcgcttggat | cctgggtgct | gggattgcaa | cagagggcac | tgaggttttg | gagtgtgtga | 2040 |
| gtggtctact | ttgagggtgg | ggaaaattaa | gaagttcagc | agaggtgctt | ttgaggggag | 2100 |

| | | | | |
|---|---|---|---|---|
| catacctcta | actacgatgc | catctccgtt | ggtgcccaaa | gcaggtgcca ggtctttgct | 2160 |
| tcctaagttt | cagactctta | aagaggctgg | ttcttaaggt | tagcaattcc tcaccatccc | 2220 |
| aggcccattg | aagtgctcag | ggtggcttg | attactctgc | ctatcaacag agtgaggagt | 2280 |
| gggagtgcct | tgcaggagga | cagggtattc | atgggtgcac | acccagttag ctccaggagt | 2340 |
| gagagggctt | tgctcggctg | acaggtttcc | tcattgaaaa | tggctttaga tcgccttctg | 2400 |
| gagcctggat | ttggagactt | ctaagaggaa | aggaaggagg | tggggagccc ttctgctgtg | 2460 |
| tccttagctt | acctctgtcc | agcctgaatc | ctgcagattg | gagggctgtt gggggagagg | 2520 |
| gggattgcag | tggcccctcg | gaaggggaa | tcgtgggaga | gggaggcagg tgaattgcga | 2580 |
| gtgttgcttg | ccacttcatc | tattctctgg | ccagctcgcc | cggggctttc ttgctcttat | 2640 |
| gatgagtttg | tgcattatgc | tctctgcaga | ctgttttgt | tctctttgac ccaggtaac | 2700 |
| aaacacatta | tacagccta | ctctggaagg | gaaaactccc | cacctcacaa tctgtcatcg | 2760 |
| agctgggtca | tccaggactg | agctttctct | gtcctggatg | gagcggaggg cggtggcggg | 2820 |
| gtgggtggga | gggttggaga | tgagagggga | tggacagaga | cctggggagg gaggtagtga | 2880 |
| ataaaagaat | tcaggccagt | gtaaagaaa | agacacgtgg | aatgtcagag tcacgatacc | 2940 |
| agggcagaac | attctacttt | ttaatctaaa | tatttctgcc | attaaaaaaa aatgtttcag | 3000 |
| catatcctga | gagtgaaaaa | aaaagtgtgt | aggtacttaa | ataaagtcta atatatgtac | 3060 |
| aggcaagtac | atatattcag | atgcatagat | ttttacaaaa | tgaacacacc cacgtatcca | 3120 |
| gcacccaggt | cccgatcagt | gccctggaag | tccccctccc | cataccgcct cctagttgct | 3180 |
| cccccaacaa | gggtaccgct | cacctgactt | ctaaggttca | ttttgcctct tttaaacatg | 3240 |
| taaatggagt | cacacagtac | gttcttttgc | cactggcttc | ttttgctcac atctgtgtat | 3300 |
| gtgactctac | tacaatctat | ccattctact | gttgatgggc | atttgtgtca tttctgtttg | 3360 |
| tgccactggg | aacattcttg | tgtcttctat | tattttttc | ccacagttct cttagatagg | 3420 |
| agtggaatcg | ccctgctac | ttttgatgc | atgtgttgtg | ggatgtgtat ttggaaatgg | 3480 |
| tgttgactaa | ggttgcagg | tcgatatgga | aagcaggttc | ctccctgtct tgtttaagag | 3540 |
| aagtgagtga | atgatccatg | aacttgtcgg | tatgctcaca | gggcctaaga gtgctacttc | 3600 |
| caaatgtaaa | ttctggcatg | gtacactggt | gaaggatgca | gtcttgctttctccacactc | 3660 |
| ggggcaattt | gtcactatga | tttcttcctc | tttcatccct | cagtgggtca aacttgaagc | 3720 |
| catcaatgac | aattaagaat | cctcatttat | ttcatttttt | cccctcttcc taagtgagga | 3780 |
| aacccaaatg | gaagtctttg | atgttcaaat | ttacattgcc | gtgttttct catgccaggc | 3840 |
| agcaagccgt | cttgaccaca | caccttggtt | tcatgttttc | attgactgga attgtgattc | 3900 |
| aaataggcc | atgagggtct | ctgatgattg | ccgaagagct | cagatctgtc agctcaaaaa | 3960 |
| ggagcatctg | tcagccttcc | tagagttccc | tccccactta | atgccactca ctccttctac | 4020 |
| caagtgccaa | ggtgaatgtc | atcttttccag | ccctccctgt | gccaccaggt ctcccactga | 4080 |
| acatgatgta | gaaactcagg | ccatcggagg | aacactggaa | gcaggtcagt gtattatcac | 4140 |
| gcacagttgc | ctgaattaca | cgtagaattc | cagcttttca | tccggtttgc agaaatctta | 4200 |
| acaagacacc | taaagtcaca | ttgacatcag | gtgacatcac | tttgacatct gtggacattg | 4260 |
| gctgattggc | actcctctca | tttttttttt | tttttttttt | tttaagaaaa gctctctaaa | 4320 |
| gagaaacttt | ctgcatgaga | agcgctggga | gacatgggag | caggttatca gactcttggc | 4380 |
| ctgtcctgag | agatagaatg | ttctagaagg | tactgccgta | gagggcagga tggtgtcact | 4440 |

```
tacgtgatcc ttgtactaga ccggcttggc tggtatttcc agaggagcaa aattctgcga    4500
agtaaaattt agcacggctt ttccaatggg agtattttca aaagggtgc aatttcttat     4560
ccacaattcc ccaatccaaa aagctccaaa aaccaaaaga cgagctcata tagaggtaaa    4620
acctaacctg aactgacttc agtttgaagt cttaatttac agttttcatt cattctactt    4680
ggtgtgcatt tgagtatgtt ttgcagcaga aatgttagat gtgcttgatg atgaggtgct    4740
gcttcagctc ctgactgtta ggtctgcatt gtagtcctgt caaactttca ggtgtatgga    4800
agttgtcttg ttaacaggat ggttctggtc cagcaggatt tgggtggggt ctgggattct    4860
gcttttctag ctagcttcta gggattcccc atgtggtaag ttcatgggct agggttggag    4920
tatccaggtt agatcataga gacatcttgt tatcattttt cttttcctta aaaatcaggt    4980
ttataggggc cgggtctggt ggttcacgcc tataatccca gcactttggg aggctgaggc    5040
cggtggatca tgaggtcagg agttcgagac cagcctggcc aacatggtga acccgtct     5100
ctactaaaaa tacaaaaatt agccaggcgt ggtattgtgc gtctataatc ccagctactc    5160
gggaggctgg caggagaatc atttgaacct gggaggcaga ggttgcagtg agccgagatt    5220
gcaccactgt acttttttt gagactctgt ctcaaaaaaa aaatagattt attgatgtat     5280
aatttatttg tagcaaaatt cacccttttg acatactggt ctgcaagctt tgacaaatgg    5340
atgtagttgt ggccaccacc caaatcaaga tatgggacag tttcatcaac cctaaaatac    5400
ccccacagtg cccctcttga gtcagcaccc cacttctcca gccccttcaa ccactgatct    5460
gttctccatc cctacagctt tgccttttgc cgaaggtcat ataaatgtaa tttcacagta    5520
tatagccttt tgaatgtgga ttcttttact cagactttga gattcattca tgctgttgcc    5580
tgtgacagta gcgccttcct ttttggtgtt gagcaggatt ccatgatatg gatggaccag    5640
agtttgcttc ccagccgaag gacattggga tgcttccagt ttcaatgatt atgaatagag    5700
ctgctataaa cattggctta tgggttttag tgggaacatt tcatttcata catttcattt    5760
ctcttgggta aattaaccca ggagtgagat tgctgagttg tgtggtaggt gtatgtttaa    5820
ttttataaga ggctctcaaa ctgttttcct aagtggttgt accattttac attcccatct    5880
ttgcaatgcg tctaaaagcc ctgagttctg aattccaaag cacgtctggc ctcgatggct    5940
taggattaag gatgtggatc tatggaaagg agtggaagta atagtgttaa atcccggtca    6000
gagaaataag aaagattaag gatgtcattc aaagctatgt gcctgcacta gagagagaga    6060
aagaaggggt tctcttgggt ggggttccac ccctccctgg tagttctacc attccccagg    6120
aaaaagtcaa gctctgaggc tgtgagaccc atgatcttta ccctgttctt caccactgca    6180
accccagtgt gtgggacaaa gcaggcgtcc tataaacgtt tgctgagcaa atgagaaaag    6240
gtacctgtct tcacccatta actaaattgt ataacatcta tctgatctac ccttgtgcca    6300
acgttttagg attttgatgg gttttagttg caggggttg agagactgtc catgagatta    6360
tcagaccaat gaaagtttct gaaatgttag tgcttgagta gattggatgc agcggcccct    6420
tgagaatgaa gtctttcttc agggacttgg agtgggaggc atctgttggg tgcgtagggc    6480
ttatgcttcc ccctccctgt ttccccccca gtagcaagca cacatataca ctttctcagc    6540
aataaaaagc accgccggga aggtggactc catccagaaa tgatcagagc ctaagagccg    6600
tgcagtaacg catttccgag aatgccagct cagctcctga gaaagggcc ggatgggatg     6660
gtgcctgctc tgaaagaggg cagagaggag agggaaaaca ctccggactc tgggtcagac    6720
tggcccaggt tcacattatt caccagccat gttatcttgg gcaccagagc ctatttcttg    6780
acatgcatga tgaggatatt ccttctagta gcatctccct tggagggctc tcaggagatt    6840
```

```
aaatggggtc gtgcgtgaaa aatggccagc acagtctcca gcacagagaa aaaccccaaa   6900
acgccagagc cgtaatacta tggagtcatt taggttccag tgttctttt tttggaaaccg   6960 gccagaaaag aggctttctg ggtgggaatg ggagcgaagt gcccccccc accacccct    7020 gcgactggtc agtgtggatt gattaacctg atcgtggcgc tctttaaagc cacctttgga   7080
cattttgcat tctccgttct ctctggaagc tttcagggga aaaaaattc gtggccactt    7140 gacccatttt tctattccct tgagtctaag gtaaaaatta attctctttc ctcctttggt   7200
ccctccctct ctctgtgggt gacaaggtga gggagtttta aagtatataa ttagcttccc   7260 tcttccccttt ttgcactccc tgtctcttcc tttggggccg gtcgagagtg cagcccagga  7320
tggccacccc aggtgtccac tgcaaactcc acagaaaaac tttgctcaac ttttggttta   7380
gaatttaggt acccccctcc ccttccaaac tttggtcttc tttctcctca ctccctaaaa   7440
aaataggaaa aacaaggaac attcctggcg agggaaccat gagtgggcac agcaacttag   7500
gtttcaaaaa ccactgggcc tcagttctta tctgagtagg gtgacccttc agccaggtt    7560 gcctgggact atcctgggtt tagcatctct ggaaactcac agtcctgggc aaactgggac   7620
gctggtcacc ctaatggtga gttcttaaca cctgagagaa agaatggtg caagagatgg    7680 tgccgttgac caagaaaggg ggagagtcag ttacttattc cctctgaaaa gccaagactt   7740
tttattggaa tgaatgcagc ttttagaagc cgtctttaag gcagctaata caagagagat   7800
tccagctatg aagggaaatg cctgagttaa gtccggatca agttttgaca tctcgcttcg   7860
gtcagacacg gctttatctg ccgttcagac tgggagcagc cgtgagtctt ccttaaaggt   7920
gcctgttgct caggcggcac ctgcagttag aaattagcag cctcccaccc ccagccccca   7980
aataacagga ttcaagagtc ccctctctga agccatgagg gaaacccaac ttagtcaccc   8040
acttgccagt aaataatatt catgctgtta agttctgttc tcattttagg cctatgtgta   8100
aaaaatatat gtaattttaa actgattttt aaagtatttt catacgaaca gcatttgcag   8160
gagggcgaag tctggatgtt accttttgt aaaagtggat ggatttgtct tcaatgagac    8220
tctggggcag acttaaaact tggcccgcag tggtgttaca tggattctga tcttccagag   8280
tctgtcacgt tcttttatct ccatgatctt tattatcttc tttattgaga atgatgggca   8340
tggtgtgtgt gggtgggagg gctatgctga ccatcactgc agtgaaatgt gttcgtggca   8400
tgttgtggcg tctgcatagg aatgtgtctg tttgattaac agcacaagca gtggaggctg   8460
taaggaggaa aagaggaggg aaggtgatat tggatggagg ggagacatat agagcttggg   8520
aacagtccac cctggctgca aatctcagct ccagctcaca gttgtggagc ctcagtcttc   8580
tcctctgtaa aacggggaca gtagtcctat gtccgaggaa ttgtaagaag gttaaaagat   8640
actgtaccca gaaagcacat ggcatatata atcatcctgt gaagtagcca actcaatgaa   8700
ttttatttta tttatttga gtcagagtct cactctgtca cccaggctgg agtgcagtgg   8760
catgatcatg gctcactata gcctcgacct cctaggctca agcgatcctc ctgccttagc   8820
ctcccgagaa gctgggacta taggcatgca ccaccgtacc cagctttaac aacataaatt   8880
tatatatata tatatatata tatatatata tatatatata tatatatatt               8940
tttttttttt ttttttttt ttttttttt ttgagatgga gtttcattct tgttgcccag    9000
gctggagtgc aatggcgcga tctcggctca ctgcaacctc cgcctccgg gttcaagcag    9060 gacgatgggc atttgggatg tttctagttt ggggtgggg attgtttgtt tgtttgctgt   9120
tatgaacaat gctgctgtaa ggaatcaata attttgaatg aatgaattcg aggtgttaat   9180
```

```
tttagtctgt gtacttggaa atctagcttc acctagaatc agctgagatt catcagcatt    9240
tatggcagga gctaagacat ttcacagctt actcatcatt ttctctaaga ggctgggtca    9300
accggttagc tcttggtcct gcttgtattc tgagagtcag aacctgtggt ttagacactg    9360
gcaattgata tggttgtaga gaagcagcat ggttgagttg agagcatgga ttctggagct    9420
aggtggctgg ggttcaaatc ccagctctac tagtcactgg ctgcgtgatc ttgggcaagt    9480
cacttaagtg ttctgtgctt cagtttccca gtctgtccca gtggtgattc taatagctcc    9540
atggggatcc taatagctcc tatctgggag gattaaatga gttaatacat ctgatgttta    9600
gagtggtgcc tgacacttag gaagcactat atgtgtttat acatggaaga gtggatagat    9660
ggatggactt atgtgggtgg ccatatttgg gcttctctga tccactgctg agaatagtgt    9720
gtggcacaca gtaggtgctg cataagtgtt aatattctgc tctttcttgc caagtctctc    9780
aactcccttg atctctgtta ttttttggcgt ctgtgttgtt aacccattct tctgaatgat    9840
cagctgaatc actgttgctc caatatataa gccaaggaga acacaatcac aaggtctcat    9900
tgattgtcca tactagaatt ccatgattcc taggcccaag taggattttc cccacgtctc    9960
agcaatcctt cttccatgtt tctaatcttt ttctctcatt tgttatgccc cattgccaga   10020
ctctccaatc tccccacagc ttccccttcc tctaactata ctgtctctag tcttaccttc   10080
tccctaaggg caccgtcttt gaagacatca aatacttcag agcaccaaat ataggttagc   10140
ttctctgagg gccttacaag gacatggagt gtttgggtct tacacaaatt ggaatggtca   10200
gaaatgttta gagacttgag ttgtctttga aagagttgtc agaatgcaaa ttttgactt    10260
gtggcctgtt tctgatcaca acgcagtctt ttaagttatg gatcatagct ggatgtttgt   10320
ggtttagagg ggatggaggc atcctctgca gttagtgttg gatgtctggg tggatggatg   10380
gatggatgga tggatggatg gatggatgga tggatggttg aacagatgca tggatgagtg   10440
gatggatgga tggatgggat gaaggaagga aggaaggatg ggtgattgga gggtaggtgg   10500
gtggataagt agattggtag atgactcgat gggtgggtgg acaaatggat gggtgaatgg   10560
atgactggat ggatgactgg atggattggt gtatgagtga atatatggct ggatgaataa   10620
ataggcagat gactagactg gattgagggg taaaaatatg gatgactgga tgggtggatg   10680
agtggatgat agatggttga atgggtgggt ggatgggtgg atgttggata tagggtgta    10740
tggtagggta gctgtctatg tgtgggtctc cctgatattt ggtgttctgt ttgacttggg   10800
aatgaccaag tctctccgct taccacctta tttgtacctt ttccagtatc aagtgaattt   10860
tgcacacttt tgtaaaaatc aataagattg tatgtttagg actttgggag gccgaggcag   10920
gcagatcaca aggtcaggag atagagacca tcctggctaa cagggtgaag ccccatctct   10980
actaaaaata caaaaaatta gccaggcgtg gtggcgggca cctgtagtcc cagctacctg   11040
ggaggctgag gcaggagaat ggcatgaacc cgggaggtgg agcttgcagt gagccaagat   11100
catgccactg cactccagct gggcgacag aacgagactc catctcaaaa taaataaata   11160
aataaatatt atatgcttag gttttaccta tgtaattaga aagctccttg agggtagggg   11220
acagtgattt gccttcctca catcccccca aagttcctgc actatatcat gcataagtat   11280
ttaattgagt aatggtgagg aaagtaaaca gtgttattga acaaagatta ttaaaattct   11340
ggaaacacct ggttttgttt cagcactggg actgaaagtg gaattccttg gattttgctc   11400
cattggtgga taggatagca tgtggtggtg gactggtaga ctctttctct tccaagcaga   11460
ttgggtaaat gccccagatt cttacccact agtcagagat tacagattac tgattgatat   11520
ggttttctc tgtgtcccca cccaaatctc atctcaaatt gtaataccca catgtcatgg   11580
```

```
gagggacctg gtgaaggtga ctggatcatg ggggtgattt cccccatgct gttcttgtga   11640
tagtgagttc tcatgagatc tgatggtttt aaacttgtgt gggcctcttt cctctctctc   11700
ctctcctgct gccatgtaag acgtgccttg ctttcccttt gccttctgcc atgatttgta   11760
agtttcctga ggcgtcccca gccatgcaga actgtgagtc aattgaacct cttttcttta   11820
taaattactt ttatagcagt gtgaaaacgg actaacacac tgatgtagca aggtccttta   11880
aggccccatg tgatctggtc cctgttttgt ctttgatctc atctctttca ttgtctacct   11940
tcctttcatt gtctattctg tctcagccct gctgaccatt ttactcacac ccatgtcatt   12000
tgcattacat gacattcctt ctgttcagca taagctattt cctctgcctg catcactgtt   12060
tctccaggtc tccccatggc taactccttc tcttcattta ggtctcagcc caaaagttac   12120
ctcctccaag aggcctatcc tttcattta ctgaacatct catgtacaaa aagaatata   12180
aaatatatgt atactctctc atccacaaaa aaatctctga agacatttta atgtatttca   12240
tcccatacct ttttatgcat gtaaactttt aggaacacat ttccatgcca ctaggtatcc   12300
ttgaaaaaat aagggccacc atgtatagtt gcacaggttg tgcactgcac aaagatagca   12360
tgtcacatat cttaagtatc atggagcttg tatgtctact atttcagtac cccagctgat   12420
aaaagcttaa gtatcttgtt ctagcaagat gaagctatta tgacaatttt tgacagagaa   12480
aggggtgttt tgtttaagtt cacaatcaga gaaatgggtg tcttgtttaa tttcacaacc   12540
agagaaaggg gtgtcttgtt taaattcata cagtggtgct gtatggggttg gtggcaaccc   12600
cagaaaagac tgttgttaat atctgataat gttccacttt atacgtgtat tatattcatg   12660
taacaatctc tggctgtttg ttttgccatt ataaataaca gtgcagtaaa catctttgtg   12720
tgtgaatctc tgtccaaggt tctgatagtt ttctgaatga aattcctgtc tatatatggc   12780
actccaagcc cataattgaa actctgctgt taccactttc tttgaatctg tagaaggaat   12840
tttgagaaca ggtgactggt atattcagga tgttgatgac aaggaacaga gaaagaacag   12900
ttaaatggtt tggaattttt cctgggctgc atgtaaagca gtgcttttga actgggagca   12960
attttccccc caaggggact tttggcaatg tctggagacg ttttgttg tcacgaatgt   13020
agggggaggg ggcaagatgc tactggcatc tggctggtag aaaccaggga tgcagttcag   13080
catcttaaaa tgcacaggac agcctttctc agtaaagaat tatccagctc caaatgtcag   13140
taataccaag gttgagaaat cttgatgtaa tcgatgtcat gggtttcttc aagaggagtg   13200
ggtggattta gggttttttgg gtgacttaaa tttaatttac agtttgtctt cctagctggg   13260
tgtctaagcc agctttctgt gaactttaga tcccacacaa gaagcaacag gcttgctacc   13320
gacagattcg ttgatgtaaa tatagatgag tgtatagaag gaaatctcac ccagagctgg   13380
aaaatgttgg aatgaaaact gcggcggcct ccccttctct ctccttcccc ttctgttgcc   13440
ctgtttgaaa atcgtgcctt actttctttg gtctcctggc atggtgaatg ctgctggtat   13500
ggactgtgtt tctatatccc cttgatcccc acacccttag gaacgtacag gagagagacc   13560
ctggagcata tcagcttaga gatggagggg aatgggaagg agtgcgttca ttcattcata   13620
aatgttgact gagcacctac tgtatgctag gtgaatggga ggacgtgagg gcagggaggt   13680
gacaaggttg gcttattctg ggctttgtga actatggtga ggattttgtt ttttttccaaa   13740
ggaaatggaa taaccactcc tttttccccc ccgatatacc taaacttttt gattttcata   13800
acaaaaatgg gcttcctttt gtatatttgt tttgagacca gccgttttc caccaacact   13860
gatcacactg cagtgagcat cctggtagag aagtctttgc acacttctgt cactgttccc   13920
```

```
ctaggacaga ttcctggaaa tggtatggca aggttgtatg tcaggctttt gggccaggtt   13980
gcaagaaaca ggaagtctgt gcccttttcaa attccaaggt cccctttccc tgacgacgtg   14040
gcccaatcag gcttgccctc ccttgatttt acatcttcac caatcagata agtgaaagtg   14100
aaatcctgtt gtggtatcct gtgcatttct ttggtgactt aagacataga gcattttcca   14160
gatctctgtg ggctgtttgg atatcctttc ctctgttttc tcaggcacat tctttaccga   14220
tgtctttgag ggattgagca agtttctgtt gaaattgagg catgtcatgg ctctgtgtgg   14280
ggcttgaggc agtccagtgt agtggaggga gggaggctgt ggagcctggc tgcctaggtt   14340
caaataccaa ctctgcttat ttccattcat atcattttag gcaaatcact tagcccctg    14400 ggcctgcctt tcctcatcag taaaagtggt ataacattag tgcctgcatt gtggggtggt   14460
tgtgaggaaa gcagcactca aaacagtacc tgacacacag tgggtgccaa ataagagtct   14520
gatgtattag tgttataggt atcggcctcc tccctcccca gtgcaatagt gtgtgtgcgc   14580
ctctgtgtac ctctgttggt gctgacaagc ccttttaaa atttagaggt gaggtctcac    14640
tctgtcccct aggctggagc acagtggtgc aatcatggct cactgcagcc tcaaccgcct   14700
gggctcaagc aatcctccca gcttagcctc ctgagtagtt gggactatcg gtgtgcacca   14760
ccacacctgg cccttagaca gccccttttat ttcaaagcga aatggcagcc acaagattta  14820
gtgcaagctc tccaagcttt aggaccagct gcaactcctc taactgacca aacaggatcc   14880
cccatgtccc caaccccaa aacctgatga aaagcaaaca gaccatttt cacattcatg     14940 acggaaaggc ccttttcttg gctcctgccc ttgctcatgt caggatttca ctccatccct   15000
gataaagagg aagcaccatg tcccaggagg acatggaaac tctctgcttt gtggtgaata   15060
gttacagtaa cagtagctcc tctctgtggg gagcttatga gcccctaagc tttatagaac   15120
tgccctggca gtttatgaga acttcatccc agccccagc gctcatggca cttattttg     15180 cccccagttt gcagatgtgc acactgagac tcagagagct aacactgctt gccaaggtca   15240
cacatctagc aaatggagaa actttatgag acaggtgaag gcacagcaag gataaaaacc   15300
cagagggaaa aatactcaag ttttctccgg gaaaccattt gcattccaga gaggttggtg   15360
tgcgagtggg caagagatgt cgcgggacga tggttaaggg acagagtctg agctcaacta   15420
ggactaggtt tcttcctttc cttccttcct tcctttcttc cttccttctt cctttccttt   15480
gtctttctct ccctcccttc cttcttcctt tccttccttt cctttctctt tccctcccctc  15540 cctcccttcc ttcttccttc cttactccttt tccttccttc ctcctttcct tcctttcctt  15600
tctctttccc tccttccctc cctccttcct tccttccttt cttttcttcc ttcctttttc   15660
ctttctcttt cctttctttc ctttccttcc ttcctctctt cttccttctt ttctttcttt   15720
cttttctctt tcttttcttc ttttcttctt tcttttcttt cttctttcct ttctttctct   15780
ctctctctct ttctttccctt ctttctcctt ccttccttcc ttcttttctt ttcttttcct  15840
ttcttttctt ttgtttttg agatggagtc tcgctctgtt gcccaggctg gagtgcaatg    15900
gcacaatctc agctcactgc aacctctgcc tcccggttca agcaattttc ctgccttggc   15960
ctcccaagtg gctgggacta caggcacgcg ccaccacacc cagctaattt ttgcattttt   16020
agtagagatg gagtttcacc atgttggcca agctggtctc gacctcttga cctcgtgatc   16080
ctcctgcctc agcctcccaa agtgctggca ttacaggcgt gagctaccac gcctgggcta   16140
ggactaggtt tctatcggtg gtgtggcttt tgggaagcta cctaatctta accactctgt   16200
ttcgtcatct ataagataag cagtgtagca ttttcttgca ggaatgttgc aaggattaag   16260
tggatggtga ctgtaaaaca tcatgcgtgg cacatagtaa attctcagca ggtagtcatt   16320
```

```
gctggtcatt tacttttctc taatgaccag caagctctta atttcctcct tggcatgggc   16380
actgggacgt agatggacaa aacacagaga gaaataaaca cacggacaaa aatccccgcc   16440
ctggtgtggc tgatattctg ggtggggaga gagagggagt ccaaggacca gataaacagg   16500
taaaggatag tttgagtgtg gtaagtacta aggctcaaaa ataaagatct cccaggtgat   16560
cttagctgca tttggaggtg acaggagata caactgagaa actgagatag gaggaaaccc   16620
aaggggagat gtgggcttga tttagggtga tctgaggagt aggagaagtc aggggctggt   16680
gtggggaggc tctgatggtt ctctctgggg agtgaagcag ggattcgttg gggagaccca   16740
aggggacagg tgaaggcccc tgaacaggtg gccagtgctg agaaaggaaa ggtggaggac   16800
ccaagtgagt tcctaatttc ttcattgctc ccctaaggtg tttgtctcac ccttggccat   16860
agtcttggat cacttacaga tgcagaccag gctgggctca atggcttgtg cctgtaatcc   16920
cagcactttg agaggctgaa cccaggagtt tgagagcagg ctgggcaaca tggtgaaacc   16980
ccgtctctac aaaaaaatac aaaaattggc cgagggtgtt ggcacatgcc tgtagtccca   17040
gctacttggg aggctgaggt aggaggatct cttgagcccg ggagacctat gctgccaaat   17100
aaggtaggca gtagccacac atggctattg caattttaga aattaattac aggccacatg   17160
tggtggctca cacctgtaat cccaacactt tgggaggccg aggcgggcag atcatgaggt   17220
caggagatcg agatcatcct ggccaacatg gtgaaacccc atctctacta aaatacaaa    17280 aattagctgg gcatggtggt gcacacccgc agtcccagct actcgggaga ctgaggcagg   17340
agaattgctt gaacccagga ggcagaggct gcagtgagct gagattgcac cactgcactc   17400
cagcctgggc aacagagaga gactccgtct caaaaaaaa aaaaaaaaa aaaaaagaa      17460 aagaaaagaa attaattaca ataaaaacag tccctgagtt tcactggcca catttgaagt   17520
gcccgatgac cctgtgtggc ttagtgacca ctgtgctgaa tagtgcagat ctagagcatc   17580
ctactggaca tgttgccagg gtccctgaac caacagaatt agcatctcct gggagcttgt   17640
tggaaatgca gaatctcatc ccctaccccc gacctgctca atcccaatct gctcttcagt   17700
gagattcctc aggtgatctt gactgcacct tctaatcact tggaagcttt aaaaatgctg   17760
aggctgggca cggtggctca cgtgtgtaat cccagcactt taagaggcca aggcgggtgg   17820
atcacctgag gtcagaagtt tgagaccagc ctggccaaca tggtgaaact ccatctctac   17880
taaaaattac aaaaattacc caggtgtggt ggcacacacc tgtagtccca gctacttggg   17940
aggctgaggc aggagaactg cttgaacctg ggaggtggag gttgcagtaa gctgagatgg   18000
cactgctgca ctccagcctg ggtgacagag tgggactctg tctcaaaaaa aaaaaaaaa    18060 aaaaaaaaa gaaagaaaa aggaaaatgc tgatgcccca agctccaccc ccacagatgc    18120
tggagagatt tgtccagggc ttcccctgga gtggggaatg tttgaaaact ccccaagggt   18180
ttctaaagtt cagccagagt tagcagaaag cccattaggt ggctaagcag gtagactgaa   18240
gttggagctg tgtgaccttg gcaagccac ttaccctctc tgaaccacaa gctcccttct    18300
ctctaaaact agagacctgc tggcacctcc ctcccagggc tgtgagaagt aaatgatggg   18360
atgattcaaa gtgctgagta gggtcagatg cagtggctca cacctataat cctagcactt   18420
tgggacgctg aaatgggagg attgcttgaa gccaggagtt tgagaccagc ctgggcaaca   18480
tttaaacatt acccaggtgt agtggtgcat gcctgtagtc ctagctgctt gggaggccga   18540 ggtggggggga tcccttgagc ccaggagttc aaggctgcag tgaacaatga tggtgccact   18600
gcactccagc ctgggggaca agagtgagac cctatttcta aaaagaaag aaacccaaaa    18660
```

```
tgctgagcga gtgccttgga ttgatagtaa gcagtgcctg tgtaataagc atgaatttta    18720
aaaaatgagg tcagcagcct tagagctaat ggttaatggg tttgggtgtg ggattttttt    18780
tttttttaatt tttaaaacat tgagataaaa ttcccataac ataaaattga ccattaacca   18840
ttttaaagtg tacagtttgg tggcatttaa tacactcagt gttgtgcaac catcacctct    18900
ctgtagttca aagaccccaa aaaggagacc ccgtactcac tgagcgctca ctccctgtct    18960
ctccccgctc ccccagcccc tggcaactac taatcttctg tctgtataga ttgacctatt    19020
ctgattttgg gggtttttga actcgccttc cctggctgac aacctctcgc catccaggtg    19080
agactgtgtg aaagcccagc tccctgcatt tctgggtctt cctctcccca ctggggctg    19140
cccccacctg tttcccctc tgggcaccct ggttctactc atcagcctgg cttaatccca    19200
gcagcaggtc catgttctgc tctcctgtgg ctgccacaaa tgagaggttt catctcagct    19260
gggtttctcc tagttaaata tttaataaat aagacctaca acttgtgatg ctgggagtgt    19320
ttgatagtga aattaatgat ggggagagag tggcaggcgg cccacaggtc catgctggag    19380
ctgggatgag gcgccctggg caggcgtccg tgccactgat gcttgggaac cacggtgggc    19440
catgccatcc catttccccc agccagggcc tcttttttag cactgtgtcc agcacagggt    19500
agccacctga taaataagtg ttaaaagaaa gagaggctgc gtgtgtaggg aagaaggaag    19560
agacagagga gacaaagagg agacacagag agagagagag agatgagaga gaaagaaaag    19620
tggaaggtga gaaagagaca gagatggaag gggagagaag gacctggatg gaggaagtgc    19680
aaggaaggca atggtgaggg aaaagagaga gagacaaaga tggaagggat gaaggagagg    19740
gagagatatg gaggtagaga aagagagaca gaaagaagag agagaatatt gcttcttgta    19800
tcttcccctt ctcctgttat ccttgaccat cttattattt ttttcttttt tctgtctctc    19860
cagttctcat ttccttaccc tcgccgtctt gccaactcgt catctctttt catttcctgt    19920
gtctatgtta tcttttaatt ttctgtctgg gtattttccc cttttctctt tctcagcata    19980
aactgttggt tggtgtatgt gtcttctttc tttttagtc tttaactgac gtgtgtgtgt    20040
atgtgtgtgt gtgagagaga gagagacaga cagacagaga gagagagaga gagacagaac    20100
aaacctagag agcagtgtag gaacatagat gaacatttta aagaccaaac catgaagcgt    20160
acacccattt tacccaggtc aagagccaca gggccaccat cagattctcc ctcatgctca    20220
tcctcaatca cagccactcc ttccctcctg gaggaaccac tattggagat tgtatgggaa    20280
ccattcgctt gctttcttgt gtggttgtac cacctaagta cgcatcctga agcaatatag    20340
tcagatatta tgtggttttg agttttatat gaataaaatc atgtgagagg agttgttttg    20400
tattttgctt cattggtttg cagttacctt tgtgagattt catcctcatt gtggtcactg    20460
cagctccttc atgatcttgt ttattcattg atgatgagca tgtgactttg ttctcttttg    20520
ggcactggca taagcagctt tgttggttgt ttatggattc tgctgctcgc ttgcagggt    20580
ctctctggag cacatcgctc tgtgtgaaat tgttggatac taagatttgt acattttcac    20640
cttgactaaa cactgccaaa caattttcca aagtgcttgt gctaatttac actcctgccg    20700
gtggtgggtg agcattcaag atgcttcaca accttgccaa cacttggtat tgtcaggttt    20760
ttaagttata gcctttctca tggtgatttc tcattgtgat tttagtttgc atccccgat    20820
tgcaaattag agtgaacata gtttaaaata tttattgact attcaagctt gcttttttgt    20880
gaagtgcctc tacatgctct gtccatttt gattaggtca cttttaaaaa aaaaatattg    20940
attttgtgggt gatccttaca tagcctggaa actgattctt catcattata tgttgtgcaa   21000
tatttttctct tggcttggct tttgatctttt tttataatgt cttttgatca ccaacagttc    21060
```

```
ttaattttga tgtggttgat tttagaaatc ttttccttta tagtttgtgg gctttgtatc    21120
ttatttaaga aaatcatttc taccctgagg ccatggatat atttttatgtt atttctgaaa   21180 gttttacagt tgtgttcact gtatgtcttt aatcagcttg ggattgattt ttatatgtgg    21240
tggtaggtag gggtccaatt tccttttat tccataagaa ttgtcccagc atcatttatt     21300
aaaaagccca ttcttgcccc aatgatctgc aagacaacct cttgactgtt taacttttac   21360
cttctttcat ctggtctgtt tttatactca acctttgaag ccacaaatat ttattgagtg   21420
ccaactgtgt gccaggcact gagttacagt gacggatatg acagatgcaa tcatggcttt   21480
catggagttt acagtctggc aaggatgaca tgtaaatagt tattactact tataatttaa   21540
aatgttatag gccttgcaaa aagggacaag tctggcttgc tctaaaagaa acatgtgaaa   21600
caacatcttc cagggaagtg ctgataaact gagtctttag tgggcctctg ctattgtagg   21660
ggtgggaatg gtggaaaaga tgttttggcc acagggaaca gcatgtgcaa aggtcctgtg   21720
gaaggtgctt aggagtttga tatttatcct aaaggcactg tcaggctact gaagcagtaa    21780
tacaatgatt ttatgtctgt gaatagttcc actggttgct gcatggagaa tgtattggaa   21840
tacagcaaga ataaaaagcc atgagaccaa ttaggaaatg atttcactca ttcagggaag   21900
tgtgccttgg gctggcatgg tggctgtgga gatggaaatc attgatcaga ttaaaagaaa    21960
ttttgagctg gcatgatttt tccctctct ccctctctc tatctctgtt tcttttctgg      22020
ttgtgttttc tgggtgagaa aagcagtttg tgatcctgcc aagggtatgt gctctggagg   22080
atgtatttgc cacagatggt ctttggaatt ctggccaaga gagtcactgg acagcccctg   22140
gcccccaggg tttctggagc caattcaaca atgactgttt attaacaaca gcaaggatga   22200
gttgctagcc tttccttcag agcaccttt aactgttacc ttactttgtt acccaaaccg     22260
acactatgga attggtgggg gagaagtgga agggttttta tctccatttt ttatagaacg   22320
ggggaagtta attggcactc ttgaaatcat acaaagatg ttggtttcag gattggtttc    22380
tggactttca gcccaatccc aattactcaa gctcacacac ccaatcccca aacatactct   22440
tttgcaaata atttccctac tgaggtgctc ctggccaatt taaaaggtcc ccatttcctt   22500
gcctataaaa tgggaattaa agtaaaaata tctacctgtt gacttgctgt gaggtcagtg    22560
ggcctgacac atggtgtgga ctcattatat ttacctatgt gaatccctta gttcccttta   22620 cttgaagag gtgaaaaact caaagggct taaacaagaa gtggggattg tattggctca     22680
tgagactgaa gagtctcagg agtgtccagc ttcaggcttg tttggatcta gggatcagat   22740
aacaccatta ggcctctgtt tctgtttctt ggctctactt tttgcagctg gctccattat   22800
ccatgactta gctgcacttc cagccctcca gtctgcccaa gaccatattc agagagagat   22860
tcttctctct ttttcagcta tcttcccgga attttcagca aatgctttct tgcttttgat   22920
tggctgttgc tgaggtcgtg tgctcatgcc agaaccaatc actgtgggga aatgggaggt    22980
ggagaacggg gtgctctgat tggcttaggc ttgggtcaca tgactttatg gagttggggt   23040
ggagccaact tctccaagtg gggaagagca gtcttcttaa aggtgtatta ggatatgctt   23100
gctgctgtaa caagcaaccc ccaagtctgc agtagcttaa ggcaatacga atgtacttct   23160
cactcaccct aaatccaatc agataatcag caagtgcat tccatgtggt gatttcagga    23220
cccggctctt tccatctgtg gctccaccat cccctaagat cagaaagtcc ttcacttccg   23280
gcctgtagga aaagagtatg aaggctcaca caggaagttt tgggaggcca catatagaag   23340
tagtgaacct tacttctgcc tgcattctgt ggactggaat ttcatcccat ggtgtatgag   23400
```

```
agagggtccc agtaggaaac ggaagacaca gaccaagaat caaattaaga gatagcttaa   23460
gaatcaaatt aagagatagc ttacaaaggt gtgggcccct actgaaatag agaaggagga   23520
agagaggaag gaggcagaga cagagagaga ctgagactca caaagacaca cacacacaca   23580
cacacacaca cacacacaca cacacacaca caagttgaga gaaagaaggg gggagagaaa   23640
gagagagagg gagcatttcc taacaggaag ctggcagaat aaatgtcccc cattgtccaa   23700
agccagaggc tgggagccc agtgagccca tccacacagg tcagcccccc atgtgacagt    23760
cctagaaggg taaagaagga aggagagtgg atttgggta atggaagaca gccaatacccc   23820 atggtccatc tgactgcagg gggaactgag aaattcagtc catggagaag aaggtttagt   23880
ggacacgtca ctttgtcttt ttcacaaagt gaaactaggt tctcaggtgg aaaaaagaaa   23940
aagaaggttt gccttgctgc tattctttt ttttttttga cacggagtct cactctgtca    24000
cccaagcggg agtgcagtgg cacgatctcg gctcactgga agctctgcct cctgggttca   24060
cgccattctc ctgcctcagc ctcccgagta gctgggacta caggcaccca ccaccacgcc   24120
cggctagttt ttttgtattt tagtagagac ggggtttcac tgctagccag gatggtctcg   24180
atctcctgac ctcgtgatcc gcccgcctca gcctcccaaa atgctgggat tacagacgtg   24240
agccaccgca cccggcctcc ttactgctat tcttattatt ggtggtagca gtggtggtga   24300
tggttattgg ttcttagttc cctctacatg ccagtatctg ctctcttctt tttttctccc   24360
ttacttcttt ccttgttctg caaattcttt ccctttaagt gaaaatcttt ccgtgttctc   24420
caagggagat aaattctatg ccaagcttga gtgtggggtc ctctgcttgg atagctgtct   24480
tctccaggag atgaggtaga actgagatag tgggggtctc tgcaggcagt ctgtgccccc t   24540 ggcaagcccc tcaccttaac ctgaggctgg gtggggaaag atgccttgat ggagtcagaa   24600
cagaaagcaa gtgatcgctg cctgaaccaa gcagtcactt tcctggaggt gaaacctaga   24660
aacggtccct caggctgggt ccagggaggt ggacttgggt cccaggggca ggaagcaacc   24720
tgcccctcac ctgctcctac ctcttttgtag cctatcttgg caaccagaag taggtataca   24780
agtgacgttg aagctgggca tgttaacaat ggtgtgagcc cgcctgactc caatctggtc   24840
cagctgtact ggccgtgcat cctcatctcc agccccagg gtcagcccag cggctgtaac   24900
aatggtctgt cccctccccg ccccacccac ttctttgaac tcctccaagg atctgtgatg   24960 ataggggctgt cactgtctta gcttccacca ttcaagctta accggccttc ttcccctcca   25020
tggagaacgg aagagcaacc cctcattgcc tctggcagct gaccagcagg tccctgcctt    25080
ctgcccactc ccaggtctag acaatgagg tgagaggtag acaggaccaa gttccccagt    25140
gctgtcttct aggtccacct atcatgagag ccgtgattcc tagttttat caccctctcc    25200 ccaactttgc cagctctcca cttctggcag tggtggctgc ccatgacttc accttcccgt   25260
gcctcagttt cctcatctgt aaaataagga cagccatggt aatgagagtt ctggtcaata   25320
tgccaggcac ctcgcttgca tcaatttagc tcatcctttc agtgccctga ggggtgggta   25380
ctgttatcat cccgtgtaac aaaaagagaa aaccgaaaca gagagagaga ctcactatct   25440
gaggtcttgc accccctcaag caacaaaagt gggatttcag cctaggctat ctagattcgg   25500
agtccacggt ctcaatgaat aataacaaca ataataatat tgtcctaatc tgatgagttt   25560
ttgatcagat tcaatacaag agcataggca gaaaagctta gcccagtgcc cagcacatgg   25620
taagaactca gcatgttatt tataaatagta ataaaccatt ttatgttatg taattatata   25680
ttcatagata aatatagttg actcttgaac aacataggg ttggggcaat gacctcctgt    25740
gcagtcaaaa atgtgtgtgt aacttttttt ctctattttt tagaaatttt aaaattagag   25800
```

```
acaaggtctc gcttttgttg ctcaggttga tctcgaactc ctgggctcaa gtgatcctcc  25860
tgcctcagcc tctcaaagtg ctaggattac aggtgtgagc ccccgcaccc agcctgtgta  25920
taacttctga ctcccccaaa gcttaactac taacagtcta ttcttgacca gaagccttac  25980
cagtaacata aacagtcgat gaagacagat tttatatgtt atatgcatta tatactgtat  26040
tcttacaata aagtaagcta gggaggagaa agtattattt taagaaaatc ataaggaaga  26100
gaaaatatat ttactattca ttaattggaa agggatcatt ataaaggtct tcatcctcat  26160
tgtcttcaca ttaagtaggc tgaagaagag gaggagttgg tcttgttgtc tcaggggtgg  26220
cagaggtgga ggtggaaggg gaggccagaa agacaagcac gcttggtgta actgttattg  26280
gaaacaaatc tacataagtg gacccataaa attcaaacct gagttgttca ggggtcaact  26340
atatatgcta caaatacgta atatgctaat atagttgtat gttattgtta tagtacgggg  26400
atcagaaaat gttttctgca aaggattagc tagaaaatgt ctagtaaata ctgtctcttt  26460
gggaccactc tactctgcca ttatagcaaa ggcagctaca ggcaatacgt aaatgaatgg  26520
gcatggccat ttgccaataa aactttgttt acacaaacaa gccatgggcc agagtttgtc  26580
aacggctggt atagtatatg ttattatata ttagctttac ttttttctgtt gctttgttta  26640 tgttcttctt tgcccttcct ttcttaaagg ccagcctttc tttctctctg ttggtctgtc  26700
ttttaggaca gcatggcagg ccactgggac atgggctctc ctgactccag gcttgtttgt  26760
ctgataagac atgaagagtg aaggtggcag gactctgagc tcaggcctgt cctcctcctc  26820
ttccctctct tcgttttttc tttcctcttt cctcttttct tcccaagctc cagaagttgc  26880
catttccctt tcccattgct gattttctct gccttgggag aaagcccgag aagatcactt  26940
ggaaaagccc acgagcatct ctggcctcac tcacccagct cctgccattg tctttactct  27000
tcctcagaca caccaggcac agtcctacct cagggccttt gcactggctg tttcctctgt  27060
ctgcattgtt cttctctcag gtgacctcat ggcttctccc tcctctcctt caggacttca  27120
ctcaaaggcc accttctcag catttgcctc ccgcccttct gccttatttt cccctttgga  27180
acttttcacc ttcttactta ctcatctgtc tgctatctgt caccctacat cactatgatc  27240
tccacaaggg aaggtgattt tattcgtttt ttgttctgtt ttgttgaaga tgaggttttg  27300
ctcttgttac ccaggctgga gtgtggtggc acgatctggg ctcactgcaa cctccacctc  27360
ccggattcaa gtgagtctcc tgcctcagcc tcctgagtag ctgggattac aggcacccac  27420
caccatgcct ggctaatttt tgtattttta gtacagatgg ggtttcacca tgttggccag  27480
gctgatctca aactcctgac ctcaggtgat ccacccacct cagccttcca aagtgctggg  27540
attactgtga gccaccacac ctgatctttt ggttttaccc accaatgtgg actagaacag  27600
cctagatcag caggtggcat gcagtaagca gttgataaat atgtgttgga tgagtgagca  27660
ctgtggcttc tgtcattctg ttgctcaata gcattcatct ggaaataacc acagtttgtt  27720
tatccattta cctgttgatt ggcatttctg ttgattctcg tttgggccat tatgaacaaa  27780
gctgctgtga aatacttata cctttgccca attcttcact tggtgaaccc ttataaatcc  27840
tttaggccag gtgtggtagc tcacgcttgt aacccagca ctttgggaag ccgaggtagg  27900
aggatcgctg gaggccagga gttcaaaacc agcctgggta acatagcaag acccgtctct  27960
acaaaaaaat aaaaaattgg ctggacgtgg caatgcatgc ctgtagttcc agctacttag  28020
gaggctgagg tgggaagagt gcctgagccc aggagttcaa gaccgcagtg agtgatcgcg  28080
tcctgcactc caggctgggc gatagagtga gaccctgtct gtaaaaatga cagcaacaac  28140
```

```
aacaataata aaacctttag gtttcctctt aaaaggaaca tccttagagc ttttcctgac   28200
ccagcaactc accccaagtc tgaattagac ttcaccccat ttctttcata acatttatca   28260
caatgacatg tttattttgt gggggcgggt ggcattctgg ccagaactgt cgacttccag   28320
agtgaaaata cggaagaacc aaataaaaca caacacacac atttgcacag cagctcgagg   28380
gaggtgctta gttctttgag tttccaagaa cagagagacg aagatttgtc tggggaggaa   28440
aaatcaggga ctgcttcttg gaggaggtgg actgttgctg ccccatccac ccacacattt   28500
gcagatgtgg tgatgagaag atgactgtca cgaggtctct gagcccaggg ggcccatggt   28560
tgagtgcaaa gatagtgggg ttgacaaata atcgtcgtat aacaaaagaa agccaccac   28620 agttgcataa tggaaaggcg gcttctatag aacattcaga tcatagttga aggcatgtca   28680
cactgtgtta ctcagaggcc actgtcagag ccaaaagtga gagtggatga gagtttgggc   28740
aggaaacaac tgaaccagat acagcatcac ctccatgagg gctcagcttt atctattttg   28800
tcttctgttg catccccagc ccttagaaca ctgcctggtc catctttgct gtgtgaataa   28860
taataaggaa cgatcgctgt gttgagtttg ggctgtgaat tcagacagtt tgctgctgca   28920
tacctgatta tgagtctcag ttttcctcct ccataaaatg ggcaaaacag tccttgcctc   28980
atggggctgt gcatttgttt agcaaacact gaaggagtat acatggtggc caaggcactc   29040
ttcaagacac aggaagcaga caaaagtccc tgccctctgg gagcttacat gctcatgggg   29100
agagatgtat gataagaaac aaaaatagta ggtaagttgc atagtacttt agaagattat   29160
aagggtaatg ggaagagaac agcagagaaa gggctgggga ggcagttgct gtattagata   29220
gagctttatc gaggcgatgg cattggagcc aagacttgag gaagctgtga ggatgtctag   29280
agaaagaagg aacagctggt gcaaaggccc tgaggtaggg gtatatgtga catgtgtgac   29340
agtgaggagg cagatgtggc tgaagccagt gagcaagaga gagggaaggt gcaaggataa   29400
ggacagagag gtgacgggac aggttttgga gggccttatg ggctgcgggg aggactttgg   29460
cttttgctct gagggagctg ggagccacgg agggcttttg agcagaggag ggacgtgacc   29520
tgactcagat attcataggc tcctctggct gctgtgaaaa gaacagactt gaaggttgg   29580 gggcaggcag ggcagaagct ggggaattag gaaggaggtg acagtgttgg tcctggcagg   29640
taatagtggg ggtggaacca ggttgttgtc tgtggagata ataatgagtg ctggattct   29700 ggttataatt tttaagtttt tttattgtga taaaatgaat tttttttattg tgataaaatg   29760 aaatttacca ctttgaggtg tgcaattcca cagcacttac tacagtcacc ctgttatgca   29820
acagtcacct ctatttaatc tcagaacatt tcatcccccc taaaggaaac cctgcaccca   29880
ttagtagtta cttccagttt ctcccttccc ccagcttctg gaaactacta attctggata   29940
taagttgaaa gttgaccagt aggatttcta ggcagacagg tggtgagggc tcaatgcatt   30000
catgcacaga aagtactcag gtggcatatc ataggtgctc aaaactgaaa tggtgatgat   30060
gagttggcaa tgatggtgag tccttccaga atccctgctc tagtgctaaa ctgacctacc   30120
tggctgtgta gaattctcac ctgctggccg ggagggtggc agaaccagga tcccttctta   30180
cttccagtct ggcttgggtt agggataggg gaggaatgat cagaagaacc aagctagcac   30240
catctgttct ggaacatcat ccaactcttg tccagatttc ccagaactga gcaggaaaat   30300
gtccagggag gaacagtgca gctgatggaa gtcctggtaa gccctggccc cagcttcctg   30360
agctgctgtt gcaccaacta gcatttgttg gaccttcagt ctgagccaag atggcagctt   30420
cagaggaaga acaagaagtg tacaagtttc tttcatggtt gtgtccccgc ctccttatat   30480
agcctcatat aaaccctgc actatcccgt tactgtttgc ctctccctga aaagagtgta   30540
```

```
aaactccccc acttttttccc tacttttttcac aatgtgtttt ggtttctaaa gatgaaactc    30600
ctttaattat gttctggttg taatttttctg gctccttttta tttctcccctt acttgatgta    30660 ttattttccc ttgttccttc tgcccccctgc ctccattgat gttttctcttc actgctatct    30720 agatttaatt ctcaactcct gccaagttca gggtgatagt gcaaaaagac atggaccatt    30780
tagtcttgaa ttcaggtccc acttctgaca ccttcaaagc tgctttactt tgggcaagtc    30840
atatgatctt cctgaggggg tatcctttac cttgttcagc taacatttct tgttttttctc    30900 tgggcacaga gtagagtgtc attttcccca cctccctgaa gttaggtatg gctgtgtgat    30960
ttggtttcat caatgaaatg tgaggggaag tgacgtgagt ccttccggac agaagcctta    31020
agggtgagca tgggattcac catgtttcct ttttcctgcc tccactgtca tggatgcaca    31080
aagatggacc ctctctcaaa gtaagtgctg gagagaggat gacatagatc agtccccatc    31140
ccacttcata gcatgagtag aaaaatagac ctggggtgtg ttcaaccact gagatctggg    31200
gattgtttgt tactgcagca ggacatagac taggctgact gtatacctca ttatctgcat    31260
tttggggctg atatctaatc acagtgtctc caggaagatt atgttgatgt atgttttagg    31320
gatggatatt catattttcc tataagggct caataggttt ggaaatgtca catgcatgta    31380
aacttctgat taacaaatat ttcttgcttt ccaatttctt cctatagtgc ttctaattt    31440 cctgttttc aatcttgaat aaaatgtgag aagtgtttga cttctccttc gaggagatta    31500
atggtttcta aagcctgggg cattgattta gtcattctca acctccttgt ttctatgacc    31560 ttttttttctc cttctctggt cacttagtgt ctgctaaggg gtgaaggaat gtctgttta    31620 actcattgca tttttttttt ttttgagacg gagtctccct ctgttgccca ggctggagtg    31680
cagtggtgtg atgttggctc actgcaacct ctgcctcctg ggttcaagtg attctcctgc    31740
ctcagcatcc caagtagctg ggactacagg tgtctgccac cactcccggc taattttttgt    31800 atttttagta gagacggggt ttcaccatat tggccaggct ggtctcgaac tcctgacctt    31860
gtgatccgcc cgccttggcc tcccaaagtg ctgggattac aggcgtaagc caccacacct    31920
ggcaaactct ttgcattttt aactcttgac atcttcatct tctttttccc acctcccctt    31980
tgcctgttcc tcccctgctc accccaccag ggagtttata atcaggttct agaacctgca    32040 atgttttttct gttgttgtct tccatcttcc ttgagtctta tgggaatcgg ccatagtcgc    32100
aaattaacaa atagctctga agcgcctcaa gcttggaggc atttccttttt gctcacctaa    32160 gcaagatcct ggagctgttg caaatatcct gcccccctact gtaaatctgt cttcatggtt    32220
gtaagagatt cagtcggggt cagtgaagac ccgagcagga gatcttggcc gaggctcctt    32280
gatgttctgt ctgcgctggg tgttgtcata ttgattaagc tcctgggact gctgccagca    32340
gcctctagga ttaaatcaat agagtttgca aaagtaaaag cttcttttgg agacacagaa    32400
tatgtgggtt tattttttaa tgataaagct tcaaggagaa tcttcatgga tggcagaacc    32460
agtgatggaa aaggcgaggc agacccaaat atttggggaa gtgcagtggg gagcaagtga    32520 gggaggttc attgggaggc cggggctttc cagaaaatct gtttaactgg agttgctaat    32580
gcaacagctc agagttagaa gtgaaggtgg aagatgcaag aaggactgcc gctgagatgt    32640
aaagagaaat gaaggagagg tggatccatt tgctcattca ataaacattt tgggaggcag    32700
gggggtgggg gggagcctgc catgtgcctg gaactgggat gtacatggtg gggacatgac    32760
agtgggcagg acagatgtgg ttcctcctgg ccctcctgga acttgtaaca ggaaaagaag    32820
gcataaaata aggaataggc aaatacagac ataattacta attgtggtaa gtgtttggga    32880
```

```
gaaaaccagc agggtcctgt gtttgtttcc tagggctgcc aggacaaatt gccatgaact    32940
atatggctta aaacaacata aatatattgt cacccagttc tgaaggctgg aagaccaaaa    33000
tcaaggcatc agcagtgctg agctcccttg gacggctcta gagaagaatg cttccttgat    33060
tcttccagtt tctggtagtt gttagcatac attggcttga ttggcttgtg gctgcatcac    33120
tgcagtctct gcctctgtct tcacatggcc ttctccttca tgtcagtgtc ttctcttcct    33180
cttctctctc tctctttttt ttttttttgt cagggcctca ctctgtcacc ctgtacaaga    33240
gtacagcagt gcaattatag ctcactgcaa ctgctgcttc ccagcatcaa acaatcctcc    33300
cacctcagcc tcctgagcag ctgggactta caggcgtgca ccaccatact cagctaattt    33360
ttaaattttt gatagagatg ggatctcact atattgccca gactggtctt gaacttctgg    33420
gctcaagtga tcctccctcc tcagcctccc gaagtgctgg gattacaggt gtgagccact    33480
gcacctggcc tcttctgtct cttataagga tctttgtcga tggattttga gcccgtcaga    33540
taatccagga caatctcatc ttgagatctc taatttaatt atacttgcag aggccgtttt    33600
actaaataag gtcatggcca gaggctccag aggctaaagc atgggtatga ttgcaccact    33660
gcactttagg ctgggtgaca gagcaaggcc ccatctctga aaaataaaat aaaataagta    33720
acctactaca ggccctttgc gtagaggata attagaagta caggggtacc acgtaagtga    33780
agacctgaag gttgttaagc acagagcaga gtgtgaacag aatgagacag agggaggaag    33840
agaatcccag gcagagggaa cagcatgtgc aaaggccctg ggaaggaac aagttcatca     33900 tgttaaaaat gagccagtgt agctagagtc tgatgagcaa agggactcac aggtgggaag    33960
acacccaaga agttggcaga gacaggtcac acaagacctt ctaggtcaag ttccggaggt    34020
gaactttatt ctacatgcaa tgagaagtcc tcagagaagc ttaagtggga tgggacagaa    34080
ctgctttact ttaaatatat atacatatat acaaacatat aatattacat atataaagca    34140
tatatatgta tacatatata catatctatc tacctgtcta tatattttt agctgggcat      34200 ggtggctcac acctgtgatc ctagcacttt gggaggctga ggtgggagga tcacttgagc    34260
ccaggagttc aagaccagcc tgggcaacat agggagaccc catcactaca aataaaaata    34320
aaaattaaaa attagctggg tgtgatagtg tgcacctgta gtcccagcta cccgggaggc    34380
tgaggtagga ggattgctgg agccccaaag gttgaggctc cagtaagccg tgattgtgcc    34440
cctgcactct agcttgagca acagagtgag atcctgtctc aataaaataa ttttttgtatt   34500 gaggtgaaat tcatgcaaca taagttaacc attttaaaat gagcaattca gtggcattca    34560
gcgcattcac aatattgtac aacctccacc tctttctagt gctgaaatat tttcatcacc    34620 accctccag aaaaccctgt atccatgagg cagttgctcc tcatcctccc ctcccggtat     34680 cccccaacc cccaccactc ctggtaacta caaatttgtt ttctgtttct atggatttac     34740
ctatactggc tctttcatat aaatgaattc aggcactgtg tgacctttcg tgtctggctt    34800
ctttcactta gcataatgcc ctggcttctc tctggagaat gaaatggata gaccactttg    34860
gagtctactg agattataga tatttctgtg ggaagggaca gtggcttgac cttggtggt    34920 gctgaagagg caatgctgag caggaggatt caaagtctaa tttcggaagt agaattggtg    34980
gggtctgata tacatcagc tgtagggga ggaagatgta ggaactggga aggtctctta     35040
gggtaacctt acctgattga gctccttact aggcagctgg tggtacaatt cataacaaag    35100
gttaatagag aaagagacat gggattaggg agggaatgga agagtttggg ccttggacac    35160
tgtagtggtt tgaatcctgt ccaccaaaaa ttcagatgca tttggaactt cagaacctga    35220
gacctcattt gaaagtagga tctttgcaga tgtcattgag tcaggattg agatgaggtc      35280
```

```
atcctggatt acagtggact cgagattcca tggtaagtgc ttttatatga gaaggtacag    35340
gggagaaagt catgtggcaa tagaagcaga gaatggagtg ctgcagccac aagccaaaag    35400
acatgtagag gcaccaaaag cgggaagagg caaggaagga tcctcccta gagcctttga     35460 agggaaaccc cctaatttca gaaccttgcc tccaggatga cgagagaata aatttctgtt    35520
gttttaagcc acccaatctg tggcaatttg tcatgactgc cctaggagac taatatagac    35580
actcctatga gatgctctaa gaagacacag agtggtatag ctattgctaa gaccacacac    35640
tgtagcaggg aggaaatcaa atggagaaat gccccaactc cccctcctct ctgatctctt    35700
gctggtgcct cccgttggcc aagccaaccc agaaggcaga agatgtggtg gagggcagcg    35760
ttgcagggct tggatgatgc agtcacagaa gtcagccctg cctctaccag gatgccaaac    35820
agggcaatga gtggatattt tagggagaaa gggcaacaag agaatggcaa aatacatcga    35880
aatgcatgca agctctagaa agaggataga gatagataaa gggtgattac ctaggattaa    35940
gccccaggga agaccaacat ttagagattg gatagaaaaa gaggagcaaa aagggaagat    36000
tgagaagtag agaccaggag gataggagga aaactagaac aacattaaga agggcatggt    36060
caagtaatct gggcacagaa aaatggccct gggatttggc agcctggggg tctttggtga    36120
tcctctttgg aagagttttg gttgagtgat gggggctaga aaccagcctg gggagggtag    36180
gagaagaatg tgcagtgagg aagtggcagg aacacgtgaa ggcaactctt catgaagggg    36240
agtagagaaa ttggttggtg gctgaaggaa aattttcagt caagggtgga ggttttaatg    36300
atggaagaat attgatttct gtaaattggg tcattcccat ccattatacc aatatgcacg    36360
ggtgtcttct ctgatatagg atgctgggat tctcaaatgc ccatttgagt ttagcatcat    36420
gaatttaatg tcaccagccc agatagttga tctcattcag gaatgctcca ctgcccaggt    36480
atggggaagg caactagttg agttcatgca gggatggatt ttttccagga gagaaacagg    36540
aggcaagaaa gtgcgatata atcaacctat gtaaggttga caaggcagga gagggtcctg    36600
agaaatggcg gggtcagtgg gttgcagggc tcgatgggat ggacgttggt ttgcatttaa    36660
gggagttagt gagctgggag gtggttaaag aggaggtggt tcagccgggc gcggtggccc    36720
acacctgtaa tcgcagcact tggggagccc gaggcgggcg gatcacaagg tcaggcgatc    36780
gagaccatcc tggctaacac ggtgaaaccc tgtctctact aaaaatacaa aaaaaaaaa     36840 aaaaattagc caggcgtggt ggcgggcgcc tgtagtccca gctactcagg agcctgaggc    36900
aggagaatgg cgtgaacccg ggaggcggag ctgctgtact ccagcctggg cgacagggcg    36960
agactccgtc tcaaaaaaaa aaaaaaaaa aaaaaaaaaa gaggtggttc aagacaagga    37020
tgctggaaac aggtgttttg gaggtggctg gtgtagcttc tgagcatgca tagctggagt    37080
ggcttggagg agacattggt tattgatgaa gaggtaggga catcctccag tgatcaagga    37140
agcaggggac cagcatggac aatggtctct ccacagggaa attggaggtc atcaaatgtt    37200
aacaggttcc gtcggagtct tagctcccag cttctgtttt cctgtggatc tcaggatctt    37260
ggctgctggt gctacctctg actttggact tcccattgag cccagcagca ctgggaggga    37320
ccttcatggc attggctggt ttaaggaaga cttccttggc tttgctgact ttcttggggg    37380
ccttcttggc tacacctgct tttgagggag ccctcctcac ctcacctgac ttcttggggg    37440 cacctttttcc accttatctg agttgggaag gtctttcttt gattctcttg ctttcttggg    37500 gccccttctca ctggtttttc tggggggccat gatggtggac atattccaga gctgagcttt    37560 cctttttgttc ttaggaacta atttgaggct gccagtggcc ccaccttggt cttagagttg    37620
```

```
atggtctgca gggaatttcc aggttaaagg ttttttatttt gtttgtttaa ttttgagaca    37680
gagtcttgct ctgtcaccca ggttggagtg cagcggcacg atcttggctc actgcagcct    37740
ccgcctcctg ggttcaaaca gttttcctgc ctcagcctcc taagtagctg ggattacaag    37800
cacgcaccac catgcccagc taacttttgt attttttagtg agacagggt ttcaccatgt    37860
tgaccaagct ggtctcaaac tcctgatctg aagtgatccg gccaccttgg cctcccaaag    37920
tgctgggatt acaggtgtga gccactgcgc ctgacctcca ggtttaagtt taaaccatga    37980
agtagatgga ctgtgtagag agagaccagg gaaatggagg attttactga ccactgaaca    38040
gggatgtcac tattgccaga gaggaaaagg attcccccttt ggtagagtga acatataagg    38100
gaaagtggtt gaaaattgaa tcaggagaca gagacctcac accactcaga ggtccctaga    38160
gaactttact gacctagaaa aaagataaaa caggagaag gtcttcagtt cttgtttgga    38220
atctgacact gaagcatcct cactcctcac tctcttcccg accccgagag tctgaaattg    38280
attaatactt tttgtttaaa acttggcttg ttgttttgtt tttcttttct gttttcatca    38340
agggatcttt atttttacttt tgtgtatttg tgtgttttcc atgagtcatg ttaattcttc    38400
catgtttaaa cttttttggcc cagaggaatt tatacatttta aattatggat ttaatttcag    38460
aaggtacata cacacacaca cacacacact cactcatctc acttttttaaa aactgtaaaa    38520
tatagccctg taaatatcca gaaaatatct aatgtgggcc gggtatggtg gctcatgcct    38580
gtaatctcag cactttggga ggccgaggtg ggtggatcac ctgaggtcag gagttcgaga    38640
ctagcctggc caacgtggtg aaaccctatc ctcactaaaa ataaaaaaat tagctgggca    38700
tggtggcagg tgcctgtaat cccagctact cgggaggatg agacaggaga atcacttgaa    38760
cccaggaggc agaggctgca gtgagccgag atcaccccac tgcgcccag cctgggcgac    38820
agactgagac tctgtctcac aaaaaaaaaa aagaaaaga aaagtcagt gtgcatcccc    38880
tctgacatcc agcaacttca catcttggaa tttatgctgc aggaaaatta tcacaagtgc    38940
acaaggatgt atggtgagat agttattatt atcattttaa aagataggg ctcactgtgt    39000
cacccaggct ggagtgcagt gaagtgatca cagctcactg cagccttgac cttctgggct    39060
cgagtgatcc tcgtgcctca gcctccccag tagctgggat tacaggtgtg agccaccatg    39120
cctggcatcc cccttttttt aaaaaaaggt tttaattatg aaaagaatat gggcttgttg    39180
ttttgtgtgg ttttttaaaa gcttaaaaaaa tgtgtagtgt gtcatttaga aggtgaaaag    39240
cccttacccc atcccacctc ccagagataa cctctgctag caatttcgtg tttgtctttc    39300
aaatttttttc ccacacacat tctttgtact ggctgcttcc cctcctgggt tactcttctc    39360
ccagacagaa acagggctca ttcccttgcc tcctccagct tttattaaaa cattaacttc    39420
cctgtagctg gatgcagtgg ctcacgcctg taatcccagt gttttgggag gtggggaggc    39480
aggaggatag cttgagccca ggagtttgag actagcctgg gcaacatagc gagacccatc    39540
tctacaaata aataaataaa taaataaata aataaataaa taatgaaat ttaaaagaga    39600
gagggaagga ctcttgaaaa ccgtccatat catgcttctc taaatggttg agggctcaga    39660
ggaaaaaaaa tcagcaattt cacatcacgg aatttattct gcagaaaat tctcacaagt    39720
gcacaaggat gcgtggtcag atgatgatga tgatgattat tattattatt attgaagaaa    39780
gtagcagcag cagcagcagt attttaaaag acagagtctc ggatgggcat ggtggctcac    39840
gcctgtaatc ccagcacttt gggaggttga ggtgggcaga tcacttgagg tcaggagttc    39900
gagaccagtc tggccaacat ggtgaaaccc caactctact aaaaatgcaa aaattagcca    39960
ggtatggtgg tgggtgcctg cagtcccagc taccagggag gctgaggcac gagaatagct    40020
```

```
tgaacccagg aaatggaggc tgcagtgagc caagatcgtg ccactgcact ccatgcactc   40080
cagcctgggt gctgacccag gttaggtgca agactccgtc ttaaaaaaaa agaaaaggaa   40140
aaaaaaaaaa aaaggacaga gcctcactgt gtcgcccagg gtaaagtgca atgagtaaag   40200
gcccatgatg ggaaccctga ggagagagtc aaggggaaag aaaaaaaaaa aagcaaaacc   40260
aaaatggaat ttaaaaaaaa tcaggtgcaa tttgcataac agaaaattaa ccattttaaa   40320
gtgaacggct ctgtggcatt tactgcactc caactgttat gtaactacca cctctgtcta   40380
gctccagaac attttcacca cccctaaagg agaccttgta cccattaagc agtctctctc   40440
cttctcccct ccccaccacc ttcctccagc ctctggcaac cacccatctg cattctgtct   40500
ctatggattt acctattcta ggtagtcaac aggatgagat atcccaaaag tccatccatg   40560
gatgaacaga taaccaagt gtgatatgcc ttcctcagat attagtctgc cttaaaaagg   40620
aatgaaatac taatctttgc tacaacatag atgaacctca aaaatatgat gtggctggac   40680
acagtggctt acacctgtaa tcccagaact ttgggaggct gaggtgggcg gatcgcttga   40740
gcccaggtgt tcaagaccac cctgggtaac atagcaaaac tccatctcta caaaacaatt   40800
tacaaaaaac tagccaggtg tggtgacatg tgcctgtagt cccagctatt caggagactg   40860
aggcgagagg atcgattgag cccaggaggc cgaggctgca gtgagccatg atcataccac   40920
tgcactccag cctaggcaac agagtgagac cctatctcaa aaacaaaac aaaacaaaac   40980 aaaaaagttg atgctgagtg aaagaagcca gacacaaaag gcaacatcgt gtttaattcc   41040
atttacatga aatgtccaat gaagattttt tttggcaaca tttatttga gtataatatt   41100 cagtgagtgg accacacata tgcatgcact gcagtatgtt cttggaaaca tttcagattt   41160
gagaggtctg ttcagctatg atgacggtag gtattgtccc ttccctccct ccttgaagaa   41220
aaggaactaa ggctggacgc ggtggctcat gcctgtaatc ccagtacttt gggaggctga   41280
ggtgggcaga tcacttgagg tcaggagttc aagactagcc tggccaacat ggtgaaacca   41340
tgtctctact aaaaaataca aaaaattagc caggtatggt gctgcacgcc tgtagtccca   41400
gctactcggg aggctgaggc aggagaattg ctcgcaccca ggaggtggag gctgcagtca   41460
accgagattg caccattgca ctccagcctg ggtggcagag caagactctg tctcaaaaag   41520
aaaagagaag agaagagaaa agaaaagaaa ccaaaagaaa aggaaagaaa agaaaaggaa   41580
ccaagaccta gaagggcaaa aataggaaaa gttggccggg cgcagtggct cacgcctgta   41640
atcccagcac tttgggaggc caaggtgggc agatcacaag gtcaggagat cgagaccacc   41700
ctggctaaca cggtgaaacc ccgtctctac taaaaatact aaaaattagc cgggcgcggt   41760
ggcaggcgcc tgtaatccca gctactcggg aggctgaggc aggagaatgg cgtgaacctg   41820
ggaggcggag cttgcagtga ccgagatag caccactgca gtctggcctg ggcgaaagag   41880
caagactcgg tctctaaaaa aaaaaaaaa aaaaaaattg gaaaagttat ttactattag   41940
cagcaattgt cataaagtaa tgaacattta ttgcatgatt acaatgagat aaattgtatc   42000
ctgtttttat aagcatatta agttttcttt tttaaaaaaa tgtatgtatt tatttatttt   42060
aagagatagg gtcttgctct gttgcccaga ctggagtgcc atggtatgat catagctcaa   42120
tgcagcctca aattcccagg ttcaagcaat cttcttgcct cagtctctcg agtagctagg   42180
actacaggca tgtgccaaca tgcctggcta gttttcttat ttttaaatgt attttttgtag   42240 agacaggatc ttgctgtgtc gcccaggctg tcctcaaact cctggcctca gcgatcctc   42300 tgccttggcc tcccaaaggg ctgagatgat aggcatctac ctctgcattt ggcccacatt   42360
```

```
aaattttcta gtcatcatgg gaaccaaaat aaacaatata aaacactcac attccttgag   42420
cacttactat atgcagggcc ctgtaataga ttattgtgtg tatcagctca ttccattctc   42480
acacaaccta tgaggttgat gctatttttct acctttttata tatgaggaaa ctgaggctca   42540
gagaaggaaa ctgccttgcc caaggtcaag gccacgtctg atccccaaat cctttcaact   42600
cctctgcact actatttttt agtgcagata ttgccagttt tctaagcaga agcatgattt   42660
agcagccctg agtagacttc tcatttcaga accaaagtgt tggacattgt tggataatat   42720
gaaaaacaaa tgacacacaa acctatttga tactgttttt aattttctct tcatttgatt   42780
ttcctgatga catgattaat cttttttgcc tctaccctgt atgtgaaatg taggtctttg   42840
cagatgtctc agagagtgtt aatagttgct gctggttttg ttttctctcc ccggggattc   42900
ccatccctgg gtgcaagtga aattaaactt gtgcctcttt gccgctggcc gtggtgctga   42960
aaacatcccg ggcagcgcta gggttgccct tgttagcatg ccatccctgc taagagtctt   43020
aggctgatca gcgagtggag agatcttttc caggcttcat tttggttaga actgtgtgtt   43080
gaagatttta aagcccatgt ctgggaactg agactgtttt ggattgtttg aagttgaaat   43140
agtcatgaat aattcctact tgagatgggc ttatgagggc gtggactagc atgcaatggt   43200
tggcctttac taaactgtgg ccattggttg ggacttgggt gaggtgtaac ccatttggtc   43260
taatccatat ggttagggcc ccaagtgcac ctgcattcta tttttttttt tttttaaata   43320
aaggcaaacc catctatctt ctaaccagga tagctcctga gtggtctttg gggaccacca   43380
gcttaaaagc atagactgtg ggctgggcac agtggctcat acctgtaatc ccagcacttt   43440
gaaaggccaa ggtgagagga tcgcttgagc ccaggagttc aagaccagcc taggcaacat   43500
ggtgagaccc tcatctctac aaaaatgtta aaagttagcc aggtgtgttg gcatgcacct   43560
atagtcccag ctactcagga ggctgaagtg ggtggatcgc ttgagcctgg gaggtcaagg   43620
ctacagtgag ctgtgatcgt gccactgtat ttcaccctgg gcaacagagc aagaccctaa   43680
ctcaaacaaa caaacaaaaa aaggcataga ctgtggagtt gggcagacct gggtgtgagc   43740
cccagctctg ccagtacctc ctatgtgacc ttgaaaattt gtttaatctc tctgagcctg   43800
gattttcttg tgtggaaaat gaggcttacc acagaaccca ccttgtagaa atgttgcaag   43860
gaattaactg aaacaaagtg cttaccacgg tatctgccca agaagcagt  tggaaacaag   43920 gcagctgtaa ttatggtcgc tgtgcttgtt aatggcccca taatagttga tcatattgca   43980
gagtgaaatt ggggtatgtg tttaatggac caaggaatat gtcttaaacc catatatcta   44040
gggttctggt accctctact cttttttcctg gtgattgtga tgagcatgga acttacatga   44100
aaatgaggtc tgtttggctt cttcacacaa gctcaatgac ctggctaact gctacaagta   44160
tctgtttcct tagaacccac ccatcagcag tccccatagt ggagacaagg tcacaaagag   44220
ttgacaaacc tgatttgatt tccgcaccaa ccacaggagg cttgaaatga gatgagggtg   44280
aagggcacca cagagggatg caaggattac ttggacactg caaggtcttg ctaagggatg   44340
ggaaccatca gccacgccca ctttgagaat tttccttcat gttctgaatc tgaagagcaa   44400
ggtcctgttc tcagatgcaa gccctccttc ttccctacgc agagtcaaac ttggtctttt   44460
ccagggtcac atacagcctc tctctggggc ctctgcaggt cctgatcaat ttcattgtgt   44520
atagagctct gtgtctcctc acctgcctgc agggctgtct gctatcctga cttccgagag   44580
ccatttcgga agccagcttt tcctcccatc agggatgctt ctcttctttc agccccgcc   44640 ccgctttggc ctcctaggat ggctgatttt tctggatccc gctgacacag gtgctttctc   44700
tccgagccaa tcagggagca gaaaggctca gctcagctaa cagaggcatt gctcaccgca   44760
```

```
gctgtgagtt agaactcagg ctttctaaat cgggaggatc aggcatgact tgaggttggg    44820
ctgagaaagc ctcgcctgcc ccccagctcg actacccagt gaaacctttg gcttctgcct    44880
cgggcgaggc atctcttacc atgccaagaa ctcagcagcc catctttctt tcatctgggc    44940
accaagtaca tcattgcata tttcagggg tttcattgtg tccttaacat gctcatggag    45000
acttggcttg agatgaagtc ggggtttcta ggcagcagga cccatgtccc cttccttcat    45060
ttcctccacc ggtgattttt gttttgtttt gttttgtttt gttttgtttt gttttgtttt    45120
tgagacggag tctcgttctg ttgtccaggc tggagtgcag tggcgttatc tcggctcact    45180
gcaaactctg cttcccgggt tcaggtgatt ctcctgcctc agcctcccaa gtagctgaga    45240
ttacaggcgt ctgccactat gcccagctaa tttttgtatt tttagtagag acggggtttc    45300
accatgttgg ccaggctggt ctcgaactcc tgacctctgg tgatccaccc gcctcggcct    45360
cccaaagtgc tgggattaca ggtgtgagcc accgcaccag gcccttccac tggtgttttt    45420
tgagcatcta ctatatagag aatgctctcc tgggcacaga ggatgaagca gtgaacaaag    45480
tagacaaaaa atccccacgt gcatagagtg tgcagtctcg tgggagagac agggaacaag    45540
ataaagaagg aaaaaaatag cagatgcttg actgggacg gggactaaag aaagaaaaaa     45600
ataagcaggc taagggggtt gatggatgtg acctttgagt aaaggcctaa aggaagtgag    45660
ggagggagtc atgtggatgt ctggggaaag actattccag gagaatgaac agcaggtaca    45720
aaggcccctg ggtacaaatg tgcctgggga gtttgggaa taaaagggag gccggcgttg      45780
ctgtagctga gtgactaagg gagagaatag aggagatgag gggagggagg taatgggagc    45840
aggtcatgca ccttgctggt gctggaagga cttttgtttttt gcttttgagt gagatgggat  45900
ccatgggaag gctttgaata cttccacatg cattaggctg aaattttctt ttctgctttt    45960
gtcgcattcc aacattgctt ttatttcatc aaaatcttcg gtttcttctc aggctcttta    46020
cccaagtggg agcagaaggc tggtacccag ggctgttcag ttctcccct ggggtcagaa      46080 cgtggaggag aaagcttgga ggagaaacag gaaccccac ctctttctgg atgactcaaa     46140
accgcaatta cctgagctcc tcctcctatc cctgaaatag aggcacttag cacttcctaa    46200
acttcccggt gcacacaaat cccctggcga tcttttaaa tgcaggttct gactcagcag     46260
gtggatgcaa ggtctaaggc tgcattccta accggtgctg gttctgggac cacactttga    46320
gtagcaaggg tctgaggtca ttgttgcaga tgtccatctg gggcatgtct gtggacactt    46380 gcggggtgc gggtgagcag agggaggggg gatgatgttg aaaagcagt gtgagtatct       46440 gtgtttgata agaagtaaga aaatgaagca aggtgggaga gtagaacctc tttatttttg    46500
cctacgtgct aaggttttat tgccataccc agagagccct gggtctgaaa tccaggcaac    46560
actggccagt tgaaaccctg atattgcagc ccataaaagt gctgcatgct gcatggtgga    46620
cttctgggac tcttcctgga accttcagtg ccagagccgg tccaaaggaa gtcacatccc    46680
tgccattgag gggcaggaga ccagggaacc ggaggagtgg gatggcagaa gcgcgtgtaa    46740
ggaggctgag ttggcaggga gagaaagcga agtcagcttc aaatcatagc gagaggagac    46800
cagggaaggg cttggcgttg ctgctctgtg tacaaatatt gtctcttatt ttccaggctg    46860
cagggtgagg cagagtggag tatttgtgca acacagccca gctttgttct ctgggctcct    46920
aatgcctgtc agctcagagg cagaaagcca atcagagatg atcgtcggca aggccggctt    46980
ttgttggctc cccaaattgc cctgagtctc ggattttgct tttcagagtg tgctttcagc    47040
tggaggcaaa ggctgaagct ggtgacaaaa ggaagcctgg ttttcctggc tttccgagac    47100
```

```
ttttactgag ggggtttcta tttcagactc cgttttccca cctggaaagc aggttccact   47160
ctccctccgg cctggaaggg atggttttat ggtgcttcca aaatgccaaa cctaactcca   47220
gggcagaaga ggagactgaa accaattaat tttccaaagg ttagagctac gaggagggga   47280
gaggtttagc atggtcaagt tccccaagac atactaattg atctctctac agaatgcggg   47340
atttcagtgc ccccagggga cactcagcaa tgtttagaga ccacttgagg ttgtcatcac   47400
tggacaggag gggctgctac tggcatctag cacacacagg ccagggatac tgttgaacat   47460
gctgcagtgc ccagacagcc ccaccaagga gaatgatcca cccctaaacc tagtgctgag   47520
gttgggaaat cctgctccgg agtaaccaac accctatggc tttttcactc aagcagccgc   47580
ttctccagcg cttacacctc ctcagagatt gccagatcca tatgcagagc ctgttggcgt   47640
gggacacttc tgaggggtgt ggcagggaga cagcggacat tcccatttac agctgatca   47700
gcaggttagg agctaatatg aaatgaacaa gatagaccct ccccacctgc cctgcagatc   47760
ctctggtggg acactaggga gggaggcctc ctaaacccaa atgacagttc ccaggatgca   47820
gggaggagtt tacctatgca aactggagag aatgcaaatg gggcatctag agatacttac   47880
tggacgaccc ctcccctgcc tcgggtcttg gaagaacaga ttctcagagg tctgccctga   47940
tcactgtaat ttttttttta ttgaggtaaa attaatataa cacaattaac cattttaaag   48000
tgacatttag ggctgggcac agtggctcat gcctgtaatc cccgcacttt gggaggctga   48060
ggaagaaagg tcgcccagga gttcaagacc accctgggca acaaagtaag actctgtctc   48120
ttacaaaaaa aaaattaggc acacatggtg ttgtgcacct gtagtcccag ctactcagga   48180
ggctgaggca ggaggatcgt ttgagcctag gaattcaagg ctgcggtgag ctatgatcat   48240
gccactgcac tccagcctgg gtgacagagc aaaattgtgt ttctttaaaa aaataaaagt   48300
aaaaataaat aagaaaagaa aggagagggg aggggagagg cgtttagtac actcacaatg   48360
ttgtgtaact gtcaccttca tctagttcta aaacattaag cagccactcc catttccctt   48420
gccattcccc aggaacaaca aatctgctgt ctgtctctgg atttgcctgt tcggatatt   48480
tcatatacat ggaatcatac aatatggggt attttatgtc tgcttctttc gcttggcata   48540
atgttttcaa ggttcattcc tgttctatca tgtatcagta cttcattcct ttttttttt   48600
ttttttgaa acggagtttt gcttttgttg cccaggctgg agtgcaatgg cacaatcttg   48660
gctcactgca acctccgcct cccgggttca agcaatcctc ctgcctcagc ctcctgagta   48720
gctgggatta caggcatgcg ccaccacacc cagctaattt tgtactttt ttagtagaga   48780
tggggtttct ccatgttggt catgctggtc ttgaactccc aacctcaggt gatctgcctg   48840
cctcggcctt ccaaagtgct gggattacag gcgtgagcca ctgcacccgg cctacttcat   48900
tcctttttat ggctgaatac tattccattc tatgagtaga ccacattttg tttatccatt   48960
cacccactgg tgaaatttag gttgtttcca tcttttggct gttgtgaata gtgctgctgt   49020
gaatatttgt gtatgagtgt tcgttggaat acctgtctta cgatccttt gtgtttatac   49080
cttggagtgg agttactgtg tgtcacatgg taactctgtg attaactttt tgaggaacca   49140
aggaatggtt ttctatggca gttgcactgg tgttttttg ttgttgttgt ttttgttgtt   49200
gttgttttga cagggtct cactcccatt gcccaggctg gagtgcagtg gtgcagtcat   49260
ggttcactgc agcctcaacc tcctggggct caagcaatcc tctctcctca gcctcccaag   49320
tagctggcac tacaggcctg cgccactatg cccggctaat ttttcatatt ttttgtagag   49380
atagagtctc agtttgttgc ctaggctggt ctcggactcc tgtgctcaag taatcctcct   49440
acctcggcct cccaaagtgc tgggattaca ggcatgagcc accgcatctg ccagctaca   49500
```

```
ccattttata ttcccaccag catgagggtt tcaatttctt cacatcttca ccaacacttg   49560
ttttctgttt gtttgtttgt ttttaatagc tatcctagtg gatgtgaagc agtatcccgt   49620
tggggtttga tttgcacttc cctgatcact aataccctca tgtacatatt ggccatttga   49680
ctgtcttctt tggagaaatg tctattccag cctcctgtcc atttttcaat tggattatct   49740
ttttgttgtt gtgttgtaaa tgttctctct ttattttta ttttttgag acagagtctc     49800
gctctgtcgc ccaggctgga gtgcagtggc acgatcttgg ctcactgcaa gctccgcctc   49860
ccaggttcac gccattctcc tgcctcagcc tcccgagtag ctgggactac agatgcccgc   49920
taccacgccc ggctaatttt ttgtattttt ttagtagaga tagggtttca ccgtgttagc   49980
caggatggtc tcgatctcct gacctcatga tccacccgcc ttggcctccc aaagttctgg   50040
gattacaggc gtgagccacc acacctggcc gtaaatgttc tttatatagt actagaccct   50100
tatcagatac atgatttgca aatagcttct cctattctgt tacttgcctt ttaactttct   50160
tgataacgtc ctttgatgca caaaaggttt aaattttgat aaagcccagc atatctgttt   50220
tttcttctgt ggatcatgca ttaggtgtca aatctgatca taatgtttta tttatttatt   50280
tacttattta tttattattt tatttatttt tgagatggag tcttgctctg ttgcccaggc   50340
tagagtgcag tggcatgatc tcggctcact gcaacctcca cctcccaggt tcaagcgatt   50400
ctcctgcccc ggcctcccaa gtagctggga ctacaggtgt gtaccaccac gcctggctaa   50460
tttttgtatt tttagtagag acagggtttc accatgttgg ccaggctggt ctcaaagtcc   50520
tgaccgcaag tgatccaccc accgcagcct ctatctattt ttaatttatc tctttttttt   50580
tttttttttt tgagacaggg cctccttctg tcacccaggc tggagtgcag tggtatagtc   50640
attgtacact gcagcctcta cctcctcggc tcaagcaatt ctctcgcctc agcctcccaa   50700
gtacctggga ccacaggtgc ctgccatcat gctggccctg ccaccatatt tgaaattgca   50760
gccctgaccc cttccactgt ctatagtctt caccatctta ctacataaca tagcatatat   50820
gatgtactgt ataacatggt atatgcagtg tactgtatag catagtatac atgatgtagt   50880
catctcattt atttgcttct cctctgggaa gcaggaggaa gcttctcctc ttgtctgctt   50940
tgctctcaac tgtgtcccta gcccagaaca gagtctggca cacagcaggt actgaatgaa   51000
tatgtgttca gtgaatattg tgggtgagat agaaggtgaa tatccacatt tcccttttaga  51060
agtcacctga tctgggtttg agatctgcag ggatctactc cagacaggag aacgaataat   51120
tccacctgtg ctgatgagtt ggaaggatct agagggcttg agatctttcc actggggtca   51180
gtgggggtgg gtgcacctcc aacacccttc ttttctttga acaagatttt tccttaattc   51240
cccaatactc cctttgaata tatgatttta gccaccatca tagcgaattg catcgtcctc   51300
gcactggagc agcatctgcc tgatgatgac aagaccccga tgtctgaacg gctggtgagt   51360
gatgtctttt ctcagggtct tctccttggc tttagcagga cattaatttt tgggggagtg   51420
gagcagggca cagaggaggc tctcagtcct ggagcccaga gccagatcat gggaagccta   51480
aatttccttt tcatttttc ttgaaccaga gtctcgctct gtcacccagg ctggagtgca    51540
gtggttcagt catagctcac tgcagcctcc acctcctggg ctcaagccat cctcccactg   51600
cagcctcctg agtagcaggg actacaggtg ccaccatgcc cagttaattt tcttattttt   51660
atctttttt gtagagatgg ggatctcact aggttgctta ggctggtctc aaactgccca    51720
ctttggcatc tgcataatt tcaggcagta tactcaaatg aacattgtta atgttaataa    51780
ttatgtcttg gccagacact gtagctcatg cctgtaatcc cagcagtttg ggaggccaag   51840
```

| | |
|---|---|
| gcaggtagat cacttgaggt caagagttcg agaccatcct gaccaacatg gtgaaagccc | 51900 |
| gtctctacta aaaaaataca aaattagctg gatatggtgg tgcacacctg taatcccagc | 51960 |
| tacttgggag gctgaggcag gagaatcgct tgaacccggg aggcagaggt tgcagtaagc | 52020 |
| caagatcgca ccattgcact ccagtctggg caacaggagt gaaactccat cttggtgggg | 52080 |
| gggaggcgaa aaaaagaaa caagaatatt acaaaggata cagatgaaga gatgcaaagg | 52140 |
| gtgagatata ggagaagggt gtggctggca gcttctaggt agcttcagga gggggactgg | 52200 |
| tcaccagaaa gaccaaggca tgattcgagg gttgcgactt tcagccccac cccccaacct | 52260 |
| ctgggagggc agaggggctg aaaatcaagt tgatcaccaa cggtcaatga tttaaatcca | 52320 |
| aacctctaat catgccttgg ttttcccggt gaccaacccc catcctgaag ctacctagaa | 52380 |
| gctgccagcc atcagtcaat ccttagcctg caaaaagaca tcccttggga gatcccaagg | 52440 |
| gttttaggag ctgtacacca ggaaacagtg tcaaagacca aacatacatt tcacaatgtc | 52500 |
| acagtcttct aaaaactata actagcctag caaacctatg atttctagat ctttgcattt | 52560 |
| tcacttaaaa taaagctaaa taaaaagcgt ccattgaaag actggtaagc aagtagaagt | 52620 |
| accagtggca agctaatgtg gaaaaaaaa atcattcagg cagagtgaaa atgattgtag | 52680 |
| ctcgagaaac gttgctgtaa cagatgggaa acattcaca ttggggctct gatggagaag | 52740 |
| agcttgtagc ttaatttcaa atatgataga ttagcagctg gaagccagaa ccagccggag | 52800 |
| gttctgcaga ggaactggag gtgaggatac tggccactta tcagccagta cagaagtcct | 52860 |
| attccaaacc tttaacaatc tacatgccag ctgagaacca tcctaagggg tcagatttag | 52920 |
| gagtgaggtc aatgcacaag ctctagcctc aaataccttg aacgctgcat gtgacaagta | 52980 |
| aattctctaa accaatgctt tccattagaa ctttctgcag tcacagaaat gatctccatc | 53040 |
| tgccctgtcc aataggattg tcacttgaaa tgtagccagt gtgactgcag aactgtgttt | 53100 |
| tttatttat tgcatttaaa ttaattttaa ttgaaatagc cacatgtggc ctgtgactgt | 53160 |
| cgtattgaat aagacaggtg caaacaaata attctgttta gctgagtgat atgtgaggtt | 53220 |
| ggcccaaaag gaatgaagga ggaaggtgcc ttctctaggc attggctttg ctcgcaaaag | 53280 |
| gctttggaca agagaactct gcaagaggca gtgaggggtg gtgagtgcag gagggtcagg | 53340 |
| ggaagtgaga gggtgatagg tactgatttc taggtgggct ggttccctga tcttgtcaac | 53400 |
| atctgcccag cccaagacgc tgaccttgcc ttctctccct tccaggatga cacagaacca | 53460 |
| tacttcattg gaattttttg tttcgaggct ggaattaaaa tcattgccct tgggtttgcc | 53520 |
| ttccacaaag gctcctactt gaggaatggc tggaatgtca tggactttgt ggtggtgcta | 53580 |
| acggggtaag tggcgcgtgc tatacgcttt ggatttaact agctgaagga ttacgaggct | 53640 |
| tttggttggt gtggtccggg ccaggctcag gaaggctgag cccttgtgtt ctccctcccc | 53700 |
| ttgttatgcg cctgcctcct ttctgccaac accccacctc catgtctcag ctgtatatta | 53760 |
| cagcagatgc tttctgttac aattaaaata atagctcatt attgttggct gcttccagag | 53820 |
| tgctttatgc ccattctcta atttaatcct tgcaacaacc cactgaatta ggaaatatta | 53880 |
| atattcccat ctgaccactg aggaatcaga aactcagagt gtaacttgct taaggccacc | 53940 |
| cagcaagtaa gtgatggaac tgggagatga acagaagatt atgcattcca gaactcaagg | 54000 |
| ttttaagtgt tgtacgtgca tgggtctctt gatttgcttg aggatatctt gcttttattt | 54060 |
| caacttggtg aatgttttt gagaatgtct gggtgcaagg gattgtgatt atgacaaagg | 54120 |
| agaaaagcaa gctaaataag gtacagttac tgtcttcaag gagttttcag atccatatat | 54180 |
| gatgaactgt ggttgaaatg tgtatatgct ttcctctaag caccctgtat gaggtagcac | 54240 |

```
ttgctggtat aacaaaagat ccaaagctag gaaatgactt aaacacggca gaagtttatt    54300
tgtcactcat agaaaattca aaattgagct gggtgtggtg gtgcatgcct gtaatctcag    54360
cactttggga ggctgaggtg ggaggatcac ttgagctcag gagttcaaga ccagcttggg    54420
caacacagtg agaccacccc cccatctgta aaacataaaa taaataaaaa attaaccagg    54480
catggtggta catgcctggg agaattgctt gagctcagga gttggagggc acagtgagct    54540
atgatcatcc aaccgtgctc cagcctgggc aacagagcaa gaccccatct cgaaaaaaaa    54600
aagtccaaaa taattgttcc tagttgacag gctcatctcc tccaatgact gacggaccct    54660
gacccttgcc atattgtggc tcttcattgt cagcccacat catccaataa ctccatgctt    54720
gtctgtatca aaccaggaag gagaagtgag catagaaggt gatacttgga aaggtttatg    54780
agtttggaag gggtgtgacc catacctgtt ccattcatat cctattggct agaactcggt    54840
cacatgacca cacatcactg caagggaagc tgggaagtat cagattgtgc ttagaagaaa    54900
agggaaatgg atttggagaa tgacctacta gtctgtcagg gaccttaaaa acttttatta    54960
gattccagta gggacattag tatctggtac caatggctgg ttcctcctct tcccactctc    55020
tactctcctc tcagctaagt ctgggctctt ctattctaag acccttcttc actggacacc    55080
tttttcatag taatcattta caggatcata gctttccatg ttttgttgct gctccaggtt    55140
ctgtctctct tggcggatgt gatgggttgc agcacccaca ctgtgctggc cgggctctca    55200
caatgcagat ttgtttcaga gcaatgttgc ctctcacaga aggagctgtg gcctattggg    55260
ctgtttctgt agaggccttc agatgtcagc agtctgttgt aaggactctg gctagctct    55320 catgggcttg ggtgttcaca gagggatctt tgttggctgt gctcacagtt cggtggcttg    55380
ggaccttggt gggttccaag gcatattat ggtactgggc acttttctct tagtctacta    55440
ggaaactcat ctagaaacag cctagtggct aacttttta ttgtttaaaa aatgtaaagc    55500
tgggcagggt ggctcatgcc tgtatcccag cacattggga ggccaaggtg ggaggattgc    55560
ttgggcccag gagtttgaga cgagcctgag caacatagca agaccacatc tccacaaaat    55620
aaaaattaaa agtgtataaa gctgggtaca gtggcacatg cctgtaaccc caattactca    55680
ggaggctgga gagagaggat tgcttgagcc taactagttt gagaccagct tgggtaacct    55740
agcaagatcc catgcaaaac taagtagaga ataatagagc aaacacctgt gtatacattc    55800
atttattcaa tgactatttta ttgaacactt ctgtgtgcca ggtcctgttc taggctctgg    55860
gacacagcag taaacaaaat agaaaaatcc cctgtcctca tggagctgag agtctactga    55920
tggagatgga cacaattgat gaatgaatct agtgtgtcag atggcggtga ggggtacaga    55980
ggaaaaataa agcaggggag ggatgggatg tgtggcaggc aggggtgagg ggtgctggaa    56040
gccagggaag acttcactgg gcatgtgaca tctgaatgaa aacctaaggg aggtgagtga    56100
gtgagccatg aggagagctg gaacagagtg tcaggcaaag ggaacagcca gtgcaaaggc    56160
tctgaggctg gactgtatct gacatgtttg atcaacagta agaagaccca catggctaga    56220
gaaggtgacc agaagaatgg ggagaattgg ggatagagaa gtaatggagt aacctgctat    56280
caaaacacaa cctttctctt tttttttttt tttttttttt tgacaagagt ctccctctgt    56340
cacccaggct ggagtgcagt ggtacaatct cagctcactg cagcctctgc ctcccagttt    56400
caagtgattc tcctgcctca gcctcccaag tagcttggat tacaggcgtg taccacaaca    56460
tctagctaat ttttgtattt ttagtagaga cgggtttacg ccatgttggc caggctggtc    56520
ttgaactcct gacctcaagt gatccacctg gcatggcctc ccaaagtgct gggattacag    56580
```

```
gcgtaagcca ctgtgcccag caaaacaaaa cctttctaac ctttctaatc cctgttttct   56640
ccctccctag acccattcct ttctctcccc catccagggg cactttcctg aattttatgt   56700
ttattatttg catttatgta ttcacacttt ggctgcctaa gtatataaga aatatatgct   56760
acctattttt acacttcaaa atatttttta aatagcatca gagtgagaat agtttacact   56820
ttgactacat gcatagataa gaaatatgtg ggctgggaat ggtggctcac acctgtaatc   56880
ctagcaattt tggaggcaaa gatggaagga ttactttagg ccagaagttt gagaccagcc   56940
tggccaatgt agtgaaaccc tgtctctaca aaatgaaata aaatgtaata aaatattcag   57000
ctgggcatgg tggtgtgctc ctgtggtccc agctactcag gaggccaagg cgggaggatc   57060
acttaagccc ataaggtcga cgctgtagtg agctatgact gcactccagc ttgggcaaca   57120
gagcaagacc ctgtccctaa aaatgtttt tgttgttgt tgttgtttt tgttttttg     57180 ttttttaat aaaggccagg tgtgatggct cacacttgta agcctagcac tttgagaggc   57240
cagggcagga agactgcttg agtccaggag tttaagacca gcctgggcaa catggtgaaa   57300
ccccatctat aaaaaaaatg caaaaaatta gccaggcatg atgacgcacg cctgtagtcc   57360
cagctactca ggaggctgag gtgggaggat cacgtgagcc caggaggtcg aggctgcagt   57420
gatccgtgat tgcaccactg cactccaggc tgggcaacaa agtaagacct tgtctcaaaa   57480
aaataaaata aaataaaaaa taaaaaaaag aaaagagaaa gaaaaaaaga gatatgtggt   57540 actgttttc aaacttcaca tttctctaac ctgacttttg tgttcaacat gagataaatc    57600
tgattaataa aaatagtttc catgcatcca ttttcatgac tgcatagtat tctgtggtag   57660
gagtatgctg ccgtgtattt atctatttgg attgtttcca gctttgggct attttgaccc   57720
aaagtgtccc tgcttctctcc caagtgagtt tctctagggc acgtacccag gagtggaact   57780
gctgagttgt atactgtgtg catcctcagc cccactaggt attgccaaat tgctctgcaa   57840
agtggttgtg ccaattcatg ctccctgggg gctggcttct gctggctgag gctggcttga   57900
ccttgctggc aggaaggagc cttaaaaatc cctgtgtggt tttttttgtt ttactttat   57960 tttaagttta ggggtacaag tgcagatcta ttacatgggt aaacttgtgt cttggggggt   58020
tgttgtacag gttatttcat cacccacgta ttaagcctag tacccattag ttattttct    58080 tgatcatctt cctcctcccg ccctccaccc tccaaaaggc cccagtgcgt gttgttcacc   58140
tctgtatgtc catgtgttat catcatttag ccccccactta gaacacgcag tatttggttt   58200
tctgtttctg cattagtttg ctaaggataa tggcctccag ctccgtccgt gttcctgcaa   58260
aggacatgat cttgttcttt ttcttggctg catagtattc catggtgtat atgtaccaca   58320 tttcttat ccagtctatc attgatgggc ttttgcagcc ctgtttttt ttttttttca       58380 taataacacg gttatgggaa cacttaggga agctcatata ttattgagca gtgtgatggt   58440
taatattgag catcaacttg atcagcttga aggatgcaaa gtcttgttcc tgggtgtgtc   58500
tgtgagggtg ttgccaaagg agattaacat ttgagccggt gaactaggag aggcagactc   58560
acccccaatc tgtgtgggca ccatctaatc agctgccagt gtggccagaa taaaagcagg   58620
cagaagaagt tggaaagagt agacttgctg agtcttctgg ccttcatctt tgtcctgtgc   58680
tgaatgcttc ctgccctcta aaatcagatt ccaagttctt cagcttttgg actcatggac   58740
ttacaccaat ggttagccag gagctctcag gcctttggcc acagactgaa ggctgcactg   58800
tcagcttccc tactttttgag gtttgaggac tctgacggat ccaccactgg cttccttgct   58860
cttcatcctt cagatgggct atcgtgggac tttccttgt gattgtgtga gtcaattctc    58920
cttataaact cccttcata tatacatcta tcctgttagt tttgtccctc tgaagaacct     58980
```

```
tgactaatac agacacctag tgggtcccaa taagtgatca ttaaactgaa ggcagtcatt    59040
cagtaggtca gtttgtcact tgtgtttgta tctccctgct tacaacaagg tggcctttct    59100
tctagtttcc tgtcatctga tggaagagat tctagactca ttcctctaga ggagaaatac    59160
ttcatctaga acagataggt cctaagggtg agagctcatc gttgggatga atgaacccac    59220 tgaaattta tgcaagaaga aaattgtgta tatgtatatt ttttttttctg gtctgtagtt     59280 tttattagat tctcagggaa tcctgatcct atcatgaaga ccttctattc tagattgggt    59340
tcctttcaca tccccttctc ctttcttgtt gaattctcca tgcatttctt tcacttgctt    59400
ttcttgctct tatttctctg gtagtcagtt atccttttg tctggtggtt ctatctcctt     59460
caaatgaggc acattgctca aattttatta ctccaaattc caaggtgctg tttagtgtcc    59520
tgttgggttg taagctagga acagggaggg gaaagtaaaa cattctgcat gagctgggtg    59580
cagcgggcaa gcacctggaa ttccagctac tggaagctga ggtgggagga ttccctgagc    59640
ccaagggttt aaggccagcc tgggcaacaa agtgagattt tgtcttaaaa aaaaaaaaaa    59700
tcccagctgg gctctgtggc tcatacctgt aatcccagca ctttgggagg cagaggcggg    59760
cagatcgctt gaagtcagga gttccagacc agcctggcca acgtggtgaa accccatctg    59820
tactaaaaat acaaaaaaaa aaaaaaaaa gcctggcatg gtggtgtggt gtgcactggt      59880
aatcccagtt atttgggagg ctgaggcagc agaatcactt gaatccagga ggcagaggtt    59940
gcagtgagct gagattgtgc cactgcactc catcctggat gacagagtga gactctgtct    60000
caaaaaaaaa aaaaaaaga aagaaaaaac acgcgcgcac acacacacac atcatgcaga    60060
cctagccttc tgccaatgtc aatggtagag aaacacagta gacacttaat tctatgtttc    60120
agagaggagg ggactcaaat atattaattt gacattgaga cagtgatgac tttaatgagt    60180
actttctttc cttttttttt ttttttttt cgggacagag tgcagtggtg ggattttggc    60240
tcactgtagc ctccacctcc tgggttccag cagttctcct gcctcagcct cctgagtagc    60300
tgggactaca ggcatgcact gctgtgcctg gctaattttt gtattttag tagagacggg      60360 gtttcacact atcagccaga ctggtctcga actccggacc tcaggtgatc tgcccacctc    60420
ggcctcccaa agtgctggga ttacaggcat gagccaccgt gcccggccta atgagtactt    60480
tctgattaac ctgttgccct ctcagattcc tgaagcaaac cacagcgtta aacgtgatt     60540 cattttgtgt ggaccaccac ggtgtttacc ttcttcttgg gtgaagtttg gtggaaaaga    60600
tcttaccccg gacatctgtt tgttctttgt aactcagagc ctcagagaaa tcctaacttt    60660
ataatgttgt caaaccttg taaggcatgt ttttattgta tttgtgttct gatcatgaaa      60720
ctgaaaatgt gtaagaggaa gatttcagaa gcttggctgt atgtctgaga tgacagttct    60780
tttactgtca ttctcaaata tatataaata ttgaagagat caaataacac aaatcgtgca    60840
tgttaagaaa agagactgtg aacctcacca gagagggtg agcacaattt ttttctttt      60900 ttattcacag ggttagcact gtcccttca cataataaat gctcagtaaa ataaatggtt    60960
gttaagccgg aaaagggtaa cacttctgat aatgagtgtc ctgggaaatt tactaagctg    61020
tttagaagat gggaccaaca cactgataga aatagtcaga tagtccagaa gtctatggca    61080
gatgccctga acatcagatg agatataaga cagagaagct ctgggtcttt gccagctctg    61140 acatttatg actctatgaa acggaaggtt ccttttaga agggtctata aactgtctca    61200
ggctttgggc cattttgttg aagatcagag gcaaggaaaa gacacaacta cacaggaacc    61260
atcagggaaa gatgttgttt tttggtcttg aagcatcatt gaattttttt tttttttttt    61320
```

```
gagacggagt ttttctcttg ttgcccaggc tagagtgcaa tggcatgatc tcggctcact   61380
gcaacctccg cctcccaggt tcaagtgatt ctcctgcctc agccttctga gtagctggga   61440
ttacaggcat gtaccaccaa gcccgggtaa ttttttttgta tgtttagtag agacgaggtt   61500
tctccatgtt ggtcaggcta gtctccaagt cctgccctca ggtggtccgc ccacctctgt   61560
ctcccaaagt gctgagatta caagcgtgag ccaccgcacc gggccgcatc attggatttt   61620
aaggctccat ggattctggc aggtccagcc cttctgtttt actcacaaac aagtggtttg   61680
tccaaagtca cacagagatg gtggcaagag atctagaata agaaggtgtc ttcaagtcat   61740
ggagccagga accctggctt tttgggcaat ggaagtggta taaatgttta atatcaccccc   61800 tcaggttctg ccactagagc ccagctctct cttccttcct cttgcccccct gactagccta   61860 tggcctcttt ccagagaata agaaagggat cctcagagaa taatcccagt tcctcgcttt   61920
ttattatata gttgaggaaa ccaagtctca gagggtcag tgtcttgacc atacacctct   61980
catgtcctct ctccttttg attaattgaa taaatacatg tagttgcttc ttacctcctt   62040
tctttcttca cccctgcccc atgcacctgc tcttagttgc cttcacatgt aaacagcatt   62100
ccaacaacaa caacaaaaca caaccagcat tctaactcat gagaccagca acagttccta   62160
taaataccag cagcatttta ttttaatgtc tctctgcagt agtttctccc ctccatggat   62220
cagtcatcct tggtaccaaa aggattcccc actgtgacac aaatgctttt tgtcattctc   62280
agtgagttat accattgaga gagcatcgat cttttattg ttcaaagctt ttggttgtca   62340
tgatatttgc tggaccatgt ttcaccagga accacatcac ttcctagcag caggagctat   62400
tttcttccat cttctaacaa caccagcagt gacagtgata ataatgatgt tagctgccat   62460
ggtcgttatt cttatcattt attgagtact tactatgtgc cagggactac attaagagtt   62520
ttatgtgtat tatcacattg agcctcgcta gcctttgtac agatgaatct gaggctcaga   62580
gaggttaagc tgctcacaag ggagtcacac agctggtaag gggtggatca ggatctcagc   62640
ctctctgcta ggacacttct ctaaacctag aataatactg gcctgtgtt aagttcagca   62700 aagagctgta ttcaacccag tgtccttagg aatgtaatgc ctgttattaa caacagtggc   62760
aacattgata agctgaaact tatgaggtgc ttacaatatg atatactata tattatatac   62820
atacataggc acccacctat aatctcagca ctttaggagg ccaagtcagg aggatcactt   62880
gagcccagga gttcgagacc agcctgagca gcatagcaag atcctgtctc tgtaaaaagt   62940 ttatttttc agttggccag gtatgttggt acatgcctat agtcccagct aatgaggagg   63000
ctgaggcagg aggattgctt gagcccagga atttgaggct gcagtgaact atgatcacac   63060
cactgcactc cagcctgggt gacagagcaa gactgtctct aaaaataaaa ataaaaataa   63120
aattatttca actctcaagg ttaaataaat actattatta ttcccatttta cagatggagc   63180 aactgaggct caaagacatt aaatgcttac tgtcttagtc tgttttctgt tgcttatagc   63240
agaacacctg aaactgagta atttataaag aaaaagcaat ttatttctta cagttatgga   63300
gactggaaag tttaagatca aggctgcatg agctataatg cacacacact attgcactcc   63360
aggctgggtg acagggtgag accccgtgtc aataaataat aatataaaat aaataaaaca   63420
aatttcaaca tgagttttgg aaggtttgaa atattcaagc cagagcatct gtctcataag   63480
tggtggaccc aggatttgaa ctaaggcaga tctggatcta gaacccattt tcttgaatcc   63540
tacgctattt ctctaaggtc aagttttgcca aggaaaataa acttgagaat ttgaatagag   63600
ctctctgaca tgggaagtca gggtgatcct tccttcccct ccctgatctt gggttccact   63660
atggctgggg gaaaacagga gcagaagaga tttcaagaaa tgagagattg gcctagcgcc   63720
```

```
atggttaaga cctggacttc agagtcagag gaagctcctc cctctatgac agtgagaatg   63780
tgggttgaac tcactgaacc tcagttttct cacctgaaaa aagggagtaa aactagtgcc   63840
tagctcctag ggtttgcatc acacacgaaa gttggtgaac tgaaggaaaa aaacttaaat   63900
tcttgtgggg gagcatgtga tagatgctac aaattctcca tgccttattt acctagctta   63960
cgtctaagtt cacctgcagc ttcctcttgg tacactccca tctctctaca tctctgttgg   64020
agggcagtct ctggcatcac agagtttgct gagccagatg cttaacaacc tcggtagcat   64080
ccctcaacca gtgagctagg gagtcagtgt ataaataccc tggcttcccc attgctcagt   64140
gggaaaacac tgaaatatgt tatacagcat catagaggtg cctcagtaaa attgaatcct   64200
agttgttcac ataaaaccca ttcactagtg taccctttac caatctctct cttcctcatt   64260
cctcacttgt aattccttgc attacctccc aaattaacca ttggacccta gttttgcct   64320 tggggtctac tcggcgctaa ctcaaggagc ggaagttgga agcttagcgg gttacaggtt   64380
tcagcaccct ggacagctcc cagcacaccg tattgtgcta aaatgttctc ttccctccct   64440
ctgcctccag ctggggtgga gagggactga gtaaaggcca gatggccagg tgaccttgtt   64500
ccatactgag cttcttggcc attttccctg tggggctgga gaagaccttg ccatccatct   64560
ctccgcaggt ttgggggccg actgaggtct tgttttctcg aattgctatg acaaatgcca   64620
gcctgcctcc aagggggcatc tgtcccactg cctctacagt ttgcatgcct aatgactcct   64680
ctcctctcac cagggcaggg aggtggctgc ctggtgggcc gcttgaagcc gggagaccaa   64740
gatcatgcca ctggactcgc aacaaaccga gactcttttt tttttttttt tttcctcgag   64800
acagggtctt gctctgttgc ccaggctgga gtgcagtggc gcgatcttgg ctcactgcag   64860
cctccgcctc ccaggttcaa gcactccac ctcagcctcc caagtagctg ggattacagg   64920
cgcacaccac catgcctggc taattttgc attttagta gagaggggt ttcaccatgt   64980 tggccaggct gatctcgaac ttctcccctc aggtgatcca ctcgccttgg cctctcaaag   65040
tgctgggatt gcagctgtga gccaccatgc ctggccaaca gaataggact ctgtctcaaa   65100
aaataatttt tttttaaacat tgctttgcaa cccagctgct tcttgtgcag gcatctctaa   65160
atgaggacag ccagtctaca tagacacgta aggaagcata gtggttaaga cctggtcttt   65220 gggggttagag tggattccca acctgactcc actgtttcca agctgtgtga ccttgggcaa   65280
gttactgtac ctccctgaat cttccatttc ttcatctgga aaatgagagt agtagcatcc   65340
cctgacttgg tggggcatgg tggctgatgc ttgtaatcca acactttggg gaagccaagg   65400
tgggtgaatc gcttaaactt gggagttcaa ggccattctg gcaacatgg tgaaactcca   65460 tctctacaaa aacaaaacaa agcaaaaatt atctgggtgt gatagtgtgt gcctgtaatt   65520
ccagctactc aggaggctga ggtgggagaa tcacttgagc ccaggaggtc aagtctgcag   65580
tgagccgtgc ttgcaccact gcagtccaac agagcgagac cttgtctcaa acaaacaaaa   65640
caaaacacaa aacaacaaca aaatactacc accttatgga gttgttttca aggttcaatg   65700
agttaatgtc tgacccatgc tgggctgggt ttatggatgt tacttgccca gggacagtct   65760
gaagaaagag aaagtgatat agtccattgg gcctcagctt cctcatctgt ggaatgggaa   65820
taataattgc acctacctca aaaggtaaaa gtcagtgaga tacatataag gcattcagaa   65880
caaaaactgg cacagaataa gtgctcaatt atattagcta ttgtaagact aataactatc   65940
attataatga tgataataat tattactact tccccaggcc cagttccata gaccagttag   66000
ttaactgtag ggaacgtttg ctattattag ttgggttccc aatatctgac ctccctttcc   66060
```

```
aatttaggga gaatcctccc ctttctataa agtactgctg gtctatggga tcccaccctc    66120
actaataagt tgaaggtgaa agggattcat tgtcacccca tcacctggta gtcagggcat    66180
gtgatttaaa caaccagggc caggcgcagt ggctcacgcc tgtaatccca gcactttggg    66240
acgccaaggc aggaggatag cttgagccaa gcccaggagt ttgagaccag actgggcaac    66300
atagtgagac ccctatctct taaaaatttt ttaattagct gggggtggta gcacaggctt    66360
gtagtccccg ctactcagga ggctgaggca ggaggattgc ttgagcccag gaggtcaagg    66420
ctgcagtgag ccgtgatagt gccactacac tccagcccag cctgggcaac agggcaagat    66480
cctgtctcaa aaaacaaact aataaaaaac tcaaccagtc acgttttcct acccaggaat    66540
ttgaaaatgg accaagtgat ccaaacatga tggtttggac tctttcatgg cctcctgcta    66600
caggagaagg tcaggctggc tacattgttc ctgctgattt cccaaatccc ctcttctggc    66660
cccctgttga ttatctgagt ttcctaaaaa tcccttttat gcctaagata gccggtcagt    66720
gtttggtttt gcaatcaaga acccagactg ggccaggcac ggtggcccac gcctgtaatc    66780
ccagcacttt gggaggccga ggcgggcaga tcatgagatc aggagatcga gaccatcctg    66840
gctaacgtgg tgaaaccccg tctctactaa aatacaaaa caaaaaaaaa aaaattagcc    66900
aggcatgatg gcggtcacct gtagtcccag ctactgggga ggctgaggca ggagaatggc    66960
gtgaacccgg gaggcggagc ttgcagtgag ctgagatggc accactgcac tccagcctgg    67020
gcgacagaac gagactccgt caaaaaaaaa aaagaaaaa agaagaaccc agaacccaga    67080
ctgatcctga gacaaagatt tgagggcaac gaatcacgag gtcaggaaat cgagaccatc    67140
ctggctaaca tggtgaaacc ccgtctttat taaaaataca acaaattagc tgagcgtggt    67200
ggtgggcgcc tgtagtccca gctactcggg aggctgagga aggagaatgg cgtgaacctg    67260
ggaggcggag cttgcaataa gccaagatcg caccactgca ctccagcctg ggtgacagag    67320
caagactcca tctcaaaaaa aaaaaaaaaa aatttgagga caagtggttt gtttggcaat    67380
accaggaaac aggggaacag gatagtcaga aagaaagag aaagctgggc atggtggctc    67440
actcctgtaa tctcagcact ttgggaggcc aaggcaggtg gatcacctga ggtcaggagt    67500
ttgagaccag cctggccaac atggtgaaat cccgtctctg ctaaaaatat aaaaattagt    67560
cgggtgtggt ggcgtgcacc tataatcaaa ataaaataaa atcaggatat tttatttaa    67620 aactctgtct tagtgtaact catatttacc tcttctgtat gctcctttgc atcagttata    67680
tattgccata atacggctgt gtaacaaaca atccccaaga cccagtggct tataatgaca    67740
agcatttatt tagctcatga ttctgaaggg tggcagttta ggctgggccc agttgggtgc    67800
tttatctggt ctcagttgag ctcattcatg catctttggt cagctgcggg tcagctgggt    67860
ggctcttctg tttggctgtt agctggctgc agactggtcc aggatgacct cggctggaat    67920
gactgtgctc cactccctat ggtctttcac cctccagcag gctagcctga gctagttcac    67980
atggcagctt ttcatcctcc agcaggctag cctgagctag ttcacgtggc agcaatggga    68040
ttctaagaga aagaggaagt gttcagcctt cttaagggct agtcccagga atggcacaac    68100
atcgtgttgg ccactgttgt ccaaagcaag caatgaagct ggtccagatt caaggaatgg    68160
ggcaacagag cccatctggt atttacctgg ggccactggg gccccattcc tgttccctgg    68220
ggccttttgc cctgacttct gtgggccctc agagcatatt tcagattcc tttccatccc    68280 tgaccctcag caatcaatgt agatgacgtg tcattactgt gtcacttgca cagagaaaag    68340
gaggaaaaaa tgtcagcaaa aactctgctg agagcagagg gccatcata cagcaagctg    68400 gaaagaaaag tgggaatgat tacacagcct cctcagatgc ttccagcttt tatcaaatct    68460
```

```
cactgtgata tctgagttct gaaccctcac aggtggttgg cgtgcaaggg aagagatttc   68520
ttgtctgcca tgctgacatg cacagacacg caacctggct ccctctgtcc actgggcttt   68580 tggatttttgt ttgttgaaat gttacccact cctgatcaga gctggatgga aacctggctc   68640
tgattccatt ggctcagggg ctcagtgggg ggcagaggcc aggctggttg ggtgtctatg   68700
tggagacctt aactcttctc cctcccgccc caactctttt tgtttctttt ttttttttttt   68760 ttttttttttg agatggggtt tcactcttgt tgcccaggct ggagtgcagt ggcgtgatct   68820
tggctcactg caacttctgc ctcctgggtt caagcaattc tcccacctca gcctcctgag   68880
tagctgggat tacaggagca cgccaccata cctggctaat ttttgtattt ttagtagaga   68940
cagggtttcg ccatgttggc caggctggtc ttgaactcct gacctcaggt gatccaccct   69000
cctcagcctc ccaaaatgct gggattagag gcgtgagcca ccacacctgg ccctttctt   69060 ttcttagctg cctccacctc tcttcccttc tgcagtgtta ggtttatgga aaccgaggcc   69120
ggcgtagaga tcaacttcag agagcatgaa ctgagcatct gctgggtctt agatcccttta   69180 catagcttat catcttcaaa ccttctcaca gttctgtgtg gctagagcca ggatttggac   69240
acagctctgc cccactgtag aaccaggctt ccttctgtcc actgtcaaat tttagaggga   69300
gaaaataggg aaagggacac cagccttctc cacgagcagc ttctgcccac tcaccccagg   69360
gactttgcac atgctgtgtg cctgtgtctg agatatgctc cctcctctgt atctgcttaa   69420
ttcttaccca gacatgatac ataaagtatt taacatccag gtggcaggga caccagctaa   69480
cctgaaaaga ggttcccctg ttgtgccaca tgtgtactca ttgtttgctg cattgtgggg   69540
gcagtccagg ggccttgaag aggggccaag gtgccaaagg ggcactctca ggcctcaagg   69600
aagtacatgt ttactgatat gatactgtct cttcctccag gaaggaagcc ttccctgatc   69660
tccccactgc atgcccacta tgataccagt ttaggtcccc tctttatggc catctgtggc   69720
atcagtgtga atcctcttaa tgttgtctat ttggttaatc atctgtctcc ttcctctggg   69780
gggtaaagac agaaccacag agcctcgtgt agaacttgag aatgggggttc agtaaaaatc   69840 tgttgaatgc ataaatgggt gattgagtga atgaatgaat gagtgaatga atgagtgagt   69900
ggatgaatga atgagtgaat gaatgagtga gtgaatgaat gaatgagtga attaatgaat   69960
gaattcatag ctgataatac aggcttcatg gcttttgtta ggcttgccca gacattgcta   70020
ggggatggac agaaggaaga agagctatac ttaattccag tcctgttgtt ctgtagcagg   70080
aggagaaaaa cagggactgc ccagcctgct ctgggtggat tcaggagcag ctgaggttcc   70140
tctcttattt gcaaacaggg aattcaaaaa gccccaacct cagaatcaca ctcgcctcag   70200
cagctgtacc agccaagggg acaatgtggg aagccttggg caccaggaat gctgagtgct   70260
tcgaaaaagc gaaggctcag ggaacaatcc ctgattttc attcccttgt cctttctgaa   70320
gaaacaggca aaggcaggcc aggcacggtg gctcacacct gtaatcccaa cactttagga   70380
ggccgaggct ggtgaatcac ttgaggtcag gagttcaaga ccagcgtagc caacatcatg   70440
aaatcccatc tctactaaaa atacaaaaat tagctgggtt tggtggtgca tccctgtaat   70500
ctcagctact cgggaggctg aggcatgaga atcacctgaa ctggggaggt ggaggttgca   70560
gtgagctgag tctgcgccac tgcactccag cctggatgac agagtgagac tccatcttaa   70620
aacaaaacaa aacaaaaaca agtaaagcct tgtgtgtttt taaattgtag gttcagcagc   70680
aaagctctgt aataaggagc tggaccctgc agtcagacag tcatgggctt ctccagtgcc   70740
cagccgagtg acccgaggga gttatgataa acaccaacat tcatccacaa tttgtaccta   70800
```

```
gtgctattct caatatcttg agtaaattat ctcatttaat cctccaggca catctttctt    70860
ggtaggtgcc gtcattgtcc ccagtgtaca tctgggaaaa tgaggacagg ctggcagagc    70920
acccttcctg ctcacctctg ctgctctgct gacctctggc aagactgttg tctctctgag    70980
cctcagtttc cccatctgaa aattggggcc tgtattagcc cgttctcaca ttgctataac    71040
gagatgcttg gctggggctg ggcgtgatgg cttatgcttg taatcccagc actttgggag    71100
gctgagttgg gcagattggg agtgtgagac cagcttgggc aatatagcaa gaccccatct    71160
cttctaaaaa aaaaaaaaaa ttagccaggc atggtgatat gcacctgtaa ttccagctac    71220
ccaggaggct gaggcaggag aattgcttga acccaggagg cagaggttgc agtgagccaa    71280
gattgcgcca ctgcactcca gcctgggaga cagagtgaga ctccatctca aaaacaaat    71340 tatttttaaa aaattaaaaa aaaaaatgcc tggctgggca cagtggctca cacccataat    71400
cccagtactt tgggaggcca aggtgggaag attgcttgag cccaggagtt ccagaccagc    71460
ctgggcaaca cagtgaaatc ctgtctctac taaaagtaca aaaattagcc aggtgtggtg    71520
gcacgcgcct gtggtcccag ctactcagga gggtgaggtg ggaggattgc ttaagcctgg    71580
gaggtcaagg ctgcagtgag caatgattat gccactgcac tccagcctgg gcgacagagt    71640
gagaccttgt aaaaataata ataataataa taaataaata aaaaccctga gactgggta   71700 atttataaag aaaagaggtt taattgactc acgattctgc aggctctaca gaaagcatgg    71760
cagcatctgc tcagcttctg ggaaggcctc aggaaactta caatcatggc agaaggtaaa    71820
gctggagcag gtgtcctcac atggccagaa caggaggaag agagagagtg gggagatgct    71880 acacacccttt aaatgtccaa tctcacaaga actcactcac gatctcgaga atagcaccaa    71940
ggcggaaatc tgcccccatg atccaattac cttccaccag gccccacctc caacattggg    72000
gattacaatt cgcctaaaga tttggttgcg gacagacaca gatccaaagt acattaaaag    72060
taatggcaaa aaccacaatt acttttgcac caacctaata tctcaggggc tcattgtacc    72120
tatttcacag gacaaatgaa ggtatcagta ataacagtag cctgtagtcc cagctattca    72180
ggaggccgag acaggaggat cacttgaacc caggaggtcg aggctgcagt gagctatgat    72240
cacgccactg cactgcaccc tgggtgacag ggcgaaaact tatctctaaa aataataata    72300
acaacaacaa tagtgaacac agatataaca tgtgtgtggc caggctgtgc ccttagggct    72360
ttgcagggat tatttcattc actctcaatc tccccatttt acagatgaga aaactgacgt    72420
tcagaaaagc tagaggactt gccccaagcc acacggctag gaagtggtgg aattggggtt    72480
taaatgagga agcttgactt cagtgtcgaa gctcttaact gccacactca atacatggag    72540
tagaggttgc tgattctgtg attatctgat tctggaaagt aaagaccctg tttccagacg    72600
tttgctgctt gacttagttc caggggatg ccactggat gatgcagtgt tgcccaggag    72660
aggttagcta gacacactgc aaccattcca ttgctaatac ttatacttgc tcttgttctg    72720
ctgggtgcta tgcagggaag gctgtctga gccctttgca agaattctcc cattggtgcc    72780
tcccagagat tctgaggttg gggctttttg catcccttat tagcagatga gacaccaaag    72840
cccaggtcaa taatctgacc tgcatccccc gcctaccagc cagaccaagg tcacttcccc    72900
acaatgcagg ccctgatcca aggctctggg tgcaaaccag tttccatgtc ctgggggtc    72960 catcttcttc agctgacttt tttttttttt tttttttttt gagacagcgt cttgctttgt    73020
tgccgaggct ggagtgcagt ggtgtgatca tggcttattg cagccttgac ctcccaggct    73080
caagcaatcc tcccacgtca gcctcctgag tagctaggac tatgggcaca cgccatgatg    73140
cctgggtaat tttttttttt ttttttttga cacagagtct cgcactgtag cccaggctgg    73200
```

```
agtgcagtgg cgcaatctcg gctcactgca agccccatct cccaggttca tgccattctc   73260
ctgcctcagc ctctcgagta gctgggatta caggtgcctg ctacctcgcc tggctaattt   73320
tttgtatttt tagtagagac ggggtttcac cgtgttagcc aggatggtct ccatctcctg   73380
acttcgtgat ccgcccacct cagcctccca aagcgctggg attacaggca tgagccagat   73440
gcctggctaa ttttaagtt tttttataaa ggcggggtct tgctatgttg cccaagctgg   73500
tctcaaactc ctggcctcaa aaagtcttcc tgcctcagcc tcccaaagtg ctaggattac   73560
agacatgagc cactgcaccc agcctgactt tttttctaac tgaaaaatta attatatata   73620
ttcatggagt acaatgggat gttctgatat atgtttacat ttttgaatga ttaaatcaag   73680
ccaattaaca tatccactac atcgcatact tatttttgt ggtgagaacg cttaaaatct   73740
actcttttag caattttgaa atatacaata ccttatgttg tatattacat tatgttgtat   73800
agtacgttga aacatacact acaatacgtt atcattaatt gtggtcacca tgctgtgcaa   73860
aagatctcta aaacgtattc ctcctgtctg actgaaactt tgtatccttt gcctaatatc   73920
tccccaatcc ctccaccacc agccctggt aaccaccatt ctctctgctt ccatgggttc   73980 aaattttta tttttgaaa ttttaatt tatttattt atttatttat ttatttattt   74040 attttgaga tggagtctcg ctctgtcacc cagtctggag tgcaatggtg ccatcttggc   74100
tcactgcaac ctccgcctcc tgggttcaag cgattctcca gcctcagcct cccgagtagc   74160
tggggttaca ggtgcttgcc accaggcccg gctaattttt gtatttttag tagagacggg   74220
gtttcaccat gttggctagg ctggtctgga actcctgacc tccagtgatc cacccacctc   74280
ggcctcccaa agtgctgaga ttacaagcgt tgagccactg cacctggcct aaaatttttt   74340
tttttttttt tttttttgag acggagtctc actctcttgc taggctggag tgcagtggca   74400
tgatctcagc ccactgcaac ctcagcctcc cgggttcaag cgattctcct gcctcagcct   74460
cctgagtagc tgggactaga ggtgtgcacc accacgccca gctaattttt gtattttag   74520 tagggacagg gtttcaccat gttggccagg atggtgtcaa tctcttgatc tcgtgatctg   74580
cctgcctcgg gcttccaaag tgatgggatt atgggccacc acgcccggcc tcaaatttt   74640 tagagctcac atataagcga gattgtgtac tatttgcgtt tctgtgtctg gcttgtttca   74700
tcttagtata atgtcctcca ggttcatgca cgttgtcgca aaagatggaa tttgctcctt   74760
tttaaagact gaatagtact tcattgtgta catatacacg ccatattttc ttcatccatt   74820
cctttactga tggacatttg ggttgtacct gcatcttggc tattgtgaag agtgctgtca   74880
tgaacatggg tgtgcagctg actctgaggt gttagaggga ttacagctcc tccaaaagac   74940
caccgtcacc caaacctgct cctcctgccc tattttctgt ttaggtaaag gcggctttaa   75000 cccctgcag tgctctggcc tcagacctcc agatcttcct ctatgcctct atgcctcttt   75060
ttctccaccc cctgcatcca atctgttagc acatcttatt ggctctacct tcagaatcta   75120
cccagaatcc accacccacc tctcaccacc ttcacagccc caccccggtc cagccccat   75180 ctttgctggc ctggactaaa ccagttgccc ctccacccca atctggtctc ttaacttcag   75240
tccttgcccc accccagga ctgttcccca cacagcagcc agagggcacc tgtgagccac   75300
tgagtcagga cctggctcct ctttgctcac aacctcactt ggagaaaaag cccaaattct   75360
cctcacaggg acccacaaac tctgcccctg tgatccccca tcccctcta ttcccactct   75420 cctctccact cactcggctt cagctacaca agttccctgc tgtcccttac acaccaagca   75480
ctccccagcc tcagggcctt tgcacaggct gttccctctg cctggaacac tcttccccca   75540
```

```
gatatctgct tggctccccc ctcacttcct ttgggtcttt gctcaagtgt ccttctaaca    75600
tgtaactgcc tcacctgcac tgtgccaccc cactccccgc ctctaggctt aatttccctc    75660
tacacccctg aagagcatct gccaagctat atttacttgt ttattggtta ttgccaatcc    75720
cctgccccca ctagaatgcc agctccatga gggcagggac ttctgtctgt tttgttcact    75780
gctattcccc cagagcctag aacacagcct ggcacatagt aagtattcac taaataattt    75840
gtaatatgaa ttgtgccagt aaaatcttcc aggggcatca agccctgcc atgactaggt     75900
ggtaacatcc tcaccccctg tccatgtgct atctcctcct gacctgcttg tctcattgtt    75960
ctaatggtgg ctcacgcctg taatcccagc acttggggag gccgaggcgg gcagatacct    76020
gagttcagga gtttgagacc agcctggcca acatgatgaa accctgtctc tactaaaaat    76080
acaaaaatta gctgggcgtg gcattgcacg cctgtagtcc tagctactcg agaggctgag    76140
gcaggagaat cgcttgaacc cgggaggtgg aggttgcagt gagctgagat catgccattg    76200
caatccagcc tgggccacaa gagcgaaact ctgtctcaaa aaatatatat atatatttca    76260
ttgtggtaac atatgcataa cataaaatgt accatttttt aagtgtttag ttgagcggcg    76320
ttaagtacat tcatattgtt gtgcaaccag gaccgccatc catctccaga acttttgcat    76380
cttgcaaaac tgaagctctg cccccaggaa actctcactc cccgctcccc cttccctct    76440
ccccgactcc cccttccccc ctccccactc cccccaccct actccacact ccccactccc    76500
ccagcccctg gcacccgccg ttctagtttc tatctctgtg aatttggcta ctttgggtcc    76560
cccctgtgag tagaatcata cagtatttgt ctttttgtga ctggtttgtt tcgtggagca    76620
taatgtcctc cagtctcatc catattgtag catgagtcag aatttccttc ttttccaggc    76680
cgaatcgtat tccattgtgt ggatggacca cactttgctt atctgttcat ccagatgggc    76740
acttggcttc cacctttggg ctattgtaaa taatgctgct gtaaacctgt gtgtacaaat    76800
agctgagtcc ctgctttcaa ttcttttgga tatagaccca gaagtggaat tttttttaaa    76860
tcaagatttg acccactggg gcccttagag gtctcattgg ctctgaagct tttttttttt    76920
tttttttttg gacgctttga aactaaaaat aggagtgagg ggcacagtga gggggggcaca    76980
catctctcgt gtcagcgttt tttaaaaaca ccccgggagg aagatgtgtg aaatccctcc    77040
cttccccccg ctcccacccc ctccaagatc tcaaaatacc tcttgtttta ggaagcggct    77100
gtgcatcag gcaggcagcg tgtggcatct gagacacaat atcgcaagtg ctgggagcc     77160
cagagaaacc aggacaggcg tgctggggat gtggactaga gatggagcta attttagtgg    77220
ctgaagaggc tgcaagaaga gagagaaaga ggggtgtgtg tgtgtgtgtg tgtgtgtgtg    77280
tgtgtgtgtg tgtacgcaca gtgatagagg ctggagggg agaaatgaca gataaatcag     77340
cttgggcaaa gaaagctaat gggcagagga gcgagaccca gctcagaagg tggtcagcaa    77400
atctaaagat gtgtgcccga gggtcaaggt ggtgggggga ttcataggca agtggtagag    77460
aggctattcc atttgcagag gctctctctg tttgaggcgt gattcacctg tgccgtcctc    77520
aaggccattc tgagaacacc actgttgttt tcctccttt atgagtaggg aaactgaggc      77580
attgaactgc ttctattctt cagtaagaag caggggaac atatggtaga agcaaagaaa      77640
tacaaacatg agggctctcg gggtctacgt gattggctgt gacatccatg agagcggatc    77700
gcaggttgaa ggaaacactg gtggcagaaa gtagctgaac atttggattt gggaatccca    77760
gtggacgtgg cgaaaattct ggcttttccc ttcacaggct gcggggccac tctgacctgc    77820
ggtttcctta tctgtgaaat ggaacgatgc cacctgtctc agcgttgttt tgaggatgcg    77880
aggagatgat ccgtgtaata tgcccactag ggggcctgct ccagggtaga ttctcagcaa    77940
```

```
atggtagtca tggtttttgt tacatttggg gatattggca ggtaaaaagg aaatacttca   78000
ttcattccaa aattgctcac tgaggttcta ctatgtgcta ggccctgatg acacatcggt   78060
caacaagaca ggcctgcttt ctgcccttgt aaaacttcag ttcaactgca ttgcactcat   78120
cagcctaata atccaggtaa attgtgatga gaataacaac tagcatttac tatgagccct   78180
ttacaaatat taacccattt aatcttctaa agagcctata agataagagc tcttgccctg   78240
cgcagtggct cacgcctata atcccagcac gtcgtgaggc caaggcaggt ggatcacctg   78300
aggtcaggag ttcaagaata gcctgaccaa cagggtgaaa ccctgtctct gctaataata   78360
caaaaattag ccaggcatgg tggcaggtgc ctgtaatccc agctacttgg ctgaggtagg   78420
agaatcgctt gaacccagga ggcggaggtt gcagtgagtc gagatcactc cactgcactc   78480
caagagtgaa actctgtcac acacacaaaa aaaaacaacc tgttattatc cacattttac   78540
ctatgaggaa accgatgccc agagaggtta agtaactgtc caaaggtcac acagctacgg   78600
agtggtagac ctgggattca gacccaggag tgtgatccca gagtgtgtgt gtatgtttgt   78660
ttgtttgttt gtttgtttgt tgttttttac cactgtgttt tcctgcttct gcaatagaag   78720
taatcaccag taacactgag cagttgttat gtgccatgcc cttaacacac atctccttgg   78780
atctttggaa agaatcctaa aagggttgtt tttcatgatc cacattttat ggagagagag   78840
agatcaaagc atagagagag gaagtaactt gcccaagatc ctgcagctga agactctagg   78900
gttgcaaatt tgggacggcc ctggaccctg cattccagct tctagcagct catagggggaa   78960 actctttatt tatttatta tttatttatt tattatttat tttatttttga gatggagttt   79020 cgctcttctt gcccagcctg gaatgcaatg gcatgatctc ggctcactgc aacctccgcc   79080
tcctgggttc aagtgattct cctgcctcag cctcctgagt agctgagatt acaggcatat   79140
gccaccacgc ctggctaatt taattttttt tagtagagac ggggtttctc catgttggtc   79200
aggctggtct cgaactcctg acctcaggtg atccgcccat ctcggccccc caaagtgcta   79260
ggaatacagg cctgagccac cacgcatgcc ctggggggga ccacttttat cggtgcattt   79320
cttccatttt ccctgtgtct gtgtaaagat aaacaccccc aagcccctttg actatgaact   79380 gtgggccata attagttaat ggaaggtaaa tgttttagag acggaaattg ctgtgccatt   79440
tttccccgct aggcattgtt gcctgcatgc taatgcaaca caatgtgcct ttcttctgtc   79500 aggcatttt agacaaattc tattttccct aaaatatttt gccaaagaaa atagcaaatg   79560
gggaagacat tcagaggctc aggcagagag aggacaccat tcccttgggt ttaaacagaa   79620
tggcagagtg gataacagca cagatcttga gttaggtgga tgccaatttg tgatttattt   79680
cccagcaaac caagatgctg gctctctgtg tgcctcagtt tacttatttg tcaaatgagg   79740
agaataatgg tacctgtctc tcaccagctt accagttgcc tctttagcta tgtctaatct   79800
gctattaacc acgcccacta tgtctttaat tccaagtatt agaattgttt cttcctaca   79860 agctgtctga tctttttaa tcctgcttca tcttttgcag tattgttttc ctacagcagg   79920
atttctcaac cttggcacaa ttgacatttt gggctaggta attcttggcc gtgagctacc   79980
accctgtgct aagatactta gagcatccct ggcctctcac cctactaaat gccagtagca   80040
gcccctcccc agttgtggca gccaaaaatg gctcagacat tgccaaacga aatgtcccat   80100
ggagggtaga aacgccccca cttgagaatt gttctatagg tattttcaag catgtcttac   80160
atttctttaa gtataatatg caaagaaaa ggctaaatct aaaaaagcc cataaatgc   80220 gaagaaattttt tataatcagt gtccaataac ttaagtatct aaaattgtta tggctttttt   80280
```

```
tctgctgtct cttgtttcct gtgattcctc attctggtgc cttgttttct tgaatgtctt    80340
gttatctttg gttgtgtgaa gctcattttc catgggacac tattttttgt tttgttttgt    80400
tttgagacag agtctcgctt ggttgcccag gctggagtgc agtggtgcaa tatcagttca    80460
ctacaacctc agcctcccag gcccaaatga ttctcctgcc tcagcctcct gagtagctgg    80520
gattacaggc gtgtgccacc acacccagct aattttttg tatttttagt agaggcaggg    80580
tttcaccacg ttggccaggc tggttttgaa ctcctgacct caagtgatca acccgcctcg    80640
gccccccaaa gtgctgggat tacaggtgtg agccaccgtg cccggcatcc atgggacact    80700
gttgaaggga gttcattgag gcctgcgatg aaggcgaacc ctccatggac aatttgcatt    80760 tacttttcc aggtgtctgg gaaactccca gtctaggacc atcttagact tttagaccaa    80820
caatgtgttg agaatttagg tcaccagtgt ctgcaaaagc cagcttgtgg ttataatttc    80880
tcaaaaactt ttgttttct cctttctgc aaagtgccaa agtaacttcc tcaaaaatct    80940 ctggaatgg aaagacggga gtaaattaac ttcaggtttc ttacctgaaa gtgatagcct    81000 attgggccc catcctactt ggggagtggt gtgtctcctt tgagactttc taacacgtgt    81060
gtaccctgga ctttgcccca cccctgctcc ctaggaggcc ataaaacttg aagcagcagt    81120
tccatgggtt agacagatgc ccttggggca aaagtggttt taatgctctg gtagatgctc    81180
aggttacctc tgggaaattc ttgacttcac ttatttattt ggggctgata actactaatt    81240
gtcaggcctt tcttgtttca acaacatgga cttcagattt tatgcaggat ttgtcatcgt    81300
tttcagcaag agagtcagtc ttattaccca gcttactgca ttagaaatag atgtctgggc    81360
caggcgcagt ggctcacacc tgtaatccca gctgtttggg aggctaaggt gggcggatca    81420
tgaggtcagg agttcgagac cagcctggcc aacatggtaa accccatctc tactaaga    81480 tagaaaaaat tagctgggtg tggtggtgcg tgcctgtaat cccagctact tgggaggctg    81540
aggcaggaga attgcttgaa cccgggaggc agaggttgca gtgagccaag atcgcaccac    81600
tgcactccag cctgggtgac aggacgagac tctgtctcaa aaaagaaat agatgtctgt    81660 tgtgtggatt atttaaaaga gtagatggcc aagaactatg acttatgcct gtcatctcag    81720
cactttgaga ggctaaggtg gagggatcac ttgaggccat gagttagaga ccagcctggg    81780
aaacatagca agaccccat ctctgcaaaa gtaaaataaa ataagttagt gtgcatgatg    81840
gtgcaggcat acctctagtc ctagctactc aggaggctga ggcaggagga tcacttgagc    81900
ctaggagttt gaggctacag tgatctatga tcatgccact gcactccagc ctgggtgaca    81960
gatcaagacc ctgcctctaa aacataaaaa taaatacaaa ttaagttaaa aaataaaata    82020
aataagtaat agaacatcca gcacagttct tggcatgcat tgactgttgt tgtttgtttg    82080
tttgtttgtt tgtgacggag tctcactctt gttgcccagg ctggagtgca atggcatgat    82140
cttggctcat cataacttcc acctcccagg ttcaggtgat tctcctactt cagcctcctg    82200
agtagctggg attacaggca cgtgccacca ctcctagctg tttgttttg tttgtttgtt    82260 tgttttgtat tttagtaga gatgggtt ctccaagttg gtcaggctgg tctcaaactc    82320
ctgacctcag gcgatctgcc agcctcggcc tcccaaagtg ctgagattac agacgtaagc    82380
caccacgcct ggccagctgt tttgattgtt aaatgaaggt ggtatgaaag ggaaggaaga    82440
acagtgacat ttgcaaggga cactccctgg agggcagggc aaggggggctg tggagggag    82500 aagtcagaga gtatgataca ggttgccttg ggtgatgttt tagattttag ccaacattgg    82560
caaagagcct catttatctc tcagagtagc tctggctact ggaaatgctg cacaacttca    82620
ggcggacttt ctagaagaaa actcttggcc aggtgcagtg actcacacct gtaatcccaa    82680
```

```
cactttggga ggctgaggca ggtggatcac ttgagctcaa gagtttgaga ccagactggg    82740
caacgtggca aaacctcatc tctacaaaaa aaaatacaaa aattaaccag gcgtggtggt    82800
gcatgcctgt atcccagcta cttgggaggc tgaggtggga ggattgcttg agcctgggga    82860
ggtggaggtg gtagtgagcc aagattgcac cactgcactc ccatttgagt gacagagcaa    82920
gaccttgtct caaaaagaa aaaagaaaa gaaagaaaa gaaaattctc tctgggattc    82980
aatcctggcc cacacagcat tggcttcact tcacctcctt ctcccctgag atacacagca    83040
ccattccccc aagcttcatc aacttaatct ctgatctggg tgctgtgact tgtccccatt    83100
cctggccaga atttaaggta gggatgaacc cactagccct ccatcacgca ctctgccata    83160
aaagcacacc acgtgctgat tgctgtcttt ggtctccttt ctgccttgcc ctctagactc    83220
tgagctgctt ggagacagag gccagttttg tccatctcca aatcccctaa agtcctgtgg    83280
ccagcaagca ggtaggacat ctgaaagttc gtcagagagg gaattgcttt tctcttgaga    83340
tgcaactaga acaagaatct tattgacctg gagtagcttc aaggttgtaa gagtatgtgt    83400
cagggttctc caagaccact ctcaggtttg aaggtttgct aaaagggctc acgggaccca    83460
gaaaagctgt gaaattcagt tatggtttat tacagtggaa gaatacagat aatacagatt    83520
aaaatctgca aagcaaaaga tgcacaaggc aatgtccagg ggagatcagg catgagcttc    83580
cagctgttca ctcccagtgg agttatgcaa acagtgctca attctcccag caatggtgtg    83640
tgacaatgta cagtgtaccg ccaaccagag aagctcacct gagccttggt gtccagggtt    83700
tttattgggg ctcagttaca ttgacatgga gcacccatgt gactgacttt aactgctggg    83760
tctccagcac actccaagat caaactgata ccgtgtgtcc cagggcccca gctgaacaca    83820
aacaggcagt caccatagat cccattgtga gcataagcta ccaggcatgg cccaaagccc    83880
tagatataca gatattcttt ccaggagcca gccaagggcc agtccttcct ttggaatatg    83940
cagagtttga actccccaac cccaaggagt taactcttta ctacacagaa tataaatctc    84000
accaagtctt tcttcttgtc aagtcctctc aaggtgaccc attgctttta gcagtgtctt    84060
tgagaccctg cgtcatctgg ccttgaccca tatcacctgt gttatctctc cactctagct    84120
acattgaact tttcttttt gagatgtggt ctcactccat cacccaggct gaagtgcagt    84180
ggtacagtca cagctcactg cagcctcaaa ctcctgggct caagtgatcc tcccacctca    84240
gcctcctgag tagctgagcc cacaggtgca tgccattaca cccagctaat attttattt    84300 ttagtaaaga tgggttctca ctatgtttcc caggttggtc tcaaactcct gggctcaagc    84360
agtcctccca tcttggcctc ccaaagtatt ggcattacag gggttagcca ccacatccag    84420
cccattgaac tttttaagga tccctagca tcctatactt tctgtcactg gatagccttg    84480
gaattatttt tccttctttt tgaaatactc ttcttctttc cacccttgc tgtcaagtct    84540 cagaataggc attatttcct ccaaaaaccc tctcctgacc ctccaaatct ggatgaggac    84600
acttcctttg cccagagagc acctgttta atcctctcag gtggctataa taaaatacct    84660
taaactgggt ggcttataca cctcagaaat ttattttcca cagttctgga ggctgggaag    84720
atcaaggcac tgacagattt ggtgtctgat gaggggccat tcttgttc gtagaagggg    84780 tcttcctact gcatctttcc atggtgaaaa gagttgaggc agctctctga aacctctttc    84840
atgagagcat gaatccctct gtcttcatga tctaatcacc tcccaaaggc cccacttcct    84900
aatatcttca cattggtgac taggtttcaa catatgaatt tgagaaagac acagacattc    84960
agaccatagc agtgctcttc caccaggttt tttatccccc tgtattataa ttgaggttta    85020
```

```
aattatctgc tttccttccc ttagattgta agctccatga gagcagggcc ctacccatcc    85080
agtcattgtc ctatcccca tgactacaac ttcctgggta cataattaat atttattata    85140
ttatgtagca aaggtatgct gccatactaa gagacccaaa aggccaccgg attaaaacct    85200
taaagaaaaa aaaataattt ctctcctata atagctgcaa ggttagccat gcaggttggc    85260
agggaagctc acttccacaa agtcactcag ggattcaggc tcctgttgcc ctcttctttt    85320
ctaccaccaa atgatcttca gcaccatttg cacaatcaaa acttaactgg tcttgaatag    85380
gcagaccttg aatttctgaa gtctcagacc caaaagtggc agctgtcact tccactgaca    85440
tatcactgat ggaaacttaa tcatgtgatc ataccaaact gctagggatg ctgggaaatg    85500
tagttttgtt gggaactcca tgacttggct aaaattccat tactgtagaa gatggtgggg    85560
gatgggggag tggtggacat ccagtggttg ctaccatatt tattgaatca aattgtcaaa    85620
caggacctat ctgataaggg gttctttttcc agaattaact gaagtattaa atcagggca    85680 aaggcatgtc acctcatctt tctctcccta tattggcttt ctagggctgt tataacagag    85740
taacatgaac ttgcggctt aaaacaacag aaatttattt tctcttagtt ctggaggcta    85800
gaagcctaaa atcaaggtgt cagcagagcc accttgacaa ctgctctagg aaagaattct    85860
tccttgcctc ttctggtggc tcctggcaac ccttggtatt ctttgtctgg catccacttc    85920
aatctctgcc tccatcttca tttgcctttt ttctctgtgt gtctatgtcc tttcctcttc    85980
ttagaaggat accagtcatt gaatttaggg cttactctaa atccaggatg atctcacctc    86040
aagatcctta attagttaca tctgcaaaga gcttatttca aaacaagatt gcattctgag    86100
gtttcggtaa acacgaattt gggggaaata gtattcaact caattcactg ctttacttaa    86160
gaaaagagac catgaagtga gcctccttct gcttgagaga gagagcgagc ctttctgtgc    86220
aataggtcaa tgaatggatg cagctgaatt ccacataact ttataaaaat agatggccag    86280
cccatggggt ttgctgaccc ctgcccaaaa attccaaagt caacagcagt ctcttttta    86340 atcatttctc tattttttaa tttattttta ttttatgtt gagatagagt cccgctctgt    86400
cgcccaggct ggagtgtagt agtctcggct cactgcaacc tctaccttcc agatacaagt    86460
gattctcctg cctcagtctc ctgagtggct aggagtacag gtgtccgcca ccatacccag    86520 ctaattttg tatttttaat agaaacaggg tttcaccatg ttggccaggc tggtctcgaa    86580
ctcctgacct caagtggtcc acccacctcg gcctcccaaa gtgctgggat tacaggcatg    86640
agccaccatg cccggccagg attttcttca ttttaacagc attcttactt gtcccacatc    86700
cattctatcc tgggtctaat tagataacaa aatctacaga tcttgtttaa ctgacattgt    86760
cctgggggat acttttatc ttttgagaca aggtctcact ctgttaccca ggctggagtg    86820
cagtggcctg ataacagctc actgcagcct cgaccacctg ggttcaagcg atcctcccac    86880
ctcagcctcc agagtagctg gaaccacaga tgcatgccac cacacctggc taattttaa    86940 atttcttgta gaggtggggt ctccctatgt taccaaaggc tggtctcaaa ctcctgggct    87000
caaaagagcc tcccaccta acctcccaaa gtgctgggat tacagatatg agccactgtt    87060
tccagccttg gaaatatagt ctaagaactg agtcaatagg cgattttgtc attgtgtgga    87120
catcatgtag agaacttaac acaaacctag atggtataaa ctactgcaca cctcagttat    87180
ggggcatacc ctattgcacc taggctgcaa acctgcacag caggttactg tcttgaatac    87240
tgtaggcagt tgtaacacaa tggtaagtat ttgtgtatct aaacatatct aggccgggca    87300
cggtggctca cgcctgtaat tccagatcac ctgaggtcag gagttcgagc ccagcctggc    87360
caacatggcg aaactcctttc tttactgaaa aatgcaaaaa ttagccaggt gtggtggcag    87420
```

```
gcacctgtaa tcccagctat tcgggaggct gaggcaggag aatcgcttga acctgggagg    87480
tggaggttgc agtgagctga gatcatgcca ctgcactcca gcctgggtga cagagcaaaa    87540
ctccatctca aaaaataaaa aataaaaaa catatctaaa cagaaaaggt acagtaaaaa     87600
tacagttata accatatggg accaccattg tataggcagt ccgctgttga tcaaaacata    87660
tcaaaacatc gttatgtagc acatgactgt accataaacc acacggcttc aaacaaggga    87720
aatgtattct ctcactgttt tggaggccat aggtctgaaa tcgaggtgtc accagggtcc    87780
ctccaaagga tccgggggag gatccttcca ttggatttgg agttgcttca ctccagtctc    87840
tgcctcagtg gtgacagggc gttctcctct tccctctcaa agttccctct tctgctgtgt    87900
cataaggata catatgactg catttaggcc ccactcagaa aatccaggaa taaactcttg    87960
ccctcatatt cttaactaaa tcgtacctgc ataccttatt ttttctaaat aaggtagcat    88020
tccagggatt aggacatcaa cataacttct ggagggttca ctgttcaacc cactacagcc    88080
agaatgcgct ttgaattcag gttctgacat ctgggactgc ctcccacgta cacacaccac    88140
taccttgtac tgaatgcctg aagggttctg cccccacctc cactccccca aatatttgct    88200
gtggacctga gaaagctgac ttcatggaag cttcattcca ttgttctaag gacttttcat    88260
acattaacaa atgtcttctc tctatgggga aaaccacaga gaaatcaaga cagagtgggg    88320
ttaagtaact cacctgagga ggaacagtaa gtggcagagc caggattcaa accaacatgg    88380
ttttgcacag ttttgacatc atttgcaaca caaatattgt cacagatacc ttttttgagca   88440 tctactgtgc taaccgccag gaaggaaaag aacatgggc cggagagct cttgacaggg      88500 gacagggctg gccatggagg tctgtgtctt ggtggaagat gctatggttc tctttttttt    88560
tttttttttt tgagatggag tcttgctctg tcacccaggc tggagtgcag tagtgcaatc    88620
ttagctcaca gcaacctcca cctcccgggt tcaagcgatt ctcctgcctc agcctcccaa    88680
atatctggga ttataggcac acaccaccac gcccagctaa ttttgtatt tttagtagag      88740 atgggttttc accatgtggg ccaggctggt ctcgatctcc tgaccttgtt gtgatccacc    88800
cgcctcggtc tcccaaagtg ctgggattac aggcatgagc caccactg ggcaactatg       88860 gttctctttt aactccttgt gctgaaatta ttgcagaagc ccaggccagt tcatcccag     88920 aaagtgaggc ataaacaggc agagctctac agaaacagag aatccacgac tggtttgatg    88980
gaggctgcct cactacctac agaatgggct ctgggtggat tgttctatct ggggagccag    89040
cccacccacc agtctcagcc cttggcgact cttcctgct gtcacagcag ctggacattc     89100
agaaaccgaa acatgacagc cttccctccc tgttcctgcc cagtggagtg gaaaccccctc    89160 gggacccaca taccgagcgt gcacagcagc acagagttgc acagttaaca cagcgcttct    89220
tctccagccc tccggatgca agctgacaga ttggcagctg gctgacttcc aaggtccagt    89280
gagttcttgg cagtcgcttt ctgacctgga cgagtggctg ccacctcctg gaacatcagg    89340 ctgcccctt ggggagaggg tgacggtctc tctggaaaga ctgtgagctt tgaggtggtc     89400
atcaaaagcc attcttggaa acattctttg agctgtaccg tgcaattcgg tcaccaattg    89460
cacgtatttg gatattaata tccgtatgtg gatattaaat tggttttggg ttttgttttg    89520
ttttgattgt ggcaaaatat acacaacaat cctcctgcct cagcctccca agtagctaca    89580
ggcatgcacc accataccca gctaattttt ggatttttta aatttgtttg tttgttttg     89640 tttttttgaga tggagtgtag cactgttgcc tgggctggag tgcagtggcg cgatctcagc    89700
tcactgccac ctccgcctcc tggattcaag tgattctctt gcctcagcct cctgagtagc    89760
```

| | |
|---|---|
| tgggattaca ggcgcccgcc aacacgccca gctaattttt tgtattttta gtagagatga | 89820 |
| ggttttacca tgtcggccag gcttgtctcg aactcctgac cttgtgatcc acccgcctca | 89880 |
| gcctcccaaa gtgctgggat tacaggtgtg agccaccgcg cccggccgat ttttgtagtt | 89940 |
| ttagtagaga cagggtttca ccatgttggc taggctggtc ccgaattcct gatctcaggt | 90000 |
| gatccaccgc ctcggcctcc cgaagtgcta ggattacagg catgagccac cgcacacagc | 90060 |
| ctaaatgctg tgcctcacgc ctgtaatccc aacactttgg taagctgagg ccagaggatt | 90120 |
| gcttgagccc aggagtttga ccagcctg gcaacatag aagacccca tctctataaa | 90180 |
| aaataaaaat aaattagcca ggcgtggtgg tgcaggcctg tggtcccagc tactcgggag | 90240 |
| gatgaggcag gaggatcgct tgagcccaag aggtcaaggc tgcagtgagc tgtgattgtg | 90300 |
| ccactgcact ccagcatggg tgaaagagca agaccttgtc tcaaaaaaaa ttaagcgaaa | 90360 |
| tttaaaattc tgtttctcac tcacacaggc tgcacttcaa gtgcttaatc atcccttgtg | 90420 |
| ggtggtggct atcatattgg acagcatgga tagagaatat ttttatcagc gtaggaagct | 90480 |
| tcatcagaga ggaccgctca gaggcctgtg gggaccagca cagtgcagta aagacacag | 90540 |
| gccagctggt gagagactgg tcttctgatc ccagatctgt ccctcacttg ctaggtgacc | 90600 |
| ttggacagct ccctcagtcc ctctggagtt ttctcttcat tgttaaatca ggaaattggc | 90660 |
| ctcagtgaat tctgaggccc catctacttt tttttttttt tttttttttt tttttttaat | 90720 |
| tgagacagag tctcgctctg ttgaccaggc tggagtgcag tggcatgatc ttggctcact | 90780 |
| gtaacctccg cctcccaggt tcaagcaatt ctctgcctca tcctcccag tagctgggac | 90840 |
| tacaggcgtg caccaccatg cctgggtaat ttttgtgttt tcagtagaga ccgggttttg | 90900 |
| ccatgttggc caggctggtc tcaaactccc aaccttgagt gatcctcccg cctcggcctc | 90960 |
| ccaaagtgct gggattacag gtgtgagcca ccacgcctgg cctcatctag ttctaaatgt | 91020 |
| tatgacccac tcagctctga agacaaggga ggaacatcct ctcagtctag ctctgacatg | 91080 |
| cagaagcctc tcaccctgtc ccccaggtca taaaggcagg cgtgttgtga agagcacaga | 91140 |
| atgggctgag aaaaatatgc agggattgcg tctatctccc ttccttccgc acgtttcctt | 91200 |
| gtcggcacca cctgcctcta ttccgcgccg cacacacacc cgccttctct ctgtctcgga | 91260 |
| ggaagacagg atcttccatc ccccaaatcc tgccctgatt cctactctga agcctctgcc | 91320 |
| ctgactcctt taagctccct gggaatacag cccatctcct atgccctcct catcccagta | 91380 |
| gttcctacct tccccaaaat cgctttggga aagtccccca atgagtaacc agctgtccta | 91440 |
| catgggcatc tcagaacttc tcttctgttg ttgttgttgt ttgttttgct tttgttttga | 91500 |
| gacaggatct ctcttttca cccaggctcg agtgcagagg tgtgatctca gctcactgta | 91560 |
| gccttgacct cccaggctca ggcgatcctc ccccctcagc ctctggaata gctgggacta | 91620 |
| caggcacacg ccaccacacc cgggcaaatt tttttagga cttttggtag aaatggagtt | 91680 |
| tcgccgtgtt gcccaggctg gtctctaact cctgggctca agcgatccgc ccacttggt | 91740 |
| ctctcaaagt gctgggacta cagacatgag ccaccacacc cggcagagct tctatttctt | 91800 |
| gagtgtgttc tcagccatgc taagacattt tctcttctca gcctgatgat gcttttggct | 91860 |
| tgtgtttctt tgttttaat tacccccttcc cagtcgctgt catgggatca tgagggtctt | 91920 |
| ctgtccatct agatgacacc tttcttgtgc cacgtgtctc caacattccc tggtttttaa | 91980 |
| acccttattg ctttcaagat actatccaag ctccttaatg tggcacattg tccttcgctg | 92040 |
| ctatctgcct gctttttttt tgagacagag cctcgctcta ttgcctaggc tggagtgcag | 92100 |
| tggcgcaatc acagcttact ctgcagcctc gacttcttgg gctcaagcaa tcctcctgcc | 92160 |

```
tcagccttct gagtagctgg gaccacaggc atgcaccatc atgccttggct aatttatttt    92220 tatttatttt tatagagaag gagtctccct atgttgccca ggctggtctc aaactcccgg    92280
actcaaagtt cattgcagtt tcaattttt ccttggctca aggatcctcc cacttcagcc     92340
tcctgagtag ctgggactac agacgggcac caacacacct ggctaatttt tgtattttt    92400 gtagagatgg ggtcccacta tgttgcccag gcttctatct gcttttatct caccttccac    92460
tcttccatcc ttcctttctt ttcttttatt tcctttccct tcccttgcct tccttttctt    92520
tctttctttc tttctttctt tctttctttc tttctttctt tctttttctt tctttctttc    92580
ttgacagagt ctggctctgt cacccagact gaagtgcaat ggcaagatct tagctcactg    92640
caacctccac ctcctgggtt caagcaattc tcctgtctca gcctcccgag tagctgagat    92700
tacaggtacc tggcaccaca cccggcaatt tttttttttt ttttagtaga cgggggtt     92760 cgctatgttg gccgggctgg tcttgaactc ctgacctcag gtgatcctcc cacctcagcc    92820
tcccaaagtg ttgggattaa caggtgtgag ccactgtgcc tggcctttt tttttttttt    92880 ttttttttta agacaggacc ttgctctgtc actcaggcca gagtgcagtg gcactataat    92940
cactttctgc agccgtgacc tcctgggctc aagggatcct cttgccttgg cctccctagt    93000
agctgggact acaggcatgt gccaccacac tggctaattt ttaaaacttt ttgtaggccg    93060
ggcacggtgg ctcacacctg taatcccagc actttgggag gccaaggcgg gcggatcacg    93120
aggtcaggag attgagacca tcctggctaa cacagtgaaa ccccatctct actgaaaata    93180
caaaaaatta gccaggtatg gtggcgggcg cctgtagtcc cagctactcg ggaggctgag    93240
gcaggagaat ggtgtgaacc tgggaggcgg agcttgcagt gagctgagat cacgccactg    93300
cactccagcc tgggcgacag agcgcgagac caatctaaaa aaaaaacaa aaaaaaaaa    93360 caaaaaactt tttgtagaga tggattcttg ctaggttgcc caggctggtc tcaagcttct    93420
aggctcaagc agtcctcttg cctgtgcctc ccaaagcctt gggattacag gcgtgagccc    93480
ccacacctgg tcctaaccca ctttctgaac ttccaaccac accatttgt cctaatattt     93540 aagtcacacc ataacatgtc ccacttcaga aatgcctacc aaagtagtct tcaaatcttt    93600
ttaaatcagt ggacccttc taccaaacaa atgttatttt ttaaatattt attttagagt    93660
aatttagact tttagaaagg ttgtagctgg gcgcagtggc taacgcctgt aatcccagca    93720
ctttgggagg ccgagacagg tagatcacct gaggttgggc gtttgagacc agcctggcca    93780
acatggtgaa acccccgtctc tactgaaaat acgaaattag tcaggtatgg tggcacgcgc    93840
ctgtagtctc agctactcgg gaggctgagg caggagaatt gcttgaaccc aggaggcgga    93900
ggttgcagtg agctgagatc gcgccactgc actccagcct gggtgacaga gtgagactcc    93960
atctcaaaaa aaaaaagaa aagaaaaaaa agaaaggtta taaatatatt ataaagagtt     94020
cccacatacc cttcacccag tttctcctgt tgtttgtatc ttatattatc accatatgct    94080
tgtcaatgct aaggaattgc tgggtgcaga gtggcacatg gctgcagtcc cagatactca    94140
ggaggccaag gcaggaggat atcgcttgag cccaggagtt caagtctagc ctgggcaaca    94200
cagtgagacc tcttttctgc aaaagaaaac aaataaaaca tctaaaaaag aatacactgg    94260
aggcggcgtg gaaacaagga tctcatttgg gagttgtctg caatgttctg agcaagcagt    94320
aacggaggcc tcaagtcagg gctgtggtca tggaggtggg gaggggtggt tggtttcact    94380
atctgtgttg acttaatttt agatttgcag actcaactga gtatgaactt taagagaaag    94440
agagaggcca ggcacggtgg gtcacacctg taatcccagc actttaggag gccaagtggg    94500
```

| | |
|---|---|
| gaaggccgct tgagcccagg agtttgacac cagcctgggc aacatagtga gacccctgtc | 94560 |
| tctacaaaaa aaaattttta aattagccag gcagggtgat gtgtccctgt aatcccagct | 94620 |
| actcaggaca gtgaagcagg aggatcattt gagcccagaa agttgaggct gtagtgagct | 94680 |
| gtagttgcac cattgtgctt cagcctggga gacaaagtga gaccctgtct caaaaaggag | 94740 |
| aatggggaga gagagagaga gagagaagga gaaagagaga gaaagagaga gagggaagtc | 94800 |
| aaggagaacc ccacattttt tgacatggtg tattagtctc ttctcacact gctaataaag | 94860 |
| acatacctga gactgggtaa tttataaagg aaagaggttt aatgcactca cagttccaca | 94920 |
| tggctgggga ggcctcacaa ccatggcaga aggcaaagga gaagtaaagg catgtcttac | 94980 |
| atggcagcag gcaagagagc ttgtgccatt tataaaacca tcagatctca tgagacttat | 95040 |
| tcactaccac aagaacagta tgggggaaac tgcccccatg attcagttat ctccacctgg | 95100 |
| cgccgcccctt gacacgtggg gattattaca attcaagttg agatttgggt gggaacacag | 95160 |
| ccaaacccta tcacatgggc aagtgaaagg atgggtttgc catcaaataa aatggggaag | 95220 |
| gagactgact aggtgggcag attaggaact cagctttcta tgaagtgcct actgatggat | 95280 |
| agagatattg tgttggccat ctattaggtt ggtgcaaaag taattgcggt tttgccatta | 95340 |
| aaagtaatgg caaaggaaat aacctttgca ccagcctaat aggaattgga gtctaaaatt | 95400 |
| caaaaaggt aagtcagagc tggagatcca aaggcaggag tcagcctcct gtggaggcta | 95460 |
| tttaaggaac tgaataaggg catagatgca ggagagcacc caggactgag cccagggctt | 95520 |
| actctccatc attaaagagg ttggggaaga tgaggaggag ccagcagaga agactgaatt | 95580 |
| ggagcaaatc agaagaatgt gggtgctggc tgtcatgcaa ggaaagtgct aagccatttc | 95640 |
| aagtatgagg gaatgatcaa tgatgtccac tgatgctgat gtgttgactc aaatgaaaaa | 95700 |
| tgagaatcaa ccattggatg tagtggcatg gagatctttc gtgacctgag ccagagctgc | 95760 |
| ttaggtgaag aggtgaaggc aagaggctac tggaaggatt actactagct cttttaaaga | 95820 |
| gttctgctgt gaagggtaga ggaagagaga tggggcatgt gttagctggt ggggaagtg | 95880 |
| gatttcagag gtttgtttcc cttaaaaaaa aaaaaaaaa gaaaaaagaa taagaaaaa | 95940 |
| aaaaaggcca ggcacaatga ctcacacctg taatcccagc attttgggag gctgagacct | 96000 |
| cgggaatttg agactagcct ggacaacata gtgagacccc atctctacaa aaaaaatttt | 96060 |
| ttttttaatta gctgggcatg gtggtgcatg cctgtggtcc tagctacttg ggaggctgag | 96120 |
| gtgagaggat ctcttgagcc tgggaggtcg aggctgcagt gagctatgat cacaccactg | 96180 |
| cactccaggc tggacaacag agcaagaccc tgtctcaaaa aaaaaagatg ggagacctaa | 96240 |
| cagcagattt tatgctgata ggaataacct attaggggag aaaaacatga ggatgctgga | 96300 |
| ggaagaagag tgtcaggagg acatctcttg gtggacgaga ggggatggca tttggtgtac | 96360 |
| aggtggaagg tttcacttta gatgacagca cacacagtta tctatagaaa caggagaaaa | 96420 |
| tgcactatat gggcatacat gctgggaggt agagagtaaa taatagtggt ggttgcttgt | 96480 |
| ggaaattctc ttctaatgtt tttatatttt tatggtttat caaggacaat ttatattttt | 96540 |
| acagtttact gcaaacaaca agttctaatt tattcaataa ttatttgtgg gtagaccgag | 96600 |
| tgcagtggtg catgcctgta atcctagcac tttgggaagc caaggtggga ggattgcttg | 96660 |
| aactcctgat tcacttctga gcttgaatca ggagttcgag atcagcctaa gcaacatggc | 96720 |
| aaaacactgt ctctacacaa aatacaaaaa ctagccaggt atagtggcat gcacgtagtc | 96780 |
| ccagctattc gggaggctaa aacgggagga tcatttgagc cctgaaggtg gaggttgcag | 96840 |
| tgagccaaga gcgagccact gcactccagc ctgggtgata gaataagacc ctgcctcaaa | 96900 |

| | |
|---|---|
| aagaaattct tattcttctt cttcttatta ttatttgagg agacatttac tttgtaccag | 96960 |
| gcgctgtgct agatgctgga gatacagaca tcaacaatga caaggctaag tgcctggcgt | 97020 |
| atttgtactt tgagtctaat aaaagacatc acacagacac acaacacaca cacacacaca | 97080 |
| cacaggattg tcaaaggatc aaccatttca catgtcaaga tcaggaatga tattggtcta | 97140 |
| ctactgcctt accatatctc ctaccatgac ctcatcttcc tcttgccaga ttttaagtct | 97200 |
| ttatacctca actcccagaa ctctcttcgc ctcacaccct atcacaatgt catccgtacc | 97260 |
| ccacggccaa tactccatca ttcgggaaag caaagttcca aagcgtcaag attgtatcaa | 97320 |
| tggacctgtc tctatggcaa cagtcctgaa tgagccaagc aaggtaaccc tggagatggc | 97380 |
| gtgaatgaga agtggcctg ttgccacgga gacgtgctga atgggaaggc ccccacgagc | 97440 |
| caggctatgt cacgaagccg aaacagtcag catgaagtcg gtatgtctat tttcaactcg | 97500 |
| gaattacaaa aatacatttt aatagagctc atgacccatc tccttcctcg tccctgcctc | 97560 |
| ccaccccact cttcagcctt catcctacaa cacaatcgag cctcaccagg aacccttcaa | 97620 |
| accccctcaag gacaccttac tgttccttca gtacacagtc cccttcctgg gctgaggtgg | 97680 |
| tattcctttg accaactact gtctcccctt tgggaccaac agtattctca aaagccatga | 97740 |
| gcttatggga agaacattaa ctacattctt tggggcaaga acagttgctc acctgtgaac | 97800 |
| cagctcagct tgcatctgtg agaatgattg caatgggtag accagttctc catcaaagaa | 97860 |
| tggccctagc accccacaca cagtggtata atctgatcat gctggtgtat tgaacatata | 97920 |
| atgttagtgc cacatgaaag gaatttgtaa aaggacttag tgcctagaaa ggtaccttg | 97980 |
| aagatcttgg aatctctgaa acttacccag gttccttata ccctgctcaa agtattcctc | 98040 |
| catttatttc ttcattcatt agttcttttg tttcaccaca tatatatttt tgaaacgggg | 98100 |
| tctcactctg ttgcccaggc tagagtgcag tggcaagatc gtggctcact gcagcctcaa | 98160 |
| cctcccatc tcaagcagtc ctcccacctc agcttcctga gtagctggga caccacaggt | 98220 |
| acaagccacc acgccaggct aattcttgta attttttgtag agacggggtt ttgccatgtt | 98280 |
| gcccagtgta ttcgtttgtt ctcacattgc tataaagaac tacctgagac tgagtagttt | 98340 |
| ataaagaaaa gaggtttaat tgactcacgg ctccacaggc tgtgcggaag gcatggctga | 98400 |
| ggaggccaca ggaaacttgc aatcatggcg gaaaatgaag gggaaacaag cacatcttca | 98460 |
| catggtggca ggagagagag agtgagggg ggagtgctac aaaaccaggt ctcacgaaa | 98520 |
| ctcactcact gtcatgagaa agcaagggg gaaatctgct cccaggatcc aatcacctcc | 98580 |
| taccaggtcc ctcccccaac attggggatt acaattcaac atgagatctg ggtggggaca | 98640 |
| cagagccaaa ccatatcacc caggctggtc tctaactcct gagctcaagc aatctgcctg | 98700 |
| ccttggcctc ccaaagtgct aggattacag acgtgaacca tatttattaa gcattgttac | 98760 |
| agcaaagaga agcattgttg cagcataaca attggaagac tccattgatg gacgtctcca | 98820 |
| tcaacaagaa ctgtcggata aactatggta cacccatccc ttagcgtgtt atgaagtcat | 98880 |
| tacaaaaaga agaagcagat ctctgagtgt caataagagc tagtacttat agggtgtcta | 98940 |
| ctgtatacaa gtgctgttag aaagtgagta ttaactcatt taattcttgt aacaagcctg | 99000 |
| tgaggtggat tctttcatat ccccatttta cagagaagga aataggaatc tctatatcca | 99060 |
| agatatgtta tcaggtgaca aaagcagttt ttgaatggtg ccgccatttt ctcgtaagag | 99120 |
| caaatctgga agattccatg agaaattaat aattgtgttt gcctctgtag cggcaccctg | 99180 |
| aaagatttgg aagtaggtgt ggaaaggaaa cttactttct tgtgtctttc tgaattttgt | 99240 |

```
actgtctacg cgttttgtct ttcacaaaac caaacagaaa atgaccattt ggtgcatttt      99300
gtgtgtcagg cattcttcta gtctagagaa gcacaggaga gcaaaatatt ttactgacga      99360
gaaaaatgag gcatggagaa gttaagtgac ttgcccaggt agcagagctg ggattccaca      99420
tcatagggtt tatacaggaa acaggtaaac agagctgtgc ttgtgtgtgg gtatgtgtgt      99480
acacatgcat acatgtgtgc atgtgtgtgt gtgtttgtgt gtgtgtgaat gtgcttgtgt      99540
gttgggagag ggaaatggca agagaagaac ctacagaagg tcagcaggaa ccaacccatg      99600
ttttgaggag tttggacttt atcctgaagg cacaagggag ccatggaagg atttagacaa      99660
ggggtggttg tgcttagctt tttatttaga aggatgactc tggctgaagg gtgatggccc      99720
agaatacagg tatatgtgaa ggactcctcc tgccctagta ggaggatgcc cacccaccct      99780
ctctgcccag tgcagtatca aagggcaaat tgggtacaga gaattctcac caagctgggt      99840
agaatccact ctgatgctgg ggagtggaca ctgaatgcac cagcctctcc tcctgctcaa      99900
tccctgaatt gaagctgttc cactaatgtt agggatcaga ttcccttcat atatatatat      99960
atatatatat atatatatat atatatatat ataaaatttt ttttttgaga cagagtctcc     100020
ctctgtcacc caggctgaag cccattgtcg cgatcttggc tcactgcaac ctccacctcc     100080
caggttcaag caactcttgt tcctcagact cccaagtagc tgcgattaca ggcacccgcc     100140
accacacctg gctaattcta tatttttagt agagacaggg attcacctat gttggccagg     100200
ctggtcttga gctcctgggc tcaagtgatc agtctgcctc agcctcccaa agtgctagta     100260
ttacaggcat gagccaccat gcccgtcctt tttatattac cttttttttat agagatgtgg     100320
tttcactatg ttgaccaggc aggtcttaaa ctcctggcct caagcgatcc tcccctcctca    100380
gcctcccaaa atgctaggat tacaggtgtg agccactgca tctgtccaga ctctgttctc     100440
cataaagctg gcatatggaa agagggaaga ccatccaggc aatatcgaag tcccattggt     100500
gctgatgtgg ctgctgagac cacatgaatg gatgcattct gactctgcca cctctcagct     100560
atgtgaccct gggccagtca gcaagtccct ctataactca gttttctcat ctgtaaaatg     100620
gcgtcaacag tagccaaccc cagcaaatac tgtgaaatat acagaacatc attataatgg     100680
tgaggatgat agagatgcta tgttatcaga ataccctgggc ttgaaccagc tccccttctt    100740
gcaagctgtg tgacttggag ctgatgccca aacctctgtg ggcctcattt gtttcatctg     100800
ttcaatgggg ataataacac tcttacttca tacagttatg gaggatttat tgaaataatt     100860
gacatacagc tcttagaaca gtatccggct ccttgtaagc gctcaagaaa tattacagac     100920
tgttgataat aatgcaatac tactaccaat aaatatggcca ggagcaatgg ctcacacctg   100980
taatcccagc actttaggag gcagaagcag gctgattgct tgagcacggg agttcgaggc     101040
cagcctgggt aacatagggg gactctgtct ttacaaaaaa taaaaataaa aatacaaata    101100
attagccagg tatggtggtg catacctgta gttccagcta cttgggaggc tgaggtggga    101160
ggattgcttg agcccaggaa gttgaggcta cagtgagctg tgatcacacc actgcactcc    101220
agccagggca acagagtgag accctatctc aaaaataata ataatggccg ggcgcgctgg    101280
ctcatacctg taatcccagc actttgggag gccaaggcgg gcagatcact tgaggtcagg    101340
agtttgagac cagcctggcc aacatggtga accccatctc actaaaaaca caaaaattag    101400
ccgggtgtgg tggcggggtg cctgtaatcc cagccactca ggaggctgag gcaggagaat    101460
cgcttgaacc cgggaggtgg aagttgcagt gagccgagat cacaccactg cactccagcc    101520
taggtgacac agtgagactc catctcaaat aataatatga gtaataataa taatatcatt    101580
tttatcatca ttcttactaa cagtctctca ctccttgccc tgcagttttg cctgttttct    101640
```

```
tggaataaca ctcttccaca cctttcccct cagggatggt tcacgtttag catcatgacc   101700 caccccctggg gattagttag ctcatttctg gaaagcactt tggagctgta ggtgctttgc   101760
aggctggaaa catcacggga cttgtaccat atttaagcaa tgccagatta ttctgcctgg   101820 caggggggagg acacagagga tacggccctg gtatcttttc tccctgccta cctcagcttt   101880
gctctgaacc attttctgtc ctgttcaggg cagcctgggc cacttgccac ttccagcttt   101940
ctcgggagag gatgccttcc tgatggcacg cctcttaaca cacacctggt gctgttgttg   102000
aaaaagcaac aattgactcc agcgccagca ctgagaggct tgtccttaaa attagcagga   102060
gctgttggaa ggtcgctgtt agctcttttg actggaacac actgttcccc aggtggcatg   102120
aggctgaata cagtgcaggg attggctctg ctctcaggtg gcctgctcca cgctcctgag   102180
ctccgggtgg aagctgtgac cattatttcc ttaacagaaa catatatagc agcattaact   102240
atgaacctta ttactgtgtg tgtgtgtgtg tatatgtgta tatatatata tgcacatatg   102300
tgcatatgtg tgcctatgaa cctgttctga gcactttaca aatgtcaatg tattttatcc   102360
tcccaacaac ccattttata aataagactt gaggcacaga gaggttacgt tactgcccca   102420
agatcacaca gctggagagt ggtgaggcca agatttgaac atatgtacca ttgtaccata   102480
tgtaccaact ttttttttct ttttgggatg cattcttgct ctgtcaccca ggctggagag   102540
cagtggcatg accacggctc attacaacct caacctccag gttcaagcta tcctcccacc   102600
tcagcctctc aagtagctag gaccacaggt gcataccacc atgcccagct aatttaaagt   102660 tttttttttgt ttgtttgttt gtttgtttgc agagatgggg tctccttata ttacccaggc   102720
tggtctagaa ctcctaggtt caagcaatcc ccccacctcg gccttccaac atgctgggat   102780
tacaggcatg agccactgca cccaggtcct ccctccttat aaaggtcgcc aagcacaatc   102840
ttgtgagcct ggccctatcc acacccatac gcaacatggt gtgtattttt caaacaaaaa   102900
ctgaatgaac acctctggtt tgggttcccc tcacacttgt cccgggtttg ttgactctgt   102960
gttgtgggcc tagacaaagc agtgtctgga gctcctagac ccagggacca gacagtctgg   103020
gttcaaatcc tggctcttcc acttctgcct gagtgctctc tctgaacctg tctttctttta   103080 tctataaaat ggagataatt ttttttaaact catcacttgg tcaaactgct ttgagcatgc   103140
aaatgagttc atatgtataa acctcttaga atgtcccagg caagaacaa cacttcactc   103200 agatcaacat ttatttagca tctactgtgt acccatgact attctaggtg atgaggagac   103260
cctctggttc ttatgaggta gtgaggtggg ggagggtgag aaccctaaac attaacgatg   103320
gtgtgttcgc aggtgggaaa atcagtaaag tcgggtaaag ggaatttggg agtgctgtgc   103380
tcaagtcctg gccctgccac tttctggggt gcaagataca gcattgaata gggtggtcag   103440
ggtaggcctt attgggaaag tgatatttga gcagacgatc tagatgtcgg cacatattgc   103500
tactgtttga tggtactaat atgagtttga gtttcacttg caagtatata tatatatata   103560
tatatatata tatatatata tatatatgtg tgtgtgtgtg tgtatatata tatgtgtata   103620
tatatgtata tatatgtgtg tatatatgta tatatatatg tgtgtatata tgtatatata   103680
tgtatatata tgtatatata tgtgtgtata tatatgtgta tatatgtata tatatatata   103740
tgaaatttgg tccatttatt tatgctgatc aattaattga tgttgaaatt ataattgaat   103800
gttttattaa taaacagata cccacatact attttttcag aaattgttag gttttggggt   103860 tttcttttaga ttttgattat tttttatttgc ttaattttct ttttctttt tttttaatttt   103920 attttttccat aagttattgg ggtacaggtg gtatttggtt gcatgagtaa gttcttcagt   103980
```

```
ggagatttgt gagaacctgg tgcacccatc acccgggcag tatacactgc accatatttg 104040
ttgtctgtta tccagtgctc acctcctact cttcccccca agtctctaaa gtccattgta 104100
ccattatttt actcacccac attctttggc ctgagatgct gagtggtcat gactcccaga 104160
tcccttcttg tttctgtatc aaagatcttt actaagatcc tggcctaggg aacctattcc 104220
ctttcctcat ccccaatggg agaaggggct tcttccccag cttatttgcc aactcatagg 104280
aaaggtatga aggagaggac tgtagttgtc ttgaagctgg tcagatgttg aagagatgat 104340
aatatttgct gatcaagaga gacaaagcaa tgctggaaga agaggctgtg ttagttaaca 104400
ccagctgcaa taaccaataa aaccaaaaat ctctggctta agagtatgca tgagtgaaga 104460
atcaacttct aaagtacaac tggtggccgg atgtggtggc ttatgcctgt aattctagca 104520
ctttgggagg ctgtggtggg agggtcgctt gacccagta gtttaacgcc aacctggca 104580
acacagtgag acaccatctc tactaaaaat aaaaaataat aaagtgaaac tggtgagggg 104640
tgcaatgagg tggagtggtg ggtgactcaa atatggctcg actccatgca gtcactcagg 104700
gatccaggct gttggaggct ctccctgctt aaacatgtgg cttccaaggt tgttctaaga 104760
gcctacattg agacagcagc tggggaaaag ggaaagtgga gtgggaggta cttatgaggg 104820
ttcctggaag tggtgaacaa cacttctgcc tgcattctat ggggtggaat ttagtcatgt 104880
ggcccaggct agctgcatgg gaggctggga aatgtagtct ctgattaggc tgccatttcc 104940
cagtcccact tgtgaatctt tagtgggaag ctcaccatgt ttgcaccagg gattcagtct 105000
acctcccact catgcctcaa ctatgtatca ggcactgtcg taagtactt acatatcagc 105060
ctacctaatg caaacaacta ctcagtgggt gctttattgg tcacatgtat tagtgagaac 105120
atggaaaccc agagccgtta aatatcttgc ccaaggtcac acagctagga agtggcagag 105180
ttggaatttg aatccaggaa atctggctgc agagccccac gcttagtata aattcattgt 105240
agtttagaaa gaggcagaag gaccctaaaa ttggcataat ccattttttg gtccctaagg 105300
aactgactga attgactact tgtaaaagtg agtcctggac aggcaacagt ggctcaggtc 105360
tgtaattcca ggactttggg aggctgaggc gggcagatca cctgaggtca ggatttcaag 105420
accagcctgg ccaacatggc aaaaccctgt ctctaaaaaa atagaaaaat tagctgggtg 105480
tggcggtggg tgcctgtaat cccagctact caggaggctg aggcaggaga atcgtttgaa 105540
cctgggaggt ggaggttgca gtgagcaaag atcacgccac tttactccaa cttgaatgac 105600
agagcaagac tctgcctcag gaccgccatg gcccctggg ttctaggtca gagtttctcc 105660
gccacagcac tgatgacttt gggggctgca ttattagctc caaaatggga gctatcctgt 105720
gcactgcctc aacttacttg atgccagtag cgcccgcgcc ccagttgtga gaaccaaaaa 105780
tgtctccaca cattgccaaa tgtcccctgg gaggtgaaat cacccctggt tgagagtcac 105840
tgttctagat tgttaaatat tatcttacac tctagcacaa gtccaaggca aactgactta 105900
gaaattacca accttgcaaa aaatagaaga tttcttaaag tcagtgagca tgatggtggc 105960
aagctgctga aatcacaccc ccagacatta gcagatggga tctggacagt attcatctag 106020
ttaaaaattg acaaggactg ggacactgca ggctcttcaa aagagaatca tttgaataac 106080
aaggggtcaa gacaggggta attggtgaaa gccctgctc ataatttgaa aatataaata 106140
ggcatcatga aaattcatcc tgcaaaagtc aaaagtcgaa tgtgcagtgt tatacatgat 106200
cagttgattt gggagggaa attgcatgca cacacatgag agcttgcaca cccacacaca 106260
cacacctgtt caagtgtgtg tgccagtgct cagtgaggac catctcccca acctgtctga 106320
tcatcttgct ttggggtgac cctatgggtg aggcagaaat tcttggatca tagttttcta 106380
```

```
atgaatatta taattgttaa cttctgatgg gtgctgactt tttcatcttt gcaacactgc   106440
gtaggtattt ttactctccc cattttacag atgagacaac tgaggctcag aaagattgat   106500
tagctctaca cgaagccagg atccaggctt agcctggctc caggaatcat gttttgagtt   106560
acgtagcttc cctgattctg agggacctcc ccacttctga atcttctac tgttactccc    106620 catggccctt tcctattgac cggaggcacc ccagctcctc actcgtccct tatcttatga   106680
aacatgacca tgatgtctga attcaaagga gagcctgggc tttgtgggga aaacgaagca   106740 gaaaagaaa ggtggaggtt ggtggttgtt tttggcatgg tgaggagcct gtcgttgctt     106800
gaggaaagca agaaggaga ttgctggggc ttggatccat ctctgggtgc ctgtgggtct     106860
gtctgtaaaa atgagaactg gtcgtgctca ttagaggatt tgaccgttag gccttgggat    106920
agcgatttgg gaactttttt ctgctaagac aaagaataat atggttcagg ttcattttgc    106980
tcctgctttc ccaagcccta catctcttct gggcttttt tttttttcctt ttctctcctt    107040 cttcttcttc ttcttcttct tcttctcatt tttggatctg gacttctgct gactcatctc    107100
tctgagcaag gaaggaggga ggaagtcaga attgctcatt aaccgttttc tttagtgact    107160
cagctgtgat tcacatttta attaatggag gagaaaaacc tgatcagtcc taaggcatct    107220
gcccaatcac gcataactcc aggctggtga taataataat acttgaaaaa agtggggtgt    107280
cctgaattaa actatggctc attccccaca ttagtcttga ggactccacc aggccctcta    107340
agttccaggt ctcaatgggg ctccctgaac cagagcagct agtccaagcc ccgagcagca    107400
tttctgcaga gttagtctga ggtcaggaca agaaacagag gctcaagccc tcctgggatc   107460
gcaggaggat catgggaatg taatattgtt tcctgagctg gtctttggct ataatcccag    107520
gctcaagcct ggcctcctc ccctcggggc ctgaaatttg tcagagccta ttgcaggggc     107580
agcttctgtg cttttttgttt gcccagagaa tgagaaaagt ccagataatc atgaccgcta   107640
cttcctgagc acttactatg catcaggtgg tgtgctcagc acttctcatg aatgatcacg    107700
ttgaatcctc actctgtcca caaaagaaa gagcttttat ataattctcc aacctcccta     107760
tgaggaaact gaggcttggc aattgcccaa tgtagacaat tagtaaataa tcaggcagga    107820
tataaaccca acccttccc acctgggagc cagagcttgc atctactata cttctctgct     107880
ttccagtcag ctgcaaagaa aaattggaag ctgatagctc attcaacaaa cacttattga    107940
acccttccac ctgctcagcc ctgttctaga caccagagat ccatcagtga accaaagagg    108000
caaatccatg gtctcatgaa actgacaatt tacctgccca agtgtattag ttactgttta    108060
taagttccta ttaagtgtat tagatatgct tgcagctgta acaaagaatc ccaacatgca    108120
taagggctca aaacaataaa aatttcgttc ttgcacagat aaagttcaaa aggtgtattc    108180
tttttttttt tttcttttgc gacggagttt tgctcttatc ctccaggcat gagtgcaatg    108240
gcccagtctc ggctcactgc aacctccacc tcctgggttc aagcattctc ctgactcagc    108300
ctccccagta gctggaatta caggtgcccg ccaccacacc tggctaattt tttgtatttt    108360
tagtataggt ggggtttcac catgttggtc aggctggtct taaactcctg acctcaggtg    108420
acccacctgc ctcggcctcc caaagtgctg ggattacagc cgtgagccac cgtgcctggc    108480
caaaaaaaaa atgtattctt aaacagcagg cacctctcct ctaagcagta agtcaggggc    108540
ccaggcttgt tccatattgt agctcctcat cttcaaccca tggcttccaa agtctccatg    108600
cttcttgata tcaagccaca gaagggaaaa gagcatgaga agggcacagg agaaatgttt    108660
ctgggacaga cccagaagta gtccatatga cttccatcta cctcccactg gctagagctt    108720
```

```
acatggcggc acccacttgc agagctggga aatggagtct aactgagcat ccaggaagga    108780
gagacagaca tgagtctttg cgtgggtcct cactgagaat caagctccac attttgatcg    108840
atgtcaccag agcgtacatg gcggcgccca cttgcagagc tgggaaacgg agtctaactg    108900
agcatccagg aaggagagac agacatcagt ctctgcgtgg gtcctcactg agaatcaagc    108960
ttcacatttt gatctgtgtc acctccttgc aagccctacc ttaggacaat tttaagggac    109020
attcctatct tcttccaccc ttaggacagt tttaagggac actcctgagt tcttccaccc    109080
acctcctctg tttcttgggc ttccagctct caggatttgc ctttgcctta caatggggtg    109140
aagcaagaat ctggaagaat gtctctcccc acaatttgaa gtcttatttg aaaaaaagca    109200
gtagagcatc cctccctctt gaggtaggga aatctagaat caaatcctgc ttctccagac    109260
tttgacctca gaaactgggg ggacttcaag gtcttcaggt gggcagcttt catgaaccat    109320
tcattcctcc cacctcatac caatcagggt cctaacagga aaagaattta acttctagat    109380
ggttcaaaag aagaccatgc catgaagaga ctccttaaag ataggaac aggtgagaga    109440 aatagataac ggctgtttga ggtcctcaga gagaagccat cgcgagccct acatttcctg    109500
gaacccagtg gaggcagagc tgtgcagaag ggactactgt cagaaccagg gagggagcag    109560
ggaagcaata ttccaatctc tttccctccc ctcatcttct gccagcgctt cccctcagcc    109620
aaaccaaacc ggaaacggag caaagcattc tgggagttgt agtcttcaag ggtccgcctc    109680
gagggcacag agcccgctgg agcattgacc tagagggcac acaggaatg actagtttgc    109740 accatcatgt gacggactgc acgccctcga ttatgtaatc cactctataa ttcaactgca    109800
gagctgcatg gtacagcagg atagccacta gccacgagg ctatttaaa tataaatgta    109860 cattcattaa aatttaacca aatgaaaatt ttagccactg agccccattt caaatgctca    109920
ttagccacac gtggctcttg gctaccatat tggacagatc agaatagaac atttccatca    109980
tcccagaaag ttctaggggc cggcgcagct gtggtgtaac ctgagcccat gcatgttatg    110040
gaatggagaa gagagaaaac agcacaagag gcagttttga agggagacag agagctgtgg    110100
atcagtaggg aggagactct ctaggcaaag gagcagttga gaagcaagaa agttgagtga    110160
gctgctttgc tgcgatggag gcttccctca cggggaagag tagagtcaga aagctttagt    110220
tcaagttcag ctctgaaatg aaccaatgag tgttctgaca agacacctgg ccttccggaa    110280
ccttggtttt gtagtggcca agggcttgac cctctgaagg ttcactgaaa aaatcaact    110340 cacaaggcat attaattgga gaaaaggcag gcagatttat ttaatgtgtt tgcacgagag    110400
ccttcagaat gaagacccaa agctgcaggg gaaattgtcc gttttttaag cttaggttca    110460
acaaagtatg gacagcggtg tagaaatatg attgaacaaa aagtgtacaa tgtaaatgct    110520
aatagactga gtggggaaac ccaaaaaggg ctgtcttgat tctccttggt ctctctgagc    110580
atgcatttct tccgggtatg ggacaagacc ctctctggaa tggagggggg gctctcttgg    110640
ttctccttgg tctctctcag catgcattcc ttccgggtat ggggcaggac cctctctgga    110700
ataagggggc tgtcttgatt cttcttggtc tctcagcagca tgcattcctt ctgggtatgg    110760
ggcaggaccc tctctggaat gggatcctta aacctacgg tcaaataacg taagttagat    110820
aatttctttt tttttttttt ctttttttg agacagagtc tgattctgtt gcccaggcta    110880
gagtacagtg gcacaatctc ggctcactgc agcctctgcc ttctgggttc aaatgattct    110940
cctgcctcag cctcccaagt agctgggact acaggtaagc accaccatgc ccagctaatt    111000
tttgtatttt ttagtagaga cagggtttca ccatgttggc caggctggtc tcaaactgct    111060
gacctcaagt gatccaccac ctgggcctcc caaagtcctg ggatttgtaa tcccagcatg    111120
```

```
agccactgtg cccagccaga tcatttcttt ttcttttttct ttttctttttc tttttttttt  111180
ttttttttgag atggagtctc actctgttgc ccaggctgga gtgctgtggt gcaaactcag  111240
ctcactgcag cctctgcctc ctgggttcaa gcaattctcc tgcctcagcc ttccaagtag  111300
ctgggactag aggtgcgcgc caccatgccc agctaatttt tgtatttttta gtagagacag  111360
tgttttgcca tgttggccag gctggtctta aactcctgac ctcaagtgat ccacccacgt  111420
cggcctccca aagtcccggg atttgtaatc ccagcatgag ctaccacagc tggccagata  111480
atttttttat aactagtttt tacaaagaaa ggtggaggga aagttagagt aacatttttta  111540
ggtgttaggg ctgactttgg ggaaaagagg tctggtttct acgacccgcc ttagggaaga  111600
gggattctag tttttgtggc tagccccagg ggagaatggg actaagagat agaagggcag  111660
gagaaggtca gagaaaaact tttgcttctg tggctgcttc ggagaacttc attttgggt  111720
attgttttct gagccccaac agtttgctta tcagtgaagt gggtataggc gcccacctcc  111780
cacagtgacg atgctgtgaa cagggctttg gaagagtaga actatgaaat atttgttgtt  111840
gccttgtggg gaaatggtcg ttaaagccaa aattgttcaa gagaagaagc aggaagagtt  111900
cctttctttc ctgcaggtat cctcttaagc tgagtcttca gaatcccctg acaacgttta  111960
atcaacactt tattaaattc accccaaccc tgcttcaaac cttcacctgg tcctcgagat  112020
cttccaactg tttcttgatg aagttagcag gcaattgtat ggcgggatca tcatctcatg  112080
ttttgttttg tttttttcct ttttacccctc tgactttgag aaatccttgt ccttttactt  112140
ttccaaacct gagagcattg cagagaagtt agaattgagc aggacatggg cttaagaccc  112200
agcccagcca tgtgctagct gtgtgaactc gaagcagtga ccccacctct ctgacctgga  112260
aagtagaggg aatgatagga cccaccaccg ccacacttgt agggtcatca tggggattga  112320
ataaaataat gcataagact tggcccacag caagcactca agaaatgtta gctacttcct  112380
aaatatattt ttaaccttttt attgaatata acatacatac agaaaagcac atgtatcata  112440
caagtagagc ttgagtgatt ttcaaaaact gagcccagtc atgtaaccag cgcctagttc  112500
aagaaacaga acatagccga gtgaggctga ggcaggagaa tcacttgaat ctggaggca  112560
gaggttgcag tgagcagaga tcatgctatc gctcccagc gtgggcaatg ggggcggagg  112620
ggaagagaga gagagagaga gagagagaga ggaaggaggg agggaaggaa ggaaggaagg  112680
agggagggag ggagggaagg gaaggaaggg gagagagaga aaaggaaaga aaagaggaag  112740
acagaaagag agagagaaag gtaaagaaag aaaaggaaag aaagagaaag aaagaaaaga  112800
ggaagacaga gaaagaaaga gaaagctaaa gaaagaaaaa aaggaaggaa ggaaaatagg  112860
gagggaagag gaggaggaag aagaagaaga agggggggag ggagggaaca gctgcagctt  112920
cgaggaagga aggagggagg gaaggaagga aggaaaggaa ggaaggaaaa aaaaacagca  112980
ccaacgttta gaaaccccct tgtgcctctg aggtcaccag taactccatc ctgacttcaa  113040
acagtctaga ttagttttgc ttgttttttga actttaagca catggggtca tacagcatgc  113100
atgcattgac ttcttttccct tgacgttgta tgtgtgagat tcatctgtgc tgttgctgtt  113160
catttgttct catcgctgtg tgtgctgaac cacctgttca tttactctac taatggtggg  113220
cagtttggtg cttttctactt tggggctatt ccagagaaag ctactttgaa cacactcaga  113280
tatgtctgtg ggtgaccact cttcatattt ctatgggaga tattcctagg accggaacat  113340
ctgagtcaga gggaggaatt ggtttagctt tggtaggaac tgcctaacaa ttggccgggc  113400
acagtggctc atgcctgtaa tcccagcact ttgggaggct gaggggggca aatcacttga  113460
```

```
gctcaggagt tcgagaccag cctggccaat gtggcaaaac ccctggccaa catggcaaaa    113520
ccccgtctcc gcaaaaaaat acaaagatta gccgagcatg gtggcgtgtg cctgtaatct    113580
cagctactca ggaaactgag gcaggagaat tgcttgaacc tgggaggcag aggttgcagt    113640
gagcagagat tgcactactg tactccagcc tgggtggcag aatacatgaa actccatctc    113700 aaaagaaga aggaaggaa ggaagggaag gaaggaaagg aaactgccca acagttttcc      113760
caagtgtttg ggatggaagg aaggaaggaa ggaaggaaaa gaaactgcct aacagttttc    113820
ccaagtggtt ggaccagtta aaactcccac cacctgtgaa tgagagtttg tttttatttt    113880
gctcctggag tgcctctcct gtagcaggtt cccactgaat gtctgggaat tcaaatgtaa    113940
tgcacttgtt catttcctca agagcttcac tccatcaatt ggattcatcc attggctctc    114000
ccatctccac tgacactatg ttctcacctc tatttggaag catcctgcc tccacctgcc     114060 caagtcacat tatcttctca ttccagcctc tcaaggagag ttttctcttt caccacctcc    114120
tctagccctg gtgattggca aggtctcgca acagtaccct tcaaaacact catgactgtg    114180
aatgcactgg ccttcactaa gtttcccatt cttctctttc tttcttttt cttttcttt     114240 cttttttttt gaacagagtt tcactcttgt tgaccaggct cgagtgcagt ggcacaaaca    114300
cagctcactg tagcctcaac ctcctgagct caaggtatcg tcctgcctca gcctcctag     114360 tagctgggac cacagacatg caacgttgtg cccagctgat tttctttttt ttctttttt    114420 ttttttttt gagacatggt ctcaccctgt caaccaagtg cagtagcatg atcacagctc      114480
actgcagcct tgacctcccg ggctcatgcg attctcccac ctcagcctcc cgagtagctg    114540
gggctacagg cacaagccac catgcctggc taattttgt acttcttgta gagaccaggt     114600
ttcaccatgt tgcccaggct ggtcttgaac tcttgggctc aagcagtcct cctgcctcag    114660
cctcccaaaa tgctgggatt acaggtgtga gccagcacgc ccggccatgg ctaatttctt    114720 cattttggt aaagacaggt ctcactttgt tgcctaggct ggtcttgaac tcctggactc      114780
aagcaatcct cctgtctcag cctcccaaag tgctaggact accgatgtga gccaccgcac    114840
ccggcaattt ccccttcttg acttctccag agctctcatc cctctcgagc tcctgtctct    114900
tctagaatca cttacctcac caccttatgg ggtttttgcc tctgttccta ctcctcttta    114960
tttaagaaaa cactgtactt taagagggct tcagaaacca cccgaaatag aaacatgtcc    115020
ttttgttcaa tccttactt taaaagacaa ataaaatgaa gaattgctct ccatgtgaaa     115080
ggttaaggag cttgggagga ccttctgtga gtggggagaa ctttacatta aaggaaaaaa    115140
aatgctggag aatagctgtg aacccaggaa gggagaagga cttcctccac tgaacttgta    115200
aagcacaaac tctaaggcaa aaaaagacat gattacatga aaactaagat atttgttcaa    115260
ataaagatgc aattggggcc aggtgcggtg gctcacgcct gtaatcccag cactttggga    115320
ggccgaggca ggcgaatcac gaggtcagga gatcgagacc atcttggtca acatggtgaa    115380
accccatctc tactaaaata caaaaaatta gccaggaatg tgtcacgtg cctgtaatcc      115440 cagctacttg ggaggcttag gcaggggaat tgcttgaacc agggaggtgg aggttgcagt    115500
gagctgaaat cacgccactg cactccagtc tagcgacaaa gcaagactcc gtccaaaaaa    115560
aaaagatgca atagcaggtg gttcgggaac caaaccttac atccagatgc tggttgtccc    115620
atttcctgtg aatccttggg tgagttatca acctctctga gcctcagttt cctcgtcaat    115680
aaaatggaga aaatagtatc tacctatgga attgttgtga gttttgaatg agttaatatt    115740
tataaatcat ttagaatagg aattagcaca tggtaaatag tggatagaat cataaaaaaa    115800
aaattgatca ggggttaact tctaactgct gtttgttata gaggtcccta gcactgtgtg    115860
```

```
gtcattttaa atttagatga tttagaatta aatgaaattt aaaactcagt tcttcattca 115920
cactagccac attttaagtg ctcaaaaccc acaggtgact agtggctacc atatttggca 115980
gcacagattg agaacagatt tatcatccag aaagttctgt cagacagtgt tgatcaaggc 116040
tacatgaggg tctgggtgca gtggctcaca cctgtaatcc cagtgctttg gaaggccaag 116100
gtgggaggat cactggaggc caggggtttg agaccagcct gggaaacaga gagacctcat 116160
ctctaccaac attttaagaa ttagccaggc aaagtgttgc atgcctgtag tcccagctac 116220
tcaggaggct gagacaggat tgcttgagcc caggaatttg aggctgcagt gaactatgag 116280
cgcaccgctg cactccagtc tgggtgacag agtgagacct gtctctaaac ataaaaaata 116340
aaaatgtagg tggggcatag tggctcccgc ctgtaatccc agcactttgg aagccgaga 116400
tgggcagatt gtgaggtcag gagatcgaga ccaccctggc taacatggta aaaccgcgtc 116460
cgtactaaaa ataaaaaaaa attagccagg catggtggcg catgcctgta gtcccagcta 116520
ctcgagaggc tgaggcagga gaattgcttg aacctgggaa gcagaggttg cagtgagctg 116580
agattgcgcc actgcactcc ggcctgggcg acagagcgag actctgtctc aaaataaata 116640
aataaataaa taataataaa gtaaaaataa aaatgcaaag actacctgag ggaatgtctg 116700
caagtcaacc agaataacac agcaacccca ataggaaaac aggccgaaaa tgtgaacagg 116760
cggatcaggg aagtgaagtc tgaaaagcta atcagcctat gacatggtac tcaaagtcat 116820
ttgtaaccag aaagatggaa atgaaagcag tatctctgta cacctttaat attggggaaa 116880
aaatatgtga ataagccaag ggtttccagc gatgcgggca cagaggaaag tcttgcacca 116940
ctcaaagggg tgtggcccag ggaggccact ctggagacat atcggtagta ctcagtccag 117000
tgaggtccag caccatcagc gcttatgtcc ccaggcatcc atcccaggga cattcttacc 117060
aggtctgtta ggggcaggta cgagaatgct tactccagca ccatctatat aaggggagct 117120
gaaggccacc tggtgtccct cctggagacc aggaggcggc atgtgacagc ggcacccatg 117180
gagcaccaga atgagtgaga gctccagacc gcatatccga cagatactac gggatggggc 117240
ttttagaaat atggttgttg ccgggcacgg tggctcatgc gtgtcatccc agcactctgg 117300
caggccaagg cgggtggatc acctgaggtc aggagttcga gaccagcctg ccaacatgg 117360
tgaaaccctg tctctattaa agatacaaaa attagctgga cgtggtggcg ggtgcctgta 117420
atcccaacta ctcgggaggc tgaggcaaga gaatcgcttg aacccaggag gcagaggttg 117480
cagtgagccg acatcgtgcc actgcactcc agcctgggtg acaagagcaa aactctgtct 117540
caaaaatttt aaaaaacaaa aaataaaaat atggttctgg gtgaaaacag gaaacaacag 117600
aatgtgtcta acttcatcct gcttatgtca gttaaaaata gacacactca aaatatcgca 117660
cgtgttttg cgagaatgca ctcctataag gccaaattaa acattctctc agttgtctct 117720
gggagggaga agaatgaaag tagggtatag agagatatag gggaattaat gcatgaatga 117780
atgaaggtat aaacaagaga caggcgtcat acagaccaaa ggtaaagata tcccgtaacc 117840
tgaggagagc aaagaacttg actctgcatt tgaagattca gaaaatgaat ttcagaaata 117900
gttttctcgc caggggtgg ctcacgcctg taaccccacc actttgcgag ggcgaggcag 117960
gtggatcact aaggtcagg agttcgagac cagcctggcc aacatgatga aaccctgtct 118020
ctactaaaaa tacaaaaatt agccaggcat ggtggcatgt gcctgtaatc ccagctactc 118080
aggaggctga ggcaggaaaa tcacttgaac ccggggaggca gaggttgcat tgagctgaga 118140
tcacaccatt gcactccagc ctgggtgaca gagcaagact ttgtctcaaa aaaaaaaaa 118200
```

```
aaaaaaaaaa aaaaagaaga ggaagaaatc gttttttcaa gaaggggaaa gctgggtgat   118260
ttaagaatga acttgaagag gatcactcag tcctcaacct aggagtggca agaatataga   118320
ctgtatggga agtggttctg ctccttggta cccatcttag aaatatttgg cctgagtctg   118380
taagaggcag gtactttatc taacctgagg ttaggggggcc actacatccc catccctcc    118440 cctgctttct aaccatgcta acatcttctc actctcctgt ctcctctcct tctcactccc   118500
ctaatctgcc tattcacatt tgggcctgt tttcctattg ggttgctgt gttattctca     118560 ctgatttgca gacattcctc tgtgtcatct ttttaatttt gttttaattt ttagaggcag   118620
gatgtcattc tgttgcactg gctgtagtga cgtagctcac tgcagcctca aactcttggg   118680
ctcaaactcc tgtcctctgc ctccacttct caactggtaa cctcacttct cttcatgagg   118740
tctctccagc cccagggcct ttgcacatgt tcccctctct tctgagtggc atatggtagt   118800
tgctcctctg taaatattta ttgacatcct gacttccaac cagcagagaa ttgacctcct   118860
tcccatgctc aggctagtga aggcatgagt ttggctgagg tcccagtggg gaaggtgagt   118920
ggggtggcag agttaaccag gagcagcatg gtagaatggg taaaaccaga cgtagcacgc   118980
aggcaccaca tgttagctgg acaagtagtt taaccccatg ggtctcaatt tccccatcaa   119040
tgaaagggag aatagaacaa gtccctggta agcagcataa aatgagctct cagaatgtaa   119100
agtaacaagc acacaacctg gaagagaata catttagtga atattggctc ctttaatcag   119160
caggttctga tatgacttag ctacaattaa gaaaataaaa atggaggccg ggcgcagtgg   119220
ctcatgcctg taatcccagc actttgggag gccaagacgg gtggggtgga tcacctgagg   119280
tcaggagttt gagaacaggc tggccaacat ggtgaacccc atctctacta aaaatacaaa   119340
aattagccag gcgtggtggc gcacgcctgt agtcccagct actcgggagg ctgaggcagg   119400
agaaacattt gaacccagga ggtggaagtt gcagtgagcc cagattgcac cactgaactc   119460
cagcctgggc gacagagtga gatttgtctc aaaaacaaaa gaagtctgga ggccaggagg   119520
ttggttgcag ggttggttcc ttggctcaac aatgtctcca aagagtcctt ccatctttcc   119580
actctaacat cgtcactgta aggactttt ttaacattta ccactcacag ccccaagacg    119640
actgcgtcag ttcttttcttt ttttccttca gacagagtcc cgctctgtcg cccaggctgg   119700
agtgcagtgg catgatctcg gctcactgca acctctgcct cctgggttca gcgattctc    119760 ctgtctcagc ctcccgagta gctgggatta caggtgcctg ccactgcatc cggctaattt   119820
tttgtatttt ttttagtaga gatagggttt caccatattg gtcaggctgg tctcaaactc   119880
ctgacctcag gtgatgcacc tgcctcggcc tcccaaaggg ctgggattac aggcgtgagc   119940
cactgtgccc ggccgatgac tgcctcagtt ctaaggtact tacccagcca tccacgtaga   120000
cagacacaaa agcatccggc caaagaagag ggagaggaag ggctgtctct taccatgtga   120060
ctcatctcac ggggaaaaaa tccttttcca gaagcaccca gcagattttt cacccagatc   120120
ctgttaggcc tacgaatggg tcatgtgaca agtgctctta ttgcaaggaa tcttgggaaa   120180
aagagactat taggcatttt ctgcctcttt gatgggaggt gggctctgcc agtaaggcgg   120240
gtagtggtgg tggctcttgg atggacaact gtgtcttcca ttcttcttct tcttttttt    120300 tttttttaa gagacaaggt ctcactctgt tgcccaggca gaaatgcagt ggcacaatca   120360
cagctcactg ctgcctcgac ctgccaggct caggtgatcc gcccaccttaa gcctcacgag   120420 cagctggagg agtgtaccac catggccggc taatttttat attttttgta gagatggggt   120480
ctctttatgt tgcccaggct ggtcttgaac tcctgagctc aaacaatcct cctgcctcag   120540
cctcccaaag tgctgggatt acaggcataa gccaccacgc ctggactctc ttctttaaat   120600
```

```
actgagcctt ccacctcttc tagaatatac tctgttaatt atcaaccaca cttttctaca    120660 ttttttgcttc attattcatt cagtaaacat ttattgagtg cctactgtat gccaggcaca   120720
gctttaggtg ctggagatgc tatgaacaaa acagatgaaa atttctaaaa aataaaataa    120780
aaaataaaaa taaattttgc aaagccaggc acagtggctt aggcctatag ttccacctac    120840
tcaggagtcc aaggcagtag gatctcatga gactgggagt ttgagtccag cctgggcagc   120900
atactaggac tctgtctcta aaaagaaaa gaaggccggg cgcagtggct cacgcctgta    120960
atcccagcac tttgggaggc cgaggcaggt gaatcgcaag gtcaggagtt tgagatcagc    121020
ctgaccaaca tggtgaaacc ccgtctctac taaaaatgta aaaattagcc aggcatggtg    121080
gcaagtgcct gtaatcccag ctacttggga ggctgaggca ggagaatcgc ttgaacctgg    121140
gaagcggagg atgcaataag ccgagatcgt gccactgcac tccagcctgg gcaacagaat    121200
gagaccctgt ctcaaaaaaa aaaaaaaaaa gaaagaaaga atagaaaata tctgccctac    121260
ggggatggac atgctagaac atcaaagtcc aatggaactt tctgcactga tgaagtatgt    121320
atgtatgcac cagccacatg tggcttggga gcacttaaaa cgtgactggt acaagcgaat    121380
ttttcattta atttaaatga atttaaatct gtatttaaat agccatgtgt ggctagtggt    121440
tactttattg ggcggtgcag ctctctaaag gccaagagat acatcatcaa cttctctccc    121500
ttgacccata ttcagttctc tcccaccctg aaaatctcct ctcctaccca ggctcacatt    121560
tccagttctt ctcctcttgt tctccctcaa ccatcagccc ccgcaagact gacgtgaccc    121620
tgatgccgta tgaaatgcat tcttcatcct ttactcttac tcacctctgt gcggccctgg    121680
agaccagtga cctctccttt ctcaaaatac tttatttctg tgtgtttttg ttgttgctat    121740 tgttttggg gggttttctt gagatggagt ttcactctca tcacctaggc tggagtgcag    121800
tggtgcgatc tcagcttact gcaacctctg cctcccaggt tcaagcgatt ctcctgcctc    121860
agcctcccaa gtagctggga ttacaggctc ccgccaccac ggctggctaa ttttcttgta    121920 ttttttggtag agacggagtt ttgccatgtt ggccaggctg atctcgaact cctaacctca    121980
ggggatccac ctgcctcggc cttcaaagt gctgagatta caggcatgag ccaccgcacc    122040
cagcctcaaa atgcttttga acttgactgt caggtatgcc attctccaca ccagtctcct    122100
cccatgtctg tgtcttctcc ctctccactg gggacccttg gctttttcca cttcactcat    122160
ctaccctggg ttatctggtc ttccataacc ctgtcctctg ccacacctca cttattcacc    122220
caccacaata tttattgagt actcactagg ccatgaaaga tgctatacaa aaaaagcccc    122280
tgtcctcgtg gagctgacat tctagaagaa agcatgaata ataaatacga cttaataaac    122340
agtacggcca ggcatggtgg ctcacgccta tcatccaaac actaagagac caagatgaga    122400
ggatcacttg aatccaggag tttgagacca ccttgggaaa cgtactggga ccctgtctct    122460
acaaaaaaaa tattaaaaat tagctggata gggtaatgca tgcctgtagt tccagctact    122520
tgggaggaca aggtggaagg attgcttgag cctgagaggt caagtccgca gtgagctgtg    122580
actgtgcact gcacgccagc ctgggtgaca gagtgagatc ctgtcttaaa aataaataaa    122640
taaacaaaca aacaaacaat ataattccag agagtgaaga ggcaggatct ctttagctag    122700
gaagttgagg gatgttctct ctgagaaggc agaatctgag tttcaacctg aagaattcga    122760
agaggccagc taggcaaaag atgagagttg aaggaatggg gacggcagag gagacagcca    122820
atatagtaat tctcaataaa gcagaaagtg agcttttcct gctggcagaa cagaaaggaa    122880
gtcggagtgg ccagggtgtt gtgggacaag gtggtcagca ggagtcacat cacgcaaggt    122940
```

```
catgtggtca tggtagactt taaattttac tccaagcctg atggaagcca ttggaagatt    123000
ttaactaagg agtgacggaa aactggcatc tcaaactcaa catgtctaca acccagttct    123060
tgatctttga aaccttcttc ctccatcttc cccatctcca ttgacagcaa cttcatcctt    123120
cagttagctc aggccaaaac cctggagtca cccttgatac ctctctcctg ctccacactc    123180 agtcttttcca ttggaagccc tagggggctgc catattgttc tccatagcac ttcacaccgt    123240
ctgacatact atatcttttc ccactattgc tttgtcctg gtagcatctt taggcactct    123300
ctgaatatct ggcacatagt acgtgctcac taaatccttg ttgaataaat gaatgaacat    123360
cactccgtgg tcctttcaga accagagcca ttcttctctt tcttcaccac cgttgccct    123420 caccccgccc aactagtcac aggagttgaa ggatgacaca gtagagaact gggattctgg    123480
agtcctgtgg ctggtctggg gttcgagttc ttactcagtg gtaggaacct ccatgtggga    123540
ttaacttatc tggtctttag tttcctcctc tgtaaaatgg gcctcaaact gccaaccgct    123600
gggatgcagg gaggatttga tgagcccagg caggctccct ggagcacagc aatcaatggc    123660
agctatatat aaaccgggc ctcttttgta ctcccactgc ctttgtccta gttccagccc    123720 tcattcacacc agcctgctct tgcggctccc tcctaacttc tgctccatca ccaccaatct    123780
gtcctttcag ctgtcaggct tgtcttctga acgccaaccc taatcacatc ccttcctgct    123840
ccaaaacctt acatgactct cactgtccac aggacaagac ccagcctcta gttgacagcc    123900
tccactgtcc agcttaccca acctctcccc taccacatac cctgagtgga gccttctgcc    123960
tccatagggc tttcttagcc agagaagcct cccttatctt cctgttctcc tcctaattcc    124020
ttcttatcct tccagggagg aggctgtgag gtaatgcatc ttgggagcca gctgggattg    124080
cacagggtgg tgagattatc tgcatttccg aggcttgaac aagttaaggc aatgggaaag    124140
gtcacacaat gagaaaatgc agggccagga tttaacccgt ctgagatgtt ctgactgtgc    124200
tatgctgcct ccccggacat gagctctgcg ataatgctgt ccccaggctg taatcattcc    124260
ctctttcatc cctgcctcct ctatccctgg ggtcagaggg acttgtagtt gaatctctca    124320
ctcactcatt ggtgtggtct ctccctaaag cagggtggag tttgtcttag cgttatcact    124380
gcatccagca caacctccct ggtccaggct tatcagcgtt caactgcgtc aatgcagttg    124440
cctcctcctc aatctcccag cttccggcct tgcccctag agagatcata ttttaataca    124500
agtcagatta catccctcct ccctcagaa ccctccatgg ctcacacctt actcagaaa    124560 aaagccaaag tcctctccac aaccacaaa gccctgcacc atccatcacc tcactgcctt    124620
cgtcccctca caccctcccc cttgctcgct ctgcttcagc cacaccaact catctctgtt    124680
tctcaaatac accaggcatg gcctagctat taaatgcacg gtccagcctg gtgcatttga    124740
agaacacgga tgaattggtg tggctggaac agagtgagtg aggggagag cgggaggagg    124800 accttgcac cagctggacc tttgcaccgg ctgttccatt tgcctagagt tttccctgac    124860
atattcatat ggctcactct cttgcttccc ttgctttctc ccagtctttta ttcaaatgtc    124920 tatttctctg cacttgtgct gttttgataca gtcaccgctg gccacatgtg gcctttgagc    124980
acttcagttg aaacacatga aagtgtagaa tattgaccag attccaagga aaaccatgtg    125040
caaaatatct tttatctctt aagatacagg gtctcgctct gtcttccagc ctggaatgca    125100
gtggcacgat cacagctcac tgcagcctca aaatcccaaa ctcaagtggt cctcccacca    125160
acagcctccc gagtagctgg gattacaggc acacaccaca atgccccgcc catttttta    125220 attgttatta ttttttttaa tagcgacaag gtcttgccat gttgctcagg ctggtctgga    125280
actcctggcc tcaagcgatc ctcctgcctc agcctcccga gtagctgaga ttacaggcag    125340
```

```
gagcttttgt gcccagcagg tctacgatct tcttagaatg cttcaggctg ggcatagtgg 125400
ctcatgcctc aaataccagc actttgggag gccaaagcag gcagattgct tgagctcagg 125460
agttcgagac cagcctgggc aatatggtaa aaccctgtct ctccaaaaaa aatacaaaaa 125520
ttagctgggc ttggtggctc ccacctgtag tcccagctac ttaggaggct gaggaaggaa 125580
gatcacctga gcccaggagg cggaggttgc agtgagccaa gattgagcca ctgcactcca 125640
gcctagacaa cagggagacc ctgtctcaaa ataaataaat aaataaataa ataaataaat 125700
aaataaataa acaaacaaac aaacaaacca ataaatgaat tttacctgtt tcttttttact 125760 tttttaatgt ggctactagc aaattttaat tttttttttt tttttttttt tttttgagac 125820
agagtcacgc tctgtcaccc aggctggagt gcagtggtgt gatcttggct cactgcaacc 125880
tccacctcat gggttcaagc agttcgcctg cctctgcctc tgagtagctg ggattacaga 125940
tgcccaccgc cacgcccagc taattttttg cattttagt agagatggag tttcgccatg 126000
ttggccaggc tggtctcgaa ctcctggcct caagtgatct gcctgcgtcg gcctcccaaa 126060
gtgctgggat tacaggcatg agccaccgcg cctggctata aaatttcata agtagctctt 126120
aatagatttc tcctgggcag tgctggtcta aacactttt tttttttttt ttttttttga 126180
gacggcatct tgctctgtca ccaggctgga gtgcagtggc gcgatctctg ctcactgcat 126240
cctctgtcac ccgggttcaa gctattctcc tgccttagcc tcccaagtag ctgggactac 126300
agacacccgc caccacgccc agctaatttt tgtatttta gtagagacgg ttttcacca 126360 tattggccag gctggtctcg aactcctgac cttgtgatcc gccagccttg gcctcccaaa 126420
gtgctgggat tacaggcatg agccaccgca cctggctata aaatttcata agtagctctt 126480
aatagatttc tcctgggcag tgctggtcta aacactttt tttttttttt ttttttttga 126540
gacggcatct tgctctgtca ccaggctgga gtgcagtggc gcgatctctg ctcactgcat 126600
cctctgtcac ccgggttcaa gctattctcc tgccttagcc tcccaagtag ctgggactac 126660
agacacccgc caccacgccc agctaatttt tgtatttta gtagagacgg ttttcacca 126720 tattggccag gctggtctcg aactcctgac cttgtgatcc gccagccttg gcctcccaaa 126780
gtgttgggat tacaggtgtg agccaccgcg cccggccctg taacactttt aacactgaac 126840
tgtttgcctt ccaggtggta aagagcaggt gcctttactg atagaaatgt caccactccc 126900
ttcatcccgc cagccccatg tcactgacgc gtcctttccc cttgctctgt ggtaactttc 126960
tcctaagcac tcatcgccct aacatctgtc atacaggtat acctcagaga cactgctggt 127020
ttggttccag gtcgccataa caaagcgaat attgcaataa agggagtcgt gcctttttg 127080 gtttcccagt gcacataaaa gttatgctta cactatagtc tgttaagtgc atgatagcat 127140
tatgtctaaa aaaaaatgta cataccttaa ttttaaaatc catcaaggct gagcacagtg 127200
gcttgtaatc ccaacacttt gggaggccaa ggcaggagga ttgcttgagc ccagggattt 127260
gaaaccaggg aacaaagtga daccccgttt ctacaaaaaa attctttta aaatagctg 127320 ggtatggtga cgcatgcctg tggtcccagc tacatgagag gctgaggtgg gaggctcact 127380
tgagcctgag agattgagac tgcagtgagc tgtgatcaca ccactgcact ctagcctggg 127440
ggacagagtg agaccgtatc tctcaacaaa aattaaaaaa aaaaaaaaaa aaggctgggc 127500
acagtggctc atgcctgtaa tcccaacagt tgtgaggcc aaggtgggtg gatcacttga 127560
ggtcaggagt tcaaaccag cccagccaac atggtgaaac cccgtctcta tgaaaaatac 127620
aaaaaaatag ccgggtgtgg tggtgcacac ctataagccc agctactcgg gaggctgagg 127680
```

```
cacgagaatt gcttgaacct gggaggcggg ggggagattg cagtgagccg agattgcact    127740
gctgcactcc agcctgggtg acagactgag actctgtctc aaaaaataaa taaataaata    127800
aataaataaa taaatgtttt attactaaaa aagttaacaa tcatctgagc cttcagtgag    127860
tcctcatctt gctggtgaag ggtcactggc tcagtgttga tgggtgctga ctgatcgtgg    127920
gggtggttgc tgaagattgg ggtgcctgtg acattttctt aaaataagac aagaaagttt    127980
tccgcatcca tcgactcttc ctttcacgaa agatttctct agcatgagat gcttgttgac    128040
agcaatttta cccacagtag aacttttttc aaaattggag tcagttcttt caaaccctgc    128100
cactgctttg tcaactaagt ttatgtcata ttctaaatct catgttgtca ttttaacagt    128160
gttcacagaa ttttcaccag gagtagaatc catctcaaga aatcactttc tttgctcttc    128220
cataacaagt aacgcctcat gcattgaagt ttgatcatga ggctgcagca attcagtcac    128280
atcttcaggc tccacttcta actctagttc tcttgctagt tccatcactt ctgcagtgtc    128340
ttcctccagt gaagtcttga actcctcaaa gtcatccatg aggatcggaa ttgacttcct    128400
caaaattcct attaatgttg atattttgac ctgttcccac gaatcacaaa tgttcttttt    128460
gttgtttgtt tgttgtggat tgttttttta tttttaattg agttgaggtc tcactatgtt    128520
gcccagactg gtcttgaact cttggcctca agtgatcctc ctgccttgat ctccctaagt    128580
gctgggatta caggcatgag ccactggaac agccacaaat gttcctaatg gtatctagaa    128640
tggtgaatgc ttttcagaaa gttttcaatt tcctttgccc agatgcatca aaggaattta    128700
tctatggcag ctatagcctt atgaaatgta tcccttaaat cataagactt gaaatagaga    128760
attacttctt gatccatggg ctacagaatg aatgttgtgg ctgggcatgg tggctcacac    128820
ctgtaatccc agcactttgg gaggctgagg caggtgggta acttgaggtc aggagttcaa    128880
gaccagcctg gtcaatatgg tgaaacccca tcactactaa aaatacaaaa attagctggg    128940
catggtggcg tatgactgta atcccagcca cttgggaggc tgaggcagga gaattgcttg    129000
aaccctcttg aagacagagg ttgcagtgag ccaagatcac accactgcag cgacagagtg    129060
agactctgtc tcaaaaaaaa aaaaaatgt tgtgttagaa gtcataaaaa caacattcat    129120
cttcttgtac atgcccatta gaggtcctgg ataaccagtg cattgtcagc agtaatattt    129180
tgaaagaaat cttttttctg gctgggtaca gtggctcgca cctgtaatcc caccactttg    129240
ggaggccgag gcgtgtggat cacctgaggt cgggagttca agaccagcct ggccaacatg    129300
gtgaaacccc aactctacta aaaatacaaa aaaattagcc aggcatggta gcaggtgcct    129360
gtaatcccag ctaccctgga ggctgaggca ggagaatcgc ttgaacctgg gagtcagagg    129420
ttgcagtgag ctgaggtcgt gccattgcac tccagcctgg gcaacaagag tgcgacttca    129480
tctaaaatac atatatatat ataacatgtt atatgtaata taattatat atataacata    129540
tatgtaatat aaattatata tcacatataa catatatcat gtgttatata tatcacatat    129600
aacatatgtg ttatatatca catataacat gtgttatata tcacacataa catatattat    129660
gtgtatatat gtcacatata ttatgtgtta tatatgtcac atataacata ttgtgttata    129720
tatatcatat ataacatata ttatgtgtag tgtatcatat gtaacatata ttatgtgtag    129780
tgtatcatat ataacatata ttatgtgtag tgtatcatat ataacatatg tgtagtgtgt    129840
tatatataac atatattatg tgttatatat ctcatatgtt atatataaca tatattatgt    129900
gttatatatt atatatatat tttttctga gtagatctca acagtgggct taaaatatca    129960
gttatccatg ctataaacag acgggctgtc attcagtctt cattgttcca tttatagagc    130020
acaggcagag tagattcagc ataattctta agaccttagg actttaggaa tggtaagtga    130080
```

```
gcattggttt caacttaaag tcaccaggag cactagctcc taacaagaga gtcagcctgt  130140
cctttgaagc tttgaagcca ggcattgact tctcctctct agctatgaaa gtcctagatg  130200
gcaacttctt ccaatagggc atttcatcta cattaaaaat ctattattca gtgttgccag  130260
cttcattaat aatctcagct agatcttctg gataacttac tgcagcttct ccatcagcac  130320
ttatcacttc accttgcact tttatattat ggggacacct tctttcctta aacctcatga  130380
accaagatct tctagcttca gattttcttc ctgcacttcc ccacctctct cagtcttgct  130440
gtgggcttgc tgtggattag ctttggctt aagggaatgt tgtggctggt ttgatcttct  130500
atccagacca ctaaaacttt ctccatgtca gcaagaagcc tgtcttactt tcttatcatt  130560
catgtgttta ctagagtagc cctttttaatt tccttcagta atttttcctt tgcattcaca  130620
acttggctaa cctctagctt atggccttt gtttgttgt ttgttttgtt tttgagacag  130680
ggtctcactc cgttgcccag gctggagtgc agtggtgcaa tcaccgctca ctgcagcctt  130740
gacttcctgg gaccaagtga tcctcccacc tcagcctcct aagtagctga gaccacaggt  130800
gtgcaccacc acacccagct aattttttta ttttctgtag agatagggtc tccctatttt  130860
gcccaagcta gtctcaaact cctaggctca agccatcctc tcacctcagc ctcccaaaat  130920
gctcggatta caggcatgag ccaccatccc tggccctatc tcagcttttg acacgccttc  130980
ctcactgtgt ttaatcattt ctagcttta atttaaagtg agagacgtgc aactcttctt  131040
ttcacttgag cacttaaagg ccattgtaca gttatacact gacctaattt caatattgtt  131100
atgtctcggg gaataggaag gcccaaggaa agcgggagag atgggaaat ggccagttgg  131160 tagagcagtc agaacacaca caatatttat cgatcaagtt tgccatcttc tatggatgtg  131220
gttcgtggca cccccaaaca atgactatag tcacatcaaa gatcactgat cacagaccac  131280
cataacagat gtaataatta tgtaaaagtt tgaaataccg taagaattac cagagtgtga  131340
cacagagacg caaagtgagc acacgctgtt ggaaaaaaaa tggccctgat agacctcctt  131400
gacacagggt tgccacaaat cttcaatttg taagaaacac aatatctaca aattgcaata  131460
aagcaaagca caatgaaatg aagtcttcct cggccggtgt ggtggctcac gtccataatc  131520
ccagcacttt gggaggccaa ggcaagagga tcccttgagc ccaggagttg gaggccagcc  131580
tgggcaacac agggagactc catctctaga acaaaacaaa acaaagcctg cttatattta  131640
ttgggtttac tctcagtctc ccccacacag agatagggcc tggcttgtta ttagtgctca  131700
gttgatgttt gtgaagtgaa atactaagga cttaaccact gcctgttctt tgctgttcat  131760
gccctgacag cttttatgtg ccagcacaga agaaaacaag gtgcaagaag agaatagtga  131820
tctctaagtc agaatttgag gaacccaaat tagtaccaga aagctgggag gagaagagaa  131880
aaataaagta aatcaaatta aagttgaat gggccaagtg cagtagctca tacctataat  131940
cccagcactt tgggaggctg aggtgagagg atcacttgag gccaggagtt ctagaccagc  132000
ctgggcaata tagcaagacc ccatctctac aaaaaaaatt ttttaatttt ctgaatatgt  132060
tgttgtacac ctgtagtccc agctgcttag gaggcagagg tgggaggatc gcttgagccc  132120
aggaggttga ggctgcagtg agctgttgtt gcaccactat actcaagcct gggtgacaga  132180
ataagtccct gtctccaaaa ataaaaataa ataaattcat tttttgtaaa gttgtatgtc  132240
atggcccctg cctactctgg cttcatgact tgctgcttga acctcaccat ccaaatccca  132300
gtggtgacac catgtcattt cttgaatttg ccaagccctc tttcagtccc aagctctctg  132360
tcatggccac tctcagcctg gaaagttctt tccccactgg ccagatttct cccctcatc  132420
```

```
tatgggaact tgacttgaag taggggggtat cccaggccct ggactagtta acacgacctg    132480
ctgtgtgccc ctcaaagcca ttgtcttcct agctgagaag gcatcacacc tgcaacagat    132540
tcactcattg tgtgcatgtt tttcttaacc acttctcttc tgcatcagct ccatggggca    132600
gggatagtct catatgtcac tctacccagc ataggata cgctcagacg cccacttgtg      132660
gatggtggaa aaggtcagcc caacctaata tgcccatctc tcctctaggg gtaatcttga    132720
gaaaaaagt tgggaacttg ctttgtgtta gtttaggatg acccagaata gatcctgaaa     132780
caagaattta gggcaatcct tgtgcaagta gttcatctga gaggtgaccc cagaagggtt    132840
ggagaaggag aggggaggtg gggcaaggaa gggtgagttg tcctgtaggc aactgagctc    132900
cgtcctactg ggagcccacg tggaactcac ctcttaagtg atccagaatg aagggtgagg    132960
gagctgcggt attgatccac caactcccag caatctttgg ttgagggctg ctcccttaaa    133020
gttcattccc tgggcctgcc ccagatttgg agacagccct aaggcaagag gtacagatac    133080
cagttggcca cagactgaag tgttaagacc caagccctg ataaaactg aaaaatcaag       133140
ccagatgtgg tggttcccac ctgtaatccc agctactcag taggctaagg caggaggatt    133200
gcttgagccc aggagttcaa tgctgtagcg agctatgatt gcaccactgc attccagcct    133260
gggcatcaga gcaagacccc atgtctaaaa taaaaataaa ctgaaaaatc cccaagttat    133320
ttgctgtgac caaccttcca ttaaccacag accctctggt attcagcatt tcttgtccat    133380
tatatgaagt tctctgatgaca gtctctttta ttgtattgtg ccttgaccac gcactgtaca  133440
tcacttagct ctgaaatgga catgttcagg aaacagggcc aggtgggacc ctgtgtttca    133500
acagcaatac ttttacaaat gaggtctcat gacagggtct tgctcggagg gtttctatgg    133560
aagcctcatc ccacctactg ctatcatcct tactaacttg catttacaaa agggactctt    133620
tttgaccaga ggcttggggt ctgtagctgc cttctagcca gctgatgctg gctggtccac    133680
acaagcagga tcacacccat ttttttgttt tcttatttat ttctgaatag gttagcatac    133740
cggtaacctg tgtgcctggc attgtgctga ccactttttg tcaacttact gaatcctcac    133800
aaccccttgga ggtattgata ctattgttat ccaggttata caaaagggg aaactgaggc     133860
acagagcagg gatgtccctt gcccaaggtt acccaactgg aaagtggcag atctgggatc    133920
tgaacccatg caggctgggc tcttaacact gaactacttt cctgccattt gttaaagagc    133980
cacaaaccag gccaggcacc atggctcacg cctgtaatcc cagcactttg ggaggccgag    134040
gcgggtggat cacctgaggt caggagttca agaccagcct ggccaacatg gtgaaaccct    134100
gtctctacaa aaatacaaaa aaaagtaccc gggcatgatg gcgggtgcgt agtaatccca    134160
gctactcggg aggctgaggc aggagaatcc cttgaacccg ggaggcagag gttgcagtga    134220
gctgagatca caccattgga gatcgcactc cagcctgggc aacagagtga gactctgtct    134280
caaaaaata aataaaata aataaagag ccacaaaccc cgaaaggtct gccattcccc         134340
cagggcccca ggccaccca caatctattg tcattgtagg ttgtgaaata tactgaatgt      134400
caccccaacc ttgagccatg gggaagattc catttctctc attgcaacat tgtgcaaca     134460
tgaaccatct gttgggggtc ttcgtaaatc accttttatc ccgtgaggca ggtactgtta    134520
agaccatttt acaggtgaca aaactgaggc cagtggtgtc gagtcacctg cctgtggtca    134580
cccaaccaat acaggacagc ttggaatccc aagcaccccc gccctgctgt ctgaccccca    134640
aaacccaccc tctgttctcc attctggctt cttctcttca gcatcttggc gacagttggg    134700
acggagtttg acctacggac gctgagggca gttcgagtgc tgcggccgct caagctggtg    134760
tctggaatcc caagtgcgtg agtttccgac cctgacaagg ggtttgctca cgggccccag    134820
```

-continued

```
gagccctcag tttcccctat gcagagcatc tcaggaggcc acatcctgcc accagcctgt    134880
gtgagggcag tctcttcttt gggactccct atagggaacc ccctaggaat atgactgtag    134940
ctccccatga gctcctgaaa gcaaactagg agccacaccc atttattgag cacctactgt    135000
ctatcgggag ccatgctaag caccacgtgt gatctcattc agtactcaca gcccTatgaa    135060
gttgatagga ctgatgtctc tattttatgg aggggaaac tgaggctcag agtggctgaa     135120
acattggagc agggttttgt ggctgagaag tggcagaact aggagtgagc aagtgtgact    135180
ccaagcctgg gccgtaccac tggtggcaat gaccattccc atttaatgag tgcctgctgc    135240
gtgcagggca ctacagaagg actttacatg aattaccttA tttcatcctc acagtcaccc    135300
agcgaacacc cattttacag atgagacggt tgaggcttaa ggaggttaaa ttactcacct    135360
gaattcttag agtggacagt aatgagctct aaaattcata ctcattcctt gctgctttct    135420
cattctccac agatacatct agtccccgtt taagggtggc tgccatatgc agggtcaaga    135480
ttaagtgtag gttgagccaa aaaaaaatgt aaaaagcaaa aataaaacag gctgtcctt     135540
tttctatctt cttgtcttgg ttaataataa taatttagcc aggcatggtg gctcatgcct    135600
gtaattccag cactttggga ggatcacttg aggccacaag ttcgagacca gcctgggcaa    135660
cattgtgagg aacaccaccc ccaccccccc gccaatatct acaaattttt ttttttttt     135720
tagaaattag ccaggttgac tgggcacagt ggctcacacc tggaatccca gcactttggg    135780
agaccgaagc gggcagatag agcgagctca ggagttttaa gaccagcctg gcaacatgg     135840
cgaaaccctg tctcaaaaaa aaaaaaaaat tagcaggcat gatggtgcac acctgtagtc    135900
ccagctactt aaaaggctga ggcaggagga tctgagccca ggaggtcaag gctgcagtga    135960
gctgtgatag caccactgca ctccagcctg gacaacagag tgagaccttg tctcaaaaaa    136020
acagacaaca aaaagtttaa aaacaaacaa tttataggct gggtgcagtg gctcatgcct    136080
ataatcctag cactttggga ggccaaggtg gatgggtgga tcacctgagg tcaggagttc    136140
gagacctgcc tggccaaaat ggggaaaccc cgtctctact aaaaatacaa aacttagccg    136200
ggcgtggtgg cgggcatcta taatcccagc tactcgggag gctgaggcag gagaatcact    136260
tgaacccggg gggcggaggt tgcagtgagc tgaaatcacg ccactgcact ccagcctgga    136320
tgaaagagtg aaactccgtc tcaaaaaaag aaaaaaaaaa attaaaaagc acttactatg    136380
tgccagacat tattctaagt atttccattt ttttaaagtc ctttatcctc caacaagcc     136440
tgtgaagtag tctcttttat tatcaccatt ttacatttta ttggcttcgt tcttccggtt    136500
cattgctacc caggtttaaa gagtaagatt cccagagga tcaccagcag gatctttttg      136560
tagaaagaag acacttctat ccaaggtctc tgcaagatcc cagcagatgc ctgcatcata    136620
ttaaattaag ggccatccca aatctaatag tcaaagagc caggtgcagt ggctcacacc     136680
tgtaatccca gcactttggg aggccaaggc aggacgattg cctgaggcta ggagttcaac    136740
accagcctgg gcaacaaagt gtgaccctgt ctcaaaaaat atatgtatat tataatagca    136800
gtagtaacaa gagtctctgt ttaatgacca cctatgactt accaggtact tcactgtgtg    136860
tgaactctct catctaatcg tatgagggag gtactattgc agtccccatt tacagatgga    136920
gaagctgagg tttggaattc actagtaagt ggatgactag gtcaggttcc cttgaagcgg    136980
atacttaggt gggtgttcag atgcacctgc tttattgggg gacggctctt gggagagaca    137040
gcaggagatc agcagggtgg ggctggggaa tggatagagc agggacgcaa tttcagctgg    137100
agtgtgtgtg acaccagagt tgtcctccaa tgcatggcaa ggatgccggc cttttgtact    137160
```

```
tctatagtca gtcactgtgg atgggaggta gagacgcagt agctcccagg tgagatagct   137220
tttgatcacc aagggcaatt ctactaagaa gagaggcagc tgggaggcat tagcaaccaa   137280
catccatagc agctggaggg cgggtacacc agaaagaaaa tgggatcttg ccagacacc    137340
aagagtatcc agcaccttaa ccactgcacc acactgcatc tgttagcacc cacattacat   137400
tttttttttt tttttttttt tttgagacgg agtctcgctc tgtcgcccag gctggagtgc   137460
agtggcgaga tctcggctca ctgcaagctc cgcctcccgg ttcacgcca ttctcctgcc    137520
tcagcctccc gagtagctgg gactacaggc gcccgctacc acgcccggct aattttttgt   137580
attttttagta gagacggggt ttcaccgtgt tagccaggat ggtctcgatc tcctgacctc   137640
gtgatccgcc cgcctcggcc tcccaaagtg ctgggattac aggcgtgagc caccgcgccc   137700
ggccagcacc cacattacat ttttaagccc ttggagtggc atggcccctc gagctatcct   137760
gacagcttcc ctctcttact gtggtctcca cccatcaaga gccatgggaa gttcctgcaa   137820
tcaagaagca aagcctcagg ctatatgttt gaaccttcat tttgatcata gactttccta   137880
gtagatacca tagtggttac aaacatagga tgttgtcatc gttcagacct gagttaatag   137940
cctcaagaaa aaaatggtag tggaaccagg tatggtgaag tgtgcctgta gtcccaccta   138000
ctcgggaggc tgaggcagga ggctcgcttg tgcccaggag gtcaaggctg cagtgagccg   138060
tgatcatgcc actgtattcc agcctgggtg acagagcaag cccatctcaa aaaaaaaaa    138120
aagccaatga taggcagaga aatactaact aaggctcttg ctctgtcgcc aggctggagt   138180
gcagtggtgc aatcacagct cagtacagcc tcaacctccc cagactcaag caatcctacc   138240
atctcagcct cccaaatagc tgggactcca ggcacacagc accatgccca gttaattttt   138300
ttgtattttg tagagacagg gtttcaccac gctgctcagg ctggtctcaa actcctgagt   138360
tcaagtgatc caccgcctc agcctcccaa agtgctggga ttacaggtgt gagccaccac    138420
gcttggccag ctattattat tattaacatt cttcgagtct tacaacagtg gaacttttag   138480
tgcaggatgc gaatttcagt attaacccct tcctctccca aaaggatttg aagcccagag   138540
taattcagcc gccatgaatg aaccatttgt tagatgagag gctactggag gctgagcttg   138600
gtaggataag agcttgcatg gggtccctga ttgatgacaa taccccaga tttaggtctt    138660
cagatgccca gttgggtgtg tcttctgttc cactgtgtcc cttcggggac tgttccctgc   138720
cttctttctt tttgagatgg aatctcgcac tttcacccag gctggagtgc aatggcgtga   138780
tctcagctca ctgcaagctc cacctcccgg ttcacacca ttctcctgcc tcagcctccc    138840
gagtagccag gactacaggt gcccgccacc acgcccagct aatttttttg tattttagt    138900
agagacgggg tttcaccata ttagccagga tggtctcgat ctcctgacct cgtgatctgc   138960
ccgcctcggc ctcccaaagt gctgggatta caggcgtgag ccaccacacc tggccccctg   139020
ccttcttatt caccaccatc tttctgaatt gggttgctca gaacagagaa agcaacatca   139080
gcacatgggg aaacatgggg cttcatttca gatggacctg ggttcaaatc ctagttctgc   139140
ctttttttttt tttttttttt tttttgaga cagagtcttg ctctgtcacc cagactggag   139200
tacagtggcg tcatcttggc tcactgcaac ctctgcctcc caagttcaag caattctcct   139260
tcctcagcct cccaagtagc tgggattaca ggcgctggcc accatgccca gataattttt   139320
tgtattttta gtagagatgg ggtttcacca tgttggccag acttgtcttg aactcctgac   139380
ctcgttaatc cgctggcctc ggcttcccaa agtgctggga ttagaggcgt gaaccgccgc   139440
cgcgccctgc ctagttctgc catttctcat gcattctctg ggtgaatcac agcatctctg   139500
ttagccttgc ttcccacttc tgtaaaatga gagtgacttt acatgtatgg ccacctcagg   139560
```

```
ggcttgtcac tagaagccag tgaaataatg ttgagtctgg ttccttgggg ttgaaattgg   139620
gaccgccaac cgctttccta cccagagcag caactagcct atatggcggc cttttatgaa   139680
tgaggaaaag acaccgcctc ttggcagaaa aaaaaaatta agaaaatggc tccctcttct   139740
gggtgcaagt tgcccaacac ccaggaatat ggctccaaaa gcaatggact cccaccccctt  139800 tcttgcccaa aagatcatca aatggaacag catgtcaaat acctttatta agtactttaa   139860
agttggctgg gctctgtggc tcatgcctgt aatcccagaa cttttgggagg cagaggctgg   139920 aagatcgctt gaggtcagga gttcgagacc agcctggata acatagtgag accctgtctc   139980
tataaaatat atatatagat ttatttgaga cagcgtcttg ctctgccact caggctgggg   140040
cgcagtggca caatcatagc tcactgcagc cttaacgatc ctcctgcctc agtccctaga   140100
gtagctagga ctacaggcat gcaccatcat gcctggctaa ttaaaataaa taaataaata   140160
aatactttaa agttaaaagt gcttttaaa aaataataag gccaggcgtg gagactcacg   140220
tctgtaatcc cagaactttg gaagaccgag gcgggtggat cacgaggtca ggagatcgag   140280
accatcctgg ctaacacggt gaaaccctgt ctccactaaa aatatgaaaa attagctggg   140340
cctactcggg aggctgaggc aggagaatgg cgtaaacctg ggaggcggag cttgcagtga   140400
gccgagatgg caccactgca ctccagcctg ggcgatataa caagactctg tctcaaaaaa   140460
aataaataaa ataataata ataataatag gggccaggta tggtggctca cacctataat   140520
cctagcactt taggaggctg aggagtttga gtccttggag accaggggtt tcaggccagc   140580
ctgggcaaca tagcaagacc ccatctctac aaacaagttt taaaacttag ccaggcatgg   140640
tggtgcatgc ctgtagtcct agctattgca gggactgagg caggaggatc acctgagccc   140700
aggaggttga ggctgcagtg agctgtgatt gtgccactgc actccagcct gggcagcagt   140760
gcaaaaccct gtctcaaagg aaaaaaaaaa cctaggaagt gttgttccca tgataaggat   140820
cagcctccgt gtggtgcttc cttcaccatt gcccaatccc caggctcctg ggtgcttaat   140880
attccctcag gaacacacct gctttgtctg ggagagacct gggcgtcttg gtggcggggt   140940
ttgggggtac ttgctcatgg gcttatgggg cctctctctg tgtccccca ggtttacaag   141000 tcgtcctgaa gtcgatcatg aaggcgatga tccctttgct gcagatcggc ctcctcctat   141060
tttttgcaat ccttattttt gcaatcatag ggttagaatt ttatatggga aaatttcata   141120
ccacctgctt tgaagagggg acaggtaggt ccacggagca tgatgcatct ttccagtttt   141180
ctccttcagg acaagctct tgggaggatt aggcaggggt gtgcttcttt ctcctggcag   141240
ctgggaggac cgtctccttc agagagcact acaggagagg cagtgagtga aatagcctct   141300
gagatcttag ctgttgaaag gggtgggggtt ccacagaagg tgacccagca gagaaagagt   141360
ttatttggga atgatcccag gaagcaccat cgggggaatg aggaagtgag cagagaaaga   141420
agggatcttt taaagagtgt gctatcaagc gggttaccac ttaaaactgg gactggatcc   141480
ccctgggcac ctctgggaga cagcaaagaa cacacaactc agctggtcac ggtggctcac   141540
gcctgtaatc ccagcacttt ggggggccaa ggcgggtgga tcacctgaga tcaggagtca   141600
gagaccatcc tggccaacat ggtgaaaccc catctgtact aaaaaataca aaaattagct   141660
gggtgtggtg gcaggcacct gtagtcccaa ttactcagga ggctgaggca ggagaatcac   141720
ttgaacccgg gaggcagaag ttgcagtgag ccaagatcac accactgcac tccagcctgg   141780
cgaaagagtg agactccatc tcaaataaat aaataaataa aaatataaat aaaaaaagaa   141840
cacacacctc agagccgtcc cagccaaggg gcaagggagc tggggtattt atacactggc   141900
```

```
ttcttttga cattggtgag gactgctcct agagtgggaa ttaatgcctg gcacatctgg  141960
ctgagtggaa caggtattct gggtgctttc agacctcgac cagtcctgac ttctaaagca  142020
agcaagaagt ggggagagtt gggccagaaa agggttattg cctcaatgca ttgtgagtgg  142080
taccttgtgg aaggtgagag acagagaaga ttccaggcac aggtgccatg ctaaacgata  142140
gttctcattt attataggaa cccatggatt tattttgttc tctgccctga gtgctgggtg  142200
agagtactgg atgagtcctc ctggtctccc ccaaccccca ggatgtacca gagataccccc  142260 aattgggagt cctggcacca accaatcaga acctagcact cagcagcatt ctgcccctcc  142320
ctgactatgc ccacattaac ccttcagtgg ctgggtctgg gggtagggtg agccccggaa  142380
aagccaggca gcgcagagac actctcccag ggctcagctc tgaaccagca gtgtggaagc  142440
agtgtgtcca ccacgatcca cactcaggaa ccaaatagcc cttggatacg ttttcagtta  142500
aatctttgcc atccaaactc tagctgcttg ctctctaaag ctccagaatg aaatggaatc  142560
aagtaggaag ggatgccttc agtatttcag tatttggacc actggccatc tgggtgcaga  142620
cagactgaat agcagttctg gttctgatga tttgggtcaa gggagctgtg aattgaagga  142680
gtggatagaa ggaatcaaga agcccaaagg ggaacccagg tgggcagaga aagaggtttc  142740 aggccccttta tttgggaaag gcagccacag aagaagattc tgtctgggag tggatttcca  142800
cccaccctct ccacccagtg acccccaagt ggatccgcag aggcagcccc tgagccctcc  142860
ctccccactc ctccccacgg ggagggaaaa cccactgggg aaggtttatt tgcaatggtt  142920
ggaggtttgg gttttttttgt gggttttggt ttgttggttt ttttttttcct cttttctct  142980 tgctcctcct gtctctttct ctcctgggct tgtgaagttt gctcaatatg gaatgtccta  143040
attatttctt tccccgatga agaaggtgtt aattgaggca gagctatttc tgctcctggc  143100
ctcgtcaccc aggcggaaat gcgagagaga gagagagaga gagagagaat gaatatgggg  143160
cagggcctct tggaaaaatc agccgtgagc agagaaacca ggactcctgg atcctaggtt  143220
tctgtgaagt tttattttat gttttctac cctagactag ctaaaggaga agaggccatg  143280
gggttggctt gggtccgagt ggggttttga ggggacagat gtgggtggtg ccaccagagg  143340
ggaggaagcc tcgatttagg agaaagactg aaaagctagc tcacgattaa aaatataaga  143400
cgtgtgagta agagacagat atatacagac acccaggcag tgggttaatt ttaaaatgta  143460
tttataaccg aattcctcag acactctgga cgcttgtttt tctagaagca acgctcagag  143520
tgtttcgtgt cggtggttgg ggggttgagg gggattgcaa agctgctaaa gatagacccg  143580
ttttcagtag cattcctcag tgtcgggagc ccagttcctg tgtgcccagc accgtgccaa  143640
tcgcttagaa ggaagcaaag ataaagtgga aggcttcctg ctttctaaga gcttccaaaa  143700
tagttagagg aaacaagacc cctcatttgc agccatttt aacagtgaag gctaatgtgt  143760
gattataccc acgccccct aaatatgaaa attcagtagc tattgtatgc ctgaaagggg  143820
ccaggtgcag tggctcacac ctgtaatccc agcactttga gaggctgagg tgggagtatc  143880
ccttgaggcc gttagtttga gaccagccta ggcaacatag ccagaccctg tctctgctaa  143940
aataaaaatt taaaattgg ccgggtgcag tggctcacgc ctgtaatccc agcactttgg  144000
gaggccgagg caggcggatc aaaaggtcag gagttcaaga ccagcctggc caacatagtg  144060 aaacccgtc tctactaaaa atacaaaaaa ataaattag ccgggcatgg tggcgtgtgc  144120
ctgtagtacc acatacttga gaggctgagg caggagaatc acttgaacct gggacataga  144180
ggttacagtg agccgagatc acgctactgc actccagctt gggcaacaga gtgagatttt  144240
gtctcaaaat aaaaaaattt aaaaattagc catgagtggt ggtacatgcc tatagtccta  144300
```

```
gctactcagg aggctgagga agaaggatca cttgagccca ggaattggag gctgcaaggc   144360
tgcagtaagc tatgatggtg cccgcactcc agcctgggtg acaaagtgag accctgtctc   144420
aaaaaaaaaa aaaaaaagag agagaggaag gaaagaagga aggaagggag ggagggaggg   144480 actgggctg tgttaactgg gctacacaaa gaggctacat ggagggtggg aattgagcca   144540
gacttggaca tggcgtggag acagagaaga ttccaggcac aggtgccatg ctaaacgata   144600
gttctcattt attataggaa cccatggatt tattttgttc tctgccctga gccttatgtt   144660
taaaagattt ttgccttcca acctgtattt atcaaataat agttcatgta ccaagtccag   144720
cataagtgag gaaggcgttt ccaacaactt aagttcatgg cgaggctaga cttggagttt   144780
ctattcagcc agagcttgaa aggccaacaa gattcattca ttcagcattg gtttatttcc   144840
ctctgctgtg tgctcagtca agggagcaga gaattggtgc tgcgaagtct gtagcacata   144900
cattgagaga tattttttgtt gagtaggaag cttgagttta cacacactca gctgtttgtt   144960
ttcttgtccg acaatgccac ggtcgtcttt gaaaaccttc aaaagcatcg ctcacagaat   145020
aaggtcctct cagacccgct gtgctggtaa aatgaggaca ctcccagatg tgagctttcc   145080
tgcctcccta ccccatcaat accttaagat ttggactgac cttttagcgtt cagcctgact   145140 gccacctccc caggaagctg tctttggttt ccagcaaaag gggtgtctgt tggcacgttt   145200
ctctctcctt gtggcatttt cacagcctgc ctcctgctat ttggggagaa agctcagctc   145260
ctgttcctta cccttaggca agggtaggaa ctgtgtgtac tggtgtccct cacccccaga   145320
acagctccct gagcccagta catcccaaga agaaaaaaat cagcaaggct tataggaaga   145380
taacacaatg cgcttgacaa atttgtccta atggatgtcg gaagaaggct gcacttacca   145440
gctacaccat gcacacggca catttactaa aactgactat attatggacc ataaagtttg   145500
tctcaacaga ggtcaaaaag ctgaaaaaaa tacaaataca aaacatattt tctgaccgta   145560
atgcaattaa gctggaaatc agtaacaaaa agagaactct aaaagtgttt gcagattaac   145620
agacatgcct ctcatttatg gatgaaatga tatgatgtct gagctttgct ttaaaaatat   145680
tctaggctgg gtgcagtggc tcacgcctgt aatcccagca cttttgaggc cgaggcgggc   145740
ggatcacttg aggtcaggag ttcgagacca gcctggccaa catggtgaaa ccccatctcc   145800
actaaaaata caaagattat ccaggtgtgg tggtggccac ctataatccc agctacttgg   145860
gagcctgagg caggagaatc ccttgaacct gggagtcgga gattgtagtg aggtgagatc   145920
atgccattgc actccagcct gggtgacaga atgagactcc gtctcaaaaa aaaaaaaaa   145980 aaaaaattct agtggcaagg caaagtgttt ggaggggata cagaggaata gatgaaacaa   146040
aatttgccag aagtaaatag gtaagtgtct aaattggtga taggtacatg gtgaatcatt   146100 atattgttttt atacttctct ctcgctctct ctctcccccc gttctctccc tgtcttcctc   146160 tccctctgt cttcatatat atatatatat atatacacac acacacacac agacacctaa   146220 taagttttttt taaaaaacaa atacatctaa attacccata ggtcaaagaa gaataataa   146280 tggaaattag aaaatatttt acttgaacaa taatgataat gcatgacaaa atgttgagat   146340
gcaggtaaag ccacacttaa aggcaattta tagccttaaa ggcagttaat ccatccatct   146400 caaaagtttta ggaaaagaat agaaaaaaaa aaaaaactca tggaaaacat aaagagaaaa   146460
gtagtaaagc tcagagaaga aattaatcaa tagaaaacca ataatagacc cccaaagcca   146520
aacattgatc tctttgaaga ctgatcacgt ttgtcccaaa agttattcgt tccaacagca   146580
ttatagagtc actggtccct atttctcaga gctggttttc cctgctcctt cccctgactt   146640
```

```
ttctcccctt cccttttgta gatgacattc agggtgagtc tccggctcca tgtgggacag   146700
aagagcccgc ccgcacctgc cccaatggga ccaaatgtca gccctactgg gaagggccca   146760
acaacgggat cactcagttc gacaacatcc tgtttgcagt gctgactgtt ttccagtgca   146820
taaccatgga agggtggact gatctcctct acaatgtaag tgatgctggg acagtgtgtg   146880
tggacaatca gagtctcagg gaggtggcct cctgggacca gtgagactcc aaggctgcaa   146940
tggagggacc ctgagctggg aaaggcagcc caaggacaac acagccccac tgaagctggc   147000
ctgaggctca ggcttttgaa gattacaggg gctcatgagc agaactctaa ctataggggca   147060 tagaagtctg gagggccccc agatgcaaca tcatttttca ttgtgcaagt gtttagatat   147120
aattttagat ttttgaatac ggaaaggtta tgtgatccaa aaaccaacac agataaaaga   147180
tagagtaata tctttggacg taggcgaggg gtccctgccc tgaggctcac ccagtccttc   147240
tccagccata ccactccccg tgggatgaga agttcctgga gccaagggga tgtgtctacc   147300
aagagcttgt gccccacttt gtaggccatg ttttaagtta ccaggatcct ggaattccct   147360
gcccatggcc agattccatg aacttgcgtg caattctcat atggatctgt tcgtaaccca   147420
actgagggcc aaggacatcc gaggggtggc tgttaacaca aatgtggcca gagcttggat   147480
gtacaagctg gaatgcccac acatatgtgt ggagcccctc tggcaggaca gagccatgac   147540
taagaagaga aagggacagg acagggctgg ctctccccac accttgaccc agtgcagata   147600
tccggattct aaattccacc ctgaccttcc aaagtgtaaa ggaaggtata tttgcaaagt   147660
agaagcacac agcatgtttt atttagttac cttttcaata tttccccgta gtatgtggtc   147720
tgcttttgta ctcttgccct agatcttaaa aatgttaggg atgtttctgg aaagatgtat   147780
ccctgccccc acttgcatgc tacttcctct tcccacaata tgcaacccct ttagttcctc   147840
agaatatcct tccaatgttt atttatgcaa ttataattat aagcataatc gaatctatgt   147900 cctccccct ctttcttatc ccaaggagta gcattctata catgctgttc aattctgtga   147960
tttttgtttt ctcataacca cacgttctag agatctttcc actgcaggac atggacagtc   148020
tcttcacggg tgcacactag tatgcccagc taattttttgt agagacaggg ttcttccgtg   148080
ttgcccaggc aggtctggaa ctcctgggct caagcaatcc tcccgcctct gcctcccaaa   148140
gtgctgggat tacaggcgtg agccaccacg cctggccttc tttattcttt tgcacagctg   148200
catagcattc tattgtgtgg ctgcccatag ttttatttgt ttgccattaa gagaaatgct   148260
tgactggctt cctgtccact gacatggaac atgatgctgc tctgccagga gcatgttgca   148320
cgtacctctt catactttg cagatatagc taggggttg gagggtctcc attcccagaa   148380
gtgggattgc aggatcaaag actaaatgca tttataattt tattttttggg gaagattttt   148440 gttttgtttt tttggagaca aggtctccct ctgtcgtcca ggctggagcg cagtggtgta   148500
atcatagctc actgcagcct taaactcctg ggctcaggtg atcctcccac cccagcctcc   148560
tgagtagctg ggaccacagg cacacaccac catacctagc taattttttaa gaacaatttt   148620 atagagatgg ggtctcacta tgtttcccag gctgctctca gactcctggc tcaagcaat   148680 cctcctgcct cagcctccca aagtgctagg attacaggtg tgagccactg cacccagcct   148740
aaatgcattt ataattttga tagatattta ggtgtgcaag ttttaaaccc cactctgtcc   148800
tcaccacagt tcaccttccc tcacctacta tgcaggtaag cagtccccag gcaggtcact   148860
tgtcagcagc tggagtgggg cagagccaag gattcaggat caaacacaag gatgccacaa   148920
ctgtagtgac cccatagagc accctggggc tgctccatac acacagctct gttgaccagt   148980
ggaggtctcc tcttcaccctg ccctaagggc tgaaattacc attgaagttt aggccagcgg   149040
```

```
ttggcctgac ccgggagcaa tacctggctt cctcctcctg tacatagaga agctgaactt 149100
tcctcttggt cctagtgtat gttccttaac aacccattta tgcctagtgt tccattattg 149160
gaatgctaat cctgtgggag ttatttacat cctgctgctc aaggtcatca ctaaggtcgg 149220
atttttcaca cacacaaaaa ttgcaacctc cggcataaat gggttaagga atttccccac 149280
ttgtgggtgg agggagattt gcaaaaactc atccttgtaa tcctgatcaa caaaggcccg 149340
ttttagttgg gagtaggcag caaaaggagc cacatgaaca gttgcgcctg tcacgcactg 149400
cacaagaatg tcattcatat catagacaac atacgatttc tactgttatc ctgataattt 149460
attgacagaa aaaaggatgt ggggaaggga catggtgttc taatttgcat gaaaacctcg 149520
tctgagtgta gcatctctgg aacatgcag cagatccgag ctcaggccct ctcttggccg 149580
tcacctgcaa acagcttgga caaagggtca gcccaattgg ccaaaactca ctggggaatt 149640
tttgtgggtt ctaggttttt actttgcaag gctggtgtga gaggaggttc cagcaggaaa 149700
tgaaccctcc tgagagggaa agagactggg aaatggagaa ggctgggaac tcagggagag 149760
aatgggagtg gggaatggga gctgaaaaaa attgtgagca taaaaagggg atatgtcaca 149820
gggttggatg accagagaaa gcgtctgggg gttcagatta agatgctggg ggcgtgccca 149880
gtggtgggac aggaagcatg aatttccaga gggctcggtt ataaacatca ttgtccaatg 149940
ggtgtttccc ttggaagcct ctaagcttag agctaagcca cctctgggga cacaaactga 150000
gtggttaaga gcagagactc aggtgtcagc ctgtctgggt tccttccgac tcttccactt 150060
ccttgctgtg cagccttcgg caaggtgctt ggcctctctg tgccactatt tccacatgtg 150120
caaaacgaag agaagcatag tcccacctca caaggcacga ggactaagta aggtggattc 150180
gcatgaagtg tttagaactg atcctggccc ggggtgacct ccgtgtaagt caaattcccc 150240
accctgcatg gtgttccttt tagaaatgtg catgaatttt tcattagaac agctccagca 150300
gtgcctgagg aagtggagtg aggtgtgaga ggtcttactt tattccctc gctggccctg 150360 ctattaacca ctaactcaga gtagctttct agcactttcc acacatttac atcccaccct 150420
cgtcctttgg ttagcagccc atgcaatgat ttggccttaa tgtgaaccta gaacacagct 150480
tctcgcccag ggatgatttc tgcccccagg ggacacttgg cagtggctgc agacattttt 150540
ggttgtcaca actggatggg aagaaggagg atgctattgg catcaagtgg gtaaaggcca 150600
cggatgctac tcaacattct acaatgcaca gcatccccca cctctgcccc accatagaga 150660
atgatccagg cccaaatgtc agtaaggttt ctgtcaggaa accctgggtc agaagaccaa 150720
ggttccttga ggacggggat gccttatact gcaatcagct gtcactctct gcctctctct 150780
ggggctgctg tgatcacctg gcctgcatgg acaaccccta ggagcagccc ccatccagtg 150840
cctggagaag tcagtggata aatacccag ctccctccct gtcgggcgtt ttgctctgcc 150900
ctgcatctct ccagtgggat caggctctgg ttgcccgcag ggttaacctg gtcacgtaca 150960 caccccttcac ttgccacctt cccttccctg tctggtattt cctgggatga acttttagat 151020
ttatttcctg gggctgctat aatgaagcac cacagactga gtagcttaaa acaacaggaa 151080
tttatggtct gacagttctg gaagccagaa gtccaacccc aagatgttag cagagctgac 151140
aacacgcccc tcaaaagcct ccgggggagg atccttcttt gcttcttcct ggcttttgct 151200
ggtttcccac aatctttggg attccttggc ttctagagcc ttcattctcc attccagtct 151260
tctgtcatct aatagcatcc tcccagcccg ggcacagtgg ctcacgcctg taatcccagc 151320
actttgggag gccgaggcag gcagatcact tgaggtcagg agtttgagac cagcctggcc 151380
```

```
aacatggtga aaccccatct ctactaaaga tacaaaaatt agccaggcgt ggtgggcggg   151440
tgcctgtaat cccagccact tgggaggctg aggcaggaga atcacttgaa cccgggagat   151500
ggaggttgca gtgagccaag atcatgccac tgcactccag cctgggtgac agaatgagac   151560
tccgtctcaa aaaaaaaaaa aaaaaaaaaa agaaaaagaa aagcatcctc ccttcgtgtg   151620
tctgtgtgtg ttctcctctt cttagaagga catcagttgt attggatcag aacctaccct   151680
actccagtcc aacctaattt taactaatta cgtctgcaat taccctattt ccaaataaga   151740
tcacattctg aggtaccagg gggttaggac ttaaacattt ttgtgtgtgt agcaggagga   151800
cgtaattcca tttataactc ctcctaaata aaacgacttg catgtgaact cttgtctggg   151860
gcttcccaaa gtgagataac ccctctctct acccctaaaa caacgagtag cgtctgtcaa   151920
tgccagggtg caggggctaa ggtgcccatc tttgagtttc tgctgaggag gacacagctg   151980
ctacgttgga gcactcttgg gttctgcctt cgtgcccagc catctccctt gggctagccc   152040
tgccctgggt ctatcctaga atgagcctcg atctgtttgg ccataggcaa gcagagtgtc   152100
tggaaatctt tgtcctccat gactggtgct ggagccgaag ccagtgggtg tggccttgcc   152160
agccaactcc atttacccag ctctgaacaa gctagtagtt gagatcaacg gagagtccag   152220
acagtcgctc caagcatctt ggaatccatg gacacaggtg taccgcagag gcttcccacc   152280
tgggtaggca gcccttttgta agatcctggc accacatttta ttctcttaac atcctttcag   152340
ttatccagta atcatttatt gagcacctac tgtgtgccag gcaatgatta ggtgattgga   152400
gacactgcaa cgaagaagac agactaaaat ctccaccctg gtaggagaga cagatgcaaa   152460
tggtaaacat gataaataat caatcaccca gaaagcagga gacactaagc aaatgtgtat   152520
gtactatggg aagcccaata ggaacgaaag ctacacaaga gaacaagtga tgggtggttc   152580
cttagtctag gtcaggcaat cagggagggc ttctcagagg aggtgatgtt tgagcagaga   152640
aggagggagc caggcagatg ttttggaaac agcattctca gcatggagaa cagtggcagc   152700
tcacctacag gatgtgtttg attcccttcc agattttgta ttcgtttctt gttttttctcc   152760 cttggcttcc tggtttaaat gccttttgaa gaaatctaag ctcaactaat cagcgatgct   152820
gttgaaggtt tatatcagga tatgcatccc agagttattt acaaaattag aacaaaactg   152880
gaagcaattg aaagcctgac aataggagat cagttaaata ccgtatggtc cttccgtatg   152940
atggcatatt atgtcatcat taaaaatcgt ctgctgggag aatattaagg atacagggga   153000
aaggctcacc atataatgat gagtgggggt gctgggcgca gtggttcatg cctgtaattc   153060
cagcaatttg ggagtctgag atgggtggat cacttgagcc caagagtttg aggccagcct   153120
gggcaacaca gtgaaaccca atctctacaa aaaaaaaaa acaaaaatac aaaaatcagc   153180
caggcatagt ggcgtacatc tgtagtccca gctactcagg aggctgagac aggaggatag   153240
gatcacttga gccctggagt cagaggtggc aataagccgt gatcacgcca ctgcactcca   153300
gcctgggcaa cagagtgaaa ccctgtcaaa aacaaaaaca aaaaaatga tgagtgggag   153360 aaacaagttt ttaaacaggg atcaaggagg ccaggcatgg tggctcacac ctataatccc   153420
agcactttgg gaggccaagg caggcagatc acctgaggtc aggagtttga ccagcctg    153480 gccaacatgg cgaaacctca tctctactaa aaatacaaaa attagccagg catggtggc   153540 ggcgcctgta atcccagcta cttgggaggc tgaggcagga aaatcgattg agcccaggag   153600
gtggaggttg cagtgagctg tgatcatgcc actgcactcc agcctgggca acagagcgaa   153660
agctgcacga gagaagaagt gatgcatggt tccctagtct aggtcagcca atcagggagg   153720
gttcctaaga ggaggtgatg tttgagcaga gaaggaggaa gccaggcaga tgttttggaa   153780
```

```
acagcattcc cagcatggag aacagtggca gctcaccctg tctagaaaag aagaaatgat  153840 aagagggaa  aatgagtttt taaaaaggaa tcaaggggag gtaaaccta  tgatctcaaa  153900 ggtacaaata tgaaaatata agtaaagaaa aactggagga cactgtacca agctgacctt  153960
cgggtggtgg gatttgggaa tcttgatatt ctcaatactt ctttgtatct tcaaatttct  154020
ctatgatgat cacagtttac ttttttttt  tttttttgag atggagtctc actctgttgc  154080
ccaggctgga gtgcagtggt gcgatcttgg ctcacttggc tcacctctgg ggttcaagca  154140
attctcctac ctcttcctcc caagtagctg ggactatagg catgcaccag catggtcagc  154200
taattttttg tattttagt  aaaaatgggg tttcatcatg ttggccaggc tggtctcgaa  154260
ctcgtaagtt caagtgatcc accaacctca gcctcccaaa ttggcttgag ccaattaaac  154320
ttgtcttgct aaatggttag cggggagaaa gaagaaggtc tcgggtcatt cctagaccag  154380
gaggcaggga gaaagggagg agaatgaacc tttcttaggc aaacagtgtc ctaggtgtcc  154440
ttatcttaca taatctgtcg agagagtcac actaaaataa atcattgatt gattgattga  154500
tacatcaata ataaatggcc agccttggtg gctcacatct gtaatcccag ctacttagga  154560
agctgaggtg ggaggattgt ttgagacaag gagttcaaga ccagcctggg aaacacagca  154620
agactcatct taaaaaaatt ttttttttta attagccaga tgcggtggct cacgcctgta  154680
atcccagcac tttgggaggc cgaggcgggt ggatcacgag gtcaggaatt cgagaccagc  154740
ctggccaaca gggtgaaacc ccgtctctac taaaaataca aaattagcc  aggcgtggtg  154800 gcacacgcct gtagtcccag ctacgcagga ggctgaggca aagaatcat  atgaacctgg  154860 gaaacagagg ttgcagtgag ctgagatcac gccattacac tccagcctgg gcaacaagag  154920
caaaactaca tctcaaaaaa aatgtttttt aattagccgg gtgtggtggt ccatgtctgt  154980
agttccagct acttgggagg ctgaggcagg aggattgctt gagcccagca gttcaaggct  155040
gcagtgagct atgatcccgc cactgcactc cagcctgggc aacagcaaga ccccatctct  155100
taaataaaca cataagtaaa taatgatca  tttttatttt attattaaat acacaagata  155160
aatgaaaaac aggcaaatct ttcttacaaa agaattccat ttaaagtatg taaacttcac  155220
tccccactgc cccaggaggt ggagactaat ctcccctact ttgagagtgg gctggattta  155280
gtgactcatt tccgaagaat agagtaggta aaggggaaaa tagaagtttt atagcggagg  155340
aacagataga taccacttta accaaatgat gaagattagt atccccagg  gatgtggata  155400 ttatgtaacc cttgatttta tgcctatata gcgttcttcc caaaaactcc taatcccagt  155460
tttttggggt tttgctctgt cttctaagct ggagtgcgat gatgcaatca tagctcactg  155520
cagctcaaac tcctggtctc aagcgatcct cccacctcaa cctcctgaat agctagggct  155580
gtaagcacat accatcatgc ccagctaatt gtattttttt ggtagagaca tgttctcaca  155640
cattgcccac gctgtcctcg agctactggc ctctagtgat cctcccaccc cagcctccag  155700
agtcactggg attataggca tgagccactg tgaccagccc agaatttttt tttaaggagt  155760
tgtgatgtcg tttaagagat gtgattcttc ataacacatc aacaacaagt cccagcgatg  155820
ggttggataa gtcttgggat ttcatgggag tattaagctt aaaagacttt gcatgatatc  155880
tgtgaactat atgtgatttc tgttggtaat ggggtcact  gattctgcgg tttgccacct  155940
ccaatcatca tggaagaaaa tgttccactt ccagtgaaag taagaggaag taagggta    156000 attattttct atctaaattc acgaactcct tgaattctgt ccacagaccc ctaagtgttt  156060
cctccccaag gtgaaactga gagaatcttg ccagtgcctt ccgcagtcac tgtggctaga  156120
```

```
aaaccccctca gaagaggtga tagtttagca ggtaactgga gttctcacca tccgtgtctg  156180
gctcagcccc catcacaacc agttacccag cccaaaatgt cagtagtact gaggttgaga  156240
ggctctgctc taggaggcca ggcctctcag aggaaggagg attggggtac tggctgggcc  156300
tcaagatgaa cctaccccct aagagctttg ggatggcgtg agtttctgtc catacccaag  156360
gactacaaat gcaggtttac tggaaattct gtgccaaaag tgaggtccaa ctcacttcta  156420
actgctacaa aacaaacctc catcaacata gccatctct gttcttgacc tggaagctcc  156480
aaggtatcca catggctccc atgcccacta gacgggcctc ttccctggac cttcctgggc  156540
cagagaaggc tctgggtagc cttgtggaat caagatgggt gatcagccac ttcctctgtg  156600
ccaccctgtt ttggctactt ccctaggcat cagcctggga ttccttgatg gtaaaaatat  156660
aaaactctct gagctagggc ctttaatatc cccattttac agatgaagaa actgagtccc  156720
agagctgtgc acagcgattg agagtcagaa ttcagctctg tctcactcag tgtcaacatc  156780
ctcagattct gccatttata gcctcccaca gcaaatagga ttgagggctg cttctctgag  156840
ctcaagggga tagaatgggg aaccccatga gtactgcaac aaaactgttt gctggagaca  156900
agagctggtg gctctgtgtt gttctagtga caggtggcct catttcacag ggaccccctc  156960
accctatgtg ccccatgtgg ctcagaaaag ccagaaattg tctccactct cacagggaa  157020
ggtccctgac cccctctttg ccagctgggc caaggcaaat tggggtcact tcatggggta  157080
caggacctac cctctcttgg ttgccccaa ggaggggatg tggagggct ggggacctgg  157140
caggaccagg gtgtcttgag ttaatttggg gctgccttta ccgagggct tctgtgtgcc  157200
tggcatcagc tttacattgt gtcttgatcc gtaaacagc cctgtgagga aagatatttt  157260
taacccatc ttccagatga ggaaacggag gcccacaggg tgacgtgacc tgccaaggtc  157320
ccctagccaa gagtgacaaa gccagggttc acacacagct ctggacacaa ttcatcaccc  157380
ttcatccgtc tctctctgac tctttctttt tccctctctc tctttgtctc tcttttttt  157440
ttttttttt tttgagacag cgtctcactc tgtcacccag gctagagtgc agtggcgcaa  157500
tctcggctca ctacaacctc catctcctgg gttcaagcga ttcttgtgcc tcaacctccc  157560
aagtagctgg gattacaggt gcgtgccacc acacccagct aattttgggg ggttttgttt  157620
tgttttgaga tggagtcttg ctctgtcgcc aggctggagt acagtggcgt gatctcggct  157680
cactgcagcc tctgactccc aggttcaagt gattccctg cctcagcctc ctgagtagct  157740
gggactacag gcatgcacca acacgcccag ctaatttttt gtattagt aaagacgggg  157800
tttcaccatg ttggccagga tggtctcgat ctcctgagct catgattcgc ccgccttggc  157860
ctcccaaagt gccgggatta caggcgtgag ccactgtgcc tgccaatttt ttgtattttt  157920
aacagagact gggtttcaac atgttggccg ggctggtctc gagctcctga cctcaagtga  157980
tctgcctgcc ttggcctccc aaagtgctgg tattacaggc atgagccacc atgcccagcc  158040
tttgtctctt ttattcttgt gttctctctc tctcttcctt ctctttctcc acctcctct  158100
ccttctctcc cttctcctca cccttctttg tgcttttctc tgtgagtttc tcttcttctc  158160
tattctctc ctttggtgaa tgtcaattag aaaagcagaa aaactgcgtt taatttgtga  158220
tcataaatgc atgtccctgg ccaggcgtgg tggctcacgc ctggaatccc agcctttga  158280
gaagctgagg caggaagatt gcttgagacc gggagttcaa aaccagcctg gtcaaaaagc  158340
aagaccccat ctttaaaaaa gaaaaataat taattagctg ggcatggtgg tgtgtacctg  158400
tagtcccagc tactcgggag gctgaggaag gaggattgcc tgagcccaag ggtttgaagc  158460
tgcaccgagc tgtgattaca ccctgcact ccagcctggg tgacagaacc agaccctgtc  158520
```

```
tcaaaaaaaa cctaataatt aaaaataaat aaataaataa atgcgtgtcc cctggccagt 158580
ggttgctaat gtttggaatc acctttgacc catgcccttt ttcattcata gatgtttgtc 158640
ttgaccaaaa tcaaagcatt agactttgga ctataaatca ctggttcatt caacaaccat 158700
cattgaatgc ctactgtatg cagacactct tctggacaca gaggagttga cgtgttggtg 158760
gggaaagcca gtgatcagtt gggataaaaa gggcagacag cagacattaa atagtttagg 158820
ctttgtgggc cagatggtct ccatcgcaac gactcaatct gctcctgtag cgtgaaagta 158880
acgacagata aagcgcgtaa gtgaatgagc atggctgtgg gccaattaaa cgttaaccta 158940
taaaaacagg tggctggccc gcgggctgta gtttgtggat cactgcctta gagatagtgt 159000
tagagggtgg tgagaggtcc gggatagaat aaaacagtag agagtttgtg cattgtcaag 159060
atgagaggtt gcagttcttc ttatacaccc cgaatggccg ggcaccgtgg ccattatgat 159120
ctataattct aacactttgg gaggctgagg caggaggatc ccttgagccc tagagtttaa 159180
gaccagccta ggcacatagt gagacccat ctctacaaaa aaaaaaattt aaaaattagc 159240
tggacatggt ggagcatgcc tgtaggccca gctacttgag aggctgagat gggaggactg 159300
cttgagcctg ggaggttggg gctgcagtga gccgatcatg ccactgcact ccagcccgga 159360
tgacagagca agaactgtct caaaaaaaaa aaacaaaaaa acaaaaaaaa cagacctgaa 159420
ggaacaaatc atatgaatgc attaaagtat cacatgtatc caaaaatat atacatctat 159480 cagcctggca cggtggctca tgcctgtaat cctagcacat gggaggcca aggcaggcag 159540 attgcctgag ctcaggagtg caagaccacc ctaggctaca tggtgaaacc ccgtctctac 159600
taaaatacaa aaaattagct gggcatggtg gcaggcgcct gtagtcccag ctacttggga 159660
ggctgaggca caagaattgc ttgaacccag gagacagagg ttacagttag ccgagatcgt 159720
gccactgcac tccagcctgg acaacagagc aagactctgt ctcaaaaaaa aaaaaaaaaa 159780
aaaaaaaaaa aaaatatata tatatatata tatatatata tatatatata tatatatata 159840
tataatcaat taaaaatttt ccttaataaa taaacatttc tctccttctc tcccttggtg 159900
aatgtcaatt aataaagcaa caaaactatg tttagttagt gatcattaat gtatgtccct 159960
ggctgggtgt gatggctcac acttgtaatc ccagcacttt gggaggctga ggcaggagag 160020
gatagtttga ggccagcaat tgcttgaggc ttttgaaag acatgaagga gatgaaggga 160080
gccatggaga tatctcaggg aacagcagcc gaggtagatg gaacagccag tgcaaaggtc 160140
ctgaggcagg atgttcctgg catttgtgag gacatgtagc tgcccagatg tccagtgggg 160200
agtgagtgag gatgaaggaa ggagctgatg aaggaagatg ataaaatact tcatggatca 160260
gccaggcatg gtggctcccg cctgtaatcc cagcactttg ggaggccaag gcgggtggat 160320
cacaaggtca agagttccag accagcctgg ccaacatggc gaaacccgt ctctactaaa 160380 aaatacaaaa aagttagcca ggcgtggtca tgcacgcgtg tactctcagc tacttgggag 160440
actgagactc gagaatcgct tgaacccagg agatggaggt tgcagtgagt tgagatcacc 160500
ccactgcact ccagcctagg tgacagagcg agactctgtc tcaaaaaaaa aaaaaaaaaa 160560
aaaaagactt cgtgaacaga cagcctatat aatttatgat ccaaaccagg acagttttga 160620
gagtgaaagg ggaaaaagag cactgaaaaa ataattagca ggcctggcat gatctataac 160680
gggtataaag tgggacacac agcctctctc acggtcactg tcagacttca gcttttcac 160740 actcaaatcc accccccatgt ttatcccata tactggagaa acgggtgttc tcctgagctg 160800
agttttgggg tttttccctt ttgttttgtt ttgtttttgt tttttaaca tcctgtatac 160860
```

```
tttttctcaa tgaaccatgc tcaaaaaaat tagaggaaaa taaaccataa aacagaaggc    160920
actgaaggat tttgctggga ctcagccatt agtttgtttg atgagtattt atggagcgct    160980
ttctaagcac caggcaccac cagcgatact gggatgaatc agtaacatcc ctcacccttg    161040
aagctctctt gggcccattg ttatttactt aaaatactat gcaagtacgg agaaggggtg    161100
aagtgggaaa aaatcagttg gttgtaaagg ccagaatgac gggtctagtc ccacccatgc    161160
catctgcacc ctgtgtgatc caggcacatc atgttgcctc tctcagcttc agttctccca    161220
tccaccaggc acagagatgg cgggaatcga ggaagatgtg gggagtattt catcagccca    161280
aaaagacttg gctaatgcga ccataattct gccttctgcc tctcctttcc cagaaaaata    161340
gcttaatcat ttggatttgg gataaacaca tttcctgtgt ttattattta aatgatccac    161400
caagctgggc atggtggctc accctgtaa tcccaactct tgggaggct gaggagggcg      161460
gattgcttga gcccaggagt tcaagaccag cctggccaac atggcgaaac cccatcttta    161520
ctaaaaaaat acaaaaaaat tagctgagcg tggtggtgcg tgcctgtaat cccagctact    161580
tgggaggccg aggcacaaga atcacttgaa cctgggaggc agaggttgca gtgagcctag    161640
atcgtgccat cacactccag tctgggcgac agagtgagat tctgtcccta aataaataaa    161700
taaataaata aataaataaa taaataaat gatccaccaa caggaacccc aggaacattt     161760
gtattgacta tgcaactaat gcttagtgag cacctactat gtccctggtg ctgatctgga    161820
cactgggatt tagacaggaa aaatctctac cctggaggag ctgatgatca agatgacaat    161880
cttgaaatgc ataagttgac aagatgattc agacagtgga acgtgctggg aagagaatga    161940
gatgtctggc tgagctgcag gaaggggcaa gtccttttga ttgagaggtc caagaaggct    162000
tctctgatgg gggcacaatg gatctaaggt tgagtgataa aagaaattg gccaagccaa      162060
gacctaaagg cagagttgct ccaggcatag gttcagagaa tggaaataat tggctgattg    162120
tgatcttgaa cttgaccttt cttttcttct gctaactttg ggtttggttt gttcttgctt    162180
ttctggctcc ttgaggtacg tgttgggttc ttaatttgta atttttttt ttttttttg      162240
cttttttgag acagagtctc actgtggtgc ccaggctgga gtacagcagc atgatcttga    162300
ctcactgcaa cctctgcctc ctaggctcaa gtgaacctcc cacttcagca tccccagtag    162360
ctgggactac tggtgcacag caccacaccc agctaatttt tttattttta ttttttagag    162420
atggggtctc actgtgttgc ccaggctggt ctcaaacccc tagctcaagc gatcctcctg    162480
ccttagcccc ccaaagtgct gggatgagag gcgtgagcca ccacatctgg cctctgtttt    162540
ttgtgatgta ggtatttgat gctataaact tccctcttag ttgcttcttg gccctttagc    162600
taaggtcaag tgtaaacttc cctcagcact gcttctgctg catctcacag gtgttggtgt    162660
gttgtgtctc tattttcatt catttccaaa attttttaag tctccatctt aatttctgca    162720
ttgacccaat ggttgttcag gagcatgttg cgtaatatcc atatatttgc atcatttctg    162780
aaattcttct tggtattgat ttctagtttt atcccacggt agtctgagaa gatgcttgac    162840
agaattccag tattttaaaa tttgttgaga gttgttttgt ggcctaacat gtggtctgtc    162900
ttggagaatg tccatgtgct gatgagaaga atgtatgttc tccatcagac atgcaagaga    162960
cagacacttt ctcacctgcc tcatgggatc cataaaagag tcaatcagaa gttggcattt    163020
aagaaagacc agaaggaggc tgggtgcagt ggctcatgcc tgtaatccca gcactttggg    163080
aggctgaagt gggtggatca cctgaggtca ggagttcaag accagcctga ccaacaaggt    163140
gaaatcttgt ctctatttta aaaaatacaa aaattagcta ggtgtggtgg cgggcacctg    163200
taatcccagc tactctggag gctgaggcag agaatcactt ggacccagga ggtggaggtt    163260
```

```
gcagtgagct gagatcacac cattgcactc cagcctgggc aacagagcaa gaccccatct 163320
caaaaaaaaa aagaaagaaa aaaaagaaag aaagaccaga aagaggtgaa ggagcaagct 163380
acagagatat caaactgtat caatctggct gggcgtggtg gctcatgcct gaaatcccag 163440
cactttggga ggctgaagca ggaggatcac ttgagcccag gagttcgaga ccagcctggg 163500
caacagagac cccctctcta caaaatataa aatttaatt aaaagatgt attggtcagg 163560 gcagccaagt tatgctgcag taacaaacat ccccaaagcc tccatgactt ttgacaacag 163620
atgtatttcc tgctcatgct acatgtccag tgcaggttgg cagtggggaa gaaggggggct 163680 ctgttcagtg cagtcacttg agacctagct aatcacctag aacattgcca cttgctattc 163740
cagaaggaaa aaaggaatgc tagaaggtcc cacactgaaa gttcaatgct ctggctccaa 163800
aatgacagct atttccactc actcctcatt ggccagcact tagcatgtgg tcctcagcca 163860
accccaaagg gactcaggaa ggaccatccc accatattgc tggaaatatt tgatggcagc 163920
attaatgggg aacagtgttc caggcagtgg aagtctttga gcccttggaa gaaagacaag 163980
gcgatctcta gagcacatcc ttcccaatat taatgaattt aacaaatgag caagccatcc 164040 tccccactc tccttcccga attcagactt gtgcatatcc ctcccttaac ttgaactgcc 164100
aaagaagaga tgagaaccag gagaagagat ctgtgacccc atctttgctg atgaactacc 164160
acagaacagc catggcatct ccagtccttg tgcttgtaaa atgtactttt cattttgctc 164220
ctgaacgaaa tccacccacc cccaccccca aaccagggaa agctcatctc ctaatccaaa 164280
actgcaccca gccttccacc accttcttcc ctgggaattg ttgattccag agtatggaat 164340
tgaataattg gatgagtttg gaagagaaaa agtgtctcta aaatcaggca gcagaagccc 164400
actccccaga gaggatggtg cagatgagag ttcaggaggg agcttggctt ggggttgacg 164460
atctgagcta tgcagggaac ttggacacac ctctcaatca gtcattcaac agacaccact 164520
tattgagcac cgactgtgtg ccagatgttg tcctaggggg ctgggaatac aggaatacag 164580
cagggaacaa aaaggacaaa gcccctccct cttgtcgaat ggacattcca gccaggaaga 164640
cgagagaaca agagaaataa gtaaagtata taggcggtga aatgcaaatg ggaaaaaaga 164700
aacaatgggg accagaaatg agggtgcaa ttgtaaaggg ccatcagggg aggcctccct 164760
cagaaggtgg catttgagta aaaaacctga aggaggtgag gggaaaccat gtagcaatct 164820
caggaaagag cattccaggc agggagggac agcctgtgca agggccgagg taggactgtg 164880
cttggcgtgg ttgagaaact gcaaggaagc caggtggctg gaaccgaatg agcgagggaa 164940
aaggggagga gataaaagca aggagatggg aggggttggag gccccctctg ccattcagta 165000
actgagtaac ttcatttatt tcctgtagct tgaaccacaa agaaccacaa atagagtagc 165060
tgaaaacaac agaaatttat ttattctctc gcagttcagg aggccaggag tccacagacc 165120
atcaaggtca gctgggccac agaccatcaa gatgtcagct gggccatggt gcctcctgag 165180
acttggtctg aaatcccttc ttgcctccct cctagcttct ggtggtttgc caacagtgct 165240
tggtggtcct tgtcttgtag acgtatcacc ctgatcccgc cttcatctcc atttcacatg 165300
gccttctccc tctgtgcaag gttgtctctg tgcccaggtt tctccttttc ttattattta 165360
cttatttgtt tgtttgtttc tttatttag acacagggtc ttgctctgtc tcccaggctg 165420
gagtgcagtg gtgcgatcat agctcactac agcctcaaac tcctggcctc aagcaatcct 165480
cctacctcag cctcctgagt agctgggact gcagatgtga gccactgtgc tctgcccaga 165540
tgtcctcttt ttataaggaa acccgtcatt taggatgagg ttccacccta atgacctgat 165600
```

```
cttaacttga ttccatctgc aaagacccta tttccaattc ataggtacca gggattagga   165660
cttcttcaat gcatctttt  ggagagaccc actgcaaccc acaacagaac tgtgggcatg   165720
taacttgacc tctcggccag gcgtgatggc tcacacctgt aatcccagca ctttgggagg   165780
ccgaggtgag tggatcgcct gaggtcggga gttcgagacc agcctggcca acatggtcaa   165840
accccgcctc tactaaaaat agaaaaatta gctgggcatg gtagcaagca cctgtaatcc   165900
caactacttg ggagggtgag gcaggagaat tgcttgaacc caggatgtag aggttgcagt   165960
gagccaagat agtgccattg cactccagcc tgggtgacag agtgagactc catctcaaaa   166020
aaaaaaaaaa aaaaaataga cctctctgtg cctcagcttt ctcacccggg aggatgggga   166080
taattatata cccactcctg gggttcatga gaggattaaa tgagctcaaa cagtccaagc   166140
ctccacgtgt gtctgttgtg gtgctgggta gcatgtcctg tggccagagg ttcccaagct   166200
tgtcgaggac ccaggcaagg gcagattcgg gtcttgttgg cagcacctga gatggacggg   166260
ctgccttggt atggaagggc ctcggctgtt tttccctttc agtcctgtcc ctctccccca   166320
tcctccaccc tgtccctgtc atctgagcct gctcctcgtg atggctcaga gtctccctac   166380
tggcggccgg tgcagagttt cgttccctgg gctatattta gccctgagaa atgggaacga   166440
gaaccctcag ccgccaaagt gatggagaga ggagcacaaa gccagtgctg ccttctgtcc   166500
agcaatgttc cgctgactcg gttctttctt ccagaacctt ccagaagcaa agcattggca   166560
tttctgagct cgttaaaaca aggatgtggg ctggtggctg gcacattcat tgtccccaga   166620
acctgtctgt gtccatgatt aaagctgact tgttagtttt tattttcagt gcttttttt   166680 tttttaatc catggcaaaa cacacatgac ataaaattta ccatcctaat attttttta   166740 actttgtaac atttttaat tgacaagtaa ttgtacttat tcatggggta catagtgacg   166800
tttcaatgca tataatgcgt agtgctcaga tcagggtaat tagcatatcc atcttctcag   166860
acctttattg tttctttctg ttaggaacat tcaagctcct ccttctagct atttgaaacc   166920
attaatatat tgttgtcatc ctaaccattt ttaaggatac agtttcgtga aattaagtat   166980
aatacattca cattgttgtg caactgtcac caccatccat ctcccaaact tttccatctt   167040
ccaaatgtaa ctctgtcccc actaaacgcg aactccctgt tcccctccc ccagcccttg   167100 gcacccacca tgctactttc tgtttttata aatctgacga ctctagggac ctcctataaa   167160
tggaatcata caggattttc cctttttatga ctggtttatt tcacatagca taatgccctc   167220
aaggttcacc catgttgcag cacgtatcag cattttcttt cttttaagg  taaagttgac   167280 tattaaaaa  aaacttctgc cgggctcagt ggctcacgcc tgtaattaca gcactttggg   167340
aggccaaggc aggcagatca ggaggtgagg agttcaagac cagcctgacc aacatggtga   167400 aacccccatct ctactaaaaa tacaaaaatt agccaggcat ggtggcgggc gcctgtaatc   167460
ccaactactc aggaggctga ggcaagagaa ttgcttgaac ccgggaggca gaggttgcag   167520
tgagctgaga tcatgccact gcactccagc ctcggcaaca gagtaagact ccgtctcaaa   167580
aaaaaacaac ttttaagaa  ttgaagtaga ataaacatac agaaaaatcc gcggattata   167640
agtgaagagc ttgattaatt gtcacaaact aaacacatcc atgtaaccag cacacaaatg   167700
aggaaacaga aacttctcag ccccagaagc ccccctcata tcctgttcct agtcactacc   167760
tccccgcaag ggtacccta  ccaggacttt gagcatcatt caccagttta gcctgttttg   167820
tattttgcat aaaatgaagtc tggcttcttt tgcttgacgt taacttttta agatctcatg   167880
tgacctgtgg cattgttcat tgcatgtatc ctctctctcc tattgataac agtgtggatt   167940
gtttgcaatt tggagctatg atgaatacca ttgctatgaa tgttcttgtg tgtgctttct   168000
```

```
gttgtgtaat tattcagaat tactatttcg gaattactat ctaattgtag tgatcttgga  168060
tcagtaacta tccaagaatt actgggtgtt ggcaaaggta catacagtta tacactgcac  168120
aatggcattt tggtcaacaa cagatcaaat atgtaacagt ggtcccataa tggaccgaat  168180
acataacagt gattatcata cagtattttt actatagctt ttctgttttt agattctttt  168240 tttttgaga cgaagtctcg ctctgttgcc caggctggag tgcagtggtg tgatctccgc  168300
tcactgcaag ctccgccttc tgggttcacg ccattctcct gcctcagcct cccaggtagc  168360
tacaggcgcc cgtcaccagg cccggctaat ttttttgta ttttagtag acggggtt  168420 tcaccatgtt agccaggatg gcctcgatct cctgacctca tgatctgccc gcctcggcct  168480
cccaaagtgc tgggattgca ggcgtgagcc accgcacccg gcctgttttt agatattttt  168540
agatacacta tagagttaca attgcctaca gtattccata gaataacatg ctgtatgggg  168600
ttgtagccta ggagcaatag gcgagaccat gcagcctagg tgtgtagtag gctataccat  168660
ctaggtttgt gtaagtacac tccatgatgt ttgcacaaca aaatgaccta gtgacacatt  168720
tttcagaatg tatgcccatt gttaagcatg acttaatttt agcatagaaa ctctcaacca  168780
atttttcaag tagttgtacc atgtgttatg ggttttattg tctcaccccca aaattcatat  168840 gttgaagtcc taaccccag tacctcagaa tgtgaccttta tttggaaata gattcattgc  168900
acatgtaaag gttttgccat tggcaaaact gccgttattt ttgcaccaac catagcagtt  168960
aagatgagat cattagggtg ggtcctaatc taatacgatg gtgtccatat aaaagggga  169020 gattttggca cagagacagg cacactcaca ggaagaatgc catgtttaaa caaaggcaga  169080
gctcaggatg atgcctctac aagccaagaa tcagcaaaga ttgccagcaa accgccagaa  169140
gctaggagag aggcataaaa cagattctgt ctcacagctc tcagaaggaa ccagcccttc  169200
tgacaccttg agcttggatt tttggcctct ataactgtaa gacaataaat ctttgttgtt  169260
taagccacct aggttgtggt tccttgttac agcagccaca ggagatgaat acagcatggt  169320
gccctcccat tggcagatta tgagggttcc agttgctcca cagcttcaca gacacctggt  169380
agtaatgacc tcatcttaac ttctttctca ttttagcctt tcttccaggc agcagcagtg  169440
tcatacatgc ttttaaaggt gggcttttaa agccacactt gagagccctg cattctgcag  169500
gtgtcacagg gtgatcaact attcaaaggc taccctgcc ctgacagctg gaggcaaggc  169560
ttcccagcac agaggttaag cccatggact ctggggccag gtggttagtg caaatccat  169620 gtccactagt gaataactct gtgatcttgg gctgatgatt ttgtctttct aagcctcagt  169680
ttcctcaata gtaacatggg cattataaca tagaggcatc atgaggatta aatgactaag  169740
tgagctaaca tacataatgt gcttaggaag gtgccagcac accataaata ctctgtaagt  169800
gctggctttt atcattcttt tctctctctc tctctctctc tctctctctc tctctctctc  169860
tctctccctc tctctctctg tctctctttc tctctccacc ccccaacctc ctctccttga  169920 tttcttccc ctcatcttac ttccttcttg ctatagtgtt ctattttctg tttcagagag  169980
tattctattt gtggactttt ttcctcttga aaattgagct gaaacttctg agaattttt  170040 gtgattggca ttaaggctgc agggaatgga gcagggagac acttgaggaa agggctcatg  170100
gaccatctgt ctggcttggt gatttcacca ggccatcaga ctctgtggtc atgcatctcc  170160
tctaagggga gtctatgact gtgttgggag aagagaagga accagggatt aattaatcca  170220
tttcaatagg ttttgtgttt tgtttggttt acttttcct tctccttctg gactgtggtc  170280
tgggaagtcc tcttgtgttt cttactccat tcccaggtca attatgttat gtgaggagaa  170340
```

```
cataattaag agagagcttt acccttggga tgttttcttc agaaaacgtt cctccatttc  170400
cccctctggg atgccagagc cccagaactc acaagccaa  gaacatttaa gacagagcca   170460
caagagaacc gagcttcccc ttccctcacc tgtcaggttc tatctgagtc ccagtcaact  170520
ctcacctgct ttccctcctc acaccctaca gagcaacgat gcctcaggga acacttggaa  170580
ctggttgtac ttcatccccc tcatcatcat cggctccttt tttatgctga accttgtgct  170640
gggtgtgctg tcagggtaag tttctgctac tccccacccc atcccactca ctcctctttg  170700
ctaacttctt tccaagtaga ggccattgaa gctttgtttt cattcactag acagagaaaa  170760
ggcttcttcc cttgtttggg ttaccagact gttattagca agccatgcac aggtgcagag  170820
gttgtgtact gctaggggta cccagtgaga gggttcatat gggctttact ttctttacat  170880
tttttttaaa aaccaatagt ttgggtttac ttctccccca ttttccaaat ataaaatcat  170940
agcatatgct ctaacggtgt attttcctga cccatattgt cctctatccc caagattttt  171000
ttggcttaat cataaatggg cttcattttt cttaccataa gaagtctggg cacttgtatg  171060
gtggctctat ggcaccatca gcaacccag attcttccag ctttccattc tgacatcttt   171120
accagaggct tccaatctcg tggatacctc atggtcttaa gatggctgcc tcacgccctc  171180
cggatggcca cttcatgttc caaacaggaa aaggaagaag ggaaacagga agaggtggga  171240
cctatggcag agaagccaac ctgctgcaga aatctttcat tcatggctta ttggtctaac  171300 ttaaagagg gctgaaataa ttattagcca aaagtatgaa gagaatgaga atgaggtatg   171360
cagccagtgg tggttggcat ggcatggttt tatcctttcg gttttttct tttttattgt    171420 tttttttga dacggtgtct agctttatta cccagactgg agtgtagggg gcgatcatag    171480
ctcactgtaa cctagaactc ctaggcacaa gcgatcctcc tgcctcagcc tcctgagtag  171540
ctaaggcaac aagtgtatgc caccatgccc agctacattt ttattttttc atagagatgg  171600
ggcccactgt gttgtccagg ctggtctcaa attcctggcc ttaaatgata ctcccatctc  171660
agcctcacaa agtgctggga ttacagacat gagccactgt gcctggcctt tttctttacc  171720
taggcacagt tgtcgggaaa tgtgtgaagc tggcagaagc acccatcact ataatatccc  171780
agtcttttcc cagaagtcct gactcctcct gttgaaaact cctgacctcc agggacttct  171840
gaatccccaa acacacacac acacacaaac acacacacac acacacacac acacacacaa  171900
acacacacac aaacgtttcc taacattttc aaaacagcca tactctggct tttctatgct  171960
tctccaggga gtttgccaaa gaaagggaac gggtggagaa ccggcgggct tttctgaagc  172020
tgaggcggca acaacagatt gaacgtgagc tcaatgggta catggagtgg atctcaaaag  172080
caggtgaggc cctttcatcc tggggcccag ggatggagat cccaggccac ggagtacaaa  172140
gagagtcatg cagtttggag aaggctaagc tgggagggtt atgatgggag gagaaagaga  172200
acctgaattg gtagtcccaa attttatcaa caagaatcca gagtctgata tgaagaagtc  172260
taagatgaag ccaggatctg acatcacgta acttgaattc tgaaatcaga cgctggttta  172320
catcccggcc ctgccacttt ttaccatgc accacacatc cctgtacctc cgtttcctca   172380
gctgttacat ggaggcgatg gtagtgccta agtcatagta ctattggagt atttagtaaa  172440
ataatctcag ctgagtcact tggggagaga agtgcctgat acacggtagg cacatattta  172500
tttgttcagc catttaacaa acatttaggg agcacctgct gtgtgccagg cactgatcta  172560
agcactgagg atatgggagt aaacaataca caccaaatcc ctgccctcag agctctgata  172620
ttctaatgag agagataaag caaacaaata catgtcatgt tgggaactcc caaattcaga  172680
gaaggaagat aaaacagact aggaagataa aacagagtag gaagttggcc gggcgcggtg  172740
```

```
gctcacgcct gtaatcccag cactttggga ggctaaggcg ggcagatttc ctgaggtcag   172800
gcattcgaga ccagcctggc caacatggtg aaaccctgtc tctactaaaa atacaaaaat   172860
tagccaggca tggtggcgca cgcctgtaat cccagctact cgggaggctg aggcaggaga   172920
attgcttgaa cccaggaggc agaggttaca gtgagctgag gtcgcaccac tgcactccag   172980
cctgggcaac agagtgagac tctgtgtcag agaaaaaaaa aagagtagga agttagaggc   173040
agggtggtca gggaaggctt ctctaaggaa gtaccctctg agcagagaga cctgaaggac   173100
gtgaagaagg aagctgtggg gatgtcaagg gaagggcat tccaggcaga gacagcaagt   173160
gcaaaggccc tgagctagga acgtatttga gacacagcaa ggaagccagt gcagctgaaa   173220
cagagtgaga ggtggggaca gctggaggag aggaagacag gaaggtgatg gagatcagat   173280
caagcagggg cttataggct gtggtgtgga cattggtttt tattttgcgc gaggtgggga   173340
gaatgttggc tattgctact gttgcggagg tggggcttga agtcacaaac cacccagcag   173400
catgttttt ggtcggttga gctgtcacca tcagtcagca gagaatgggg gtggccgggc   173460
agacccttct tcctggtcca agggagaact catcctccaa atgcaggagc ttaactctgt   173520
gctcttcctc ttcagaagag gtgatcctcg ccgaggatga aactgacggg gagcagaggc   173580
atcccttga tggtaactgc tctaaaccca cctcagggt gggtcccagg ggagaaggga   173640
gaagctgtgg tggggagtcg ggggagagca ggtgactggt ctaaggatc ttgcagaggg   173700
tagacgttcc tcttggagga attttaggac ttccatgcag agtttcccta ttctggcctc   173760
cactttttg ttttaaccat ggacctggtt ttttctgctt tgtgccttgg tttttctcat   173820
ctgcaaaatg ggtatgatat aaacaatacc ctagctcacg agattgtttc tcagaatgat   173880
attcgttatg gcaaatagaa cacctgggat agtgcctggc atgggtcag cacgtttctg   173940
tttgctaaat aagtaataat tccaccaata atccagttta ctgtgaacgg ctgctgtctc   174000
ccatgttaga aacttaacga gacagaacca tgactttctt tcttttcttt ttttttaat   174060
tgagacagag tctcgctctg tcacccaggc tggagtgcag tcacacgatc tcacctcact   174120
gcaacctctg gctcccaggt tcaagcaatt ctctgcctca gcctcatgag aagctgagat   174180
tacaagcatg agccaccatg cctggctaat ttttatattg ttgatagaga tggggtttcg   174240
ccatgttggc cgggctggtc ttgaactcct tgcctcaaat gatctgcaca ccttggcctc   174300
ccaaaatgct gggagtgtag atgtcaattc atggtcccct ggaaacctga atatgaaagg   174360
agggaccatt aaaaaggtgt ccaaaagccc aacctcccca gcatagctgg gagtcagggg   174420
acagactgta agagtcactg tgtatccaac ctgaggcttc atgaaagtaa gtttcctag   174480
aatttagaga tagggttgga tgcggtctgt ctgtggctca catctgtaat cccaacactt   174540
tgggaggcca agacaggagg aacacttgag cctgggagtt caagaccagc ctgggcaaca   174600
taatgaggtt ccgtctctac aaaaaataaa cttagccaga tgtgggggca cacgcaccta   174660
tggtcccagc tactcaggag gctgaggtgg gaggatcact tgagcccaag aggtcgaggt   174720
tgcagtgggc accactccac tccagcctgg gtgacagagt gagaccctgt ttcaaaagaa   174780
aaaaaagaa tttagagata ggccagaata atatgtctgc aatataataa taacagcaat   174840
aagaaaaata atagtactcc ctgaaaaatg caacttcttg cttgagattt atcttctcat   174900
actttagaaa actggttaga cagggggctgg gcgtggtggc tcatgcctgt aatcccagca   174960
cttgggagg ccaaggcggg tggatcactt gaggccagga gttcaagacc ggcctggcca   175020
tcatggcgaa accccatctc tactaaaaat acaaaaatta gctaggtgtc atggcacacg   175080
```

-continued

```
cctgtaatcc cagctactca ggaggctaaa ctacgagaat tgcttgaacc tgggagacgg    175140
aagttgcggt gagccgagat cacaccactg cactccagcc taggcgacag agcaagactc    175200
tgtctcaaaa aaagaaaga aagctggtta dacagggtga tgacttttga ttaaaaatct    175260
gagagatttg agggaaataa aagaactggc actgcgtccc agaaggttat aaaatgaatt    175320
ttattatctt agttggggag gggagattac ctaactcccc taaatgagtt aggtaatcta    175380
actcatttag ggtacctaaa tcttttttatt ggaagtctac acctgaactt gtctgctgtg    175440
gagcccctgg ggtgtatagc ttgaatatgg gggcagaatc ccaaaattgc agcctgccta    175500
gcgagtatgc tacaggtcaa ggggtggact gttttcataa gaaagtgagg tttcttagaa    175560
tttaaaaata gaggctgagt ggggcggctc acgcctgtaa tcctagcact tttggaggcc    175620
aaggcaggca aatcacttga ggtcaagagt ttgaccagcc tggccaacat ggcaaaaccc    175680
catctctact aataatacaa aaattagcca ggcgtggtgg tgcatgcctg tagtctcagc    175740
tactcaggag gctgagggag gagaatcgct tgaactcagg aggcagaggt tgcagtaagc    175800
caagatcaca ccactctctg ggtgacagag caagattctg tctcaaaata aataaacaaa    175860
taaataaata aaccagaagg aaaatagtgg ctgagggccc agacctggag tcggactgaa    175920
cccgacttga ttcttgtctt taccccttta agcaaagtga tagtgccacc ttgaacctca    175980
gtttacacat ctgaaaaatg ggtatactat tagttcccgt gagaacagtt gccgtgagag    176040
ttaaatccaa ggacacactg tgtccatatg gtctgtgttg caaaagggt aacgtctttt    176100
tctcttgcca tgtttccatt gttggagctc tgcggagaac caccataaag aaaagcaaga    176160
cagatttgct caacccgaa gaggctgagg atcagctggc tgatatagcc tctgtgggt    176220
agtcccttcc tctgccacct atcagttgtt catcacctat cgcccaagag acatggtggg    176280
gtgggggcag agggcttgca aaccgtgctg cctggatttg ggtctcagct ccacccttc    176340
ccacctgtgc gtgtgtcctg ggcagattac atcattatgg gaataacatc cgtgcctagc    176400
ttctcattat tttgtgggaa ttcaactaaa tgatccccat gaagcatggc aaaccagcac    176460
ctggcaggga cgaagctccc agtcaagttg gtgaatgttt gtgactcatt cgggaagtat    176520
tcatggggga cctgcttata ttaggtgctt ggttgcaaac aagacaaggc agtcacgagg    176580
ctgagctggg aggatcactt gagcctggga agtggaggct gcaataagcc attattgtgt    176640
tactgcactc cagcctgggc acagaaaaaa aaaaaaagac acaaactgag ccaggcacag    176700
tggctcacgc ctgtaatccc aacactttgg gaagctgaga tgagcggatc acctgatgtc    176760
gggagttcga gaccagcctg gccaacatgg tgaaaccctg gctctactaa aaatacgaaa    176820
aaaattagcc tgtagttcca gctactctgg aggctgaggc gggagcatca cttgaacctg    176880
ggaagcagag gttgcagtga gctgagatct catcactgcc ctccagcctg gcaacagag    176940
caagatcctg tctcaaaaaa aaaaaaaaaa aaagacaca aaccaaatcc ctacctacat    177000
ggagctcaca gtccagtgca ggaaatagaa attaaacaga gaattacaca aataaacctg    177060
taatggtaat ggcacttcag ggagaggctc tgggcttagc ttgctctaga aggatgggga    177120
gcagtcaggg aaggctacct ggaggaagtg acggttaagc tgggaactga aggatgggta    177180
ggagatcact gtggtggtga tagcagaagg aacagtgtga gaggcagggc tcagaccttt    177240
gccaccacaa gggccagagt tcgagggagg agggaacatt tattctttcc cttctcactc    177300
ctctgtccta ttgattcatt ggctgtgatg atgttgattt tgaccttcta aagtgagaat    177360
gtattgttat tgttgttgtt gttctttaat gggttttgt ttttaatgga aggaagagca    177420
tccaggcaga ggaaataaga ctggaataag attgagggga gaaggaattt aggctgcttg    177480
```

```
ggaaactgtg tggccgcagt ttagaggaag aaaggatggc aagagaaaga ggaagggagg  177540
aagagaagga gggagagaag tgaaggaagg agggaagtta gtacatccat gtgtttctga  177600
tccatagttt ctgatccact atttcgtatt cccctttat cgctcgcccc tagtttataa   177660
ccttattgct gagtttaggc ataatttcca ttgcgatcac atatctcgta gggtggatac  177720
actatggttt gtttagccat agctctatta tagggtgttt gagttgtttc caataatttc  177780
tcttacgaag aacactgctg tgcacattta cgtacaatga ctcccccac cctttgggcg   177840
tatttccttg gggataatta taggatcaaa gatattaaca gcttttcaac tcattattca  177900
aagagccatt ctgagtttca aaaacatgga acccatttat aaacctgcca agtatgcata  177960
tgttcatgga ttccccaccc aggccatcga atattaccaa tttaatttcc tttcccagtt  178020
aagtgggttt gtaatgaaac cttaaagctt gttttcattt gcattttaa tttccagcca   178080
aaacacgctt ttctttgtaa tggagaactc attctgcttc cactcgtgtg tgcatctgtt  178140
taatttcctg taagcaaatg tcaagaattg gagcgctcag taggtgtctt gagtatttga  178200
tcaattatgt ctgtctcacg tgttacgtta cctccattgt ttaaaatctg ttttatgacg  178260
aggtacagtg gttcacgcct gtaatcccac tgctttggga ggccagtgca ggaggatctc  178320
ctaagatcag ccgttcaaga ccagcctggg caacataaca aggctccatc tctgaaaaac  178380
aaaatgttga aaaacttagc caggcattat ggcacacacc tatagtccca tctatttagg  178440
aagctaaggc aggaggattt cttgaaccca ggaattcaag gttgcagtga gctatgattg  178500
tgccactgca ctgcaacgtg ggcaacagag tgagaacctg tctcttaaaa aaataaaata  178560
acatacattc ttaaaaatct actttgctgg ccgggcgcgg tggctcacgc ctgtaatccc  178620
agcactttgg gaggctgagg cgggtagatc gcttaaggtc aggagtagga gaccagcctg  178680
gccaacatgg tgaaaccgtg tctgtactaa aaattcaaca attagctggg tgtggtggcg  178740
tgagcctgta atcccagcta ctcaggaggc tgaggcacaa aatcacttga acccgggagg  178800
cggaggctgc agtgagctga gatggcgcca ttgccctcca gcctgggcat caagagtgaa  178860
actccatcaa aaaataaaa aatctgcata tacatatata tgtatatata ttttaatttt   178920
ttttaatttt ttttttttt tctgagatgg agtcttgctc tagcacccag gctggagagc   178980
aatggtgcca tctcggctca ctgcagcctc cgcctctgtt aacaaggcag gtgacattgc  179040
agctttctaa acagacccaa aacccaggcc agtggcttgt tctttcatag ccacgtttgc  179100
tacaggcaaa tccaccaaaa cccacctcat cagcctgatt actcaaaaag acaagaaag   179160
gagccccaa tctagccagt ggttttctag accaccccaa aagagatctc tggaattcca   179220
ggattctggc aaggaatcac atttagcttt atttatttat gtaaagaatg caacaataca  179280
ggctgggtgt ggtggctcac gcctgtaatc ccaacatttt gggaagctga ggtgggagga  179340
tcgtttgagg tcaggagttt cagaccagcc taggcaacat agtgagaccc tgtctctatc  179400
aaatattagc tgggcattgt ggcacacgcc agtagtccca gctactcgtg aggctgaggt  179460
ggatcacctg agcccaggag gtcaaggctg cggtgagcca cagcatgccc ctgcactcca  179520
gcctgcgtga cagagacttc atctcaaaaa aaaaacaaa aaaagtaat aatacagtaa   179580
tgcatatttc aaagtaaggt gggagctatg tggtatttgc gttcacgttc acattatacc  179640
acagtatgca cagtcctttt tttttttttt ttgagacagt gtcttgctct gatgttcagg  179700
ctggagtgca gtggtgcagg catagctcac tgcagcctca aacccctgga ctcaagtgat  179760
cctcccacct cagcctccca gtagctggg actataggtg tacactgcta cactcagcta  179820
```

```
agttttttat attttttact agagatggga tctcaatatg ttgcctaggc tggtctcaaa  179880
ctcctggcct caaacaatcc tcctacctcc acctcccaaa gcagtgggat tacaggcgtg  179940
agccaccaca cctggcccac atgcagtctt atataattgg tgattctact gcgctgttga  180000
atcagttgat aaacgcacta taaagcaggt tcattcctaa ttgatgaact tactgctgaa  180060
ataaggaact tgaatcattt acatgaaaag ttgagccatg ttgctgaaag gatatcaatt  180120
ttttttcttt ttttttcttt tttttgaga tggagtctta ctctgtcgcc caggtgggag  180180
tgcagtggtg cgatctcggc tcactgcaac ctccaccttc caggttcaag cgattctccc  180240
acctcagcct ccaagtagct gggactacag gtgcacacca ccacgccctg ccaattttg   180300 tactgttagt agagatgggg tttcaccatg ttggccaggc tggtctcaaa ctcctgacct  180360
caagtgatct gcccacctca gcctccgaaa gtgctgggat tacaggtgtt agccaccgcg  180420
cctgacagga tatcaaattt catttagact gcaggaatac gttcaagaga tctattttgt  180480
acagcctggc gactgtatta ataacaatgt attatatact tgaaaattgc tcagagagta  180540
ggttttaagc attctcaccg tgagaaaagt gataagcata tgtaataatg catatgttaa  180600
ctagctcaac tgagccactc catagtgtat acatatggtc aaaatatcat gttatgcact  180660
ataaatagat acagcctgta tctgtcaatt taaaataaat gaataataac tttaaaaaga  180720
aaaataacag tatggctggg cacggtggct cacacctgta atcccagcac tttgggatgc  180780
caagacaggc ttgaggccag gagtttgaga ccagcctggc aacatgcg aaactttgtc  180840 tctaataaat atacaaaaat cggctgggca tggaggcggg cgcctgtaat cccaactact  180900
tgggaggcag aggcatcact taacctggga gatggaggtt gcagtgagcc aagatctgca  180960
ctccagcctg ggtgatagag tgagcctta tttatttctg taaagaatgc aataatacag  181020
gcctggtgcg gtggctcatg cctataatcc caatgttttg gaaggccaag gtgagaggat  181080
catttgaggc tacaggcgca tgccacagtg cccagctaat acttgataga gacacggtct  181140
cgctatgttg cccaggctgg tctcaaaacc ctggcttcaa atgagcctcc caccttggcc  181200
tcccagagtg ttgtgattac aggtgtgaga cactgtacct ggcctgtatt aaaaaaaaaa  181260 aaagaagaa gaagaagaag aggaggaaag aagaagaagg aagaaggaag aagaagaaga  181320
ggaggaggag gaggaatggg aaggggaagg ggaagaagaa gaggaggaag gggaagggga  181380
agaagaagag gaggaggaag gggaagggga agaggaagaa gaaggaggaag aagaagacga  181440 agaagaagca caatgataaa taagtaaaat gtggagcata tgaaaacaaa acaaaaaaaa  181500
gttgatccat tatgaatgga agctgccatt gtaactctgc ttttttagga aaaccagacc  181560
ccatttagat gatttttattt gttttttaaag gcaggttctt gctctgtcac tcaggctgga  181620
gtgcagtgat atgatcatag ctctctgcag cctggagctc ctgggctcag gcgatcctcc  181680
cagcttagcc tcccaagtag ctgggactac aggcaccacc acacccagct aatttgttgt  181740
tgttgttgat gttgttgttg agatggggtc tggctatgtt gcccaggctg gtctcaaact  181800
cctggcctca agtgatcctc ctgccctggc ttcccaaagt tctgggatta caggcatgat  181860
tttttattaa tttatttgca gctgacaaat ggtaattgtg tatgtttatg gagtgcagtg  181920
tgatgtttta atctatgtat acatcataga atgattcagt catgctaatt aacacatcca  181980
tcgcctcacc acctcaccgt ttttttgtgtg tggggaaggc attaaaaatc tcttagcaat  182040
tttgaaatat gcaacacatt actatttatt aataatgcaa tataaataca caataatgta  182100
ttaatgcatc actaaatgcg atgcaatgca atgcaatgca atagatcact aaaacttact  182160
cctccagtct aactgcaact tatacccttt gatcaacatc ttctccttct caatccctcc  182220
```

```
tcctccsctg cagcctccag gaaccacctt cctgctcttt ctatgagatc aattttttt   182280
agttttaagc tcccacatgt gagatcatac tgtaattgtc tttctgtgcc agcttatttt  182340
actcagtata atgtcctcca gttctgtccc tgttgtcaca cattacagaa tttcttctt   182400
ttagggctgt atagtattct atttgtatac ataccacatt ttctttatcc attcatccat  182460
tgtgggacac ttagtttgct tccatatttt ggctattgtg aataatgctg aagtgaacgt  182520
gggagtgcag atgttctgaa aagacttaaa tgtcagacct gaaatggtaa agatgctcca  182580
agaaaacata aggagaaagc tccatggcat tggtctcggg aatgatttt tggacaggac   182640
ctcaaaagca caggcaacag aagccaaaat ggacaaatgg gatcgtatca aactaaaaaa  182700
tttgtgcaca gcaaaggaag cgttcagcag aggaaagaga caacctaagg aatgtgagaa  182760
aacgtttgca aacaatacat ctgataagga gctaatatcc aaaatatata aggaactcaa  182820
acaactcaac agcaagaaaa caacccaatt aaaaatgggc aaagacagct actcgggagg  182880
ctaagatgtg acgatccctt gagcccggga ggaggaggtt gcagtgagct gacattgcat  182940
cactgcactc caccctgggc gacagaagga gaccgagacc ctgtctcaaa ataaaaaata  183000
aaaatgtgca aaggatctga acatacatat cccaaaagaa aagacataca agtggccaac  183060
aggtatatga ataaaatgct gaacatcact catcatcagg gaaatgcaaa tcaaaaccac  183120
cattagctat cacctcacac ctgttagagt agctattatc ttttttgtttg tttgtttgtt  183180
ttttgttttt tgttttgttt ttgagaggga gtctcactct gtcacccaag ctggagcgca  183240
gtgttgtgat ctcagctcac tgcaacctct gcctcctggg ttcaagggat tctcctgcct  183300
cagcctcccg agtaactgaa attacaggca cacgccacca tgcccagcta acttttgtat  183360
ttagtttcac tatgttggtc aggctggtct tgaattcctg acctcaaatg atctgccctc  183420
cttggcctcc caaagtgctg ggattacagg tgtgagacac tgtgcccagc ctagagtagc  183480
tattatcaaa aagacaaatg aggtttgttg aagttctaac ccctggtacc tgcaaatgtg  183540
gccttacatg aaaatagggt cttttgcaggt ggtaatcaag ttaagatgag atcaaactta  183600
attagggtgg gtcctaaatc caatgactgc tgtctttata agaggagaag caggctgacc  183660
aacatggtga aaccccatct ctactaaaaa tacaaaaatt agctgggtgc agtagtgcac  183720
acctgtagtc ccagctactc aggaggctga ggcaggagaa ttgcttaaac ccaggaggtg  183780
gaggttgcag tgagcagacg tcatgccact gcactccagc ctgggtgaca gagtgagact  183840
ccatcttaca agaaaaaaaa aaagacaaa tcataacaag tgctggcaag gatgtgggga   183900
aacggggatc catttacatc attttaataa cacaggctct atatgggtgg tattgagttc   183960
ccagagttgc cattacaaaa tgtcacaaac ccagtggctt aaaacaacag aaatttcttc   184020
tctcacagtt ctagaggcca gaagtccaaa ctgaaatcaa ggtgtcagca gagccaccac   184080
gttccctcag aaggttttag gggagaatct gttccatggt attttcttag tttctggtgc   184140
tgccagcgat acttggtgtt cctcagttca tagatgcata attccagtct ctgcctctgt   184200
tgtcatatgg tcttctttct gtgtttctgt atgcgatttc tttttttttt tttttttct    184260
gagacaagtc tcactccatc acccaggctg gagtgcaatg gcacgatcac agctcactac   184320
aaccccaacc tcacaggctc atgccgtcct cccacctcag cctcccgagt agctgggatt   184380
acaggcgtgt gccaccatgc ccggctaatt tttgtatttt tagtagatac ggggtttcac   184440
catgttggcc aggctggtct cgaactcctg accttacgat ctgcccatct cggcctccca   184500
aagtgttggg attacgggca cgagcccacc gcacctggcc ctaattactt tatttttttg   184560
```

```
taaattttt  tttgtaaatt  tcatgtagcc  tgagcataca  gtgtttataa  tatatacagg  184620
agtgtacaat  aatatcctag  gccttcacat  tcactcacca  ctcaactcac  tccctcacca  184680
agagcaactt  ccagtcctgc  aagctccatt  catgccaagt  accctatgca  gctgaaccac  184740
cttttctctt  ttatactgtg  tttttactgt  acctttccta  tgtttagata  tgttcagaca  184800
cacaaatact  atgatgttac  agttgcctac  agtattaagt  acagtaacat  gctgggcagg  184860
tttgtagccg  aggagctaca  aaccacgtag  cctgggtgtg  gagtaggcta  caacatctag  184920
gtttatgtaa  gttcacttta  agatgctcac  acaaggacaa  aattgcctaa  caatgcattt  184980
ctcagaacac  gtctccctca  ttaagccaca  catggctgta  ttacaattta  catataattt  185040
taagcgtata  taaattgcca  gaaatcacca  gatgaatcct  tggcggtgac  atacccctttc  185100 ccccaccata  gaacattgca  gactggcccg  gacgcccagt  atctcatgcc  tgtaatgcca  185160
gcactttggg  aggctgcagc  gggcagatca  cttgaggtta  ggagttcgag  accagcctga  185220
ccaacatggc  aaaacaccat  ctttactaaa  aatacaaaaa  ttattcggac  gtggtagtgg  185280
gcacctgtag  ttccagctac  ttgggaggct  gaggcaggag  agtcacttga  acttgggagg  185340
cagaggttgc  aatgagccaa  gatcgtgcca  ctgcactcca  gcccgggtga  cagaatgaga  185400
ctctatctca  aaaaaaaaag  aaaaaaaaaa  aaaaggaaa   agaacatttc  agactggtac  185460
cagttacacc  ggctcttgat  cccttgaatg  tggctgaccc  tgaactagga  tgtacttcat  185520
aataacacgt  ccggctggga  atacttagta  caaaagaaag  agtataaaat  atcttttgaa  185580
tccaccttga  tattgattcc  atgttgaaat  ggtaatattt  tggatgtatt  gggttgaata  185640
aaacatctca  tgaaagtgat  ttttaaaaat  ctagaaattg  tctgcaatta  taattccaga  185700
ccacagagaa  aaacgagaga  caggaatgta  tagaaaaagg  gaacgtggga  caaagtgagt  185760
atgaaattca  actaacagaa  gtgacagtgc  ctagcatggg  gtccagcact  tagtaggtgt  185820
tcaattaata  ttcatttccc  tctcccttac  cagtgaaggg  tatgcctgtc  gtgggaatg   185880 tgtcttcagg  ctgagtgatc  aggaaggact  ttctcaatgg  ctggcacgtg  aacctagtca  185940
tgatttcagc  tcttgaggtt  gtactagaag  atttatatcc  aataatcgta  aggtaccact  186000
tagcatcacg  ctaagatgta  ttaattcatt  tatgcctttg  gatggccctt  tgaggtagga  186060
agtgtggttg  tctccagttt  accaaggtgg  cttgcccaag  gtcatctgct  ggttggtgat  186120
taagccaggt  tttcagtgtg  gctccagcag  gagtgggggc  tggggacctt  ctacctgctg  186180
tggtttctct  ctctctctct  ctctctctct  ctctctctct  ctcgatctgt  ggaacatccc  186240
ccctgtcccc  caaggtccca  agggtcttat  ttcttttggc  caagcccttt  ggagacctgc  186300
agatctggac  acatctttga  gagtttcagg  aactagggcc  agaaatgctg  gcagggtca   186360 tgaggagctg  ccactggggt  tgagaaggtg  atggacatga  ggggaagggt  ctttgcagaa  186420
aggagaggcg  tccctgtaag  caggtcacag  ccactgggcc  tggccaactg  cagccgagtg  186480
gaatgtgccc  ctgccccatg  accatatgcc  ccaggtgtgc  aatgtggcgg  cccagagcac  186540
acactctgaa  ccatcttgac  acatcttcac  tggttactag  accccccctca  gcctgtttcc  186600 ttggctgtaa  aatggggatg  acgctggtcc  ctacttccta  gggctctgag  caggagtaag  186660
tagcttgtcg  tataaaacat  gttccctgca  gtgcctggtg  cctgctaaat  gttccataaa  186720
cgtcagctgt  tattttcatt  caggggaagc  tgaaatccat  attttcatgg  aaaatctccc  186780 agttttttaaa  tgtggaccaa  taatttcagc  tttcacaaac  ccagtatgag  tcggtatggc  186840 ccctaggggtg  ccaactcaaa  atctctgttg  agaattttgc  tgataggaag  tggcctcctt  186900
ggaggtgttt  gctgtgtcct  gtgtctggca  agtggggtgg  ttttgataaa  cgtgctggat  186960
```

```
ggatgtatgg gtgaatggat aaatggagga atgaatggag aaacaaatga gcaaatgaat  187020
aatgaatgga tggatgaatg gatgagcgaa tggatggatg aatggatgag caaatgaatg  187080
atgtacacac aaaggaatgg ataaatgatg aatgtgctaa tgaatttaag aatgatgaaa  187140
gaatgaatga ataaatgaac aaatggatgg atgaaagaat gaatgaatgt actaatgaat  187200
gaatcaatca atgaagaacc atttaaaaat gaatgcaact gagggtttat aagaaaaggt  187260
atcttaagcc tgggcatggt aattcatgct ggaatcccaa tgcttaggga cgctgaggcg  187320
ggaggatcgc ttgaacccag gagttcaaga ccagcctggg caacacaggg agacctcatt  187380
gctaccaaaa acaaaattgt tttaattaag cgggcatggt ggtacgtgcc tgtagtcata  187440
gctacttggg aggctgaggt gggaggatcg cttgaaccca ggagttcaag gctgcagtga  187500
gctaggatca agccactgca ttccagcctg ggcaacaaag caagatcctg tctcaaaaaa  187560
aaaaaaaaaa gatgtatttt agaaggtaaa ttcaatctgt ccaaaactga gctctgacct  187620
tcccctaaac ctgtgcccat tcagtggatg agagctccat cccttaaggg gttcaccaat  187680
tcatccattc ctttgtatgt acatcattca ttcaccttgg ctcatccctc tctcttacat  187740
ccacaccgtt ccatcagcaa atgttgaatc tgtcttaaat gattcatccc aaatcctccc  187800
cgcttaacta ccacccaact ccagccccca tccatcatca tcatcacttg cctggatggg  187860
ttcagtcacc tccagcctgg tctcccagct ccgtcctca cctctcactg tctactctcc  187920
cactcggcag ccagagggtg cctgtgaaca cccaaatcag gttccatccc tcctctactc  187980
agaaccctcc acggctcccc cctcactcag ggtaaaagcc aaagtcctcc ttgtggtcca  188040
ccaggccatg catgatctgc ctgtcacctc cctgccttca ccacttcct cttttcccct  188100
caaccactcc actccagcca cactgacttc cttgtgctct tccccaaaaa tgtcgggcag  188160
acacattcat gcttcaggac cttaaatttg ctgtttcctc tacctaagat actaaagtga  188220
caagtcaaca cactcacctt gaccatgcaa tttaatgttg cagcctaccc tgtggactct  188280
ccaagggctc ccagtccctc tgtgatgctt tacttttct cttaaaaaaa aaattgttat  188340
ttaaagaac ttgtctcgct gtgttgccca ggctggtgtc aaactcctgg cctcatacag  188400
tcctcccatt ccagcttccc aaagtactgg gattagaggc atgtgccact gcacccatcc  188460
caacttttt tttcccatag cacttttcat tttccatccc actgttaatt tacttattac  188520
gtccactgtc tgtctcctcc ccttagaggg tcagaccccg gaagtccagg ctctgttgcc  188580
taatgtatcc tgagcccctg aacagagcc tggcacaaaa taggtactca ataaatgcat  188640
aagagcaaaa ctatatgtag gcagaggaca cacccagctt attcctcagt gatcacttct  188700
aaagttaaat gtccatggaa aacagtctca tccacatctc tttctggagg ccttccaagc  188760
gtgctccatg cagctctgtt gcctgcccct gcatcaggga atggaggctc tgctttatcc  188820
tgccctgtgg tgtgactccc agaggcatca gatgtggctg ggagtgggag acatggaaaa  188880
ttggctcctg caacagagaa ctatcagcct tccatcaat tggttacttc taattctgtt  188940
attttttcagg ggcactgtct tctcataagc tccatctatg caaaactaag cccatgggtc  189000
atgatggttc cctcaggcca gaggcttgct ggagagacta atggatcccc tggctaaaat  189060
ctgtgcttgg gctgcacatt ggttaatttc ttctgaagga acagcctgag cctgacattc  189120
tccatctttt ccctggcagg ttctcccttc gcccgagcca gcattaaaag tgccaagctg  189180
gagaactcga cctttttca caaaaaggag aggaggatgc gtttctacat ccgccgcatg  189240
gtcaaaactc aggccttcta ctggactgta ctcagttttgg tagctctcaa cacgctgtgt  189300
```

```
gttgctattg ttcactacaa ccagcccgag tggctctccg acttcctttg tgagtatcac    189360
ccagccccac ccctgccaac tccctgatcc ctccctcaca ccctttttcc acttctcttt    189420
ctctggtagt atgtgtatct tctttggtcc tcattgaatc tgcccttttcc tttagccatt   189480
tctataactg tcactggggc caatgttact gttgctatga caatggaacc catctcccctt  189540
agacctgaga gctggaagct ggaattcaga ccaacaaatg ctcctgtgat tcctttctaa    189600
gagagaggga cagaggggtg ctggtgaagg ggatgttgga agagagacag agaaagacgg    189660
agctcataag atagacagat agaaacagaa acatacatgt attaataatt tttatgtaca    189720
tctctggaaa tgttcataac ttatggttaa gagaggatgc cttagaaata aggagtggct    189780
tatatgttgc cctcattttc tctacttatt tctgactcta cttctctctt ctttcaaacc    189840
ttctgcttct ttcctgttag gttggtgcaa aattaattgc gttttttgcc ttttttttt     189900
ttttttttaa ccacagttac ttttgcacca acctaatact tcctcccctg cccttttttgg   189960
cttccttatt cattcataga acatcccctc cagtatctgc gagagcgttt tgctccctca    190020
aggtacaagg cccactaagg ctttgccctc tgggcctatt cccagattct atgtgagtta    190080
gcatgagata gtatcaaaat tgagggccaa gtgagggtga ggaaaagcag caaaagatgg    190140
ggagatgtct gagcaggatt taaaaagtaa agagctcgag gaatcaacaa gagcagcgac    190200
tggggccagg catggtggct cacacctgta atcccagcat tttgggaggc tgaggtgggt    190260
ggatcacttg aggccaggag ttcaagacca gcctggccaa tatggtgaaa ccctgtcttt    190320
acaaaaaata caaaaattag ccagatgtga tggtgcacac ctgtaatccc agctactcag    190380
gaggctgagg cactagaact gcttgaatcc aggaggcaga ggttgcagtg agccaagatc    190440
atgccactgc actccagcct gagcaacaga gagagtgtct gtctcaaaaa ataaagtaaa    190500
ataaaataaa ataaaataaa gagtagtgat tgggcagtga gggggggcagg tggatgccct    190560
ggctttggct cacaggcccc aagtaaggac ttctcaaaac gtcttttgcc tactggctgt    190620
ctaatttatt cactgacctt ctgacctggt tcagaattga cttaggacag caagaagaga    190680
cagtctagtc tttgacctag aaaggcccgt gagcctagtc caggccattg tcttcttata    190740
accctccttg ttcccagtca cgttggctga ccccccagga caccctcag gaaccagttc     190800
tccttcccag ggccctgacc tagtttcaaa cttagtaatt gttttttagtc cctctggagt   190860
ctcttataaa tgaggactct acttcgtgtt ttaacttcct ctaatactct atttttaatc    190920
tcctatattc tctctactaa tcatcttgta cagtctgtcc tggttcagga acaagggact    190980
gagacttcct gcctgggtcc tcagtgtcta taaaggtcct ttactcattc ccacttttccc   191040
tttgagaaaa ctgagacaca gagaggttaa gtagattgcc caggatcaca cattagcttg    191100
gcatgatggc gggcgcctgt aatcccagct acttgggagg ctgaggcagg agaatcgctt    191160
gaacctggga ggcagaggtt gcagtgagcc cagatcatgc cactgcactc tagcctgggc    191220
aacagagcta gacgccatct caaaaaaaaa aaaaaaaaa aaaagataca cattaatttc     191280
agagatgtca aaatataaac aaaaatgtat atcttggcat cagtgaagtg tagttgtttc    191340
tctggatctc agactccaca tctatgtggt agaaaccgga tttgatggtc ctgaaagttc    191400
ttccagatgc aacaatgcta aggataagta attctttcaa gtcttgtgca tcacctgcta    191460
tcatgttttcc atggtaactg aggaacaaga tctcagaaac tcttcagtcc tcccagagtt   191520
acttctggtg ggtctaggaa tgtgtcagat gttacaaaca gacttcctct gctgatattt    191580
tggtcctagg aaccctagag ttcccctcag acactaagat ctccttagcg tcctataaat    191640
aaggagaaat tttggtgata aatactgtga aggactttga cggtcagttc aaaacacctc    191700
```

```
ttaaaagcat gacatagcaa acacccttgg caaatatctt agttcatttg tactgctata  191760
acaaattacc cgagactggg taatttgata agaacagaaa tttattttct cacagttctg  191820
gaggctggga agcccaagat caaggcattg gcaggtttcc ctgtctggcg aaagctactc  191880
tctgcttcca agattgcacc ttgaacactg tatcctctgg aagggaggaa cactgggtcc  191940
ttacatggca gaaggtggag gagcaagagg gacaaacttc ctctgtcaac ctcttttata  192000
agggcaccta atcccattca tgagagctct accgtaatga cttaatcacc tcctgaaggc  192060
cccacctctt aatactgtta cattggcaat taagtttcaa cgtgaatttt ggaggggaca  192120
caaacattta aaccatcaca accaccaaac acaattagct ttgtggcctt aattagctat  192180
atgaaattca tggaagttag tttcagtcct ctgtctcttt cctttctgta tgctttctgc  192240
tcctcagaaa ccctcctcat ctctcctttc tatccattaa gtacccacgc ccttcctaac  192300
tcctcatctt cctaccctac caagaaagcc ctctcagaaa aggatctgat gtcagccatt  192360
tatttgctgg agcaaatgca tatccatgtt ttacccctcc ctgaggcatt tgcaatttta  192420
tgcttgctca tcaaagaaca aaaggctttg tcttactcaa gacttttttag gtcactcaca  192480 acacaggatt tctaggggac ataagacaag ttttctgagt taggagaaaa gccatacctt  192540
aggtgggttg cctgtgtcgc tccaactaag tacttaactt caggattaca aataggatat  192600
cattatgatt tctatttcct tttatccttt ggagctcagt cacgtagaag tagattaaat  192660
ataattgtta gatcacagca ccctggcatt atggggccgt tatggtccat tgttattatg  192720
tgaattattc agttaattag ttttattttt aaatgtgata aacacccagg aacccaccag  192780
tcaacacaaa agtccttggc aataatctat atccgatcct tctcatcgaa ccagggcaaa  192840
aactacaaga tggagaccca ctgatatttt tctcattcct tttaaaatcg gcctaaggtt  192900
ggttagcttg ttggttggag ggtagggcat aattgttgct tttttttttt tttttttttt  192960
ttagacaagg tcttgctctg tcacccaggc tacagtaggg tggcccaatc ttggctcact  193020
gcaacctcca cctcccaggt ttaagtgatt ctcatgcctc agcctcccaa gtagctgggt  193080
ttacaggcat gtgtcaccac actggctaat ttttgtattt ttagtagagg cggggtttgc  193140
catgttagcc aggctggtct caaactcctg acctcagttg atctgaccgc ctaggcctcc  193200
caaagtgctg ggattacaga cgtgagccac catgcccagc cagctcttcc tttttaacag  193260
aggggaaact gaggcccatg ggaaggacac cttggacagg gcgtggccac agtgggtcat  193320
gtatataatc ccagcacttt gggaggctgt gctgggagga tcacttgagg ccaggagttc  193380
aagaccagca agggcaacat agtgagaccc ccatctccac ataaaaattt taaaaagaaa  193440
aaagataagt cagaagttgg gtgtggtgac acatgcctgt agttctagca tgttggaggc  193500
caaatcaggg aaactgtttg aggccaggag tttgaaacca gcctaacagc atagcaagac  193560
ctcatctcta caaaaaataa aaagtttaaa aatgataata aaaggaaagt cagagccacc  193620
tggaacccct accctcagca agcctaacct cctctctgtt tcctccttct cccttctaga  193680
ctatgcagaa ttcattttct taggactctt tatgtccgaa atgtttataa aaatgtacgg  193740
gcttgggacg cggccttact tccactcttc cttcaactgc tttgactgtg gggtaagtgc  193800
tcttgtttct aagagttcat ttctccagct cttgcctgga atgacagata cctgacaca  193860 ttaaagggag aaaggtaaag tcacccctga atatgagaga ctcagatgga tgcagaagga  193920
atgagaaaac aatcccaaac actggcaagg atacagtgta cccagaaccc tcaaccaccg  193980
ccagtgggag gaaaacgtat agacccccctt tggaaagcta agtgggggac ataagacaag  194040
```

```
ttttccaagt tgggagaaaa gccatgcctt aggtgggttg cctgtgtcgc tccaactaag   194100
tacccaactt caggattaca aacaggacat caatatgatt tctatttctt cttttccttt   194160
gtagctcagt catgtggagg tagatgaagt ataattgtta gattacaaca ccctggcatt   194220
atggagccat tatggtcctt tgttattttg tgaattactc agttaattaa tttatttttt   194280
aaatgtgatt aacacccagt aacccactag tccacacaaa acctaagtcc tggagaataa   194340
tctacgtcca atccttctca tcgaaccagg caaaaacta caagatggag atatgaccca   194400
gcattccatt gctaggaatt catcctagaa aatctcaccc agatacctag gagacacagg   194460
ccagaatgtc cctgcagctg gaagtgaaat taaggttgtt cgcaaataag tggagaatgc   194520
ctggcccagg gcagccctaa tcatttacca tagtcctgtt ggtctcagaa aggcttaata   194580
atttatttat ttttttttat tttttgtttt tattttttgt ttttgagatg gagtctcgtt   194640
ctgtcaccca ggctggagtg cggtggcgcc atctcggctc actgcaagct ccgcctccca   194700
ggttcactcc attctcctgc ctcagcctcc cgagtagctg ggactacagg tgcccgccat   194760
catacctggc taattttttg tattttttagt agagatgggg tttcaccgtg ttagccagga   194820
tggtcttgat ctcctgacct cgtgatccac ccgccttggc ctcccaaagt gctgggatta   194880
caggcgtgag ccaccacacc cagccagctt aataatttat aataactgaa tgttgtactg   194940
ttttctgcca ttatagaaaa ttatgttgtt ggagaaaaca aaatacatac aaacaagcaa   195000
accttcccta cataaatgac ccaagtagtt aaagaataaa accaatttct ttccattaaa   195060
aagaaaagaa agccgggtgt gatgcctcat gcctatagcc tcagctattc aggaggctga   195120
ggcagcagaa ttgcttgagc ccaggagttg aaaaccagcc caggcaacat agcaagaccc   195180
tgtctctaca aaaattaata ataattagcc aggtgtggtg gtgcacacct gtagccccag   195240
ctactcagaa ggctaaggtg ggaggattgc ttgagcccag cagtttgagg ctgcagtgag   195300
ctatgatcac accactgccc tccagcctgg acaagagagt gagacccccat ctctaagaaa   195360 taaaagtagg ccaggcacag tggctcacac ctataatccc agcactttga gaggcggagg   195420
caggtggatc acctgaagtc aggagttcaa gaccagcctg ccaacatgg cgaaaccccg   195480 tctatactaa aaaatacaa aaattagcca ggcgtcgtgg cacatgcctg taatcccagc   195540
tacttgggag gctgaggaag gagaatcact tgaactgggg aggcagaggt tgcagtaagc   195600
tgagattgca ccactgcact ccagcctggg tgacagaatg agactccgtc tcaaaaaaaa   195660
aaaaagaaaa attttaaaat gtcctgagca accttgtttg taatagttcc aagtctcaat   195720
atccgtgtat cccttgctg tagaacagat aaatattttg tggcatatct atataatgaa   195780
atactctgtg acaatcaaag tccaccaaca gcagccacat gcccaacaac aggaatgaat   195840
ctcacccatg taacatggca cagaaggagg caggagctag caacgtaagt ccatacagtt   195900
catgcaaagt tcaagtggac aaaattaaac tctctctctc tctctacata tatatatata   195960
tatatatata ttttttttt tttttttttt tttttttttt tttttgaga cagagtctca   196020 ctctattgcc caggctggag tgcagtggcg caatcttggc tcactacaac ctccacctcc   196080
cgggttcaag ccattctccc gcctcagcct cccaagtagc tgggattaga ggcatgcacc   196140 accaccccg gctaatttttg tatttttgt agagaccggg attcagcaat tgcccaggc   196200 tggtctcgaa atcctgatct caggtgatcc acctgccctg gcctcccaaa gtgctgggat   196260
tacaagcgtg agccaccacg ccccgcctta aactgtattt tttaaggatg atacttgaat   196320
acgttaaaaa ggcgaggacc ttgaaaacac aacgctcggg aaaagaaacc aaacacaaaa   196380
ggtcaagtat tgcataattc catttgtatg aaatgtccag agcaggcaaa tccatagaga   196440
```

```
cagaaagtag attagtggtt gctagggtct gggtgaggga gagtggggag taactgctca 196500
tggggacagg gcctcctttg ggggtgatga aaatgttttg gaacttgata gaggtgatag 196560
ttgcagaata ttgtgcatgt acctaaaggc actgaattgt gtaattcaaa gtgtgaattt 196620
tatgttatgt gaatttcacc tcagtttttt ttaaggtaag aaaatggtta ttacaaaatt 196680
caggatggta gttatatcac agtgtctctg gaaacttcca gggtatccac atgtcccttt 196740
ttattttatt ttattttta ttttatttga gatagggtct tgctctgttg cccaggctag 196800
agtgcagtgg caggatcatg accctctcct gtctcaaatt cctaggctca agctatcctc 196860
cctcctcagc ctcctaagta gctgggacta taggcacatg ccaccatgct tgactaattt 196920
tttttttttt tgtaaagtca gggtttccct gtgttaccca ggctggtctt gaactcctgg 196980
gctcaagtga tctgcccacc tcggcctccc aaagttccag aattacaggc atgagccact 197040
gccctagcct tctcctaatt gttgacatag gtagtagttg catgacattc actttgtaat 197100
tatgtgtttc aggaattctc aggcctgtgg gagctcttaa taaataaaaa agaggccagg 197160
tgtggtggct cacgcctgta atcccagcac tttgggaggc cgaggcaggc ggatcacgag 197220
gtcaggagtt cgagactagc ctggccaaca cagtgaaacc ccgtctctac taaaaataca 197280
aaaaattagc cgggcgtggt ggcgggtgcc tgtaatccca gttacttggg aggctgaggc 197340
aggagaatcg cttgaacctg ggaggcggag gttgcagtaa gctgagatcg cgccactgca 197400
caccagcctg ggtgataaga gcaagactcc atctcaaaat aaatgaataa ataaaaataa 197460
ataaataaat aagaggccgg gtgcagtggc tcaatgcttt ggaaagtgga ggccaacagt 197520
tggagagacc aaagcaggag gatggcttca gcccagaagt ttgaggccag cctgggcaat 197580
actagcgaga cactatctct ataaaaatgt tttaaaatta gccagatgtg gtggggcaca 197640
cctgtaatcc cagctactca agaggctgag gtgggaggat cacttaagcc caggaggaca 197700
gtgctgcagt gagctatgat tgcgccactg cactccagcc tgggtgacac agtgagaccc 197760
ggtctctata gataaatgaa tggatgaatg agggggtcaa ggatcctcac ccggcttcca 197820
tttggaggga ggagtttggt tgagttcttg caaggttggt acctaggaaa tgcttgccag 197880
ttctggagcc cagacactgt ccctggacat gagaccaggt tctctgccct aggttatcat 197940
tgggagcatc ttcgaggtca tctgggctgt cataaaacct ggcacatcct ttggaatcag 198000
cgtgttacga gccctcaggt tattgcgtat tttcaaagtc acaaagtaag tctttggggt 198060
tcctggacat ttgtacaggg ggtggggatg ggggacatgg tggggccgcc tccagaaagt 198120
tgggaaagtg agcctcgtgt ttcgagggct gactccgggg ccctgcctcc ccgcctggc 198180
ctgagtcctc gcctggcctc tgtcggcagg tactgggcat ctctcagaaa cctggtcgtc 198240
tctctcctca actccatgaa gtccatcatc agcctgttgt ttctccttt cctgttcatt 198300
gtcgtcttcg cccttttggg aatgcaactc ttcgcggcc agtaagtcct tcacaggaat 198360
tccaactcct ggttccctgg ggtcaggctc agggaacaca cagtcccctc caccgtgcag 198420
gctgccttcc tcgtagccca gacacccatt gcggtcaccc aaatgggcag ggccctgggt 198480
accactcagg gtttcctggg gacagagatg atggagacgt tcgtttcctt ggagatgaga 198540
tactgagcca cacgctcaga gcaccccggg tggggccaac gtgaaatgtc tgtgtcctcc 198600
ctgcaggttt aatttcgatg aagggactcc tcccaccaac ttcgatactt ttccagcagc 198660
aataatgacg gtgtttcagg tacagcctcc acctggcccc acgggccaac acctctcagt 198720
gtcacagatg aaagtgcctg ctccacatcc aaggggcttc cctgaactcc tccttctcta 198780
```

```
cctggcctttt tcacaccact ttgaaacaca gattttatgg ttatcattat tcaattatgg   198840
tgaggccaac agatcaggag atgaatgtca ttggaaagat agtttgtggc tgggcacggt   198900
ggctcacacc cataatccca gcactttggc caggtacggt ggctcacacc tgtaatccca   198960
acgctttggg aagcccaggt gggcggatca cttgagatca ggaattcgag accagcctgg   199020
ccaacatggt gaaaccccat ctctactaaa aatacaaaaa ttagccgggc gtggtagcac   199080
atgcctgtaa tcccagctac tcgggagatg aggcacaaga attgcttgaa cctgggaggc   199140
agaggttgca gtgagccaag atcgcgccac tgcactccag cctgggcaac agagtgagac   199200
tccatctcaa aaagaaaaa gaaaaaaaa accactttgg gaggtcaaga tgggaggact   199260
acttgaggcc aggagtttga gacaagtctg gcaacatag tgagactccg tctctgcaaa   199320
aaaataataa taataattag ctgggcatgg tgatacatac ctcctagcta ctagggcagc   199380
tgaagtggaa ggattgcttg agcccaggag gttgaggctg cagtaagcta caatcacacc   199440
actatactcc agcctgggcg agagagcaaa gccctgtctc aaaaacgaaa agaaagtttg   199500
ttatactcac agatcctcag agaaggagca caccatgcag gaccaagcag agaagcaaca   199560
gggtcaagca ggaagagaag gaaaatgtgg gcaagaggct tgattgtggt ttccatggga   199620
cggaatgggt gaggcagagt aaacagctcg agactggcta gttttggatca tttcagtggg   199680
ctctggggca gaggagctgt tcctacttgt ctaggacctg gccttggggt gattagggca   199740
ggtggatagt gctgggaaga taaaggaggt ggttgggata tgggctggtt gggatattgt   199800
ttggtttgct tttaaaaagc ctgctcaggg ctaaattgtt tactacctct agggactggc   199860
tagtgctgga ccgggcagtc cctccagagt cagcaagacc ccagatgcat cagaataaag   199920
aaaataaaat gcgtggccag gccaatgagg tggttcatgc ctgtaatctc agcactttgg   199980
gagaccaagg cggaggatt gcttgagccc aggagttcaa ggctgccgtg agctccagcc   200040
tgcaccacag agcaaggccc tgtctcttaa aaaaaggca gagaaaaaa atggctaata   200100
cacccatcaa atctgaagat accttggtct catattccag ggtgatcaac ccaaagcaac   200160
ttctgcaccc atgtgggcgc attccctgag gcttgggact ggcccagccg ggaccttcag   200220
agcatctttg gtggattctt tctctttgag ggactgagag tgtatagaaa atgtgacttc   200280
actctctcct tctcctgggg aggtagtttc taaatgagac cccaagacag ggagttgaag   200340
aggaaacctt ccatgaaggg aagttctgag cccccacata agcgattttt ttttttttt   200400
tgagatggag tctcgctctg ttgcccaggc tggagtgcga cggcacgttc ttggctcact   200460
acaacctctg cctcctgggt tcaagcgatt ctcctgcctc agcctcccga gtagctgaga   200520
ctacaggtgc atactaccat gcctggctaa ttttttgtatt tttagtagag acagggtttc   200580
actatgttgg ccaggctggt ctcgaactcc tggcctcgtg atctgcctgc ctcggcctcc   200640
caaagtgctg ggattacagg catgagccac cacacctggc ccataagcga ttattaatag   200700
cactgatcgc tagtcatgta tcttttagctc agaggttctc acccaaggac aagtctgtcc   200760
tccaaggaca tgtagcaatg tctgcaagca ttgttggttg tcacagctag ggagagggtg   200820
ctactggcat ctggtgggtg gagactagga atgctgctca atatcctaca atgcacagga   200880
cagccccaaa tagaataatc tggccccaaa tatcagcagt gctgaggctt agaaaccctg   200940
ttttagcaga ttcatgtttt tggagttctt taacatttac tttatcctca tggggatatg   201000
gatagaagga aggaagttgg atcttttta aaggagcatg taggtgctgt ttgaatatcc   201060
ccttggttct ttcagtatgc atcagcacaa cttgcgtctg tcaacaccta atcctttgcc   201120
ttggtctttc tctggtcccc tgctctgccc ccaaggaact gcagtccagc agtactgtga   201180
```

```
atttttttgtg ccacacctta aaaggagcag ccgttggtgg ataaataccc cagctccctc  201240
accctcaggt gggatgaccc ctagagctcc ccagcaagac caagcccggg ttacctacag  201300
tggaaactcg cttgatcaca tactgtttac gttccaccct cttttcccctt ttctcacttc  201360 tcctctcccc tactggtgct tcctgagatc acctcccaga caaaccactt gcacccgaac  201420
ccttgttcca gggtctgcct caggcagggg gaccccaaac gtgtccttgt gctacatttg  201480
tgctatccac gtagtagctt gtttaatcat caccatgacc acatgaggaa cacaggtaaa  201540
tattaaaatc ctgtcttagt ctgctcaggc agccataaca aaataccaca cactgggtgg  201600
cttatacagg aaacatttat tctctcatag ttctggaggc cgggaagtcc aagatcaaag  201660
tgttagcagg gttagttagt tcctggtgag ggccctcttc ctagcttgca gatagccacc  201720
ttcttgctgt gtcctcatat gtcaaagaga gagagagaga gttgtgatgt ttcttcctgt  201780
tctttttttt tttttttttt tgagacaaaa atctcaaaaa aaaatctatt ttttttttag  201840
gcaaatcaca ttttttttgtc acccagcctg gagtgcagtg gcacaatcat agctcactgc  201900
agcctcaaac tcctaggttc aaacgatcct cccacctcag cccccttgagt agctgggact  201960 acagatgggc accagctaat ttttttaaat tttttgtaaa gatggggtct tgctatattg  202020
cccaggctaa tcttgaactc ctgggctcaa gtgatcctcc caccttggcc tcccaaagtg  202080
ctgggattac aggcatgagc catggcatgc ggtctcttcc tgttcttata agggcactaa  202140
taccatcatg aagtccccca tgacctcatc taaccctagt tacctcttaa aggccccatc  202200
tccaaatacc atcccatcat aggttagggc ttcaactcat gaatttggag gcgggcacaa  202260
tttagtccat aacaaatccc cttaatcaca tcaagtaaga cagagttaca ggagggtctg  202320
tgactcctcc agggtcccat tttcctagaa gccaggctaa gagccccacg acgcaggaac  202380 ggcccttttct actcgcaaac aaagagaaaa gccaaggaga agccaacacg gagtctggct  202440
ctgcaaaccg ggcaggattg ttaaagacct cctgggctcg gggatggggt gggcggattc  202500
cggctccaca gctgcatctc caaggggccc gtggctgaga gggggggttgg ctgtgtgttt  202560 cttcctcccc tttcagatcc tgacgggcga agactggaac gaggtcatgt acgacgggat  202620
caagtctcag gggggcgtgc agggcggcat ggtgttctcc atctatttca ttgtactgac  202680
gctctttggg aactgtatcc ttcatggaga gagagaaggg gacaggcctg gacctctggc  202740
agaggagagg ttgcaggggc tcaagggagg gtactgagag acccagatac ccagggccca  202800
agtggtgtcc caccagtggt tgcttttcct gactcagaca tttgcagaca ccctcctgaa  202860
tgtgttcttg gccatcgctg tggacaatct ggccaacgcc caggagctca ccaaggtgga  202920
ggcggtggga gaatgtttct ctggcaaagt taccacctgc ccatggcaga tcaggacggg  202980
ggtgggggtg gggtgggggg tggggtggg gcatgggaa cagggttaga acttttgccg  203040
gggatgcacc atgcaaagag aaggcgcctc tcccccccact cccagaaaca gactgtccct  203100
catcaagcaa attctacagc caagagggtg ggaaggggga aggcagtgag gtcgctgcag  203160
gaaacggatg gcaaactcaa ccaaaaggcc gtttacaggg agtaagcagg gtttccaagg  203220
aatggtgtag cccccaggct agtggatggg agagggagtg ctgttatggg gacccagtca  203280
gagctggggc caaggaaaaa gggctgccac cagccctggg accttagaga acccagaacc  203340
atggcaaggc acagatggag tggccaataa atgtccccac cttctctctt cctctggctt  203400
cccgctggag cctcccctta gccaaacgca gcatgttaag agctagcctc cgtccagcct  203460
aagcctctcc ccaaggaccc tattaagtta agattacatg taacaggtac agggtcttcc  203520
```

```
tctcagccct ggggtctccc tcagcattgc agccccacct ccagtgcctc gaggtattca  203580
ggacatgttt gtgaaattga accaaaccaa gcagacgttg ccaacgctcc atctgccggc  203640
cctggcagga gggagagaga gtttcccggc cccagctccc agtggaggga agcggaagtc  203700
tctgccatcc caagcacacg gccacaagcc tggccactgt ggagctggct ggcatggctg  203760
agccgagggc tgatccagcc atgagctcat ccaagttcca agagtccatc cttagggget  203820
ggtgcaggag ggtagcagaa ggggaggag aaaggccagt tcgtttatct cctgggaggt  203880
gtggacattc ctctccagat ccacattctt tctttcattg atcctacaag catttcttgg  203940
tcatttaata cgtgttttta atcctattca gtcctcatgg aaaccttagg agccaagttc  204000
tctgagcccc attttacaga tttcatcatt cagtaagcac ttaatgagca cctactgtgt  204060
gaccaaggcc ctggtctagg acttagggat taagcagtga acaaaaaaag gcaaaaatcc  204120
ctgcctccgt ggagcaggga ttcaagaggg gagacagaca agaaacaaga taaatttgta  204180
aacatacgta gcttgtcagt tggtgataaa cacaacagag aaaaattcag tagggaaagt  204240
cagggagagt tggaattta gatgagatgt gtgtcgcaca gagaggttga gagacttgcc  204300
caaggccaca cagcagtaag ttgtggagct gggatttgaa cccaggccgt ctgggtctgc  204360
agcttgtgct cttaactgct gtgtaccagt tgcttgaatt tgggcatgtt ttatgctcac  204420
ttgggaacct gtgggaaatg cagattccag ggcccagcac tggttctata gattatttgg  204480
ggagcctgag gatctgcatt ttaggtgttt ctgaggcaga tggtccagag acctagctct  204540
gaaaaatgct gggaatggtg ccaggagggg tggggtggc cctatgagag cagggtggcc  204600
agccagatcc catctccatg ttgtctctga cagtgtcctg atctgaccat ttccaaggtg  204660
gtaaggttgc tccccgttcc agtgattcgg agcacagcgg gagagctgcc tgcaatggca  204720
tgactttct tatgggcggg ttcatttctg gccatttctt tctcgttgcc ttttctttgc  204780
tttttctttg ttggcttttc tgttttacga atgaggccct gcatgaaggc tgaagaagga  204840
tttaaagtcc aaaaacgtct ttttctgtat gtatttttaa aacctcttcc cccattctcc  204900
tcctctctga acctaaccac cagtgagcag cagcaccctg ggcagttggc tgtagcccaa  204960
gtgccctgct ctcctctccc caccgccttc ctgtcatggg ggctgggaat ataaattcct  205020
ctcctcattc tccttctggg ggctgttgac agtgcatggc aggggccatc ggatgccagg  205080
ctcttctgtg tgtgagggta gttggtgttt tttgaaagtt ggttcagaga gttcacatgg  205140
ctcagaaagc ctagtgagag gaaaatcttt gcactgcttt ccagctcatt aagacaggat  205200
gcaggggcca ggcatggtgg cacatgcctg gaatcccagc actttgggag ccgaaatgg  205260
gaggatcatt tgaggccaga agttcaagac cagcctgggc aacatagtga gaccctgtct  205320
ctacaaaaaa aaaaaaaaaa ttaaatgtat acaggcatag tggcatgcac ctgtagtccc  205380
agttgcttgg gaggctgagg tgggaggatt gcttgagccc aggagttcaa ggttacagtg  205440
agctatgatt gtgccactgc actccaggct gggcaaccaa gggagactct gtctctgaaa  205500
acaaacaaaa gaaaaaaaaa taggctgcag gaaagtcttc attgtaggaa gagaagggac  205560
atttttattt tttgttatct ggctgtgtgt taaaataggc ttcataatga gttagatgtc  205620
aaacttatac acagagggga tagcaataca cttaaccaat agcaggtacc cattccaatt  205680
ggggagcctt ggttctgatt ggtcgaaata tttcaaatgt tgcccctggt cagcaacagg  205740
gtcagaagtg agtcccccaag gcctagttca tgttttgtga acaaagattc cacgtgcctt  205800
ttaggacgag caagaggaag aagaagcagc gaaccagaaa cttgccctac agaaagccaa  205860
ggaggtggca gaagtgagtc ctctgtccgc ggccaacatg tctatagctg tgtaagtgcc  205920
```

```
cctaatccct gggatgctac cctggctcct gaacgtccac actatcccag gcacagattt  205980
gggaagcagt gggggtggtc cttgacagaa ctgagcttta ggaagagaca cttcttgtcc  206040
ttccacccac tttcactcaa taaatatttg gttagcagct gttatgtacc cagcactgtt  206100
ctaacttctg gggatacagc attaacaagg aggaaaaaaa aaatcccacc tgtgtgtagc  206160
cattctagca agggaaggag tcaataaatt agataaataa gtaaattata tattgtgtta  206220
gaaggcgatg gaactacaga gaaagtaggg gagggaaata gcaaatgctg ggagtgaaga  206280
gagttgtgat tttaaacgaa gttgtcaggg aaggcatcac ctagaatagg ggtccccagt  206340
cccggggctg tggactggta ccaggccgag gcctattagg aacggggctg cacagcagga  206400
ggtgaacagt gagcaagcaa gcattaccgc ctgagctcca cctgccgtca gatcagcagg  206460
cagcattaga ttctcatagg aacacaaaca ctattgtgaa cggtgcatct gagggatcta  206520
ggttgcgtgc tcctttttaag aatcgaatgc ctgatgatct caggtgaaac agtttcatcc  206580 caaaccacc ccccacacct aggtctgtgg aaaaactgtc ttccacaaaa ctggcccctg  206640
gtgccaaaaa ggttggggac tgctcaccta gaaggttaca tggcctgaag gaggtgaggg  206700
aggagccact gggggggcctg ggaagggca tcccaggcag agggaacagc ataggcaatg  206760
gccctgaggc aggaacatgc ctgatgtgaa ggaggcctgt gtgactagaa tcgaatagta  206820
agtgtgagga ggtgaaggca aggaggtgac aagcagatta cacagggcct tctgggtcag  206880
gggggaggac ttgggctttt gccctagcc aggtgggagc catggagggt tcttgagcag  206940
aggaggctgg gacctgactc agatgctcac agactcctag cattcagtgg ggagtagagg  207000
gtggagagca ggagtgggag gctgagatgt gggttggttc gcctgggtca tccatccaag  207060
ctacagtgcc tagcaatgct ctaagtcctg tgaccatgcc actgcaggaa agagcaacag  207120
aagaatcaaa agccagccaa gtccgtgtgg gagcagcgga ccagtgagat gcgaaagcag  207180
aacttgctgg ccagccggga ggccctgtat aacgaaatgg acccggacga cgcgctggaag  207240 gctgcctaca cgcggcacct gcggccagac atgaagacgc acttggaccg gccgctggtg  207300
gtggacccgc aggagaaccg caacaacaac accaacaaga gccgggcggc cgagcccacc  207360
gtggaccagc gcctcggcca gcagcgcgcc gaggacttcc tcaggaaaca ggcccgctac  207420
cacgatcggg cccgggaccc cagcggctcg gcgggcctgg acgcacggag gccctgggcg  207480
ggaagccagg aggccgagct gagccgggag ggacccacg gccgcgagtc ggaccaccac  207540
gcccgggagg gcagcctgga gcaacccggg ttctgggagg gcgaggccga gcgaggcaag  207600 gccgggacc cccaccggag gcacgtgcac cggcaggggg gcagcaggga gagccgcagc  207660
gggtccccgc gcacgggcgc ggacggggag catcgacgtc atcgcgcgca ccgcaggccc  207720
ggggaggagg gtccggagga caaggcgag cggagggcgc ggcaccgcga gggcagccgg  207780
ccggcccggg gcggcgaggg cgagggcgag ggccccgacg ggggcgagcg caggagaagg  207840
caccggcatg gcgctccagc cacgtacgag ggggacgcgc ggagggagga caaggagcgg  207900
aggcatcgga ggaggaagta agtggaggtg acctcgaatc cgcagaatga cggtaacatt  207960
aataatgaca acagccaaag tagcacgtgc tgtgtatttg tttataaaaa tatattataa  208020
aatgctgtat ttggccaggc gcagtggctc acgcctgtaa tcccagcact ttgggaggcc  208080
gaggcggatg gatcacgagg tcaggagttc aagaccagcc tggccaagat ggtgaaaccc  208140
cacctctaat aaaaatacaa aaattagccg ggcacggtgg caggcgcctg tagccccagc  208200
tactcaggag gctgaggcag gagaatcgcc tgaaaacagg gggcggaggt tgcaatgagc  208260
```

```
cgagatcaca ccaccgcact ccagcctggg cgacagagtg agactctgtc tcaaaaaaaa   208320
aaaaaaagtg ctgtatttgg ccaggagcag tggctcatgc ctgtaatccc agcactttga   208380
gaggccgagg cgggcggatc acttgaggtc aggagttgga gaacaggctg ccaacatag    208440 tgaaaccccg tctctactaa aaatacaaaa attagtggtg gtgccacct gtattcccac    208500 tactcaggag gctgaggcgg gagaatcagt tgaacctggg aggtggaggt aggttgcagt   208560
gagctgagat cgtgccatca cactccagcc tgggcaacag agcaagactc tgtctcaaaa   208620 aaaaaaaat gctgtatgtt tttgttttt tgacacaggg tctcgcctgt tgcccaggct     208680
ggagtgcagt ggcagtcata gctcagtgca gcctctacct cccgggctca agccatccgc   208740
ctcagcctca caagtagctg ggaccacaga catgtgccac atgcctggct aatttttgta   208800
gagacagtgt tttgtagaga cagggtttca ctgtgtttcc caggctggtc tcaaactcct   208860
gaactcaagc attccgcctg ccttagcctc cctaaagtgc tgggactaca gggttgagcc   208920
accacactca gcctaatttt tttacctta gtagaaatga ggcctggctc tgttgcccag    208980
gctggtcccc aactcctggc tcaagcaat catcccacct cagtctccca aagtgttcgg    209040
attagaggct tcacagatgg ggaaactgag agattgagtg agctcctcaa ggtcattcct   209100
ctaaccagtg tccttgaacc caggctctct ggcaccagag gccttgagca tttcaggaa    209160 actattaaga gaagccccac tgtcgtccag aattatatag tcttctgtgt tcttgctgtg   209220
tgacttttgc aaagtgactt catatctctg ggcctcacac aatggaaata gtgggatcta   209280
attgggtcat tgccaggatt gaatgaggta atgtatgcaa agggcctgga agagcagctg   209340
acacataata agtgctcggt aaatttagag cattttggc catttcagc caactctatt     209400 tacctaatgc tattctttgg aagtttgaaa agccactctg ttgggaggcc aaggtgggag   209460
gatcacttga taccaggagt tggagaccag tctgggcaat agaggcagac ccatctccta   209520 taaatataa aaaattaaac agatgtggtg gcatgcacct gcagtcccaa ctacttggga   209580
ggctgaggca ggagggtcac tggagcccag gatgtctagg ctatgatgag ctatgattgc   209640
accactgcac ttcagcctgg gcgacagagc aaggctttgt ctcaaaaaat aaaataaaaa   209700
ataaagaaaa agaaaaggca ctttgggccg ttagaattga agggagagca gagtttcaaa   209760
gctttggatg cagcgggatg tggtggctca tgcctgtagt cccagcactt tgggaggcca   209820
aggtgggagg atccacttga gccccggagt tcaagaccag cctgcgcaac atagtgagac   209880 ctcaccttt aaaataaat aaaatgtta gaaagctttt gaggcatctt ccaggccagc      209940
aacttatcca ttcagaacca gcatcctctt tttcataacg acattttgta atactttcta   210000
gcagatgcta tagtgattct gcatataggg actcaacaac ttacccatta aaatagacat   210060
cgtagacatt gtcctattac aaattaacct gctcttagtc ctcttttata ttaccatcag   210120
ggcataatat tgattttttt aatgatgggt ttaagtgatc ctgttgtatg acatatgagg   210180
taggccagca cttctcaaaa tctaatgtgt atgtgaatcc ccagggatct tgttaaaaca   210240
caaattgtaa ttccgtaggg ctaaggactc agtggagcct gagattctgc atttgcaacg   210300
agctcccaga tgaggctgat actactggtc cagggaccac attttgagta atgagactct   210360
ggaggacata gtgaagtaat tctgatatgt acaccataca caaatcacc atgaagtgac    210420 aggcacaaat gatggctaac tctgggttgt gtggacaatt caaccacat gagggagtt     210480 gccagcagtg tcaagatgtt ccacaatgtt gaacacctct tggcaaagtt ccatatacaa   210540
aagagtctag tctttcttcc atttatttaa tagttgcatt gcaggaaaat gcaatgtata   210600
ttaaaaacat acaaaaaata tgttgtgttc ttatgtaaaa gagttaggtt taaactaaaa   210660
```

```
gcacaggatc aggtgcagtg gctcccacct gtaatcccag tgcattggga ggctgaggaa    210720
ggagaatcgc ttgaggccag gagttcgaga ccaacctggg cgacataagg agacctcgat    210780
ctctacaaaa gaagtttttt aattagccag gtgtggcggc aggtgcctgt agttctagct    210840
acttggaagg ctgaagcagg aggattgctt gagcccagga gttcaagatt acagtgagct    210900
atgattatgc cattgcattc caacctgggc aacagaacaa gtccttgtct caaaaaaaaa    210960
aaaaagaaag aaagaaagaa aaacccaaa caaacaagca aactaaaagc acaggtaatt    211020
acaagcaaga ttttttcacct ctttgaggga cattagaaag tcatgaagag gaaagataa    211080 gtctttccca tatgggactg tcatgtacat ggtagggtat ttagtataac tgcctaccat    211140
tctctaagtg cctgcagtgc ccctcaatca ttatgttatt aggtttccac gtagttctac    211200
aacagttttc tgaaaaccat tgttctaggt cattctttcg cttcaatctt ctcctatggg    211260
tttatgcatt cattcagtta gtatttacta agtgcctact atattctaag ctcatgctgt    211320
gagttcagtc acacaactgc aagtgaagtg gtctgagaca ttctgagaaa tacgaccaag    211380
aaactgctcc cagggtctca gggcaggttt ccagaggagc aatctgagaa gggagtagag    211440
tgtttcagtc taacaacagc atgtgcaaag gccctgggt ggaccagaag gaggccagtt    211500
tgcaggacat gactagtgac gagaaagtga caaagaaatt gaaggtgcat tgatgagact    211560
ctggggctgt cagtcactca ggggaatgag agatcaaaac gggagtttag gtggaataaa    211620
gtgtttacca cagcactctc tgtatagtaa agaccaatga agagccaggt acaggccagt    211680
gtgatggttc acgcctgtaa tcccagcact tgggaggca gagacaggtg gatcacctga    211740 ggtcagggt tcagaaccag cttggccaac atggcaaaac cctgtctcta ctaaaaatac    211800
aaaaaattag ccaggcgtgg tggtggacgc ctataatccc agctactcag gaggctgagg    211860
cacaagaatt gtcctgcgag gcagaggtta cagtgagctg agatcacacc actgcactcc    211920
agcctgggca acagaacaag actctgtctc aaaaaaaaaa aaaaaaaaaa aaagccaggt    211980
acagtggtat gcacctgtaa tcccagctac tcaggaggct gaggcaaagg attgcttgag    212040
cccaggagtt cgagaccagc ctgagcattt agagaatggg aggccagtat actaaatacc    212100
ctaccatgta caagacagtc tcatatggaa aagaattatc ctttcctctt catgactttc    212160
tagtgctcct cacacaggtg aaaaatcttg cttataatta tctgtgcctt tagtttgttg    212220
gtttatttag ggttttgttt gttttttttt ttttttgag gcagggtctt gctctgttgc    212280
ccaggttgga ttgcagtagc attgctcatt ttagagatga gcaagacctc atgtctaaaa    212340 aaaaagaaa gaccaatgat tattaattac tcttgctatt attactaata ttactgttat    212400
tatcagcctt attaacagat ctactgttat tgaaggaggc agagtgacag ggacaaaatg    212460
tctctcccta acaatatgcc aggaagagtt tttgaaagac aacagtaaac attggaaact    212520
acaagagcag caaagcctgg ttgtgaaagg caaggacttt ggggcaggca gtcacattcc    212580
tgccctatca cttccaggct gtgtgacttt cagaatttca ctcctctctg ggcctccatt    212640
tcctcatcta taaaatgaag ataagaatag tagctacctc cttctctggg tataagattt    212700
aactgagccg ggcgcggtgg ctcatgcctg taatcccagc actttgggag gccgaggtga    212760
gcggatcaca aggtcatgag ttcaagacca tcctggctaa tatggtgaaa ccccatctct    212820
actaaaaata ccaaaaaaaa aaaaaattag ccgggcgtag tggtgcacg cctgtagtcc    212880 cagctactcg ggaggctgag gtaggagaat ggtgtaaaac ccgggaggcg gagcttgcag    212940
tgagccgaga tcgcaccact gcactccagc cggggagaca gagcgagact ccatctcaaa    213000
```

```
aaaaaaaaaa aaaaaaaaaa agatttaact gagttagtac gtgtaaaatg ctttgagtgg   213060
ttcctggctt ataccaagag ctcaataaat gttagcaatt ttttgtagca ttttggggtc   213120
tcactatgtt gcccaggctg gtgtcaaact cctggcctca agaaattctc ccactttggc   213180
ctcccaaagt gctggattta cagacatgag acaccatgcc tggccatgtt agctattatt   213240
aatatgaata ttattaagta ctcaatgaat gctatttta gcagtaatag taagcactca    213300
ggaagtgtca gctaatactg ttagtaatac tctcatcaat aaacataaaa agcaataagg   213360
acccagcttg cccaaatccc acagatggtt cctgctccct ctcttcttca gaggaagaaa   213420
ctatctcccc actttcaccc ccatagcctc agctggccag accccattc tgaaccaggg    213480 gagtactgct aattccatta ttaatagaca catcaaacaa tctggccggg agagacatta   213540
ttcatttggc tgataaagag gttctaaggc tctttggaaa taaagttca tgaagattca    213600 tgcactttaa gagaaaaaaa ttcaagatca gtcattcatc tgctttaaaa aaagtggcaa   213660
agataaaact ttatttgaga atataaaata ataaaaagac attttcgttc tctgttgtga   213720
caaagccagt ggccttcgga ggtctgcctt gtacattttt cctcttcttc agtcattcct   213780
tgaggctttt tgcaaacgta ccctgtgttt ttcattctcc agcatattga aattttttt    213840 tttttgagac atggtctcgc tttgtcatcc aggccccgga gtacagtggt acaatcatgg   213900
ctcactgcag ccttgacttc ctgagctcag gtgattctcc cacctcagcc tcccgagcag   213960
ctgggactac aggtgtgcat gaccatgcct agctaatctt ttgtattttt tgtagacaca   214020
gggttttgcc acattgccaa ggctggtctc caactcctgg gttcaagcga tcctcccacc   214080
tcagcctccc aaagtgctgg gattacagga gcgagctacc ttgccaggcc gatcatattt   214140
ttttcctttt tattcacttt gtcttctcct cattcctacc ttcatctgtc tttcagtggc   214200
tcactccagt gaaaagtgga ctgacgcaca ttctatttca tataattcaa tggctgctgg   214260
ccccagatcc cccataccag gtggccgagc ccagtggccc tgcagggtgg acaaaatgag   214320
ggtggaactt tccagactg tcagtaaaaa tctatgaggt acagagcttc tgcctctccc    214380
ttgcaaccag gcagtgcctt ctcccaggcc tatctgcttg caagggaac ttttgccaag    214440 acctgctcca ctctagaatt cttatctctg ctgttcgcat cctaattcca cctgcatctg   214500
tcaccatgac aacctgctcc ccaaaaggaa caggaagaga gatgctggac ttttgagctc   214560
cacagtttat cctgcatggg ggtagggagt ggttaattac ttagcactct aattcttacg   214620 gtaccccaa tgggcccaag ttggtttttt taaaaaaaaa cagtcttgct ctgttaccca    214680
ggctggagtg cagtggcaca atcatagctc actgtagcct caaactcctg gactcaaatg   214740
atcttcccac ctcagcctcc caagtaactg gaacaacagt ctcgtgcaac tacgcccagc   214800 taatttttt ttttttttt tttttttaga gatggggtct cactatgttc cccagactga    214860
tctcaaactc ctgggctcaa gcgatcttcc ttcctcagcc tcccaaagtg ctaggattac   214920
aggcgtaagc cactgtacca agctgcccca ttaaagcttt gaacaccaga gagcccagct   214980
cagctgtttt ccagctgggt aactctgggt aactttgcct ctctgaacct cagtctcctc   215040
ctgtgtgaaa tggggctgat cactataccc atctcggatg gtggtagttg cagggattaa   215100
atgagttaat acgtgaggtc cttaggacag ggggtgggga cacgagataa gcaataaaca   215160
ggaactgctg ttattatcac ccccacataa tccgatctca gggtctgagt gtgccccagg   215220
caaggtgtcc acagccctct gcagaaggat gcccaagtga tcagctggca caagaacgcc   215280
acgcacagca ggtgttatgc aactggccac ctattccagg cagaggatgc cagatcccca   215340
gggagaaggg ggtaggggtg cagcttcaaa gttttctgcc ccttttgagt tctccttgga   215400
```

```
gacactttgg aaatgaaacc tcccggaaat tgatattagg cctctgcagg ctgagcttgt 215460
taaaatttcc aacaaacag agccaacaga cgctctacaa ggaagcaaaa acaagacaaa 215520
acacattggc agacccttt ccatctgctc ttggtagatg gtattcctct aagaaaatgc 215580
cgccacgagt ttctccatgg cttcttgagc tggtggccaa aggatttagg ttctctttga 215640
aattataact taactgggcc tgctttatgg cagggatatc actctctgaa atgtgtatat 215700
atatgtgtat gtatatatat acacatatat acacatatac atacacaggg ccaggcgtgg 215760
tggctcacac ctgtaatccc agcactttgg gcggccaagg caggtggatc tcttgagccc 215820
caggagttca ataccagcct gaacaacata gtgagaccct gtctctacaa aaattaataa 215880
aaataaccag gcatggcagt gtgtgcctgc aatcccagct acccagggtg ggaagatcgc 215940
ttgagcccag gagttaaaag ttgcagtgag ctatggtcat accactgcac ttcagcctgg 216000
gcaacagagc aagaccctgt ctcttaaaaa tatattatta ttattataca cacacagaca 216060
cacacagaca cacacacaca ttacagatga tgagaaaata ctctcagcca ggttttcatg 216120
atacacaact tctcaaaaag catcacaagc aggttagaat tagggatttc tttgtggact 216180
gtccaagatg ttgaggaaat attggtttag aatttacctc atttaggcca gaaatggtgg 216240
ctcacgcctg taatcctaac actttgggag gccaaggcca atggatctct tgaagccagg 216300
agttttagcc tggccaacat ggcaaaatcc tgtctctact aaaactacag aaaaaaaaaa 216360
aaaaattagc cgggtgtggt ggcacaggcc tgtagtccca gctactctgg aggctgaggc 216420
aggagaatca cttgaacctg ggaggcagag gttgcagtga gccgagatcg tgcattacac 216480
ttcagcctgg gtgacagagc aagactccat ctcaaaaaat aagatagata agataaatat 216540
atataatata tatgttatat atataatata gaaactacag aacaagtgat ctttgtatgt 216600
ttccagaata taacagcggg acaggcatag gatagacgtt cccattgcaa aagggagaaa 216660
ttggaaggga taaagaggtc accagtccta agcaagtgct aaatccagca agacaaatcc 216720
cattaggttt caaggcctga gaataatcct cggtgactct cagctcatta acatacttag 216780
ttctcagagc cagactcaat gaggttacgg cccgcatgtt atgggtcagg aactgaggct 216840
aagtaactca ctggagatta tgtggtaaag aaggtccagg atcattgctt cagtctccag 216900
gatatgggga aggttctact cctgttatcc caaattttaa aatgtgggaa ctaaggctca 216960
gagaggttaa gcaaatcaca cagggttgca cagctagtga tgttgctgag atttccctgt 217020
gtgtagtggc tcatgcctat aatcccagca ttttgggagg ctgaggcaag agggtcgctt 217080
gatcccagga gtttgagacc agcctgggca atatagtgag acctcatctc tacaaaaaga 217140
aaaattaaaa agttagccag gcgtggtggc aggcacctga agtcccagct actgggaagg 217200
ctgaggtggg aggattgcct gagcctggga ggtggcgatt acagtgagct gagatcgcgc 217260
cactgcacta caacctgggc gacagagtga gaccctgtct caaaaaaaaa aaaaaaaaa 217320 gacattgccg agattcaaac ccaggtcagc ctgtcttctg aaatgtccct ctatgaccca 217380
ctcacaaaac tgagaaggca gaaagttgct tggacctgtc tatttcccct gtgcagtctc 217440
agagaaacag tggaactgcc tcggtttctc cttccgggaa gtattcatag aagcatccca 217500
cttacctact ttggtctgaa aataaattag cttgtctctc ttccacttac taaaaacacc 217560
gtgggttttt gcaagttaaa atgcaaaaat aaaatgagga gaatggtgct ggtagtttag 217620
ccagtgggaa gccctctggg gaaagccagc ctttttattta ttacttattt atttatttat 217680
tctttctaga tagatttatg ggaaaccagg gctgtgttgt ccagggggtct gtagtccaga 217740
```

```
aggcatcaga tgggctacta agtgagtctt tgtccacctg tagatggcaa gaggcagggc    217800
ccaggtgtcc atggcttgga gaggcagggg ttgatgggag gtttgaggct gtgggatctc    217860
tcctggggcc tcagtatcct catctggata atggggacat tctggccagg cacggtggct    217920
ctatatatcc agcacttagg gaggcctata atcccagcac tttgggaggc tgaggtgggt    217980
ggatcactgt aggccacgag ttcaagcagc ctgggcaaca tggcgaagcc ctgtctctac    218040
tgaaaataga aaaactagct gggtattgtg gtgcacgctg gtaatcccag ctattcggga    218100
ggctgaggca cgaggatcac ttgaatccac gaggcagagg ttgcagtgag ccaagatcct    218160
gccactgcac tccagcctgg gcaacagagt gaggctctgt ctcagttaaa aaaaaaaga    218220 aaaagaaaa agaaagaaag aaaagaaaa tgggggtatt catttatcat ttgacagtaa    218280
gtttacccag cattgactgt gtgagaggcc ctgtactagg cagtgaaaac tcagctaaga    218340
ataagaaagt taaaaacaag ctgggcattg tggtttacgc ctgtaatccc aacattttag    218400
gaggccgagg aggaagaatc acttgaggcc aggagtttga gaccaccctg gcaacatag    218460 tgagacgcca gtctctacaa aaaattgtaa aattagccag acatggtggc gtgagcctgt    218520
agcctcagct acctggaggc tgagatggga ggatcactgg agcccagaag ttcaaggctg    218580
cagtaagcta tgatcctgcc actgctctcc agcctgggca acagagtaag accctgtctg    218640
aaaaaaaaaa aaaaaagag gccaggtgca gtggctcaca cctgtaatct cagcactttg    218700
ggaggctgag gtgggtggat cacttgaggt caggaattcg agaccagcct ggccaaaatg    218760
gtgaaacccc atctctactg aaatacaaaa aattagccgg tcgtagtggt gggcacctgt    218820
aatcccagct actcaggagg ctgaggcaag agaatcgctt gaacctggga gccagaggtt    218880
gcagtgagcc gagatcacgc cactgtacga cagagcaaga aaaagaaag aagaaagaa    218940 aagaaataag atgatgggga gttgtggaaa cctgtccatg gcacgtgaa ggtcttgacc    219000 tctgaccaag aagtgaacag gctcctctca attccaggca ctgcagggat ctgggacatg    219060
acttctccat gaccaaactg tacccttttcc ttttcttttt tgttttttg gtgacagggt    219120 ctcactctgt cacccagact ggagtgcagt ggggcgatca cggctcactg cagcctcaac    219180
ctcccaggct caagcaatcc tcccacttcg gcctcccaag tagctagaac tacaggcaca    219240
cagcgccacg cccgtcaatt tacacatttt ttgtagaaat agggtctcac tatgttgccc    219300
aagctggtct tgaactcctg gccttaagca atcctcctgc ctccgcttcc caaagtgctg    219360
ggattacagg cgtgagccac tgcgcccagc ccaaattgta ctcttgaaag atggaatctt    219420
agctaggatc ctgaactgtt gcctttatc ctaaatcagt tgttggttct ttttcattca    219480
cttgccttcc tcagagagaa ccagggctcc ggggtccctg tgtcgggccc caacctgtca    219540
accacccggc caatccagca ggacctgggc cgccaagacc cacccctggc agaggatatt    219600
gacaacatga agaacaacaa gctggccacc gcggagtcgg ccgctcccca cggcagcctt    219660
ggccacgccg gcctgcccca gagcccagcc aagatgggaa acagcaccga ccccggcccc    219720
atgctggcca tccctgccat ggccaccaac ccccagaacg ccgccagccg ccggacgccc    219780
aacaacccgg ggaacccatc caatcccggc ccccccaaga ccccgagaa tagccttatc    219840 gtcaccaacc ccagcggcac ccagaccaat tcagctaaga ctgccaggaa acccgaccac    219900
accacagtgg acatcccccc agcctgccca cccccctca accacaccgt cgtacaaggt    219960
gagaccctct gctctcacat cactgggcag gggacctggc gtccctggag ccagaggctc    220020
tgctgagtga ccctgactg tgaccccatc tctctggcct cagtctcctc ccctggaaaa    220080
tgggcatagg cgtagttcc taccccacag ggctgtggag ggttcagtga gataatttgt    220140
```

```
gcacagtgcc tggcacgggg ttgtgttcag tcgggttagc aatatcttct acgtccttcc   220200
ttcccaaggg gagccaggaa gccacccat  ttgaggagca atagggtcct ctgatggaag   220260
cttgaggggg tcagatgatt gattctctcg gcccagcact gtccaaaaga aatgtaacac   220320
aggccacatg caaatgtcag tttaaactct ctagtcgcca cattaaaaaa ggggccagat   220380
gtactggctc atgcctgtaa tcccagtact tcaggaggcc gaggtagagt gagccaagat   220440
ggcacctctg tactgcagcc tgggtgacaa agcgagactg tctcaaaaaa aaaaaaaaaa   220500
aaaaaaatg  gtgaactgct gggtggatta tgtcttaagt tcatctagtg tcagttctat   220560
gtgagagatt ttcatgagtt tgctggataa aggctttcca tggtcctgag acctaagatc   220620
ctaaggtctt gtcactgtgc ccattttata gatgtaggga ctgaggctca gagaggctca   220680
gcctgcccgt gggcacataa gcaggctggg ctgcagaatg gaagctccag aggctgatgg   220740
ctcctccccc tgagtcaaga gagggtgct  aatgggggca tgccatgcag tttatgggag   220800
gtctcagtat ttctatctgt tcagtgggtc tcttggcact ctccctacct gcctgcaagt   220860
gagggtgtga aggtccaacg aggatagggg caggtctgtg ttaatatccc atgagggccc   220920
caccgcactc aaggctatag agtggttgag agcaggctct cggggccag  gccgcctggg   220980
ttccaaatgc cagctctgcc acttcctgct gtgtgacctt agacaagtca ctttacttct   221040
ctgtgcctca atttcctcat ctgtaaacag gagatcagaa tatatcaacc tcagggctat   221100
acaagggttc agtgatgtca taagatgcct ggtatataca gcaggcactt tagaaatgtc   221160
agccgcttct tgcctgccct gggagtacac aggagttccc agagacttgt gggaaattgt   221220
ggagggagcc ctgtgttggt tcttgtccca acagtgaaca aaaacgccaa cccagaccca   221280
ctgccaaaaa aagaggaaga gaagaaggag gaggaggaag acgaccgtgg ggaagacggc   221340
cctaagccaa tgcctcccta tagctccatg ttcatcctgt ccacgaccaa cccgtgagta   221400
tggcccccag caagggcagg gggggcctgg ggctcccacc agggtggcgg aagtcaggcc   221460
agatagaggg caatgagtga gtgttgacca ccatgagtcc agggatacct ttgaacaagt   221520
tgaaaatgga tgctccttcc gtaagtcagg taagatgatt tgtcacaata tactttgttg   221580
gaagagaccc ctgtcctgcc atccactaga aaatcattgt tatttatgac aataaataaa   221640
caaatttgtc ataaataaac aaataaattt gtcctaaaca acaaataaat ttgtcataaa   221700
taaacaaatc ttcactgtga tgtaagaggc acccccttag aaatggctgc cttgtgcagt   221760
acacagcctg aacaactgca cgtggcagcc ctaggacctg aactctgttt ctaacctaga   221820
ctctgtaagg gtttagattc tgggcggata gtgtctgagt tccatggcct tctgtcttgg   221880
gcatctttga aatggataga ctatttaggg gagaaattta tcccatgaat gtcgtagtgg   221940
ctcggaggtt gttttagaat tgaatgtctc ccagggatat ttcttgaaag cctgaccgct   222000
caaaatgctt cttgacaatg aaggatcatg tcagataaga tggggagaa  gctgctttct   222060
ataatctgcc tcttggcaac tcaccctggg tagtaataaa taaagtacc  tttaaagtac   222120
tttttatt   agttgactta tcgattttac taaggaaaca cttatgtggt atctactcag   222180
tgccaggcac tgttctgagt gccttaaaat ttttttaat  ttctctgagg ttgttactat   222240
gcttagctcc atttgacaga tgaaaaaact gaggtccaga gacgtgaatt cacctgccca   222300
aggtcacaca gcaagccagt gggagagctg gagtttgagc ccagacactg gctctagcct   222360
ccttgttctt aaccactcag ctctgctgcc attcacacaa ccttatgaac tatttattat   222420
tggctccact tattaagagg ttaactggca catcccattg gcacattcaa ggctctgata   222480
```

```
aggcctgcaa ttcataattt caataactaa cttttttggag cccctatcat gagccaggca 222540
taaattaagt cttgggtctc atgattttgt gaagtaagca ctagtattac ggctatttta 222600
cagatgaggg caccaaggca cagaggggac aagtaacttg cccaaggtca cacagctaat 222660 tttttaaaaag aaagaaagaa atctacttaa cccatagatt cacaatattg tttggccctg 222720
ggacatttaa tatcgaaaag cctttttatc tcctacagaa ttaaggaccg tatttcttca 222780
acctagcttg gggatcaaga tacttcaaga gggtcgtttg ggagtgatag gaactttgct 222840
aaacagggca tgtgaatgtc ttctctcacc gaggtcccct ctgccttctt ggggttccag 222900
gacccagaga gggcccccac ctggaggagt ttaatagttt gttgtgtagg aggccttggg 222960
ggttggagat ctcagtagtg gtaggtaaca tgagattatg gaagaaaagg gtttgtgagc 223020
ctgtggtctg agtggacctc tgcacgccca tctgtctcca acagccttcg ccgcctgtgc 223080
cattacatcc tgaacctgcg ctactttgag atgtgcatcc tcatggtcat tgccatgagc 223140
agcatcgccc tggccgccga ggaccctgtg cagcccaacg cacctcggaa caacgtgagt 223200
cccacagagc acacccttc ctagcctggc tgctctgcct caggccactt tctcctgcat 223260
ccaaaatgct cataggtagg gtgggatgtt ggggtcaccc ctaggcatag cccttatggc 223320
tgctggttga gaggggaagc tctgattcct tggggatgct cttgggagca agacattcct 223380
tgaggcagtt tctctgtgag cctggtgggg tggaggtggc ccagagtgac tggggctgaa 223440
aattgctgga ttctctaatg gaggcgtgag actagcagga tatggatgtt gcacattctc 223500
tacatggaat agggggggtta ctggggcagg ggcggtgctc agaggtggtc ccctccgcag 223560
tagacatttc cctttgtaca cgaagctttg aaagaaacaa ctatttggct cagaaacaca 223620
gcctaagctt ttggttttta tgaaagcaag cccctttgcg gatggtgggt ctgttgacaa 223680
cccctgttaa ttgagcactt gctgtgtccc aggaagaaac tcagcatgca gtatctcatt 223740
taatcctcac aatgcgcccc cccaacccc cgcccaggca tccccatttg acagatggga 223800
aaactgaggc tcagggggaat gagagagtgg taagtggcct gtccagggtc acacagcaga 223860
attccaactc tgcatccccc aaagctccca ctgcttcccc caactgtctg catttactaa 223920
tcacctactg tatgctacgg atgggtgtgc atagccccctt tgagtcctga caagcaggaa 223980
tgagtgcatg cttgtggttg agatggggaa accgaggcac caacaggcaa gggcgtgcct 224040
cagtcatggg ctgcgggcag aggcttgacc ccagggcctg gtagagggtg gactggtggc 224100 tcctgttttcc ctccccagct ccctccccca acccttccct cccaacccag agccaaaaaa 224160
gtgtgttttc tgctggtcca aggctctgct gccctggcta agtaggttag gacccaggca 224220
aagctggcga gccccatccc tcaagcccgc ccacagctta ccatgcactt tcccttcctt 224280
cccaggcctg gcaggccccc ctggggacct gatgggggag atggaaggaa ataattagaa 224340
cgcagctcct ggaggaagct agagccagtg ctcagcctcc tcacagtccg cttagttgct 224400
tcccgcagcc tggtttcccc caggggcctc caggagccag gcgtggggag gaggtgtccc 224460 tggagggggtc cacaaacccc ctgctgacgc gaggatgctg aagaaggcgt tgccttcggc 224520
agggagggca caggcatgga tgatccaggg ggcacggcag ctcccagggc tgaagggaat 224580
ctaggcagtg ctcagaccag gcccaggga ctgtttgcaa agagcgttca gctcccggc 224640 cccctccctc gtccatctcg cagtcgaaac ttctctacaa gaacactgtg gccccataac 224700
gttcacacca cgtaaccacc atccagggca agaaatagaa caaaaacgcc ccacgcggca 224760
tgtgcctcct cgatccccca cccccaccgc cttcttcccc tctagagctg ctgggacac 224820 tgtctggaga cattttttggt tgtcacgaca ggagggggga ggtgctcctg gcatctggtg 224880
```

```
ggtggaggcc agggatgttg ctcagcaccc gccgatgccc aggacagccc ccactctaga 224940
ggatgatcca gacccaaatg tccacagagc ccagcttgag aaaccctgcc ttaccggtaa 225000
ccacgacccc agcttctgga atgagcgttt ttggcttctc tcttttttccc acctgcacag 225060
gcttttttttt tttttttttt taagagacaa tgtctctctc tgtcgcccag gttggggtgc 225120
agtaacgtga tcatggctca ctgcagcctc aacgtcccgg gctcaagtga tcctcccacc 225180
tcagccccccc aggtagctag gaccacaggc atgcaccacc acacccagct aattttttaaa 225240
tgcttgtaga aacgggcctc gctatgttgc caggctggtc tcgaactctt gacctcaagc 225300
aatcctccct cctcagattc ccagagctct ggaattacag gcatgtaatt ccaattctta 225360
catgcctgta attggccaac actggccaat tcttaaaaac tgaatttatg tttgctcttc 225420
tgtaacattc aataaatgag acacttctat gcttcgcatt aaatgagtac atgttgcttt 225480
tgcaggattg atgggcattc tttttttttt tttttttttt gagatggagt cttgctctgt 225540
cacccaggct ggagtgcagt ggtgcaatct tggctcactg caacctccgc ctcccgggtt 225600
taagcgattc tcctgcctca gcctccagag tagctgggac tacaggcagg cgccaccaca 225660
cccggctaat ttttgtattt ttagtagaga cggggtttca cactatcagc cagactggtc 225720
tcaaactcct gacctcaagt gatccgcccg ccttggcctc ccaaagtgct gggattacag 225780
gcgtgagcca ccacgcccgg tcaatgagca ttctttatga tgctgttttg agatttactg 225840
tgtggcatgg gatgtgttat ccatccctg ttgacagatg tttgggttgt ttctaagtgt 225900
gaatactgtc cccatgccac gcccctcaac atgtttcctg agtcacctgg acagtaattt 225960
ctccaggagg ccagatgcag tggctcacgc ctataatccc agcacttcga gaggccaagg 226020
tgggagcaat gcttgaggcc aggagttcaa gaccagcttg gcaacatag tgagaccccc 226080
acctctacca aaaaaaaaaa aaatttttttt tttttttaatt aaccgagcgt ggtggtgcac 226140
acctgtggtc ccagccactt gggaggctga ggtgggagga tcacttgggt ctggaaggtc 226200
aaggctgtag tgatccatgt tcataccact gcactccaac ctgggtgaca gagcgagacc 226260
ctgtctcaat aaataagaat tcctccaggg tataaaccaa aagcgaagtt tctagagcat 226320
ataatttgca agtggttggc ctcagtaaat gcagcttgaa tgtttattgg acaataaaca 226380
cagtgacccct ttgggaggcc aaggcgggtg gatcacctga ggtcaggagt ttgagaccag 226440
cctggccaac atggtgaaac cccgtctcta ccaaaaatac aaaaattatc tgggcgtggt 226500
aacacacaac tgtaatccca gctactcggg aggctgaagc acaagaatca cttgaaccca 226560
ggaggtggag gttgcagtga gccaagatgg cgtcactgca ctctagcctt ggcgacagag 226620
cgagaccctg tctccaaaat atatataaat aaataaaaat aaacacagtg gccgggcac 226680
agtgggccgg gctcgcacct gtaatcccag cactttggga ggccaaggtg ggtagatcac 226740
gtgaggtcag gagttcgaga ccagactggc caatatggta aaacctggtc tctactaaaa 226800
atacaaaaat tagccgggcg tggtagcatg cgcctgtaat cccagacact ggaggctga 226860
ggcagaagaa ttgcttgaac ccgggaggca gaggttccag tgagccaaga ttgtgccact 226920
gcactccagc ctgggtgaca gagtgagaca ccatctcaaa aaaaaattaa aaataaatg 226980
aacgcagtgg cccttgcacc agtagctcat gggaactcct gttcttccac atccttgtca 227040
acacttggta ctgtcgactg tttcatttgg ccgatctgct gggtgtggag tgagatctta 227100
ttggggttgt gcttggcatt tccctgtaat gaatgagatc aagcacttttt ttggattaga 227160
ctgagccaca ggaaataaca ttttcaaata gatgaaaaag atctaagtat taggaatact 227220
```

```
tgaacctaat ttattggtct tttgatttcc tcttgcacag cttattaaga gctccagaat   227280
tagattcacc tgaccccac ggcctgccct ttcccagctc cctctcttcc ttctttcctt    227340
ccattcattc ctttagtaag tatttgataa gcaactacta tgtgccaggt actgagcgag   227400
ccagggagga ttgacagggt atgagatggt ccctgcactc ccagagccca caaaccacca   227460
ggcctttgac caggctgtgc ccactgcctc gtgcacctga atactctcc caccaccatc    227520 ccctctgccc acccaggtct ttcaagccaa tccccttgca ccagcccctc cctcaggaa    227580 gtcacctcac cctgacccca ggcactctgg tctctgattc ctcttcaagc accacatata   227640
acaggaatat aagttataac cacacagatc acagagccca gctcctccag acccagtac    227700 agccccaact gttgatgcat tcattcaaca aacatttctt gagcacctac tgtattcctg   227760
accctgtatt ataagctgga gacgccatgg tgacagacag acatccctgt ccttgtgggg   227820
ctgacatttg ggtggggag atggacaatg agattatcag taactacaac aaatgttcag    227880
ggagtgataa gtggccgggg gtgtggtggg cagaggaag gagagacttc gtaaaggaga    227940
tctcaagcac caggagatgg aatttaaaca gccggtcagg ggagtcctca ctgggaaagt   228000
gttatttgag ctaagtcata aaggaggaga aagacggaat caaatgggat gtgggggaaa   228060
gcattccaga gagacagaac agcctgtgca aaggccctga ggtggaagca tcttgggaa    228120 caaaaggaag tgagcaaggg agagaatgag aggaagtgag ggcagggagc tgaatggtca   228180
gatcgtgcag gggcttgagg gcctcgggga ggactttgac ttttatccct gaatgaggtg   228240
ggagccacgg aggattgtaa gcagggggaag gatgtgcctg acttctttgg tgttcacagc   228300
gccctctggt ggccatgttc agtaatgctc agcccttgca gcttctgggt ggatctgatt   228360
tttttttttt tttttttttt agacagtctc tgtctcccag gctggagtgc agtggcacga   228420
tctcggctca ctgcaacctc cgcctcccac gttcaagtga ctgtcacgcc ttggcctccc   228480
aagtagctgg aattacaggc acacgccacc atgcccagct aatttttta attttttagta   228540 gacacggggt tttgccattt ggttaggctg gtctcgaact cctgacctca agtgatctgc   228600
ctgcctcagc ctcccaaagt gctgggatta caggctcgag ccaccgtgcc cagccggtgt   228660
ccaccccatg tctagcacca gccagacact gtgccggcgc accctcatct tcaggcctgg   228720
gtgacaccag aggtgtgcta tggtgtgtcc tggacagggg ctgggccaga ggacattgct   228780
cgtccaggca gaaacatcag gcctggggag gggcacagga aaaatcaacc taccctggca   228840
ggggcctggc cttgaagcag gaagagatgc cgtggcagga agttggcccc agtgtttaaa   228900
aaaaccacgt agcaactatt tctcgcccag gatgccagg aaagcaaggg tactggggga    228960
ttagatccat caccaagaag gatacagtca gccctgaact tctctggggc cgcttctaat   229020
ccactacagg gcttggggca aattttaaaa ggtaccttc ccgtgggtta gcgaactggc    229080
ctagtacagt gatttttttg ttaggatttg ctgccatctg ctggacaatt tcattcacaa   229140
catacaaatc tgcagtatga aaagagatgg gaggggccct tgtgcagtgc acgccctgcg   229200
caactgtata tagcagctgt gtttcctctt ctgggtagaa actctgctcc ccagtaggcg   229260
atcgttagtt ttaccggggc tctgctggaa caggccagtg atccactgct ctcttgcttt   229320
tatcccttac aggtgctgcg atactttgac tacgttttta caggcgtctt tacctttgag   229380
atggtgatca aggtgagtgc agattataag tgagaacaca cggtaatttt ttttttttaag   229440 caagtgcagg gctgggcaca gtggatcatg cctgtaatcc cagcactttg ggaggctgag   229500
gcaggcagat cacttgagat caggaggttg aggccagcct ggccaacatg gtgaaacccc   229560
atctctacta aaaatacaaa aattagccgg gcatggtggc acatgtctgt aatcccagct   229620
```

```
actcgggagg ctgaggcagg agaatcactt gaaccctagg ctgcaatgag ccgatgtgga  229680
ggctgcagtg agccgagatc ttgccactgc attccagcct gggtgacaca gcgagactct  229740
gtcaaaaaaa aaaaaaaaaa aaagagctgg gattccagga gatcctgagc ctccaagaat  229800
gccccccttg agaggatgag tctcccagag gattagaaat gcctggtgtg tttgaagagc  229860
agcaaggaag ctggtgtggc tgggcggagt gagagaacag tggggaaacg aaggacagag  229920
agatgagtgg ggaggtgagg gggcaccttg tgccggggat cacagagagg gctcttcggc  229980
tcttactttg agtgaggtga gggccataga gtgttctgag cagaggaggg acttgatcca  230040
ggtgttcaca ggtgccctttt ggcatctgtg ggaagccaga ggacctgtga gcaggtgatc  230100
acactggtcc ccatgggcga tgacggggac aggatcaggc tggtgaccaa agaagaggtg  230160
agaagtggac agattcttgg aaggttctgg aaatagagcc agtgagtttt gctgatagag  230220
ccaccaatga gggatttggg acaaagaggc atcaaagagg atcccaaagt ttggatctaa  230280
gagccggcaa gccagagctg gcttccatca ggcaaagggg ggccgcctca tggggcaggg  230340 gctcccccact cctccctgga gtcctctggc cactgcccat ccctgcaaga tgaggtggcc  230400
tcattggctt ccctgcctct ccccgagagg ctagagagtg ggtggcagca ccccagggtg  230460
gggatcaggt gggggttctg agcaccctct cttctccccc acagatgatt gacctggggc  230520
tcgtcctgca tcagggtgcc tacttccgtg acctctggaa tattctcgac ttcatagtgg  230580
tcagtggggc cctggtagcc tttgccttca cgtaagtctc ctcgcaaggg ttcctcttgc  230640
ctcttttccc ccaaccccca gcctgggcca cacatcggat tacaggacat gttctcaggg  230700
tctagggatg gggtgtgtgg gctccgggga cgtgggagat atcagcatgc caccaggaag  230760
agcttcgatg gcttttttgca tgatgtccat ggaggaagaa ggagaaggga ccccccctcc  230820
tgccaacctt ctacctcctc acacagcaac gggcctcagc cacatcactg gccccttgct  230880
gtgcagcttc ctgtagacta gcctcgccgg aacatctcat ccccctacta ctccacaagc  230940
gccgcccaaa ccgctgtctc tttggaaagt ccctaaagag acaatcagga aacgaatgtg  231000
catgagaatt ctgaccccct ccctatgcct gaaggccccg tagttgtaga cctggtgact  231060
ccctttgtgt gtctttcact tctcctggca gtcctaggat tctctgccct ctgaaaggcc  231120
atgtgtcatc ctgcagctcc aagatggcgc cccagttgta ggcagccatt tcaggatggc  231180
acccaagctc ttagtagtca tcccaagatg gcatccaagt tctgggtggc cattccaaga  231240
tggcccctga gttctgagct atcattccaa gatggcctct gaatttgggg tggtcattct  231300
tagatggtcc ctgagttcca aggtgacctt caagttctgg gtagccattc caggatggtc  231360
cccaagctct gggtggctat tccaagatgg ccccaagttc taggcagcca ttgcaagatg  231420
gcccctgagt tccagggtgg ccccccaagtt ctgggcaacc attccaaggt ggcatccaag  231480
ttctgggtgg ctattccaag atggcctctg atttctgggc taccatgcta agatggcctc  231540
tggattcttg gtgccattc ttacatggtc cctgagttcc aaggtggcct tcaagttctg  231600
ggtagccatt ccaagacggt ccccaagtct tggatggcta ctcgaaggtg accccccaagt  231660 tctgggcagc catctcaagg tggcacccta gttctgggta accattccaa atggcaccc  231720 aagttctagg gcaaccattt caaaatggcc cccaagttct gggtgactat ttcaagatg  231780 tacccaacag gtgagtggcc attagcccctt agggccctga tagcagactt agcagtacat  231840
tcctgaagtt gtagacattt ggagcgggat gaaaaatatc taatcagtct ttaatcaaga  231900
aacaaatctt ggggaccctg gctgtgccca tcatggtgaa tgattccctg acaggttttg  231960
```

```
aaaggatctt gacacattca ctcccatcgt gagagaatca ggggcttcct cctgtgcctc 232020
tgcctctagg ctccctcctg agccaatctg gaggggccct tgaatggtct ccctcaccaa 232080
acaatgagga cttggtttgt caggagggcc aaaatagtgg cccatttcca gtagaagggc 232140
tgttaagtag gccacactta gattcttctc tgggaacaca atgaggtcaa gttgtgttag 232200
aacaaaaaat ctccagagtt tttggatgcc tcagagctgg agatgtatca tgaaggttgg 232260
gaggctgatt atacttcttt ctcttttctct ttcactcctt cctcctcttt ctcctctctt 232320
tttgttcgtt tactctttc tttttctctt ctcctctccc tccccacatc cttccctctc 232380
ctcaaagctt ttcagtgtct atttgactac tagagcaatg cacggtggct tacacctgca 232440
atcccagcac tttgggaggc tgagacaggc agattgcttg agcccaggag gccaagacca 232500
gcctgggtaa catagggaga ccccatctct aaaaaaaaaa aaaacaatt agccaggcat 232560 ggtagtatgc ctgcactagc agctacacgg gaggctgagg tgggagaatt gcttgagccc 232620
aggaggttca aggctgcagt gagccgaaat cgcaccactg cacccagtc tggggaacac 232680 aggaagaact tgtctcaaaa aaataaaaag tttaaaaaat taaaaatcaa tgaatttgct 232740
atttagaata ttatgcttta tatggttact gaataatttt aatagtgatg agtacaaaaa 232800
aaacaggttt agcaagctgt tctgtaggtt aaaaagtaaa taaataaata attaattaaa 232860
caaaatacaa tgcacatcaa attaggggac aaagattgtg acgaataaga caaggagtcc 232920
atgtctttaa aatatgaaaa gcagttacaa atcaataaga aacactactt ctcaatggat 232980
aaatgggcaa aggacataaa cagaaatctg atagaatgct ggcaactagt aaaaatggag 233040
gtaaatcaac ccttggaatt cagagaaatg taaaataaaa acgagataca attcattccc 233100
tatcaagtta gcactgttcc cgccgcaccc ccacacacac acaaaaaatg atttttttag 233160
ctaataaaca gcatatataa gaatgtatta taataggctg ggcacagtgg ctcacgcctg 233220
taaccctagc attttgggag gccaagggag ggggatcacc tgaggtcagc agttcgagac 233280
cagcctggcc gacatgacaa aaccctgtct ctactaaaaa atacaaaaat tagccaggca 233340
tggtggcgga tgcctgtaat cccagctact caggtgggta aggcaggaga attgcttgga 233400
cccaggagat ggagactgca gtgagccgag atcatgccac tgcactccag cctgggtgag 233460
aaagcaagat tttgtctcaa aaataaaaaa aggaatgtat tataataaaa tatacttttc 233520
tccccctcta tcacctattt aagcaggtcc ttcaagttgt caggtagaca tcatgctatg 233580
agaaaattta aatcctgaaa agccagaatg ttttaccacc ctcagcctgg aatgaatcct 233640
tctcctatgg aaataaccta cgggtttctc caccctctc tgcctttcag cccctttcct 233700
ccctctcccc tccttttctt tctccctctt tctcttcctc ctttccctc tcttccctct 233760 ctcttcttcc ctctctctgt ctctttctgt tcgtctttct ccttttaccc cctctcagtt 233820
tctatctttt tattttcctc tttctctctc tctctccctc tctttctctc tcactccctg 233880
cactgttgat gacctatgtc cttgggtgat gtgggcctcc cctggaccgt gtagcttgga 233940
gaaagctgac cctctgtcat cggtctggca acagggactt ggcccccta ccctgcattc 234000 tgatgaggaa tggtattcag acaaaggcag atcccaggac acaggaggac atgctcaggc 234060
agggaccccc gcccctttcc tctggggcaa ggtctgctca gcagcctcca agattcctag 234120
ggctcaagag gtggcaggta gctcagggca ctagggcagg cagtggggtg aatatgtcac 234180
tcatatccac ctgtccacac acaatgctta ccttggccac ctgtgcccag gggaatgggt 234240
tttatcctgt gaatcctccc agtgaccacc actgagtgtg gcacagataa atggtaccaa 234300
gcccaagctg ttcaggtctc caatgtcact ttcctctcag acctctgttg tagctgacat 234360
```

```
actgtaatgc tgaggagggc cgggcacagt ggctcatgcc tgtaatccta gctctttcgg   234420
aggccaaggc agatggatca cctggggtca ggagttcaag accagcctgg caacatggt   234480 gaaacccag  gcaacatggt aaaaccctgt ctctactaaa aatacaaata ttagccaagc   234540
gtgatagcag gcgcctgtaa tctcagctac tcgggaggct gaggcagaag aattgcttga   234600
acctgggaag tggaggttgc agtgagccaa gattgcacca ctgcactcca gcctgggcaa   234660
cagagcaaga ctctgtctca aaaaaaaaaa aaatgctga  ggaggtgact gtcccacctc   234720
catcctccga gttgaccatc acaatttagg gaggggaatg acctacaaag gacccagaag   234780
caagcctttc aattgttgag cttttgccat tatgggccat cgtttacaac atgctgtttc   234840
taggttctct ggaggtaaaa ttagcctcct cttttaaaca agctaatct  gcaaaagcga   234900 accaaaaatt cttttccacc agagatcaat tagcagaatg agctgggtgc gatggctcac   234960
acctgtaatc ccagcacttg ggaggccga  ggcaggtgga tcacttgagg tcagggtcc   235020 aagaccagca tggccaacat ggtgaaaccc catctctact aaaaatacaa aaactagctg   235080
ggtgtggtgg ggagggcctg tagtcccagc tactcgggag ggtgaggcag gagaattgct   235140
tgaacccagg aggtgaaggt tgcagtgagc caagattgtg ccactgcact ccagcctggg   235200
tgacggagca agactccatc tcaaaaaaaa aaaaaaaaaa aaaaacagc  agaatgattc   235260 ttttggggag ttgactttt  tttaatttc  tgagttttct ttttaaatat caagttatac   235320
aagggcattc aaattggcct acaactcaca ggaatttggc agcctgtttg cagagtcaag   235380
cttttacatt gttctcatga aattggtaca ggcataaagc cacccttcac tcttgaaaat   235440
ccattttgaa tgttgttgtt ttaattctta tgcaagaaaa ggatctggat agggatttca   235500
ggccatcctg tcaaccctgg caggcttgta gatcatgcag gaactgggag gtgtgagatt   235560
ttgccagtag gatcctggca agtgcctggg actctcccag ggttttggaa gagccgacgg   235620
acatgagtcc aacagggagc atctttatat catggccgaa gggatgagag aggagaccct   235680
caaacctcac gcctaccaca ccctccccac cccactgtca agagtccatc tggtactgct   235740
gttcctcccc cagggcaggg ctgcaggccc agcacagctg gccaggtgcc ttgatcaagc   235800
cattcctgca cacctaagag ccaaactgct agaaaaccag aataggagct actgcttttt   235860
tccctaaaaa gttttggaat cttctccccg ttacaggttt ctggcctctt ttgcctgaga   235920
aggtctctca ccctatgagg actttgctta ttgtctttcc ttgttatcgg atagttggca   235980
cattggaagg agcatggatg ctctgaggtt ctcagcctga gcgctgaact ctccacccgc   236040 ccccaccc   ccaccccagg gtcctctgct tatttccttt ctggtctttt aacttgcttt   236100
gtctgtcctc tgtgcatatc ccctcataga caaggctgag agccccacaa gtattagatt   236160
gaccttattg ttttaagaaa ttgtccctcc aggtctgttt gatttctctc tagatgtgca   236220
agtcctttag cctctctgtg cctcagtttt tcccatctag atgaggaaac tgcggcccag   236280
agggactgtg gagggaagta agtccgacaa gatcactgag gttgggttca gctgtcgat   236340 gctacccatc tcccagccct gaatacggag gctcacagtg agcagaatga tgctcagcag   236400
cctggccagc ctgggttctt tgaggcctgg cagggctgcg agatccaggg gaagggaata   236460
ggggaaggga gcataaggtt attccccttcc ttgttgaaag gaaccttgcc attctggcct   236520
gttggggtca aagcaaggat tcttccccca gtgctgtgat tgtggcctcg tctccgatat   236580
gggagaaaac tatccctgtg gtcccaccaa gggatgtatt gaagctcttc tgaagatgtc   236640
cacccctcct gcacctcacc caaatatctg tgtgtgtgtg tcctgctcaa ttcactgact   236700
```

-continued

```
gtgtcccttg tatccatgcg tctaccataa acaccccatt tcatgagcca tcacacgtgg   236760
tatcacgctc tgtgcccatg catcagggcg gccaactgac atttctcagc agctggcaga   236820
tcatgatcct gccctcaccg ccaagagtcc atctggcgcg gctgttcttc ccccaaaggc   236880
aggaccgcaa ctggcagagc gccttgatca agctgctcct gcatacccag gagccaaact   236940
gtcaggaagc caaagatgga gccctcaggc tgctatctct tgatcctcat cttcaaaaca   237000
gcccccaccc ctgaaggcat tattttttctt gtgtatgatg aaatggaaag aagattagag   237060
tgcgagatac ccacacctgg gtttgaatct tagtctgtct tcccagctgt gtgcctgccc   237120
ttgggcaggt cactcttttt ctctaggcct cagcttcctc atctggaaaa tggtcataat   237180
ggtgctgtct tcccataggc aaatgcagtg atgtccagaa gactcccata ttaaacctaa   237240
agtcagcaga ttaggcaaaa atcactgtca ttgaaaactc cctcaatcat ccgtaaagaa   237300
gctgggtgtg gtgtctctca cctgtagtcc cagctacttg ggaggctgag gtgggagaat   237360
cacttgagcc agggagttca aggctgcggt aagctatgat tgtgctactg cactccagcc   237420
tgggcgacag agcaagacca cgtctctaaa aatataaaat aaagccgggt gcggtggctt   237480
acgcctgtaa tcccagcact ttggaaggct gaggcagcct ggcaacagag tgagaatcca   237540
tcaaaaaaaa aaaaaaaaa aaaaaagta gaatctatat gattctacgt atgcaataat   237600
tcctagatac actgaatttg agaaccccaa gtcagactac aggaaaagga gatgaggggg   237660
tgtggaggag aatccacttg gaatatttgt agacatttaa accattctgt gttttaaaaa   237720
atatcacagc cgggcgcggt ggctcacacc tgtaatccta gcactttggg aggccaaggt   237780
gggcggatca cgaggtcaag agatgggac catcctggct aacacggtga aaccccatct   237840
ctactaaaaa tacaaaaaaa attagctggg cgtggtggtg ggcgcctgta gtcccagcac   237900
tcgggaggct gaggaaggag aatggcgtga acctgggagg cggagcttgc agtgagccga   237960
gatcttgcca ctgcactcca gcctgggcga cagagcgaga ctccgtttca aaaaaaaaa   238020 aaaaaatcac taacttccag aggggtcgtg gatggaaaat tccatagagt ccgcttggcg   238080
acagggtttc cgccattctg atggcggtca agtctttcta acctggatct ccagtcattg   238140
ttgaaggcgc ctaatgagcc ccaagcctga ttccaatgaa tcacgagagg accagctgct   238200
aggtgctgat agctttcccc aggcccgcat ttgctcagag ggcttcagag ttgcttctaa   238260
ttccatccca agtcagaact cttttgctgac cccctccttc ataaagagca aagccaaggc   238320
catagctttt gttaatcaaa catcagaatt ccacagacct gagttggttg gttgtttgtt   238380
ttaagagaca gagtcttgcc caggatgcag tggctcacac ttgtaatccc agcgctctgg   238440
gaggcctagg caggaggatc acttgagccc aggagtttga ccagcctg agcaacataa   238500 tgagaccccc gtctctacaa aaaatggaaa aatttgcctg tatttccagc tacttgggag   238560
gctaaggtgg gagaatcacc tgagccctgg aggttgaggc tacagtgagc caagatcccg   238620
ctactgcact gcagcctggg caacagaggg agaccctgcc tcaaaaaaaa aggagagaag   238680
gagagagaca gggtctccct atgttgtcca ggctggtctc gaacttctgg cctcaagcaa   238740
tcttcccaac tcgtcctccc aaggtgctgg gattatagct gtgagccacg gcacccagtc   238800
tgggcctgtt ttgcagatga ggataacgag aggcagagtc aggattcaaa cccaggtccc   238860
ctcaacttca aagctcacaa ccttttagac attctaaaac cttgcagctc cacaacgcct   238920
ggagaagagg ggtttctccg gctcttggca gtgactttcc gtggtgaatt cacctttggt   238980
aactgacagc tttgcagctg tcctgctacc tggaaatttg gctttcttag tgctttcttg   239040
ggcagtgcca ggtgcctgcc aagggcgggg gactgaatgg aggtgggggc ggcttccaga   239100
```

```
tggaaggatg gacatcggcc agcgccatga gcctgaggct cccccaactg ctgcccgggc   239160
gggactcggg ggtgctcagg ggtgcgtgtg tgtacgtgcg tgttctgtgt tcttttttct   239220
gaggccactt acgatctgtc tctccctccg atgccacatc accaggagca gtacacggta   239280
aagtctctct ctatctttct ctctctctct ctttctctct ctctctctct catattctgt   239340
ctctcgtgat ctgtcccctg gtgcagcctc gttagttctg ggcctgtttc tgtggccttg   239400
tgtccttgct gccgctgtcc tgtcgcttca aatgaccaga actcactccc tgcgaaggag   239460
gcatcccaaa gggtcttgcc aatgcctccg cccatgcccc accagttctt gcagagaaca   239520
gaaggggcag aggttcagtt tcaataggca agctgggtgg agcagttatc agaagcaatg   239580
aaagtgggcc agacacggtg gctcacgcct ctaatcccag cattttggga ggccgaggcg   239640
ggtagatcac ttgaggtcag gagtttcaga ccagcctggt caacatggtg aaacccccatc  239700 tctactaaaa atgcaaaaaa ttatctgggc ttggtggtgc acacctgtaa tcccagctac   239760
ataggaagct gaggcaggag aatcacttaa acctgggagg tggaggttgc agtgagctga   239820
gattgcacca ctgcactcca ccctgggtga cagagtgaga ctctgtctca aaaaaatata   239880
taaaataaat tgaacaataa aaaaataaaa tggccatgga atcgttttca gatgaggaga   239940
tgcagaatgc ccatggagac atgctcccaa ttgtcacttg tttgggacat caagatttta   240000
gccagttcca tgtgcaacct ggatgtacag ttccttgact ttttttctat caacatgtat   240060
tctaaagttc aatttcaaaa ggaaacttta gccaggtgca gtggtgcatg cctgcagtcc   240120
cagccatttg ggaggctgag actgaaggat cacttgagcc caggagttgg aggctgcggt   240180
gagctatgat cgtgccactg cactcccccc tgagattcca tctctttaat ttaaataaaa   240240
aaaaaggaaa ctatattatc cacttacaac cagcattgct aacctaagat aaatctgcaa   240300
ctgcaaaagt aaatgtaggc cagacatggt ggctcacacc tataatccca gcactttggg   240360
aggccgaggc aggtggatca cttgaggtcg ggagttcgag accagcctga ccaacatgga   240420 gaaacccccgt ctctactaaa aatacaaaat tagccggacg tgatggcaca tgcctgtaat   240480
cccagctact cggaggctg aggcaaaaga atttcttgaa cccgggaggc agagactgct   240540
gtgagctgag atcacgccat tcactccagc ctgggtaaca agagagaaat gccatctcaa   240600 aaaaaaaaa aaaagtaaa tctaacagaa accagacaat gttgttgcct tcaagctggg   240660
ctctttgtta aaaggaaaat tactaagtgt tagggaggtg ttaaaggcct attagcatct   240720
acctgaggct tcctttctcg caaaagcaga gcgtctgaaa gatacgtgga aaagaaactt   240780
aaagtataat aaaaaagaaa gaaagaaaaa gaaatgatta tgcccctctg agatccaatt   240840
atttaatctg tgcccctgtt ctgcctaaaa ttatctcagt gactgtccaa cgtgtgtctc   240900
acacttgggg gcacagcctt gagatgataa tgatgatgtt agttttaaaa agaaaaaaaa   240960
aggttcagag ttctgaatcc tggagtatat ctctgcctag caggctaaaa tacaattatc   241020
gtctttgttc cctgaaaaat gaaaaaaatg gagtcccttta aaaagcaaat ggtgtgaaga   241080
atgatgtttt tgcactggat actgagaccc atcgtgatgg gggtctctgg ggcagctctg   241140
ctcatgacct gggaggtcac tgtagggaga tgttttctag gtgacctccc cacccaaata   241200
ctccaaccgg aggcattcac gtgtcctgag accacacgcc aggcgcaggc taggggctag   241260
gacaagaatc aagattaaag gggaaatggc caggtgcggt ggctcatgcc tgtaatccca   241320
gcactttggg agtcaaggcc agtggattac ttgaggtcgg gagttcgaga ccagcctggc   241380
caacacggtg aaaccctgtc tctactgaaa atacaaaaat tagccaggtg tggtgactca   241440
```

```
tgcctgtagt cccagctatt cgggaggctg aggtgggaga atcacttgaa cccaggaggc   241500
agaggttgca gtaagccaag atcatgccac tgcactccag cctgggcaat agagcaagac   241560
tccatctcaa aaaaaaaaaa aaagattaaa gggaaaatga acacagagaa gagtagatta   241620
cactgtaagc cttttgaagag ttttctgtct aaaaccagag accgaagaaa caaacaaaga   241680
ttaactccga aatagcacat aggagctggc aggagccaga ggtaggcagt caggaaatgc   241740
tgtcggaggg agcaacaggt aatttgggct ttgaggaccg ggtagttctg tgactggaga   241800
agtggaggaa gggcatttct agcagcggga acagtatatg cataagcaga cagaggcaaa   241860
agaatgtggc tggggcttga gatatgtagc cataaatggg aatgcaaagg tgaaggtaag   241920
ttggactaga ttttcaagag cattgaatgc catgcccaga agtttgcact tgctcttctg   241980
agaattcacg tgctccagaa gaattctgag caagagaaag agtgacaagg tcattggctt   242040
tagccactgt gtgcataaaa catggaagaa aaggcaggga atgaggagca agttgggaga   242100
cgggtgaggg gggatggcac ccaggaatgg atggcgggat gttaaggaag gtgacccact   242160
ggggatgggg atgggatag agggcaggca gttgaccatg actctcaggt ttctggtgtg   242220
gacaactgga tgggtcatga gtgccatgaa ccacaagcta ttcatggtcc cactcaatac   242280
cctcctcttg gggggcctga gtcatggttg gccaaggtg tcatggcatc tctgggtct    242340
gcattgctaa gctcagttcc aacagacctt ggactgaact tctgtgcagt cctctctggc   242400
aaagatgggc tcagagaccc ttggagcaat gcagcagaga ccatggcagc agccacatca   242460
gcatctgaaa acagcggcac ccggttattt tccctccttc agactcaggg aatatggtgg   242520
gggaggggag atttggtata agggccactt taagtatctt ccagaatccc attggaaggg   242580
ggagaaaatc ccatttttt aagagcccac tgataccacc tttaaaaaga atacacaggg   242640
ggccaggcgc agtggctcac acctgtaatc ccaacacttt gggaggccaa ggtgggtgga   242700
tcacctgagg tcaggagttc aagaccagcc tggccaacat ggtgaagccc catctctact   242760
aaaaatacaa aagttagctg ggcatggtgg cacgcacctg tagtcccagc tacttggaga   242820
ggctgaggca agagaatcac ttgaacctgg gaggtggagg ttgcagtgag ccaagatcat   242880
accattgcac tccagcctgg gcaacaagag tgaaactcca tctcaaaaaa aaaaagaat   242940
acataggga ccactaaact cctagaccaa gggctttttt gaaaatagct gtgaccaggt   243000
gtagtggctc acacctgtaa tcccagcact ttgagagggt gaggagggca gattgcttga   243060
gctcaggagt ttgaaaccag cctgggcaac atggtgaaac ctcatctcta caaaaagaca   243120
aaacaattag ccaggcgcag tggcgtgtgc ctgtagtccc agctacttgg gaggctgagg   243180
tgggaggatg gctttagccc aggaggcgga ggttgcagtg agccgagatc gtgccactgc   243240
actccagcct tggtgacaga gccagaccct gtctcaaaaa agaaaaaaga aaagctgtgc   243300
agaaatgggg gtggggaatc agccaacccc cttgtgctgg gtctcaggga cacccaatac   243360
agctgctcag gcccagccag atggcaaagg gccctcaacc aaccctggga ccagaaccac   243420
aaaaagccac gtacttactg gctcccgagc ccaagcttaa caggtgaaat ggaccactct   243480
tcaccaggaa gggcagggct gtgccaagct caccccagac ttctaggcct gggagggtag   243540
ggtcccatgg agctgtgggc tgccccctac ccaacctgac ctctgcttcc tctcttccct   243600
tcttcccacc taaacattcc tccacagtgg caatagcaaa ggaaaagaca tcaacacgat   243660
taaatccctc cgagtcctcc gggtgctacg acctcttaaa accatcaagc ggctgccaaa   243720
gctcaaggtg agattgggag atggtggggt gcggtggggg ggactgtcag ggttatcatg   243780
tacagctgag caggttgtac actgctcaag gacaacacat taaggaggt gctgataaca    243840
```

```
tcctagccat cgtgtatgga tatttgtatt attacaactt cccagcagat ggcagtaaag 243900
tgagctgacc taaaataatc tgtgtattat ggcagttttt ctttagatga agtgtcttgg 243960
ggttaagatc cttttccta attcgcatga aggcatcata tggatttaaa agggtataac 244020
cgtgatctgg gaagcaggaa ctagatttct tgttccataa aattttgact tttcatctac 244080
ctattctagg ctctagtatc tcccattcca aaatagcatg aaccagcatt tcccaaaagc 244140
ctgtcattca aaaacatata tatatattaa gggaaataaa atccagtcat tagagcaccc 244200
actttcactc tatgcttcac ctgggggtcc ccagtattat ctcttatgta atatgtttct 244260
ttaaatcaag tcacacccgt aatccctgca ttttgaaaga ccaaggcagg agtgttgctt 244320
gagcccagga gaatgagacc agcctgggca acatagttag actctgtctc tactaaaaat 244380
taaagacaga aaacagatac tgttatggaa atctaaccaa atatggctgc ctgcctaagg 244440
ctttgtgcat tgacaactgc tctttcttgg ttaaagaggg aaaatgtcaa tggtaggtgt 244500
taacatggta gcaactaagt aaaaatttct ccttcactca aaaggattga gagagttgga 244560
aaggaagtaa ctttgttacc ttgttttttct gtgttgggct cctgtatcac ttaaaagcat 244620
ctctggtatc ccatctggga gttttagatc catagaatgc caggattgag tccaactcct 244680
ccaacgctta tttctgaaag ctgggggggac cttaccctag tgacttgact tatgaccttg 244740
cctgtaaaat gggaatgatc atggcagtat tttggtatga tgggccactg gaggcagaag 244800
gttgggcagg tccccagccc ctcatgctct ctgtcaactc caccccacag gctgtgtttg 244860
actgtgtggt gaactcactt aaaaacgtct tcaacatcct catcgtctac atgctattca 244920
tgttcatctt cgccgtggtg gctgtgcagc tcttcaaggg gaaattcttc cactgcactg 244980
acgagtccaa agagtttgag aaagattgtc ggtgggtctc cactttccag cacattccca 245040
ttggaaccag caggtgggca ggggggaagt ggctagaggc attggccact tgggctcaga 245100
gactggagaa gtgatgagcc ttggaagtga ctcagttgca accagcttgg atcttggta 245160 gaaagaaaac cggttttaga atttgagtca ccacccagag ccacagaatg agtcataagc 245220
aaattgattg accttttcagc caccgccttt gtcatgtgag ggatattaat acacatccac 245280
agttccttac ttgaaatcgt tacaggcaga tgtgtttcaa agttgagaat attttgagat 245340
tcccatgtgg gacatgacac cctcagctgg gtctaaggca gccctataat caaacacaat 245400
atttctgcca taaaatgtgt aactatttac atcaaatggg gtaaataaca agtataaaga 245460
gcttcatgtc caatcagatc aggtttcatt accaaataag ttaggtaaga ggccaggtgc 245520
agtggctcac acctgtaatt ccaacacttt gggaggctga ggtgggagga tcacttgagg 245580
ccaggagttg gagaccaggt tgggcaacat aatgagagcc catcctacaa aataaatttt 245640
aaaagttagc ggggcatggt agcacacacc tgtagtccca gctacccggg aggctgaggc 245700
gggaggattg tttaaacaca ggagttcaag gctgcaatgc actatgatgg taccactgca 245760
ctccagcctg cgtgacagag tgagaccctg cctctcaaaa atatatacat ataggccggg 245820
cgcagtggct catgcttata atctcagcac tttaggaggc cgaggcgggc ggatcatgag 245880
gtcaggagat cgagaccatc ctggctaaca cggtgaaacc ctgtctctac taaaaataca 245940
aaaacctagc tgggcatggt ggcagacgcc tgtagtccca gctactggg aggctgagac 246000 aggagaatgg cgtgaacccg ggaggcggag cttgcagtga gcccagattg gccactgta 246060 ctccagtctg ggcaacagag ccagactcca tctcaaacaa acaaacaaac aaacaacaac 246120
aacaaaaata tatatatata tatatgtata tatatatatg tacacgcaca cacacatatg 246180
```

```
tattatatgt gtgtgtgtat atatatgtat gtgtatatat agtgatattg ttaccagtgt   246240
aaagtggcat tttgcaacac atggtagcct gttgttatct tgatggctat ttattgaaat   246300
taggaggatg ccagatgtct ggataggagt ctggaactaa cccttgtttc ctgccttgaa   246360
aaggagtagc aacctccctt agcctgatga acctctaaat gtccctatg tctctctgcc    246420 tcctcctaaa ctccctccac cccacccca gcaagcctga ggctctcacc ctgaggacta    246480
gaagttatca cgttggaaga gggtgctgga ccctgggtca gctctcccac caggagtaag   246540
gttgtgccat cacccatgga tttatctcaa agtagatgca cacgtcatcc cctatgaagc   246600
acaggaacac atggtggcag gatggggagt cactgcttcc caagcagtct aggctggtgg   246660
accactcttc ctttccctcc ccctgtctct gataaccaaa gacaagtgca agacagcccc   246720
tctttcccat ttactaacag tccccactct ctgtggcaga ggcaaatacc tcctctacga   246780
gaagaatgag gtgaaggcgc gagaccggga gtggaagaag tatgaattcc attacgacaa   246840
tgtgctgtgg gctctgctga ccctcttcac cgtgtccacg ggagaaggct ggccacagta   246900
agtggcccga ctggaaatct atccaggagg agccctgggg agcaggagga taaagggcct   246960
gagagcttag caataagaaa ggtcttggag gccgggcatg gtggctcacg cctgtaatcc   247020 caacactta ggaggccaag gcagatgtat cacttgaggc caggagtttg agatcagcct    247080
ggccatcatg gcaaaactcc atttctacta aaatcccaa aaaaaaaaaa aaaaaaaaaa    247140 aaaaaaagc tgccaggcat ggtggctcac acctgtggtc ccggctactc aggaggctga    247200
gacacgagaa tcacttgaac ccaggaggca gaggttgcag tgagccgaga ttgcaccact   247260
gcacttcatc ctgagtgaca gagcaagact atggcctccc cgccttcaaa aaaaaaaaa    247320 agtgaggctg aatcatggac ttagtctta tttaaaattt tgagccactt gtggtggctc     247380
atacctgtta tcccagctac tcaggaggct gaggtgggag gatcgcttga gcccaagagt   247440
tcaaggctgc agtgagctgt gattatgcca ttgtactcca gcctagacaa cagaaggaga   247500
cccctatccc tgaaaaaaaa aagaagaag aaattgatat ttgttcatca tggacttttt    247560
gcattaattt tgattttta aaatattgga gcaaagatt atcttgatta ctgagatttt     247620
cagtaccccc ttaatttgca cccaaaacaa atgcctccct ccctcacctc gtccaagtaa   247680
tggtctttct ctcagaggtc ttggaaatgc caggctggaa gcttggtaga ttccagcatg   247740
tgccctcagc atcctcacct ccctcctct ctcagcaaat atgccaacct gaacatgccc    247800
tactacccac tctcagacac atccagtact cacacatgtg ggaataatgc taacccacaa   247860
ggcacctttg agcaaagttt ttttaaacac ctttctcaac agacttcatt tccatctgtc   247920
tgaaaatcat cgcaatagac ttaaatgatt ttgttcaaac aaggcactga aggaccacct   247980
gccaaaaaat tgtcatcatg aatacacaaa tctatcatgc ctatcatgtg aaggtatcgc   248040
ttagacacag agcctttgag cagtgtgcaa cctgcactac tgtacagagc tgctgtgcac   248100
ttacccactc tcatatatat ccccattgta cctcctgagc acccagcacc acctgtgctc   248160
aaatacccac tctacatgca tacacccacc tctactccct ccattgccac aacctgtctt   248220
taaatcccaa cttggccact tataagtggg tggtcttcag cacgtcccct taaattgctg   248280
aacctcaagt tcctcatgtg caaagtggag ccagtaataa cctccctggg agggttgctg   248340
agccggtggg gatgaattgt tgaatattgt ttccagcaca cagcaagccc ttcatgcaca   248400
gcagtagaaa tgactgacat tggccaggcg tggtggctca cacctgtaat ctcaacagtt   248460
tgggagaccg aggcaggtgg atcacctgag gtcaggagtt caagaccagc ctggccaaca   248520
tggtgaaacc ccgtctctac taaaaataca aaaaaattag ccaggcttgg tggcgcatgt   248580
```

```
ctgtaatccc agctacttgg gaggctgagg caggagaatc atttgaaccc gggaggcgga 248640
ggttgtagtg acccaagatc acgccgttgc actccagcct gggcaacgag agcgaaactc 248700
catctcaaaa aattaaaatt aaaattaaga ataactgac attgttgtca gcctttcaaa 248760
aaacagcgac tacttaaatt tcttttttcat ttccctctgt tcctgttctg ccatctcact 248820
tccaccctct ctccaccttc ctcatcaccc cttgggtccc tgtctctctc cttcctgccc 248880
cttccctctc cctgccccat tccttgcagg gtcctcaagc attcggtgga cgccaccttt 248940
gagaaccagg gccccagccc cgggtaccgc atggagatgt ccatttttcta cgtcgtctac 249000 tttgtggtgt tccccttctt ctttgtcaat atctttgtgg ccttgatcat catcaccttc 249060
caggagcaag gggacaagat gatggaggaa tacagcctgg agaaaaatga ggtgccactt 249120
ccaattccat ctgtccttta aaaactgggg acacacacaa actttaaaac acacacaaca 249180
cccaggaacc cctttctagg ggtacctggg ggagggaaca gaagcattgt cccaaccgaa 249240
tccagtcttc agggcagccc ttcatggagt ttccagagga aacacatcat atagtgtatg 249300
tatcagtcag tttagactag gttatgccgc agtaacaagc aaccccagat ttcattgcca 249360
aatatccaca aagggactta ttttttgctc acactgcatg tcaacatcag ttgtggatct 249420
tgccatcttt attctggttc ccaggctggc agagcagcag agcagcctcc ctctgagatg 249480
ctccagatga aaagagagt atgtcagact gaggttcagt tcttcaggct tgtgctcaaa 249540
aattacacat gtcacttctg ctcacatttc atcagccaaa gcaagtcaca catccattct 249600
gacatcagtg gagtgggcaa atacaatctc ccctagcgaa gggtggtgaa tatttatgaa 249660
tgaaaagcca agccaggtgt ggtggctcac acctgtaatc ccaacatttt gggaagctga 249720
ggcaggagga tcacttgagc tcaggagttt gagaccagcc tggccaacat agcaagaccc 249780
catctctact acaaatcaaa aaaattagcc aggcaggatg gtgcacacct ttagcccag 249840 taacatggga ggctgaggtg ggaggatgct tgagcttggg agttcgaggc tgcagtgagc 249900
tatcattatg ccactgcact acagcctggg caacagagca agaccctctc tcaaaaaaag 249960
aaaaggaaag aaaatccagt cccctgtcta ccagagagta tagacatgac tctttgcctc 250020
tctggcatca tccaagctaa atagaggacc tagaatatat cctctgctcc cttgacccctt 250080 aagacttaat aaccactatt cctccttctc tctccctcaa agagaaggag aagacgcagc 250140
aaagtattca gtaagaaaga atgggctggg cgcagtggct cacgcctgta atcttaacac 250200
tttaggaggc caaggcagga ggattgcttg agcccggaag ttcaagacca gcctgagcaa 250260
catagtgaga ccccatctct atgattaaaa aaaaaagtt ttaattagct gggtgtggtg 250320
gtgcacgcct gtagtcccag ctactcagga ggctgaagcg ggaggatcac ttgagtccag 250380
gaggtcaagg ctgcagtgag ctgtgattgc actgcactcc agcctgggtg acaaagcaag 250440
cccgtgtcaa agaaaaaaaa aaaaaagga aggagggagg gagggaggga aggaaggaaa 250500
tgagagagag aaagaaagga gggagggaag gaaggagata gggaagaagg aatgaagaag 250560
aaagaaaggg agcgaaggaa agaaggaaga agagaaag gaaggagaa aggggaaagg 250620 gtggaaggaa tgaagggaag gaaggaaaaa ggaaagtgaa ggagggaggg aggaaggaag 250680
gaaaggaggg agggaaggag ggagggaagg agggagggag gaaggagggg aggagagaa 250740 ggagggaggg agggaaggaa ggagggagga aggaaggaag gagggagggga gcgagggagg 250800 gaggaagggg aagaaggatt aggcttcaat ttgatttggc acactcggta gctgtgtcac 250860
ctcaggcaag tggtttaacc tttctaagcc tctattttgg tgatctgcaa agtgaggcca 250920
```

-continued

```
ttgatagtac ccacttccca tgtttgtatt agccatgcaa taatgggaa  atgtcagtgc  250980
aagtttggc  agttggtgac atctcaagca actgtagctg ttgggataag aaagcaatgg  251040
tgagaaggaa gagagagccc aggaatcctg gctggggca  agagaggcag agactcaagc  251100
agaagcactt gagaaccgcg acgagttaga cagagggtgc ccggtgtaca gccaccttcc  251160
tcctgcctct gccgctctca ccactggcct ctctcccgca gagggcctgc attgatttcg  251220
ccatcagcgc caagccgctg acccgacaca tgccgcagaa caagcagagc ttccagtacc  251280
gcatgtggca gttcgtggtg tctccgcctt tcgagtacac gatcatggcc atgatcgccc  251340
tcaacaccat cgtgcttatg atgaaggtaa gtgccccaca ccagccccca gcactactta  251400
acccccacct cgttcctgcc tctaccctga taaaatgaaa ccatctgcag tttcccagac  251460
agaccacact ctggatcacc tctgagattt tgttcctgct gttccctcta cctgacacac  251520
tgttcccacc actcccccgg ccagcttctt cttcccagct gtacctgcag acctcttcct  251580
ccagaaagcc ttccctgacc acccaagact gcttgaggtg cccatcttag caggcatcct  251640
atctttatgt cgcctgccac aaaaatctgc gtcaggttgc atgacagtgt cccccaccca  251700
tttatgatga cctcagccct gaattcctag aggccaacaa ggatctggct cagacggaac  251760
aagaagctct ctataaatgt ttgattaatg aaatgagggg gctgggcgcg gtggctcatg  251820
cctgtaatcc cagaactttg ggaggccgag gcgggcggat cacctgaggt cacgagttcg  251880
agaccagcct gaccaacacg gagaaaccgc atctctacta aaaatacaaa attagccagg  251940
cgtggtggtg cgcatctgta atcccagcta ctcgggaggc tgaggcagga gaattgcttg  252000
aacccgggag gcggaggttg ccatgagccg agatagcgca attgcactct agcctgggca  252060
acaagagcaa gactccatct caaaaaaaaa aagaaaagaa aaagaaagaa atgagggaga  252120
aggggtaggt gaggacccta aaatccccag ggctaaggag cggcttccaa aaaaaaactc  252180
tgaaaacctt tcaccctgtg ctttggactc caaagcgtgg attcaagccc agctcttcca  252240
tttaattcat ttaccttgt  acaagcaacc agtgactttc tggggactca gtttccctgt  252300
caataaaatg ggaatgataa taagagcaca tttgcccct  ccagaggagg tgagaggatt  252360
gaatgagaaa gttcatgcaa ggaccttagc tccttctcgg cacttcaaaa acgatcaata  252420
gtggccgggc aaggtggctc acacctgtaa tcccagcact ttgggaggtc gaggcaggcg  252480
gatcacttga ggccaggtgt tcgggaccaa ctggccaaca tggtgaaatc ccgtctctac  252540
taaaaataca aaaattagct gggcgtggtg gcgcatgcct ataataccag ctgcgtgaga  252600
ggctgaggca tgagaatcgc ttgaacccag ggggcggaag ttgcagtgag ctgagatcac  252660
accactgcac tccagcctgg gtaacagagt gagactccgt ctcaaaaaa  ataaggaagc  252720
cggggacggt ggctcacgcc tgtaatccca gcactttggg aggccgagga gggcgatcac  252780
aaggttagga gatcaagacc atcctggcta acacggtgaa acgctgtctc tactaaaaat  252840
acaaaaagtt agctgggcat ggtggtgggc acctgtagtc ccagctactt gggaggctga  252900
ggcagggaa  tggcatgaac ccaggaggtg gagcttgcag tgagccgaga tcgccccact  252960
gcactccagc ccgggtgaca gagtgagact cctcaaaaaa aaaaaaaaa  aaaagtata   253020
attcagccaa gcacaatggc gtatgcctat agtcccgact atcaggaggc taaggtagga  253080
ttgtgagttc aagcccagcc tgggcaaaat aggaagaccc cgtctaccaa aaaaaaaaaa  253140
aaaaggttgg gggaggtttt tgttttttg  gatgtgaaaa gaagagccta gtccggcgga  253200
gagcggggct ttcctgaact gtgcctccta ccagtgaggt tgctcagacc ttgcctgggg  253260
ctggagtgtt gcctggagaa cagccatgaa gctgcctccc cacttcccac ttcccacccc  253320
```

```
tgctcgctga cccctgctac tcctgcttct ttccctagt  tctatggggc ttctgttgct 253380
tatgaaaatg ccctgcgggt gttcaacatc gtcttcacct ccctcttctc tctggaatgt 253440
gtgctgaaag tcatggcttt tgggattctg gtaagtacca ccttggggct acagctatgg 253500
gcttgggaga agcccaaggg ggaacaatgg gtcctggatg atggtctccc aacgtggccc 253560
caagaacccc aacctcaagg gtggcttcag tatcctgcca gtggccacag atcctactta 253620
ggcattcttg tgtttgccaa ggagtcccag ggagacccaa cctgtgagtg ttaccatatg 253680
gctgcttatg tatccagttc ctcaaaatga tgggagtcat catggctggg agtctttagc 253740
atccatttta gagataagaa aactgaaatc aggctgggcg aggtgtctca tggctgtaat 253800
tccagcactt tgggaggcca aggtgggcgg atcacctgag gtcgggagtt cgagaccagc 253860
ctgaccaaca tggagaaact ctgtctctac taaaaataca aaattagccg ggtgtggtgg 253920
cgcatgcctg taatcccagc tactcgggag gctgaggcag gagaatcgct tgaacctggg 253980
aggcagaggt tgtggtgagc cgagatcaca tcactgcact ccagcctggg caacaagagt 254040
gaaactctgt ctcaaaaaaa agaaagaaag aagaaaact  gaaatcaggc tgagcacagt 254100
ggctcatgcc tgtaatccta gcacttcagg aggccaaggc aggaggatcg cttgaagcta 254160
ggagttctca accagcctgg gcagcaaagc aagcccctgt ccctacaaaa aaaaaaaaa  254220
ttttttttta attagccagg catggtaact cgtgcctgta gtgccagtta ctcaggaggc 254280
tgaggtggga agatattttg agcccaggag gtggaggttg cagtgagcta tgatcatgcc 254340
actgcacccc agcctgggca acagcaagac tccatcttta aaaacaaac  acagaggtca 254400
ggcacagtga ctcacacctg taatcccagc actttgggag gcagaggcag gcaaatcact 254460
tgagcctagg agttcgagac caccctggcc aacatggcaa acccccatct ctactaaaac 254520
tacaaaaaat tagcctggcg tgcttgtggg tgcccatgat cccagctact caggaggctg 254580
aggcaggaga atcgcttgaa cccacaaagt ggaggttaca gtgagctgag atcacaccac 254640
tgcactccag cctgagcaac agagcaagtc tcaaaaaaat aataataata aaataaata  254700
tgtctttatt tttcaccagc cactaactaa attttaacat ttccttccat cttaaaggga 254760
gataacaaac ccttagtatt agtattatca acccttaata ttatcaacat gacctgtgtc 254820
acttataaac atcagatatt ttcatactgc attataagag ctgcagatac cttaacattt 254880
aatttgcatt catcattgct ttaaaatgtt gcttgtgatt aaacctacag ctagaatttg 254940
ttactcagtg ttttttttgtt gttgttctgt tttgttttgt ttgagacagt ctcgctgttg 255000
cccaggctga agtgcagtgg cgcaatctcg gctcactgaa agctccaccc cctgggttca 255060
cgccattctc ctgcctcagc ctcccgagta gctgggacta caggtgcctg ccaccacacc 255120
tggctaattg tttgtatttt tagtagagat ggggtttcac catgttggcc aggatggtct 255180
tgatttcctg acctcatgat ccgcccgcct cggcctccca aagtgctggg attacaggcg 255240
ggagccaccg cacccggcct actcagtgtg ttaatggaga agtatattca ttgttagatc 255300
gccattttta aaactttttt tttttttttg agacacagtc ttgctctgtt gcccaagctg 255360
gagtaccgtg gcacaatctt ggctcactga aacctccacc tcctgggttc aagcgattct 255420
cccatctcag ccttctgagt agctgggact acagatgcac accagcatgc caggctaatt 255480
tttatatttt tagtagagac ggggtttcac catgttggcc aggctggtct cgaactcctg 255540
gcatcaagca atctgcctgc ttcagcctcc caaaatgctg gattacagg  catgagacac 255600
tgtgcctagc cttaaaaaat attttgatag ctattttatt acaaaaggta accttgaagc 255660
```

```
ccttgctatt ttgttatgca tttacaagcc tttatgcata aaataaaata gccagcacta   255720
ttctcacatg gccaaggttc atagcacaca cacaaaagta tagttggctg agtgcggtgg   255780
ctcacacctg taatcccaac actttgggag acagaggtgg gtggatcatg aggtcaagag   255840
atccagacca cccttgccaa catggtgaaa ccccatctct actaaaaagt acaaaaatta   255900
gctgggtgtg gtggcgcatg cctgtagtct cagctactcg ggaggctgag gcaggagaat   255960
catttgaacg tgggaggcgg aggttgcagt gagccgagat cttgccactg cactccagcc   256020
tgggtgacag agtgagactc catctcaata aataaataaa ttaaattaaa ttaaattaaa   256080
attatttttt aaaaaattgg gggctgagtg tgatggctca cacctgtaat cccggcagtt   256140
tgggagcttg aggagggcag atcccttgag gtcaggagtt caagaccagc ctggacaaca   256200
tggtgaaacc ccgtctctac taaaaataca aaaattagcc aggcatggtg gcgtgtgcct   256260
gtaatcccag ctactcgtga ggctgaggcc caagcatcgc ttgaacctgt gaggcggagg   256320
ttgcagtgag ccaagatggc accagtgcac tccagcctgg gtgacagagt gagactttgt   256380
ctcaaaaaaa aaaaaaaatt aaggtgaaga aggcttatac tagtgggctg ggacttgaag   256440
tgaagtgaat tcttgaaggt ccccagtgag tggccaaggt gggacttgaa ccaggacatc   256500
tgttctcttg accaccagct tagtccatcc ctttgaagag agtgacctac agtctgggtc   256560
tcagccaggg tctcaggaaa ccaggttccc accttggctc acggaggtgg ttaggggcat   256620
cagctttagc accagagttc agatcttgcc tcgtcctata taagctttgt cacctcccca   256680
tcattaaaag gagccatcct ccccctccac ctcagcagag ccctggtaaa cagcaaatgg   256740
actaacgtgc atctagaggg ttgaggatga agcctggcct ggcatgggca ctcaataaat   256800
gctaggggcc aggcacggtg gctgacacct gtaatcgcag cactttggga ggctgaggca   256860
ggtggatcgc ttgagcccag gagtctgaga ccaacctgga caacatagtg agattctgtc   256920
tctacaaaaa gtacaaaatt agcctggtgt ggtggcgtgc acctgcagtc ccatctactt   256980
aggaggctga ggtgagagga tggattcagc ccaggatgtc agggctgcag tgagtcgtga   257040
ttgagccgct gcacccccacc ctgggtgaca gagcaagacc ctgtatcaaa ataaataaat   257100
aaatgctagg aaagggatcc tactaatgga cctttttcct ccaaaacagt ggctttcatt   257160
tggtggagat gctacttatt agaagcactt gaggccaggt gtggtggctc atgcctgtag   257220
tcccagcact tgggacttc tgccaaggca gaagaattgc ttgaacccag cgtttcaga   257280
ccagcctggg caacatagca agacctcatc tctagaaaac attgaaaaat tagccagcat   257340
agtggcacat gactgttgtc ctaactactt aggcgaaggc aggaggatta cttgagctca   257400
ggagttcaag gctgcagtga gctgcgatca catcactgcc ctccagcctg agcaacaaca   257460
caagacccgg actctaaaaa tcaaaaaaga agcacttagg gaaatttctt aaaattaaat   257520
gataccctga gcaaaccct agatgttctg attcatttgg tttggtgagg tgggagggaa   257580
tcactgaatc tgtaatttat tattattttt ttttttttga gatggattct cactctgttg   257640
cccaggctgg agtgcagtgg tgcaatcttg gctcactgca acctctgctt cccgggttca   257700
agcaattgtc ctgcctcagc ctcccgacta gttgggatta caggcgccca ccatcacgcc   257760
cggctaattt ttgtattttt agcagagacg gggattcacc acgtcagcca ggttggtctc   257820
caactcctga cctcaggtga tccgcctgcc tcggcctccc aaagtgctgg gattataggc   257880
atgagccacc gtacctagcc tgcagttatt ttattctgag ttgatcttct gctggtgaag   257940
tgagtcttcc actggggcct ggagctgcat ctccctcacc ctgccaatcc tgcaagagcc   258000
agcactgagc ttccctctg ctttctcttt tttttttttt tttttttttt tgagatggga   258060
```

```
tcttactctg ttgcccagcc tgttcttgaa ctcgtggcct caagcagttc tccctccttg 258120
gcctcccaaa gtgctggaat tataggcatg agccaccacg cctggtctcc cctttcagtt 258180
ttaaatgaag ccacaagttc cctgtataac atttgggaga tagaggggag ctctctagcc 258240 tagggggttga ggtctgtgac caaacgccta taaagttgtc tttgtttgga ctcccccaga 258300
agcagagcct gagacaagga ttgagtgcaa ggaatttatc tgggatgcag ggcagtaagg 258360
gagagaggaa gtgacacagg gacagaaagg caaccaggaa agagtgtatt attaagccag 258420
ttcctgctgt gaacaaatgg ggctcagttt cagtggatac ctccaggagg caacagagag 258480
cacataccac agagtcatcc cacctcacag ggagggaatt ggagtattta tcctccagtg 258540
cccatcagac ataatcacag gccactccca ggggagctat taattcccta acacttgtgc 258600
agccacagag agaccctggg caaagtagtg tacctcaggt gtgtagttga gctatgggca 258660
gggccccagc aacacctgcc aaaatgccaa aagtgccagt gggacctgaa ttcctttttta 258720 tttatttatt tatttatttta ttttattttta ttttatttatt tttgacggag tctcgctctg 258780
tggcccaggc tggagtgcag tggtgcaatc tctgctcact gcaagctctg cctcccaggt 258840
tcacgccatt ctcctgcctc agcctccgga gtagctggga ctacaggcgc gcaccaccac 258900
gcctgcctga tttttgtgtg cgtgtatttt tagtagagat ggggattcac catgttatcc 258960
aggatggtct tgatctcctg acctcgtgat ccgcccacat cggcctccca aagtgctggg 259020
attgcaggcg tgagccaccg cgcccggccc cctgaattcc ttttttaggc agttgtgaaa 259080
caacaacatc ccatctgttg ggcacctact gtatattcca tgctcagcga cgcacattca 259140
ttgtctgatt gctgtgttac cactgccttc cagagaaggg cgcagaggcc ccaggcactt 259200
cgcctaggag ggaagcacag ctctaaggtc aggctccttc tctgtaaggt agaggggcta 259260
cttcagggtc acactgaccg ccccaacccc tgacctggcc tctgcttctg cgaagatgct 259320
gagaaggccc tgtgttttgt gttttgggtc ccactgaccc cagaggggag ggccatctct 259380
ttgacccaga ctcttggatc caaactgggg tgccacccat caccatgtca gtacccggtt 259440
gaggggagtc agagatagca ggagaccttg tgggacttga ggctgtgact gttctccaaa 259500
caatgtggag tatttccata ttttaacaaa agagaggcca ggcgtggtgg ctcacgcctg 259560
taatcccagc actttgggag gccgaggcgg atggatcaca acgtcaggag atcaagatca 259620
tcctggctaa catggtgaaa ccccgtctct actaaaaaat acaaaaaatt agccaggcgt 259680
ggtggtgggc gcctgtagtc ccagctactc aggagactga agcaggagaa tggtgtgaac 259740
ccgggaggca gagcttgtag tgagccgaga acgtgccact gcactccagc ctgggcgaca 259800
gagtgagact ctgtctcaaa aaaaaaaac aaacagagag ttatgcttg tgtttcccct 259860 tgagccagca cccagcccag gaatgcagca gtcaggatag atcaagtgaa gctgcagtaa 259920
caaacagccc ccacatctca gtgacttaaa ttgatgggaa gggttttttta cattcagcag 259980 ggaagctgtt tgcctcatag ttacccaggg acccaggctc acagagtagc tgccattcaa 260040
aatgttactg gtcgccaagc ccagggttga gaggctagag agtccaacac tgaccagaaa 260100
gtgaccacac tgcttccaca cacagcacat cactgcacct agacacacat ggccccatct 260160
aaacacaagg ggaccaggaa gtgcgtgtgc ctgaaaggcc ccaaagcccc gtccagtgcc 260220
tgttctgcac cctgttactg tccgcctcca gatcaggaaa tggaggccca gagaggttaa 260280
gccacttgcc catagccaca cagctgtggt agcagagctg ggatttgaac ccagagtctc 260340
cttcttttgc gagtatgctg ccaacctagt ggggacctga acacagactg tgggctctct 260400
```

-continued

```
gaggcctggg ttcaaatcct ggctttacat ctctgtgctg ctagcctcag gcagatgagt   260460
ggcttggtta cctcctagaa aatgggtata cctgggagtg gtggctcacg cctataatcc   260520
caacactttg gaaggccaaa gtgagcagat cacttgaggt cagaagttcg agaccagcct   260580
gaccaacatg gtgaaacccc gtctctacta aaaatacaaa aattagctgg gtgtggtggc   260640
atgcacctgt ggtcctacct acttgggagg ctgaggcagg agaatcgctt gaacccagga   260700
ggcagaggtt acagtgagcc gagatcgtgc cactgcactc cagcctggat gactgagcga   260760
gactccatct caaaaaaaaa aaaaaaaaag agaaagaaag aaaaagaaaa tgggtgataa   260820
cccttccctc caggatcttc atgaggagct cagtgatgtc atttataaag cccctggggt   260880
ctcgggagcc ctcaaaaatg ctggagagac aggccacagc tctgaagagc agccccagcc   260940
ctgtggagct gaagcagggt ctggaggccc cctctgggc caggccaatc atgggaaggc   261000
ccccaggagt tcccagggag ggagactcag cacagatgat gtcgaacagc ctttaccgca   261060
gcccttcgaa caaccataac tgtcccgggc actccgctga tgggcaactg tgcctctaac   261120
atgcacccgg ccagcctagg gggccgggaa ccaagccctc tgttggcatc tctgtcttgt   261180
gggtccccat tctagaatta tttccgcgat gcctggaaca tcttcgactt tgtgactgtt   261240
ctgggcagca tcaccgatat cctcgtgact gagtttgggg taagtctccc tccagcttct   261300
ctctgggtga ctctgggctg gacgaggcag gcggcagggg gcggggagc ggtcccagag   261360
gcagtgtgtc ccggaagcca tagctgcttg agccagcact tggccatgac cagagaggga   261420
gaactggggc cccggggaca agggcagccc ctcaggaggg cattgtgggg agatgggggt   261480
aaccaaagct tggctgtagg gccagcactg aggggtgggc tttcctgcat cctggcctag   261540
gaattaataa tgcagatgag tacactgagg gaactgagac actcaaaagc tctgaaagct   261600
gagccggctc ccaaacacca ccctatgtca ggagcccaga aagaatgggt ttcaagtcaa   261660
ttctgtttga accaaccctc tcctagttag tgggcaggag agagccacag ccctcaggcc   261720
agtgtgggga caccactccc agggccatag aggggtcccc agggtgtctt ccctcctcta   261780
gccccgggcc tgggagactc tcaacatggg agtctctgga cctctctgtg gtggcccac   261840
aggccacatt gcccttctcc ttttctggaa gactcagggc cccagaggtc ctgtcctaga   261900
ccctctcctt ggccatctgc caatgagccc aggcttgggg tccctcagga gattggggg   261960
agggtagaag atccttgcag ggggaagcaa tggtcaaaaa agggtgtcaa agccaagggt   262020
caagggtgat accaatgtca tcttactaac aataaaaata acaatagctc acgagaatcg   262080
cagccttgct gtgtgccagg gaactgtgcc aagtggttta cgtggattgg ctcagggtag   262140
aggtcttggt ctcagctcgt aagagaattc cctcggaggg ttcaactgaa ggcacccaaa   262200
tgcagacctc actggtggag gggaaggaa gggtacccac aagggtgca aggtgtccag    262260
cgaccaccca ccgtggggag ctgtcacctg cccaggtgct gaagtgggga gggaacctga   262320
gccgaggcc aggagaagcc accaagtggg agctgtcctg tcaatgtgga gagacagaga   262380
ccagggccca agcaggcaga gagcaatagg ggagaaacac cccaacccttt ctctcccctc   262440
atcccttatc tcctgccaga gcctcccatg gcccaaagta aaccggaagc aagctgaata   262500
tgatgctcag agcaggcagg gaagtcagga gaatagatct gggtgtggtc gggcctgagg   262560
aagagggtgt tgcctcattt cacagatggg aaaactgacc tcagctgggc acggtggctc   262620
atgcctgtaa tcccagcact ttgggaggcc gaagccggcg gatcacctga ggccaggagt   262680
tcaagaccag cctggccaac atggtgaaac cccatctcta ctgacaatac aaaaaaatta   262740
gccaggtgtg gtggtgcatg cctgtaatcc cagctactcg ggaggctgag gcaggaaaat   262800
```

```
tgcttgaacc cggaaggcgg aggttgcagt gagcgacggt cataccattg cactccagcc    262860
tgggtgacaa gagcgaaaac tccatctcaa aaaaaaaaag aaagaaagaa aactgatctt    262920
caatgcctgg ggaagtgaga gacactccca aggtcacaaa gccaggcctg ggtgactcct    262980
gagagtacac tgacagctcc tggggtgtcc cagtcagatc cccctacaga aaaggatctg    263040
tttgcctgct cttccgtcct agaaggccag gaggggctgg ggaactacac aaaagagggg    263100
gccattcttt gatatgtcct acggcacccg cacccaagtg atacacactt atttgccttc    263160
agctccagtg agccagaatt ttccccttcc cctcacccta tccctgaaac cttcctctag    263220
agggttcttg cccacatggg ggctctctcc actggggtgc ccccacctgg tcattctccc    263280
ctgtcctgag tttctagaga gggctggagc tccagctggc aatcaaaata tcttgccatc    263340
cggctacata caagacagcc ttgaaccaat gtcccttt gg gtcaagaggt tagaaggatg    263400
gtccagctcc ccagaagggc aggtggggtg gaggaagtta gctgaaacct tcaatcacca    263460
gtaagagagc tgtagggaca gactccaaca gcctgttctc ctggctggca ggaagatggg    263520
gcatggggtg ttcatgggac atcaggaccc ttgcagtagc caaacagccc ccagccctcc    263580
ctaccagctg tttgatcttg acaacttgc gctatctctt ctcatgtaga gtggggctaa    263640
ccattgcaac caacctcaga cacttgcaag actcacagtg atgcatgcac tcaaaagaca    263700
ttcattgagc acctactgtg tgcctggtgt gattataagt gctggagaca gaacgagaag    263760
gaggggtgcc aaacaaaaca gaccaagaat acagagtgtc tgctcccata gagctgacat    263820
tctaaggaga gagacgggaa cttttttacaa gtaaaagcat caacaggccg ggcatggtgg    263880
ctcacgcctg taatctcagc actttgggag accaaggcag gtggatcact tgaggtcagg    263940
agttcgagac cagcctggcc aacatggtga aactctgtcc ctactaaaaa tacaaaaatt    264000
agccgggcac ggtggcaggt gcctgtaatc ccagctactc aggaggctga ggcaagagaa    264060
tcacttgatt tcaggaggc gagaggttgt agtaagccaa gattgtgcca ctgccctcca    264120
gcctgggcga cagagtgaaa ctctgtctca aaaagaaaag gaagaaaaag aaagaaagaa    264180
acgtgaagtg cttggcacag aacctgccag gaaaccagga gtttgaaaat ggtggttgtt    264240
aactattact gctgttgtta ttgttattgt gaatgggtgt gtagttttgt tagccagccc    264300
tgagttacag tcaatttgag ggaaagatag ggggtgggtg tttgggtcct tctgggacaa    264360
ttaactccca acctggagta gggagaggca tgtcctggca ggcaaggagg tctcagttgc    264420 cccttctgc ctcccaggta agcccactag ttctgaggcc agggcttggc caggctgaga    264480
caggaaatgc cagatgcttg ggcgggcagg tccctgggt ttaggggca gagggcatgc    264540 ggcagtacta accagtgctg tctcagctgc tgccccaag tggctggggt gatgtgggtt    264600
tgccctgtgt gcaatggata atgactgtgt ttcttgtctt gtctctttc atgcctgctc    264660 ttaaaactgt atattggcgc aacgccgtct gaaaaactca tccaatcaaa atgcactatg    264720
aaattcattt gttcatccat gacatggtct gtgtgttcat acaccaatga cttatctccc    264780
aacccaccgc caccaccacc cccactcccc gcccgggaac cgaaacccat ggtttttttg    264840
gcactggtta caaatcaacc taaaaaatgc tgaacacgcc tccccaactg ccccgcccg    264900 cccgctcccc ctcatcttca acatctgcat ctagaatccg gttggtctta cttcttttctg    264960 aagtctaaat gccttacatt aactgtgaac gcatctcctc gcgtcggcat tgcatgccac    265020
accctgcctc tccaacgtgg gatgcctgac gctctcctca accctccgct ctcctctgtc    265080
tgtctgtcct cccgccccca gccctgtgc ctcccacttc ctgtagactc tgtctctctg    265140
```

```
tttttatcgg gttctgaatg gggttttct gtttggggtg gtttgcgtct tttgcagaga    265200
aagggatggg ttttcccagc gcagcacctc tctcttgccc catcccgcac acacatcccc    265260
tacactcaga gacaatagag gcaaatccac tcccagccac ctctcaccac tcctgtcccc    265320
cattcagctc catggacccc aggcccagg aaagctgcca actgtctcct cgcccctcca    265380
gctctctcca tcctgctgtc cccaatcctc catctcaagc ccacaagatc tttggccttg    265440
accagcagag acttgactct ccaagtctga taaaggagac ctgaaggcca ggcagtgtgc    265500
cggcaaagac tctcaggcag aggaactcag aagtgccaga cttggatctg gtagcttcat    265560
gtggggctgg cccactgagg ccctctcctg gagccttgaa ctgtacgtgc acacgcagtc    265620
acacagtcac tgcacacaga cactgcacac acagtcactg tgcacacact cagtcactgc    265680
gcacacactg tgcacacagt cactgcacac agacgctgca cgcagtcact gcagtcactg    265740
cacacagtca ctatgcacac acagtcactg cacacagaca ctgcacacac agtcactatc    265800
cacacacaca gtcactgcgc agacactgca cacactgc acacacaa tcactgcgca    265860 cacacagtca ctgcacgcag aaactggaca cacagtcact atgcacacac tgcacacacc    265920
actatgcaca cactgtgc acagtcacta tgtacacaca ctggcactgc atgtagtcac    265980
tatggacaca cactgcacag tcactgtgca cacatacact gcacacactg tcactatgca    266040
aacacagtca ctgcacacag tcactatgca cacacactgc acacagtc actgcacaca    266100 gagccactat gcatgcacac acagtctgca ttcacacatt gaacacacag tcgctataca    266160
cacacagtca ctgcacacac agtctatgca cccacacact gaacacacag tcactgcatg    266220
tacagacact gcacatagtc atgacctctt ctcttttct cactcattct ccaattctct    266280
ctctctctcg ctcttttttt ttttttttt tagacagagt ctcgctctgt cacccaggct    266340
ggcgtgcagt ggcacaatgt cagctaactg caacctctgc ctccccgttt caagcaatta    266400
tgatgcctca gcctcctgag tacctgggat tacaagcatg taccaccacg ccaggccact    266460
tcttgtattt ttagtagaga cagggtttca ccatgttggc caggctggtc tcgaactcct    266520
gacctcaagt gatgcacccg cctcagcctc ccaaagtgtt gggattacag gtgtgagcca    266580
ctacacctgg cctctaatcc tcattcactg ttcctgtctc tgtgtctctc acatacagtc    266640
atgcatgcat gcacgcatgc acacacacac acactggccc tctctgctac atctacccac    266700
cctgtacccc cactccagta catactgcac acatctctct ccctccccca cttctcagcc    266760
ccttgcacac ccttgttct gttaaatctc aactgcctct gccctctcc tacccaccaa    266820 tgaggccctt agagggacgc cccaatggca tctttgccct ggaatcatcc cttccctgct    266880
ggcaatacac atgcattcac ccaccaaaca tttaatgagc ccctatttgg tgccacagat    266940
ggaattatgg gcagaagcag acaccattac tgtcccctct taccacatac agtcaggtgg    267000
gggaggcagg catcggtcaa ataacccctt gactccactt aaaattatac ctgcactgcg    267060
agctgaagga tgagcagcat taacaaggca gagagagatg cacagagcat tccaggccca    267120
ggacagcaca tgcaaaggcc ctgtggtggg acggaacctg tgagggtca ggatctgcaa    267180 gcgagggaat gtggctgatg caaagacagc cgagaaaggc tggcctggag acagccgaag    267240
aaggcagaag gggacaggac ccggggctgg ggagggcggg gctatattgt ggaatatggg    267300
cttctcccta agcaccagga agggcctggg aggataggaa gcaggggagg cgcgactggt    267360
catgtgacta gacaagctcg ctctggttgc agggcaggga acagcttgac aggaggctgg    267420
gctggaggtg ggcaccagga atcgcagcaa gagatgacag tggaggagag agaacagtgg    267480
gagggttgtc ctctgcagga cccagggaaa gatcaggtct gaactgagat gaggtgcctg    267540
```

```
ggagcagtcg ggtctggctt aaaactggga gataggctga gcacggtgac tcaagcctct 267600
aatcccagca ctttgggagg ctgaggcagg aagatcacct gaggtcagga gttcgagacc 267660
agcctgacca acatggtgaa accccatctc tcctaaaaaa tacaaaaatt agccaggcgt 267720
ggtggcaggt gcctgtaatc ccagatcctc aggaggccga gacaggagaa tcacttaaac 267780
ctgggaggtg gaggttgcag tgagccgagg tcgtgccatt gcactccagc ctgggcaaca 267840
gagtgagact ctcttaaaaa aaaaatactg ggtgatagag gtgagcgagt gcaaggaaag 267900
gaccaggttg ggggaagaga ataggtgtgg gcatagcaag tttgaggtgc ctttaggaca 267960
tcccgaaata agtcagatag gcaggtgttg tgggggctgc agcttggagc tgaggtctac 268020
aagtagtagg acttttctgg agcccttagg tgggtggtct ccatatcctt ctgagcactt 268080
gaggaacatc tgagcacagc actggaaaag aaaagaccac aaggacgctg tcctcatgtc 268140
ttccaggggc tgtgtcccac ccccatcaca ttctagccag gaagttcagg ggaggtgttg 268200
aagagaggaa gctgcacctc ccaagccatg gattgaaatg tggaaggcag gaagagggaa 268260
cttgtcagaa gttctggggg cagtggaaag aattggtact gatgcaggaa gagatggagg 268320
gtggatgagg gcagactagt acccttcccc cactgcccca aacccttccc gtctccaccc 268380
ctacctgcct catgtgtctc ctcccccact tggctccaag aagggaagca tgttttctgc 268440
acgcatctcc ctgccagatc cctggctttt ttgcatggtt gcaagcttcc cctgctctcc 268500
tccaaacccc cctcctgagg ctgcttccag ggtccgcctg ccttcgcatg cctggccgag 268560
tccacatgtt atgatccgcc ccatgaaagg gatggcttgt actctggggt tgaacggag 268620 ggggctgggg atacctgagc catcggcccc atccccaggt ggagctgggt ggccaggcag 268680
ggatgggggt cagggcagca gggcacagag agtgactctg ttagccaagc tgggtttggg 268740
gcttgttcga ggcactggag acattctcac agcacttgag cccagtgtgg tcagggtagg 268800 atccccagc cccttcccc atcctagagg cctaaggacg cactgatgtg tcccagagag 268860
catcctagac attgccatca aacccagagg cctcagaaat tccttgaact ccagtccttg 268920
cctctcagct cccaggccaa agccagcaca agacacagat ctggcagcca gaaagccctc 268980
tggaagccac caagtaggat gcccatgtca cccaaactag gacacttttg aaacaggagg 269040
gaggctgtga ctgtatggtc accctgtgcc atttgggggg tgaaggttag accaagttaa 269100
atcttgctac gtgcctgta gcaaatccta caaatcccat agaacaagtc tgattaagcc 269160
ccttccctta gtgtggagag accctctact cctcctgcct tcaccctgct gggtactggc 269220
cagcgaagga gggtttccat gtctgcctga ggctggggtc tcaaactcaa atgcctctgg 269280
gggccaggca gacaccagtc aaccaggaaa gcaagtgcca tttctaaaac gtgaggaccc 269340
tggaaaactg gagatcatgt ggcctgcttc cagggagcaa tcgcagcagg cctgggttg 269400 ccagaaagcc agattggtgg gcaaaatctc ttgatttta aacaatggca ataatttta 269460 attaaaaaca aggacaaatg aaaaaacact gctcgggccc aacaaaacag ttttattagc 269520
tagatttggc ccactcgtga cttcgagagt cccacccccc ccaccaaggt cccttgaagc 269580
cccacaatgg ccacttaact ctagctggtc tcctccctga ctctccaact ctctggcccc 269640
ctggttcttc tagcttgggt gggaggaggc agaggcagtg actagacagg gggttttga 269700 gcagaggcag tggccaccca gggaggtcct gggggcaggg atggcccac ctcccggccc 269760 ccagcacccg ccccttggtg ggccgggct gatttctgag ctcacccacc catgggagct 269820
gagtgcttcc tgcttcctgc aggcctggtc ccgtgctact ccacccagcc ccagaagctg 269880
```

```
agaagccatc cctgagaggg gggaaaaggg ccccaaatgc atcttctccg actcagcggg   269940
cagcgaggac tcaccctgca gccgaacagt cccagctccc tcccgtcctc cccattcccg   270000
ctcgccaagg gggtaagaaa agatgctctt ccgcttctcc caattggctc gagccgctgc   270060
tcctcttggc cgtggggtga ggtcaggcg ggcaggagcg ggtgggcagc tcggcagggc   270120
agggcagggc agggtgcccg gtgagtcccg tgacagatgc atttctggcc cggagcgtaa   270180
catgccctcg gaacccgcac atgtccacca ggcctgactg tgctggcgac ctccaccccc   270240
accccgccc tggtgtttgt gcatcgtaca cgtatgatag attccgcaac ttgaccggct   270300
tgtgtccttt cgtctcagtg catttggttg ttgggagaaa caaaaaccat ctcgattttt   270360
ttcctgattg gatgattcgg atatattttc tttttcttgt tcttttgtta tttcttcccc   270420
atccccgttc cttttcctc cttttcttt cttttcttt ccccattgtg ggtggggctg   270480
gcagggaggg cttatgcttt tgagttgatg ccttttcctc cctcccaccc tctctctccc   270540
aacattattc cttttcgag ttttcctct gcatcattgc attaatagtg ctttctctct   270600
ccctccttat ttggggtctg gcttgctttt ttcctgttgg ttggcttcat gtaggggcct   270660
ctgtgagtgg tgacagctct gagccttttg gggtgggtgg atggtcaccc ctcttcctcc   270720
atctccccag aataacttca tcaacctgag cttctccgc ctcttccgag ctgcccggct   270780
catcaaactt ctccgtcagg gttacaccat ccgcattctt ctctggacct tgtgcagtc   270840
cttcaaggtg agtcctcgtc cctgctgctg gcccagggct gagaagacag gtgaccctca   270900
tgctctggct gaatgtagaa gtcagattgg aagtgcctct gtgatgtagt cgtgcagaga   270960
atctgttatc tccaaggctg ttgtcaaact tcctgtccct ggtgtgtctt cagagctgta   271020
agggcctcat cctagagccc ccagagatgc ccaccagccc tggaaggact ctggcacgtg   271080
gcatatggcc acccaaccca gtggggcaga gcactgggac aagggaggaa gacagtgcgg   271140
ctgagggacc cccagcactc ttcttcattg cctttttcc caccaggccc tgccttatgt   271200
ctgtctgctg atcgccatgc tcttcttcat ctatgccatc attgggatgc aggtgagtgt   271260
cgtgtcccta aggttcccag agcctcccaa ggagggcagc cacccttaga aagggtggg   271320
tcagaggagc ctggttcaca gaagcagcca tggaggttga gctgggtttc ccagaagcca   271380
ctggaggaat ggcagcccct ggtcgtcacc ctccaattcc acaggtgttt ggtaacattg   271440
gcatcgacgt ggaggacgag gacagtgatg aagatgagtt ccaaatcact gagcacaata   271500
acttccggac cttcttccag gccctcatgc ttctcttccg gtgagaaggg gacctgctct   271560
gataattctg tttccgtggg gtggggtgcc tgccttcatc cttctgttcc catagaggat   271620
gtaccctcct cttccaatgc aagacgtgcc ctcctccttc tcttctggca ggggcgcgcc   271680
ctcacccttc ttttccggta ggggcgtgc ccttctcttc cggtagggga cgtgccggcc   271740
ttctcttccg ataggggcg tgccctcctc ctccttttct ggtgtgggg tggccagatg   271800
tgctcttatc cttcttttcc cgtgaggctg gaaatgggtg tcgtgggggg cccaggaatc   271860
ctagcagggc agaagcagag ggccctggga catagtcatc aaggtcattt ccaggcatt   271920
atctctgaat cttcctgacc accctgtgag gaagggattc ttggcagccc tatccgacaa   271980
ataagaaaac aggcttacag accgtgaggc ttgattcttt ggttcatcat cttggctgca   272040
cacaaaagtt ccttcactcg ttcagtgtag gttttttggg ggggcttttt ttttttttt   272100
ttttttttt ggagatggag tctcgctctg ttcccaggc tggagtacag tggcgcgatc   272160
tcggctcact gcaagctccg cctcccgggt tcacgccatt ctcctgcctc agcctcccga   272220
gtagctggga ctacaggcgc ccgccaccac gcccagataa ttttttttgta tttttagtag   272280
```

```
agtcggggtt tcaccatgtt agccaggatg gtctcgatct cctgacctcg tgatccgccc   272340
gcctcggcct cccaaagtgc tgggattaca ggcgtgagcc accgtgccca gcccttttt   272400 tttttttttt ttagatggag tctctctctg ttgcccaggc tggagtgcag tggcgccatc   272460
tcggctcact gcaagctcct cttgtggagg tgtattgagc acctacagca tgccaggcag   272520
ggctgaaaaa cgaggatgca ccaggaaata gagaaagag acattttaag cactttggaa   272580
gctaacatcc ccatggggaa gacgaataat caggaaacaa attatagagg atgctggaaa   272640
aagataaaat tcaagaataa aggggaatag ggccaggtgc agtgactcgt gcctgtaatc   272700
ctagcatttt ggggaggccga ggtgggagga tcgctttagc ccaggagttt gagaccagcc   272760
tgggcaacat agtgagaccc cgtctctaca aaaaaattgt ttttaattaa ctgggcatag   272820
tgccacacac ctgtagtccc agctacttgg gaggctgagg caggaggatt gctcgagccc   272880
aggagttcca ggctacagta agctatgatt gtgccactgc actccagcct cggcaacaga   272940
gcgagactct gtctctaaaa agaaaaatat atttttttaa tttttaaaaa aagttacaga   273000
ggtagatagt ggtgatagtt gcataataat gtgagcttac ttaatgctac tgaattgtac   273060
acttcaaaat ggttaaattg ataaacttca tgctgtgtgt attttgccac agtaaaaaat   273120
aataatgttt ttaatctaac aacaaaaaaa gaatagaggg ccggcaggtt atgcctctct   273180
gaaagtgtga catttgagag aaattggcaa gggagggagt cagtgggtat atggggaagg   273240
gcaggccaag ccgaggggac tgcctgtgta aaggccctga ggcaggagta tggctggcat   273300
gtttgaggac tgtgaggagc ccagcatacc tagaacagag tgatctaggg agaatatagt   273360
atgagatgac tgtcaccttc atggagggga gcttttttt ttttttaatc tgagacagag   273420
tttcggtctt gttgcccagg ctggagtgca gtggtgcgat ctcggctcgg cgcaacttct   273480
gcctcccagg ttcaagcagt tctcctgcct cagcctcccg agtagctgag attataggtg   273540
cccgtcacca cgcccagcta atttttgtat ttttagtaga cggggtttt gccatgttg   273600 gtcaggccgt tctcaaactc ctgacctcag gtgatccacc cgcctcagcc acccaaagtg   273660
ctgggattac aggcatgagc cactgcaccc ggcctgaagg gagctttttt ttttttttgc   273720 tttttttga gacagaatct ccctcttgt cacccaggct ggagtgcagt ggcgcgatct   273780
cagctcactg caacctccgc ctcctgggtt caagcgattt tcctgcctca gcctcccaag   273840
tagctgagac tacaggtgag cgccaccaca ccgagcaaat ttttggtatt tttagtagag   273900
atagggtttc accatgttag ccaggatggt ctcaatctcc tgacctcgtg atccacccac   273960
ctcagcctcc caaagtgctg ggattacagg tgtgagccac cgcgcccagc caagagggga   274020
gcttttaaag cataacagtg accagcctga gcaatgcagt gaaacccccat ctctacaaaa   274080 aaaaatagtt taaaaattag ccaggagtgg tggcgtgtgc ctgtagtccc cagctactca   274140
ggaggccgag gcgggaggat cacctgagcc tgggaagttg aggctgcagt gagcagtgat   274200
tgtgccacta cactccaacc tgggtaacag agcaagaccc tgtcaaaaaa aaaaagaga   274260 gagagagaga aagaaagga aagaaagag agagagaagg aaaagaaaag aaaaaaacat   274320
atcagtgtcc tcaaatccca ccctagacca actgaatcca agtctgctgg ggtggggcac   274380
gggcattggt atttttttcaa agctctctgt ggacttcagt gcacagccaa gaatgtgaat   274440
tcccttctct cagctcccag taaaaggagg tggtccacct ggggcttgcc tggccagctc   274500
cagagcccaa gtgctcaacg tgtgtgctcc acctcctggg gaggcgttgg tacccagtca   274560
gggctgggtg tccgagtctc tgatttctcc ctgtcctcag gagtgccacc ggggaagctt   274620
```

```
ggcacaacat catgctttcc tgcctcagcg ggaaaccgtg tgataagaac tctggcatcc   274680
tgactcgaga gtgtggcaat gaatttgctt attttttactt tgtttccttc atcttcctct   274740
gctcgtttct ggtgagtctg tggacactgt gagggccgtc tgggctccct aagcctggct   274800
tcctttcagg ggagtgggtt tctgtggaat gtggctgtgt cgaaggcttg ttccctccaa   274860
ggcttctctg aaccagcctg ggatcaggtg accctgagcg tctcaaactc agcactgttg   274920
acatttgggg gtggctgatt ctttggggtg gggccatcat gtgcactgca gtgtatggca   274980
gcatccctgt cctcccccca ccagatgctg gcagcacacg ccacccgttc ctcctgttgt   275040
gacaaccaaa aatgtctccg gacattgcca ggtgccccca gggggtgggg gtggggttgg   275100 gagtggggc cagaattccc ccatttgaga ctcaatgaaa tatttcagct gggcgtagtg     275160
gccgatgcct gtaatcccaa cacttcggga ggctgaggtg ggagggtcac ttgagcccag   275220
gaatacaaga ccagcctgga cagcatggtg tgaaacccat ctctttaaaa aaaaaaaaa    275280 aaattgaatt agctgcacac gtggtgctgt gcacctgcag tcccagctac tcaggaggct   275340
gaggtgggag gatcacttga gccttggagg tcgaggctgc agtgagccat gatcacacca   275400 ctgcaccca gccagggcga cagaatgaga tcctgtctca aaacaaaca aaacaaaca       275460 aaaaaaaaa aaacattgcg agggaagaaa tacctcactt tggccttgtt gggggcagat   275520
gtgggaggat ttggggtcac agtggttctc ttggtgttgg tccctgtttc agaagcctcc   275580
cctccctctc actgactctg tttctttcca tcattcttgg tctttgtctc tctctctctt   275640
tttttttttt ctttgaaatg gagtctcact ctgttgccca ggctaaagtg cagtggcgag   275700
acctcagctc actgcagcct ccacctccca ggttcaaccg attcttcagc ttcaacctcc   275760
caagtagctg ggattacagg tgcacatgcc accacaccca gctaattttt gtatttttag   275820
tagagacagt gtttcaccat gttgaccagg ctggtctcaa actcctgacc tcaagtgatc   275880
tgtccacctc ggcctcccaa agtgctggga ttacaggcgt gatccaccgt gcccggccag   275940
tctttgtctc tttgtatctc tctctctcca tctctctctg tttctctctt cctcttccc     276000 atctctccac ttgatctctc tctcactgga cctccttgtg tgagtgagca tcacctctcc   276060
attccccagt ctctttctgt ctctgtctca tttcctttcc ccatcttctc tctatccctc   276120
tctccatctg ggcctctgtg tacatgtctt tgggtctgtc tgtccgtctg tctgtctgta   276180
tccttctcac tcactcattc attccctcgg tctctgcccc cattctctct tggtccccgg   276240 ggtcccaca gatgctgaat ctctttgtcg ccgtcatcat ggacaacttt gagtacctca   276300
cccgagactc ctccatcctg gcccccacc acctggatga gtacgtgcgt gtctgggccg   276360
agtatgaccc cgcagcttgg taagaagtca ccccgaatcc tccagccaca atactcacct   276420
ctccctggaa ctggaacacg ggctaggtca ggccccagac tctggagcac tgaactcctg   276480
gggtcctagc aggggtctca caggttcagt caggagagaa gatataagaa tcatcaccct   276540 tgcataccc agattaaaca cgtagggtgc caaccctgcc caaaccctgg actttctggg   276600
aaatgaggga gggcgtcaac catgagatgt cctgaagagc cctctcctcc tacgagtctc   276660
tcctgtctct cactgtgaag tctccagatg gtgaggatgc attagccagg ctccagggag   276720
aaaaccaaca gcatcccagc ctcagttctc ttgagtgtg ggaggagg gctggcctac       276780 ccttggcaga caggattggc agcaacatca gagtagcaga actcagctcc cactgggacc   276840
cgtgaacctg ggagtgagag gacatacagg ccaggggagg acgcagagcc tcaggggccc   276900
atgcatcttt gtggccacaa agggagtggg cgctcccatc tgggtagaca ccagagggt    276960 ccctctccac tgacgggcaa tggtttcaga gggtgggttc caccttgtgc acgtgtattg   277020
```

```
agtgcccacc caacaccaag ccttgaagga cactcagagg ctttatctga atacctggaa 277080
cccaccagcc actaactgag gatttagttc aggctggtct tggggcctga agaagcatta 277140 ctgggggggcc ctcagcagcc taagccccat cttcctctgg cctcagcacc agagaggagg 277200
ccgtcacgag gaaggtgggc aggaggtggt cttggctatt cccatagcct caaacaagta 277260
ctccatgaga ccgagaggct ggggagagcc gtgggtctgg ggctgggctt tggctggttc 277320
ctaactcttc ctcttttgat tttaggtcac agcaattgga tgctgtcccc aaggcctcta 277380
ttccacaagc cccccccac ccctgtagcc catgtagact gtggaggagg cagatgcaga 277440
gagagcccca ggggaggtgc cctgcagtcc cgaactcgac tgacatccta cacccctggg 277500
tctccccagt gtctgggaat gtactgggga ccttcacttg tccccagtct ctcccactcc 277560
ttcaagccag ggacacccca gcctcgggca tcatgacctc gctgtgtgcc cagggagccc 277620
gtgtgaaccc attgcctgca ctaaccccct tcttctcct tcagcggtc ggattcatta 277680 taaggatatg tacagtttat tacgagtaat atctccccct ctcggcttag gcaagaaatg 277740
tcctcatagg gttgcttgca aggtttgact tccactaaaa cctgctagca tccatggaat 277800
gagtgtggct tggggttctt caatatatat atttcatata tatatatata tatatctctc 277860
tctctctcta aaaaaacaga gccatctctc tttcttgcat taaactagaa aactctctta 277920
gccaacagaa tgcagtcatg tagactcgat aaagcatgga acatatttcc tccttccctt 277980
cagccttcag ccatctttgc ttgctcttag ctgaagctgc ccatcctggg gtctccacgg 278040
caccccaaat cagatacatc ccctgggga ttgtaacttt gcatttctcc cccaaccatc 278100
acctccactc tctccccctc caccctcac ctcccaaagc ccctagccct cctccctcc 278160 ctggcactgg cccctgctcc ccacctaggc cccctcagag accagcctca gccaaaccag 278220
agaacgtgac ccaactgtag aaataacagt gatggccggg cgcagtggct catgcctgta 278280
atcccagcac tttgggaggc caaagcagga ggatcgcttg agcccaggag tttgagacca 278340
gcctgggcaa catagcaaga accccttct ctataaaaaa ttagccaggc attgtggcgc 278400
atgcctgtag tcccagctac ttgggaggct gaggcagaag gattgcttga gcccaggagg 278460
tggaggctgc agtgagctat gatcacacca ctgcactcca acccaggcga cagagagaga 278520
ccctgtctct ttaaaaaaa aaaaaaaaa aaaaaaggc aatgaacaaa agcatggctc 278580
tacgtcttcc aaagtgagaa ttctccctcc cctccgcatc cctccagaac tgtagctcag 278640
agcccacgct gaatctgact tttctctttt ctctctctct ccctgctccc gagcagtgaa 278700
gtaatctttt tttactgacc ttttcttcca ttttttttcc tcctctttc cattgatttg 278760 aaatatctat tttatcattc tctgcatctt tctctctcta ttttttcggc tcgtgtggat 278820 ttctttttc tttcttctgt ttctccccac ctctcttcct ttggttctct gttcccattc 278880
ccgttttgtt ttttttgtttt tgttttttgtt tttttcattt tcggtgctgc caggggccgc 278940
atgccttacc tggacatgta tcagatgctg agacacatgt ctccgcccct gggtctgggg 279000
aagaagtgtc cggccagagt ggcttacaag gtagactacc cttgccgacc accgacgtcc 279060
aggcactggg tttttttttc ttcttcttct tctttttttt tagtgctgac cagaaacacc 279120
cggccgactc tcttttccca acgtttctct tcttttttgt ttttgattct ttttttcctt 279180
ttctcgagtc aactgatcat gaccatccct tgattctaag cagcacactg tgtccgtcct 279240
ttctgatgag tgtcttcgtg tttttgagact ccattatggc cgacatgccg gggggagggg 279300
gaggggagcg cccaggtccc cttgcacctg gtctcccagg taccaaattg gaaacaaaca 279360
```

```
cgcttcttca gggagtcaaa acccatgctt cccacttctg cccacccaga gcggccccca 279420
tgcccaggct ggggcaggcg ccttgcagag aggggcttta gccccgaaa gcaggcgagg 279480 tcccgggtcc ccgcccctgc cacgcacacc tgaagctgat ctctgaccta gggccttggg 279540
gattcgagac cttccaagga gcaccaagaa cctctcttcc cctcccttcc ttcccctgga 279600
gtttcgtccc cagccccgt ccctaatccc cccaagacac cccaacatgc ctctccattg 279660
ttccagagtg ggcaggcggc cgcagctgga cccctggacg gtggcacact gatgcaggcc 279720
atgcacgctg ccttggcggg gcctggggcg ggcaggcacc atggccgacg ggggtggtg 279780 catgctggct gagagagcga gcgtcctgcc gccaagcggc tggcccgggc cacccctcca 279840
gatccctgtc ctggaatctc ccttggtgcc caaggacaga tgctctgttc cctccattca 279900
tccacaagaa gttcagggat gacctttaaa gattctcccc acccaaaaag tattacccca 279960
tcatcctatt ctcccatcca ccttgatctt ccctgcgtcc ctatccatca atgctatttg 280020
tacctgcccc gtgttgccac ctcattcctt tccttcctct gtgcacccct cctcacctaa 280080
cctatatgtc tccctcctt ctcaatcaaa gccggggaca aggttgtccc accagcatct 280140
cagacaatga gcctcctg gcacctgtcg ctctgtgccc ctccctgccg ccccccccc 280200 cccccggt tttcctcaag tcgcttctct cagtctctgc ttagatgaat gtgtgcgcat 280260
gtgcaagaga gggagggcga gcccttcctc tcctggtctt tgtgcaggac caccatgggt 280320
ccataagaca actttgtgca aatttgaaaa aggcacccct tccacagaac atgcctgttg 280380
gaaaattgtt gcaatctacc aatgtggtga gaacaagaca cttttttct atcacctggg 280440 aagctgttat atttaatata caaatcgggg gctgggcgtg gtggctcatg cctgtaatcc 280500
tagtgctttg ggaggctgag acgggaggat cacttgagcc cagttcgaga ctagcctggg 280560
caacatagcg agacccatc tctacaaaaa gaaaaatat tttaattaat aaataagtac 280620
ataaatctat catttccaag atgggagccc tttgtgcggt gtacaacctg cacaactgtg 280680
cacagtggcc cagtctatgt gtgtttctct atttccacc tccttcccca ccctaccccc 280740 agtgtccct ccagtgtcct gctctggatt taccataccc ctccccatct tcaactctgt 280800
gtttcctgcc cacttgtgtc tgaatcccca cccaagttgc cctcacccc cttctctgtg 280860 ccacttcagc ctgggctggt gcacaccagc ccagcatcct ctcccatgcc accaagcatg 280920
gtggacagag cccctgcctg ggacatgggg aatcttttct tccctgggct ggaagggagt 280980 gccctcacc cttcccct gccattgcac agagagccaa gatctggaca tgcccctgag 281040
atacacttcc cacggagcta tgaatgagtc tcgagattcc gtctgcatgc gcccctgtct 281100
gtgctgttct gtgtcacagc ctcgctgcat gcctgcgagg ggcctgcccc gtcagtgggg 281160
ggctgcctgc ctgctgcttc tcagaggaat gatgtggtct gtgcccatct gctctgtcct 281220
ggtctgggcc aagccaggga ttgggtgtgg ggagccagtg gcaccccca ccagcggctg 281280 tggtcctggc cccctcagcc ttggctgttg catgcactgc tcaaatccag cttgtgctct 281340
ttttctttgg ggtcagactg aaacgggcc atccagaaga actctgggc agggcggggg 281400 tggggcaagg gttgaggcaa accctggaaa tgccagctct caggtcaagc aggtggggga 281460 aaaaggaga gggcagggga ccagaagtac aagagagcct tttgtgccct ccctgcgggc 281520
caccaagaga aactgagtac tgggacaggt aacctaagta agagacacct cagccgccac 281580
agctttcaga gttcttcctg ggactccctg ggtaggggcg ggcgcggctc acgggagacc 281640
caggagggat gcctgggaat gactgcgctt gccttgggtt ttctgtagcg gcttctgcgg 281700
atggacctgc ccgtcgcaga tgacaacacc gtccacttca attccaccct catggctctg 281760
```

```
atccgcacag ccctggacat caagattgcc aagggtaagg aagggacagg ggcgggcaca    281820
gacaggcgtg acagggtgga accggggatc tccctcccta ccccaaacta gaggatctgc    281880
tgtcaccacc cggatcttca ttcactcttc cattcattcg ttccacaggg ttttttgggg    281940
tttgggtttt tggtgttttt ttttttttt ttttgagaca gagtcttgct ctgttgccca    282000
ggcagcagtg cggtgacatg atcgcaagtc actgcagcct tgacctccca ggctcaagtg    282060
atccttccac ctcagcctcc ccagtagctg ggactacagg cacacaccac catactcggc    282120
taattttttt ttttttggtg tgacaatttc cctctgtcac ccaggctgaa gtgcagtggt    282180
gtgatcttgg ctcattgcta cctccgcctc ccggggttcaa gcgattctcc tgcctcagcc    282240
tcccaagtag ctgggattat aggtacccac cagcacaccc ggctaatttt ttatattttg    282300
ggtagagatg ggtttcacc atgttggcca ggctggtctc gaactcctga cctctggtct    282360
caaactcctg acctcaagtg atccacctgc ctcgacctct caaagtgctg gattacaggc    282420
gtgagccacc atgcccaacc taattttta tatttttat agagatgggg tttcatcagg    282480
ttgcccaggc tggtctcaaa ctcctgggct caagcagtcc tcccaccttg gtctcccaaa    282540
atgctggtat tacaggcatg agccaccaca cccggcccat ttggcagata tttagtgcac    282600
tccttcaatg tgccagagac ccgtccaagc agggaggac ccagcagctt acactttaga    282660
tggatgggga ggccgccact gaggaggtaa ggcagtgtct catggatccc tgggggaag    282720
gtgctccagg cagaaggact ggcaaaggcc ctgacagagg ggtgaacaca ggacacccgg    282780
ggcattgagc tgactcacct tctgagtgag ggcacgccac gcaggttcag agcagaggag    282840
gaacctgacc caactcacat ttgaacaggt tccctccggc cactgagggg atgggagacc    282900
gaaaggaggc cagtgtgggg gctgctgata tcatctgggt ggagacaggg cggcagctta    282960
gatctagggg taggctcgac gtggtggctc acgcctgtaa tctcagcact tgggaggcc    283020
aaggtgggtg gattacttga ggtcaggatg accagcctgg ccaatgtggt gaaacccccg    283080
tctctactaa aaatacaaaa tttagccaga cgtggtggtg ggtactgtag tcccagctac    283140
tagggaggat gaggcagaag aatcgcttga acctgggagg cggaggttgc agtgagccga    283200
gatcacgcca ctgcactaca gcctgggtga cagagcaaga ctctgtctca aaaattaaat    283260
taaattaaat taactggaca tggtggcata tgcctgtggt cccagctact caggaggcag    283320
agatgagagt attgcttgaa gccaggagtt tgaggctgca gtgagtcatg atcgcaccac    283380
tgcactccag cctgggcgac agaacgagat cctagctcaa acaacagaa agaaaaagaa    283440
aaaaacattt ttttaaagc tgagaagggg ctgggcgca tggcttacgc ctgtaatccc    283500
agcactttgg gaggccaagg tgggtggatc acgaggtcag gagttcaaga ccagcctggc    283560
caacatggtg aaaccccatc tctaccaaaa atacaaaaag tagccgggtg tcatggtggg    283620
cgcctgtaac cccagctact ccggaggctg aggcaggaga atcacttgaa cctgggagac    283680
agaggttgca gtgagccaag atcgcgccac tgaactccag cctggatgac agagcaagac    283740
gctgtctcaa aaaaaaaaaa agctgaggcc gggcacgctg gctcacgcct gtaatagcag    283800
cactttggga ggccgaggcg ggcagatcat gaggtcaaga atcgagacc atcctggta    283860
acacggtgaa accccttctc tactaaaaat acaaaaaatt agctgggtgt ggtggcacgc    283920
acctgtagtc cctgctactc agaaggctga ggcaggagaa ttgcttgaac ccgagaggca    283980
gaggttgcag cgagccgagc ttgtgccact gcactccagc ctgggtgaca gagtgagact    284040
tcatctgaaa aaaaaaaaa aaaaagccg agaaggctgg acatggtggc tcacacctgt    284100
```

```
aatctcagca ttttgttgag gccaggcaca gtggttcacg cctgtaatct gagcacgctg   284160
ggaggccgag gtgggtggat catttgaggt caggagttcg agatcagcct ggccaacgtg   284220
gcaaaaccct gtctctacta aaaatacaaa aattagccgg gtgtcgtggc gtgtgcctgt   284280
aatcccagca ctttgggagg ctgaagcggg tggatcactt gaggtcagga gttcaagacc   284340
agcctggtca acatggcaaa accctgtctc tactaaaaat acaaaaatta gccaggtgtg   284400
gtggcgggta cctgtaatcc cagttactag ggaggctgag gcagaagaat cacttgaacc   284460
cgggaggcag agattgcagt gagccgagat cacatcactg cactttagcc tgggcgacag   284520
agcaagactc catctcaaaa ataaaaataa aaataaaaaa taccgagaaa ttcccccaaa   284580
gacctagctc agggctcact ctccatcatt aggggggaaag aagaagagga ggccagggag   284640 gcggcagag accagggcag tgtgggctcc tggaggcagc ttctatgttt aaaagggcgg   284700
cttcaggagg aaggggacca accgtgtcag gcactgccca gagaccaagg atgacaagga   284760
tcacaagtga ctggtcatca tggtcacttt gaccagtgca gctttggcgg aggggtcagg   284820
ggtcccctgt ctggagtgca tttcggaggc ccgaaagggg atgtgatgtg atttggcagc   284880
tgattaagga cagcagggca gagagacagg cgcacaattg ccagaagaaa cggggacctg   284940
aggctcacgc ctgtaatccc agcactttgg gaggctgagg aaggtggatc acttgaggcc   285000
aggaatttga ccagcctg gccaacatgg cgaaacccca tctccactaa aaatacaaaa   285060
attagccagg catggtggtg cacacctata atcccaacaa cttgggaagc tgagcacaag   285120
aattacttga acctgggagg cagaggttgc agtgagccga gatcaaacca ttgcactcca   285180
gcctggggga cacagcaaga ctctgtctca aaaaaaaaa aaaaaagaaa gaaagaaaga   285240
aaagaaaaaa caaatgggac cagaaaaaag gagtgggtgg gagaggagca ggtggatagt   285300
cccacacatg ggaaggtgct gagcccagct gaaaccacta gtaagtcagg aggagggaag   285360
actgagcctc gagacatatg tgccttccag ggtcttgagg gaaagaaggg aggaagagcc   285420
aaggccacgt ggcaagactc aaggaggaag tggcagggaa ggtgggggac tggaggggtg   285480
gaggacagat attgttaatg ccaggaacaa agtgaaggta agagagcac aaggaagttg   285540 ggagcagtgg ctcacacctg taatcccagc actttgggaa gccaaggcag gaggatcact   285600
tgaggccagg agttcaagat cagcctggcc aacacagaga gaccccatct ctacagaaaa   285660
ttttaaaatt agccaggtgt ggtgatgtgc acctgtagtc ccaactactt gggaggctgg   285720
agtgggagga tcactgggga ctgggatgtc aaggctgcag tgagctatat gatgaccaca   285780
gacatagcag cttaagacac acctatttgt cagctcacag tcctgtaggt cagaagtcca   285840
aaaagctgga ctgggctgtc tgctgagggt ctcacgaggc tgaaatcaag gtgtcagcca   285900
agctgggctc ctctctggag gatctggggg agaatctact tccaggttca ttcaggtgtt   285960
ggcagaattg aagtccttgt ggctgtagga ctgaggtctt gttttatcac tggctttta   286020 gcttttttgct cctggaagtg catgtaatcc tccatgtgct ctcattctct ctgacttccc   286080
catctgccac ccagcagaga caatactgtg cttttcaagg gctcacctga ttggggcagg   286140
cctaccctga tcatctctgt attttgaggt cagctgactt gatatttttt ttttttcttg   286200
agacagaatt tcactcttgt tgccaaggct ggagtataat agtgtgatct cagttcactg   286260
caatctccgc ctcccaggtt caagcaattc tcctgcctca gcctcctgag tagctgagat   286320
tacaggtgcc caccaccacg cccagctaaa ttttttttgta tttttagtag agatgggggtt   286380 tcacaaggtt ggccaggctg gttttgaact cctgacctca ggtgatccac ccgcctcagc   286440
ctcccaaagt gctgggatta caggagtgag ccaccatgcc cagcattttc tttctttttt   286500
```

```
tttttttttt tgaaacggag tcttgttctg tcacccaggc tggagtgcag tggcgcaatc    286560
tcggctcact gcaacctcca tctcccgggt tcaagtgatt ctgcctcagc ctcccaagta    286620
ggtgggacta cagatgcgtg ccaccacgcc cggataattt tttgtatttt tagtagaaac    286680
ggggtttcac catgatagca ggatggtctc gatctcccaa cctcgtgatc tgcccacctc    286740
ggcctcccaa agtgctggga ttacaggcgt gagccaccgc accgggcctc cggtatttta    286800
attatatctg caaagtccct tcatagcctg gcaatggtc cctagattag tgtttgaata    286860
aacagaatct tggcagaagg gcagcttttg aattctgcct accacagttc cttcgtttgt    286920
acaacgggtc taacaacacc cccactcttt gtatgtaatg ccatcgtaac tcagcttctg    286980
tggcactctg agaatctgtg ttcaggggtc ccaaaaccac ccacaggttc agtgattccc    287040
tggaagaact cagaactgag aaaagttttt atactcacag tttattacag tgaaagaata    287100
tagattaaaa tctgcaaagg gccgggcacg gtggctcacg cctgtaatcc cagcactttg    287160
ggagggcgag gtaggcagat cacttgaggt cacgagttca agaccagcct gaccaacatg    287220
gtgaaaccct gtctctacta aaaatacaaa aattagccag gcgtggtggc tggcgccagt    287280
aatcccagct acttggaagg ctaaggtagg agaatcactt gagcccagga ggcagaggtt    287340
gcagtgagcc gagatcccgc cacttcactc caggctggac agagtgagac tctattagaa    287400
aaaaaaaaaa aaaaaaatc tgcaaagggc ctggcatggt ggcttacgcc tgtaatcctg    287460
gcactttggg agggcaaggc gggcagatca cttgaggtca caagtttgag accagcctgg    287520
ccaacatggc gaaaccccgt ctctaccaaa aatacaaaaa ttaggcatgg tgccagaccc    287580
ctgtaatccc aactactcag gaggctgagg caggagaatc gcttgaccct gggaggcaga    287640
ggttgcagtg agctgagact gtgccattgc actccagcct gtgtgacaag atcaaaactc    287700
tgtccaaaaa gaaaattagc caggtgtggt ggcatacacc tgtagtccca gctactccag    287760
aggctgaggc acaagaatcc tttcaaccca ggagatagag ctacattaag ccaagatcac    287820
gccactgcac tccagcctgg gcaacagagc aagactctgt ctcaaacaaa caaacaaatt    287880
ccaaaaacat aaaatgcgca aaggaagggc atctggggaa gggtccagga gacaccaggt    287940
gcgagcttcc agttgtctgc ctccagtgga gttgcacaga caacgcttaa ttctccctgc    288000
agtgtgtgac aacacgcacc gtgtactgcc aaccagggaa gctcacctga gccttggtgc    288060
cccagggttt ttattgaggg tttgtcatat aggcagggct gacgtagtta ctcagtctcc    288120
agtccctcca gaggtcaaac tgataccacg tgcccaaga ccccaacgat aaatcgcatt    288180
gttagaatga actgtatgga aaattatcca ggcgtggcgg cgggcggctg taatcccagc    288240
tactggggaa gctgaggcag gagaatcact tgaaactagg aggccgaggt tgcagtgagc    288300
caagatcgca ccattgcact ccagcctggg caatagagca aaaacaccat ctcaaaataa    288360
ataaataaat agaatgaact gtattggccg ggtacagtga ctcatgccta taatcccagc    288420
actttgggag gctgaggctg gaggatcgtt tgaggcagg agttcgagac cagcctaggc    288480
aacatagtga gaccctatct cttttttta aaaaaaaaa aaaaaaaaa aaagaatgaa    288540
ctatacagtg tggcccaagg cccctgctaa ataaagaca ctcttcaggc aggacatttc    288600
aaaggcttag agatcaccct ccaggagcaa gtcaatgggc cagtcctttc atcggaatgt    288660
gcagggtttg gacaacacta gcctactgag ctagtcctta ctgcttagca ccccagcttc    288720
tatgacacct actggattcc cttcctgagg gtttcaaaga ctcctggaga tgtctctgaa    288780
tttggctgtc acagttgtta cttgtacccc agatgccact cagttccctg aagacaatga    288840
```

```
tcccccagat ttctcagcca ggagcccctc cacctcttgt cctcagtggg tgccaggcct  288900
catcctggag ttccacagct gagccaggct ctcggggtta cggaaggtca agagggtgtg  288960
gggacaacaa tggaagagtg ataacagtgg cagcccttig agcagatgcg ggtctcagga  289020
gaacataacg cgcttictit tcatagttca gctcactttc taagcacact gagcttcctt  289080
tccagcaggc taagggggctg caaaggggg acagattaac ctcattcttc agattctcaa  289140
aaatggtgtc accattcatt gctggagact gggagaaagg gggcaagtcc atctcattct  289200
ctctgtctct gtctctctct ctctcttccc tgtccatctg tttctctctc ccacccaccc  289260
ctctgttctc tctgcccaga agaatctcta tittggtittt ggttttgtttt gttttgtatt  289320 gttttgagac ggagtctcgt tctgtcgccc aggctggagt gcagtggcgc agtctcaact  289380
caccactgca gcctccacct cccaggttca agcgattctc atgcctcagc ctcccgagta  289440
gttgggatta caggcgcacg ccaccacgcc cagctaattt ttgcattttt actagagact  289500
ggtttcacca tgttgaccag gctggaccct atcctctttc aagcccccca ccccaggcat  289560
tgagggcaga gccaactacc tgcctgaacc aattagcata ttaaacgtaa acccagttag  289620
catatccaaa tagcagccca cagtgacatt ctgactgtca gaatgtggat tgcttgagcc  289680
caggagctca aggcttcggt gaacaaagat tgtgccacag cctgggcaac agagtaagtc  289740
cctgtcgatc gatagataga tgatagatag atagatagat agatagatag atagatagat  289800
agatagatag ataaatttt aaaaaaaata ataggcagg cacagtggct catgcctgta  289860
atcccagcac tttgggaggc cgaggcaggc agatcacctg aggtcaggag ttcgagacca  289920
gcctggccaa catggtgaaa ccctgtctct acaaaaatat aaaaatagcc aggcagagt  289980 ctgtaatccc agctactcag gaggctgagg taggagaatc gcttgaactc tgaaggtgga  290040
ggttgcagtg agccgagatc atgccattgc actccagcct gagtgacaga gcagactcc  290100 atctcaaaaa taataacaat aataaaata ataaatatg ctctggcccc aaagtggcac  290160
attacatggt gcacacccca ttagcaagga ctcatcacat ggccctgcca accacaggag  290220
gaaccccccc atgtactcag gtaggagggc caggaaacac cgtcagagag ctttaatgac  290280
tcaccccatg actggggtga gggacgaggg actggctgca ggccaagggc atgtccgtgg  290340
cagtggagac ttgggaaagg ggaaaagacc tcctctgagc cacgcacagt ggctttcatc  290400
tgtaattcca gcactttggg aggctgaggt gggaggatct tgagcccagg aggtcgagac  290460
tgcagtgagc tatgtttgtg ccacggcact ctagcctggg cgacagagca aaccctgtc  290520 tcaaaatca aataaaaacc aaaaccaaaa cttcctctgt tggggatgct ccagggcgtc  290580
ccagccttga acagatgggt cactgcagta ataatcctat ggcagacact gtcccaaggc  290640
tgcacgcacg ttactttgat catcaaacaa ccaggtgata gccaggcatg gtggtgcgtg  290700
cctgtagtcc cagctactca ggaagctgaa gcgggagaat ctcttgaacc tgggaggcgg  290760
aggtaacagt gagtcgagat cacatgactg cacttcagcc tgggaacaga gagagactct  290820
gtcaaaaaaa aaaaaaaaac aggccagacg cggtggctca cgcatgtaat cgccagcact  290880
ttgggaggct gaggagggtg gatcacctga ggtcaggagt ttgagaccag cctggccaac  290940
atggtgaaac cccgtctcta ctaaaaatac aaaattagtt gggcgtggtg gtgcacacct  291000
gtaatcccag ctactcggga ggctgaggca ggagaatcgc ttgaacccag gaggcagagg  291060
ttgcagtgag ctgagattgc accattgcac tccagcctgg gcaacaagag tgaaactcca  291120
tctcaaaaaa aaacaaaaa aaaacaacc agccaggcgc ggtggcttac gcctgtaatc  291180
ccagcacttt gggaggccga ggcgtgtgga tcacccgagg ttaggagttc gagaccagct  291240
```

```
tgaccaacat ggtgaaactc cgtctctact aaaaatacaa aaaattagcc aggcatggtg    291300
gtgcatgtct gtaatcccag ctactcggga agctgagaca ggagaattgc ttgaacccag    291360
gagtcggagg ttgcagtgag ccaagctcgt gccactgcac tccagcctgg gcaacagagc    291420
aagactctgt ctaaaaaaaa aaaaaaaaca cacacacaca cacaacaa ccaggtgagg      291480
caagtactct tgctatcatc tccatttcac agatggagaa actgagttac taagtggtag    291540
agtaacctaa gtcatgcagc cgataactgg gagacaagat tgggacccag gtcgcccagc    291600
tgttctccat gccgggctgt ctcctgcaca gctgctccat ggtcctggcc ccaccgaaaa    291660
ccagagccca caaggtcatt ccagcagcac tgcccagggc ctcctctggg ccaggccgtt    291720
ggggaactgg agaccccatg gggaccagaa agattggggt ctcgttctcg ggagcctatg    291780
gctttgcagc tgacccagag tccagctgac acccaggcag gcagtcaggg tctgtctaca    291840
cccccattgc aggaggagcc gacaaacagc agatggacgc tgagctgcgg aaggagatga    291900
tggcgatttg gccaatctg tcccagaaga cgctagacct gctggtcaca cctcacaagt     291960
gtaagagctg agcccagccc tgggatccaa tccaccagga cagatggagg gggagggaaa    292020
ggggaggcct ggggagagtg ttggcctggg ctggtataca cagggaccca ggacaagggc    292080
cccaaagagg cctgcccttg gtgagctcac cgtgtgtgtg cccccagcca cggacctcac    292140
cgtggggaag atctacgcag ccatgatgat catggagtac taccggcaga gcaaggccaa    292200
gaagctgcag gccatgcgcg aggagcaggt gcgctgttcg ccgctctggg gacatctggg    292260
ctggggacag tggcttgcat gtcaccacgg gaaccaactg gaatatgagg gtggctgagc    292320
cccagggcag gtccctgaaa agtagggct gtgcacagca gctcacacct gcaatctcag     292380
tgctttgaga ggccagggca gagggatcgt ttgagaccag gatgagacca ccctgggcaa    292440
cacagtgaga ctccatctct acaaaataaa acattagcca ggcatggtgg tgcacacctg    292500
tagtcccagc tatttaggag gccaagatgg gaggatcact tgaggccagg agtgggagac    292560
cagtctgggc aacatagaaa gacccatatc tctacaaaaa aaaaataaaa ttagctgcat    292620
gtggcgccat gcacctgtgg tcccagctac ttgggaggct gaggcaggag aatcacttga    292680
acctgggagg tggaggttgc agcaagccaa gatcaagcca ctgcactcca gcccgggtga    292740
taagagcagg actctatctc aaaaaaaaaa aaaaaaaaa aaaaaaagt tcttgccaag       292800
gacacatcat gtggattcat tcttcattca gctgctccac caacacttat tgagtattac    292860
tgtgtgcagg gcgctgttct cagtcctcgg ggatgcaccc atggggaaaa taggccagaa    292920
tccctgccct cagggagcag acattccaag tggggaaatg ccaatggtag caaatgactg    292980
aatcgtgcaa catccagcaa agagaaagaa agtgtcgtgg gggaaagtgg agaagaatcc    293040
agaagatagg agtatccagg ggaggagggg atgcggtggg aaatgggtag ttggggagcc    293100
tccctgagaa agtgacatgt gagcaaaggc ttgaaggaaa aggggagagg gagtgagcta    293160
agcaatacct ggaagggtgt tccaggcaga ggaaacagcc agtgcaaagg ctctgaggct    293220
ggaccgtgcc tgggttgttt gggtaacagc aaagaggcca gtgtggtgga aaagagcagg    293280
gaggagacaa gggcaaggag gtgacagggc agatccttca gggccatggg agctgcagga    293340
aggactctgg cttttccc aagcaagtgg gagccatgga gggttctaag caaggaggg       293400
ataggacctg actcaagtgc tcatgggcgc cctctggtgg ctcttgtgga acagtggggt    293460
tgaaggtagg agcgggagac ctgggagaag gtgcctgcag tgagagatga ggacgtggga    293520
ccaggctggg gctatgactt gggtggagga gtgagaagtg gtccagttct gcgtggaatt    293580
```

-continued

```
ggaagggtct agatggatga gacctgagag agtgtgtgtg tgtgtgtgtg tgtatactgg   293640
ggatgtcgca atgccttctg ggtaccaccg tcccaccacc ccaccttgt ccacacactg    293700
ctctctgccc cattccccag gaccggacac ccctcatgtt ccagcgcatg gagccccgt    293760
ccccaacgca ggaaggggga cctggccaga acgccctccc ctccacccag ctggacccag   293820
gaggagccct gtgagtgtca cccctgccag ggaggtggag tgtgggggtg ccgtggtccc   293880
cacgttctgg aagctgccca agcgcccact gctaccccgg cctctgtccc ccatgcagga   293940
tggctcacga aagcggcctc aaggagagcc cgtcctgggt gacccagcgt gcccaggaga   294000
tgttccagaa gacgggcaca tggagtccgg aacaaggccc cctaccgac atgcccaaca    294060
gccagcctaa ctctcaggtg cctctgtccc ccaactcccc aatggctccc agggcccggg   294120
tggttcaggt ggaagggatc tgggcccccc acacacacac acctgcagct ccctccctct   294180
gcagacacca gggatctgga ggtcaggccc cagagctcat ctggctttgc catctgctcc   294240
gcagtccgtg gagatgcgag agatgggcag agatggctac tccgacagcg agcactacct   294300
ccccatggaa ggccagggcc gggctgcctc catgccccgc ctccctgcag agaaccaggt   294360
gagggctttc accactgccc tggggctgga cccctcactc tgcactgggt agggccaggc   294420
ccccccacaa gcagcccagt gcatcccctc cctgccggac tcaggcctgg gtagggactc   294480
cttcagtctc tgaagcagtc tgcaggcccc acccaccacc tggtcacacc tggagcacct   294540
gcagaccctc ctccctcaca gaggacagag aggaaagtgc tcccctggg gcagagggca    294600
gtggccactg caaaatggtc tctggctgcc ctggttggag gctgcagaca ggggaggttg   294660
tggaagattt gtgggtgcag cagggttcaa cagggccagc tgagacctgc cacgaagatc   294720
accccctacac aaacacacac acacatgctc aacatacatg cacacacatg tgcagctgtg   294780
cgcctactca gatgcttgca tacacacacg tgtgtgcacg tgggcatata cacactgcac   294840
atgtactcac acatgcacac atgtacgtgc acacgtgtct gcatatggga acttggcagg   294900
tcctaggata cagtagcaga gtctgggggtg ggtctggggg cagctgggct cgtattttct   294960
gtctggtctc tgtgggagtc attgggggc acagggtgt gtgcttgatg tgtgtctgtg     295020
tgtggccgct tcacccagct gccaggccca cctgcaggtg atcccgttgc cttggactca   295080
tgggacagag ggcccagagg catagctggc tgcccacccg gcctgaacag cggggccca    295140
tgcacgcagc ccgcctctgg aggagaacag ggcatggctg tgagagcctg ccccgggtgc   295200
gtggcatgtg tggctgtggc gagctttccg tgtgccgtgt gtggcgtctg cacggggcag   295260
gaggctgtgc tgtgcctggc tggaccaggg tcacctgagg gcctgcctc tggctgctgg    295320
gaacgtgggt tggggagcac ccagcgtgca tgctgctgct ccctcaggac cgagctgctg   295380
ggccccagga gagggttggg acaagcccag ctgacggcca ccacatggaa gctttgagca   295440
tcggccggag ccaggggttg gggtgtgcat cgcatgaggc agagcccagg gccaggggct   295500
cgaggctgcg ccgtcctgtc tttcggtccc atgcctctgc catttgtctg tctgcatctc   295560
ctgtctgtct cctctgtacc catgggaata gaggacgccc agccccgggg gcctgggaca   295620
cccacccgcc aggactttaa cttttctttt cctccctgcc ttctccctcc gatttctctt   295680
gatgccagtg ccactcccct ccttggcttc ttctccatgc accacctcct cactctccct   295740
cttgcctttt atatttattt tcttctttct gttttttctg tgtgcaccat cccatggggc   295800
tgtgacagag gagaagggc cggcacgtg ggaataacct cagtgtatgt accgcgcctg     295860
cccagcgccc agcagggctc cggccccctc ttcctcccca ccccccctcc agggagtccc   295920
gtcatctctc accgtccccg gaccccaccc tttctttggc aatcgcaccc tctccctcc    295980
```

```
atggagccca atccttgtgt gtggtgtcct gtgtgtgccc ctcacccata agccctggtg   296040
ggcggggcca tccccatcct caccccctacc cccttttctt cagggccccc cacgccggag   296100
gacactggct ctccaagagc ctggcccact ctgcacctct ttctgggggg cttcttctcc   296160
tgacaccacc accaacccct ggtcctgcag ctcctacctg gagcagggcc accagcgctc   296220
agctgggctg gaccctggga ggcgggcgtc tgccccatct ccctccttcc ctcctctgcc   296280
tgctgcagag aaacctgtgt gtcagggctt gacccaggga tgaagcacca gggaaaagag   296340
tgggccccca gagcctccag tgcctgggta tcccccaccc ccacccagag ctccctagct   296400
tgggcctcac cagaaggact cagacttgtg ggggcagcga gcacagcccc gttagccggg   296460
aggacccaaa gctgccatgc cgggcacctg gtcctgagcc cataggtcag ccagccacag   296520
tcggaggctt ctcaccctcc caggagagca agctggggca gggatgagtg cggcagtcca   296580
gggctcccag gtttgcaccc tggatgtgga gagggcttcc ctctggccag cctgagcctg   296640
cccaactgtg gctgggcccc caggactgga gagtgaggat cagatctttc tggtcagaac   296700
ccaggatggg ctcaaaagga gcagtcctgt ctctgaggga cagaggaatc ctcaggctcc   296760
accctcagag gcctggccac acccagagcc ctgattgatc aggggagcc aaggccccat   296820
ggcatcccct ggccctgcc ccaggatggt cacaccgcag tcaccgaagg ccaccaccag   296880
gctgccacaa tggggcagga aggacccgga ccacttggtg ctagctgctg accccagccc   296940
accggcctgt cccctccccc agaccatctc agacaccagc ccatgaagc gttcagcctc   297000
cgtgctgggc cccaaggccc gacgcctgga cgattactcg ctggagcggg tcccgcccga   297060
ggagaaccag cggcaccacc agcggcgccg cgaccgcagc caccgcgcct ctgagcgctc   297120
cctgggccgc tacaccgatg tggacacagg tgggcagccc tgtggtgctc agggacaagc   297180
agaacagagg agaggagagg ggaggagaag gcagggcgga ggagacacta aggaagaaga   297240
aagggagagg cctccatgga gaggggacag aggggccag gcagcagctg caggaacctg   297300
ggtactaccc cctccccca acccactgac ctgcctcggt tcagggggatc tctagggccc   297360
ccacaccttc caggtggcct cctgtgtgtg catctgcccc acctctccct cacgaccacc   297420
tgtgtgtctg tctgacccctc acccggccca ggcttgggga cagacctgag catgaccacc   297480
caatccgggg acctgccgtc gaaggagcgg gaccaggagc ggggccggcc caaggatcgg   297540
aagcatcgac agcaccacca ccaccaccac caccaccacc atccccccgcc cccgacaag   297600
gaccgctatg cccaggaacg gccggaccac ggccgggcac gggctcggga ccagcgctgg   297660
tcccgctcgc ccagcgaggg ccgagagcac atggcgcacc ggcaggtggg tgcggctgca   297720
agtgacccca ggctgggctc ggccgggagg cggggaggag agaagggat acccccatcca   297780
acagccactc taggcaaagg tccccggatc ccggctgtga ccacctccca tcctgccccc   297840
aagccaccgg ggtgcccggc ggccggagcg gacacggatc cccaccacac cagctgccta   297900
tgctgtcccc ccagccccct tgcccacccg ccgccccctc ccgccgcccc gcagctgctt   297960
gctcctcggt tgtggatcat atttgagttc tgggccgtgc cgcccgacct ttcactttcc   298020
tttaacccgg cttctgtttt tgtttcaatt atgatttctg tcctctggac gcctgtgagt   298080
aatttttgaa acttctgcta tttttaaccc cgaaacttac aaaactccat ttctcatttc   298140
tcttttcact ttgttgtgtt ggttttcgac tcctccctc cctgtctcac tcccctcct   298200
cccctccctc ctccctgtgg ctgttgcttt tttccattca atgtcctgtg tccccctct   298260
cctcctcctc ctcctcctcc ccctcccct cctccctctc ctcccggccc ctctcccttc   298320
```

```
gctcccctct cttcctccca atcccgtgtc tcctttgatt tgttgtatc ttttttttttg   298380 atttccttg tttcaattt cgtgtagggc agtagttccg taagtggaag cccagccccc   298440
tcaacatctg gtaccagcac tccgcggcgg ggccgccgcc agctccccca gaccccctcc   298500
accccccggc cacacgtgtc ctattcccct gtgatccgta aggccggcgg ctcggggccc   298560
ccgcagcagc agcagcagca gcagcagcag cagcagcagc aggcggtggc caggccgggc   298620
cgggcggcca ccagcggccc tcggaggtac ccaggcccca cggccgagcc tctgccggga   298680
gatcggccgc ccacgggggg ccacagcagc ggccgctcgc ccaggatgga gaggcgggtc   298740
ccaggcccgg cccggagcga gtcccccagg gcctgtcgac acggcgggc ccggtggccg   298800 gcatctggcc cgcacgtgtc cgaggggccc ccgggtcccc ggcaccatgg ctactaccgg   298860
ggctccgact acgacgaggc cgatggcccg ggcagcgggg cggcgagga ggccatggcc   298920 ggggcctacg acgcgccacc ccccgtacga cacgcgtcct cggcgccac cgggcgctcg   298980 cccaggactc cccgggcctc gggcccggcc tgcgcctcgc cttctcggca cggccggcga   299040
ctccccaacg gctactaccc ggcgcacgga ctggccaggc cccgcgggcc gggctccagg   299100
aagggcctgc acgaaccta cagcgagagt gacgatgatt ggtgctaagc ccgggcgagg   299160
tggcgcccgc ccgccccccc acgcacccca cgcacacacc ccacccgagg agccgcgcag   299220
aggccgcggg ggcccagcac agagggcccg ggagagggcc agccgggaga ccccagactc   299280
tggagaggcc agggctgggc cacaagggtg tcccgcagag accctcggcc aaaagagacc   299340
ctcctgggca gccacggcgc ccccaacca gccccgatcc ccccacccac gacaggggct   299400
ctcgggtggg aggcagggag cagacaaacc acacagccaa gggatttgaa ttaactcagc   299460 cattttggg gaactttggg gaacatgaaa aaaaaaaaa aaaaaaaaa aaaaacatt   299520 tttaaagaa aaacgggga gaaaaaata gcttctattg atgagtttta tcatctcaat   299580
tgaatctttc ctttccctga tgaagacagc tggtggccga gtgcggcaaa gaagccagaa   299640
ggaaccagaa tcccagtgcc ctacacccac caccagacac actcacaccc acacgttc   299700 tcagacacac acaagagtgc ttgccggtta taccaaaccc tactattact gcctgcagaa   299760
atcaatttaa aaaataata ataacaataa acaatttaa aaaggacaaa aaattaatg   299820 attgagaaaa gaggcatttt tttctgacat ttggtcctgc ttgaaacaac aaagaagaa   299880 gaaaaaaccca ccatcaccac cgattccttt gcttctttt tcctttttc ctaccttgtt   299940 tgaaaaccgt gggcttggga ctgtgaatta ttgcatgaca ttcaaaaga aaaaaaaat   300000 aaaaaaagt tgaatcaaa                                                 300019
```

<210> SEQ ID NO 44
<211> LENGTH: 1000
<212> TYPE: DNA
<213> ORGANISM: Artificial Sequence
<220> FEATURE:
<223> OTHER INFORMATION: Construct
<400> SEQUENCE: 44

```
atttcattta tcaggtgttc agtgaatgct tactatgtaa cagcacagtt atcagcactg     60 gggaataga tgagtaagat aagatttgca ctttcattag cttacatgcc ataaagaggg    120
aaataaagag aacaccagat gatgataagt ttatgctgag aattaaaatg aagtgatgaa    180
ataatgggaa tgtcaggtgg ctacttttgg tgggatggtc aggaaaggca tctctgggga    240
gataaatttt aagctcagac ctgagtgaaa agaatgagcc agccatggaa acattatgtt    300
aactcacatg gtagtttgaa atgctttatc tgatcaaagg tacttatttt tggtgactt     360
```

```
caacaatatt aagggtctat aaaccaacac tcatttgcat aagaataact accagtgaat    420 cttttttgtat gataggtttt ttgtttgttg ttttttttgag acagagtctc gctctgtcgc   480
ccaggctgga gtgcagtggc gcgatcttgg ctcactgcaa cctctacctc cccggttcaa    540
gtgattctcc tgcctcagcc tcccaaagta gctgggatta caggtgcctg ccaccacgcc    600
tggctaattt ttgtattttt agtagagatg gggtttcacc gtgttgtcca ggctcgtgtc    660
aaacttctga cctcaagcca tccacccgcc tcggcctccc aaagtgctgg gattacaggt    720
gtgagccacc actcctggcc atgataggtt attttgtgat gaaaatacct acctcttaat    780
ttgtctgata aatttaaatt ttatgtctag atttcctaag atcagcactt ccatatttta    840
aagtaatctg tatcagacta actgctcttg cattctttta ataccagtga ctactttgat    900
tcgtgaaaca atgtattttc cttatgaata gttttctca tggtgtattt attcttttaa    960
gttttgtttt ttaaatatac ttcacttttg aatgtttcag                         1000
```

<210> SEQ ID NO 45
<211> LENGTH: 214
<212> TYPE: DNA
<213> ORGANISM: Artificial Sequence
<220> FEATURE:
<223> OTHER INFORMATION: Construct

<400> SEQUENCE: 45

```
acagcagcaa aagcagcaac agcagcagca gcagcagcag caggggggacc tatcaggaca    60 gagttcacat ccatgtgaaa ggccagccac cagttcagga gcacttggga gtgatctagg   120
tgatgctatg agtgaagaag acatgcttca ggcagctgtg accatgtctt tagaaactgt   180
cagaaatgat ttgaaaacag aaggaaaaaa ataa                                214
```

<210> SEQ ID NO 46
<211> LENGTH: 135
<212> TYPE: DNA
<213> ORGANISM: Artificial Sequence
<220> FEATURE:
<223> OTHER INFORMATION: Construct

<400> SEQUENCE: 46

```
aacttgttta ttgcagctta taatggttac aaataaagca atagcatcac aaatttcaca     60
aataaagcat ttttttcact gcattctagt tgtggtttgt ccaaactcat caatgtatct   120
tatcatgtct ggatc                                                    135
```

<210> SEQ ID NO 47
<211> LENGTH: 208
<212> TYPE: DNA
<213> ORGANISM: Artificial Sequence
<220> FEATURE:
<223> OTHER INFORMATION: Construct

<400> SEQUENCE: 47

```
tccccagcat gcctgctatt ctcttcccaa tcctcccct tgctgtcctg ccccacccca     60
ccccccagaa tagaatgaca cctactcaga caatgcgatg caatttcctc attttattag   120
gaaaggacag tgggagtggc accttccagg gtcaaggaag gcacggggga ggggcaaaca   180
acagatggct ggcaactaga aggcacag                                      208
```

<210> SEQ ID NO 48
<211> LENGTH: 214
<212> TYPE: DNA

```
<210> SEQ ID NO 48
<211> LENGTH: 214
<212> TYPE: DNA
<213> ORGANISM: Artificial Sequence
<220> FEATURE:
<223> OTHER INFORMATION: Construct

<400> SEQUENCE: 48
ctacttcttg ccctcggtct tcaggtcgtt gcgcacggtc tccaggctca tggtcacggc      60
ggcctgcagc atgtcctcct cgctcatggc gtcgcccagg tcgctgccca gggcgccgct     120
gctggtggcg gggcgctcgc aggggtggct gctctggccg ctcaggtcgc cctgctgctg     180
ctgctgctgc tgctgctgct gcttctgctg ctgt                                 214

<210> SEQ ID NO 49
<211> LENGTH: 110
<212> TYPE: DNA
<213> ORGANISM: Artificial Sequence
<220> FEATURE:
<223> OTHER INFORMATION: Construct

<400> SEQUENCE: 49
ctgtaaatga atgagaaaac cggtttagaa agtgcacagc tgtcagggaa gtcaacactt      60
cagtgagcat gtgaccatgt ggagtcagct tcctgtttcg tgctgcaatc                110

<210> SEQ ID NO 50
<211> LENGTH: 374
<212> TYPE: DNA
<213> ORGANISM: Artificial Sequence
<220> FEATURE:
<223> OTHER INFORMATION: Construct

<400> SEQUENCE: 50
gtaaggcctg ctcaccattc atcatgttcg ctaccttcac actttatctg acatacgagc      60
tccatgtgat ttttgcttta cattattctt cattccctct ttaatcatat taagaatctt     120
aagtaaattt gtaatctact aaatttccct ggattaagga gcagttacca aagaaaaaa     180 aaaaaaaaaa gctagatgtg gtggctcaca tctgtaatcc cagcactttg ggaaaccaag     240
gcaggagagg attgctagaa catttaatga atactttaac ataataattt aaacttcaca     300
gtaatttgta cagtctccaa aaattcctta gacatcatgg atatttttct tttttttgaga     360 tggagtcttg ctct                                                       374

<210> SEQ ID NO 51
<211> LENGTH: 136
<212> TYPE: DNA
<213> ORGANISM: Artificial Sequence
<220> FEATURE:
<223> OTHER INFORMATION: Target site

<400> SEQUENCE: 51
tttaagctca gacctgagtg aaaagaattt gagacagagt ctcgctctgt cgcctttcct      60
aagatcagca cttccatatt tggtgacttt caacaatatt aagggtctat aaaccaacac     120
tcatttgcat aagaat                                                    136
```

METHODS FOR TARGETED INSERTION OF DNA IN GENES

REFERENCE TO RELATED APPLICATIONS

This application is a continuation of previously filed application U.S. Ser. No. 17/366,290 filed Jul. 2, 2021, which is a continuation of U.S. Ser. No. 16/800,444 filed Feb. 25, 2020, now U.S. Pat. No. 11,091,756, which is a continuation of U.S. Ser. No. 16/601,144 filed Oct. 14, 2019, which claims the benefit of previously filed applications U.S. Ser. No. 62/746,497 filed Oct. 16, 2018, U.S. Ser. No. 62/830,654 filed Apr. 8, 2019, and U.S. Ser. No. 62/864,432 filed Jun. 20, 2019, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Oct. 14, 2019 is named 2019-10-14_BALTES_P12987US03_SEQUENCE_LISTING_BA2018-4WO.txt and is 517,077 bytes in size.

TECHNICAL FIELD

The present document is in the field of genome editing. More specifically, this document relates to the targeted modification of endogenous genes using rare-cutting endonucleases or transposases.

BACKGROUND

Monogenic disorders are caused by one or more mutations in a single gene, examples of which include sickle cell disease (hemoglobin-beta gene), cystic fibrosis (cystic fibrosis transmembrane conductance regulator gene), and Tay-Sachs disease (beta-hexosaminidase A gene). Monogenic disorders have been an interest for gene therapy, as replacement of the defective gene with a functional copy could provide therapeutic benefits. However, one bottleneck for generating effective therapies includes the size of the functional copy of the gene. Many delivery methods, including those that use viruses, have size limitations which hinder the delivery of large transgenes. Further, many genes have alternative splicing patterns resulting in a single gene coding for multiple proteins. Methods to correct partial regions of a defective gene may provide an alternative means to treat monogenic disorders.

SUMMARY

Gene editing holds promise for correcting mutations found in genetic disorders; however, many challenges remain for creating effective therapies for individual disorders, including those that are caused by gain-of-function mutations, or where precise repair is required. These challenges are seen with disorders such as spinocerebellar ataxia 3 and spinocerebellar ataxia 6, wherein the disorder is caused by gain-of-function mutations (expanded trinucleotide repeat) at the 3' end of the genes.

The methods described herein provide novel approaches for correcting mutations found at the 3' end of genes. The disclosure herein is based at least in part on the design of bimodule transgenes compatible with integration through multiple repair pathways. The transgenes described herein can be integrated into genes by the homologous recombination pathway, the non-homologous end joining pathway, or both the homologous recombination and non-homologous end joining pathway, or through transposition. Further, the outcome of integration in any case (HR, NHEJ forward, NHEJ reverse; transposition forward, or transposition reverse) can result in precise correction/alteration of the target gene's protein product. The transgenes described herein can be used to fix or introduce mutations in the 3' region of genes-of-interest. The methods are particularly useful in cases where precise editing of genes is necessary, or where the mutated endogenous gene being targeted cannot be 'replaced' by a synthetic copy because it exceeds the size capacity of standard vectors or viral vectors. The methods described herein can be used for applied research (e.g., gene therapy) or basic research (e.g., creation of animal models, or understanding gene function).

The methods described herein are compatible with current in vivo delivery vehicles (e.g., adeno-associated virus vectors and lipid nanoparticles), and they address several challenges with achieving precise alteration of gene products.

In one embodiment, this document features a method for integrating a transgene into an endogenous gene. The method can include delivery of a transgene, where the transgene harbors a first and second splice acceptor sequence, a first and second partial coding sequence, and a first and second terminator. In some embodiments, the first and second terminators can be replaced with a single bidirectional terminator. The method further includes administering one or more rare-cutting endonucleases targeted to a site within the endogenous gene, where the transgene is then integrated into the endogenous gene. The transgene can be targeted to a site within an intron or at an intron-exon junction. The first and second partial coding sequences can be oriented in a tail-to-tail orientation, such that integration of the transgene in either direction (i.e., forward or reverse) by NHEJ can result in precise alteration of the gene's protein product. In other embodiments, the transgene can include a left and right homology arm to enable integration by HR. These transgenes can be harbored within an adeno-associated virus vector (AAV), wherein the transgene can be integrated via HR (through the homology arms) or by NHEJ forward direction or NHEJ reverse direction (through direct integration of the AAV vector within a targeted double-strand break). In an embodiment, vectors with a first and second coding sequence and a left and right homology arm can further include a first and second site for cleavage by one or more rare-cutting endonucleases. Cleavage by the one or more rare-cutting endonucleases can result in liberation of a linear transgene with homology arms, capable of integrating into the genome through HR or NHEJ. In another embodiment, vectors with a first and second coding sequence can be flanked by a first and second site for cleavage by one or more rare-cutting endonucleases. Cleavage by the one or more rare-cutting endonucleases can result in liberation of a linear transgene, capable of integrating into the genome through NHEJ. In another embodiment, vectors with a first and second coding sequence can be flanked by a left and right transposon end. Delivery of a CRISPR-associated transposase (e.g., Cas6/7/8 along with TniQ, TnsA, TnsB, and TnsC) can result in integration of the transgene through transposition.

The methods can be used to alter the C-terminus of proteins produced by endogenous genes. In some embodiments, the endogenous gene can include the ATXN3 gene or CACNA1A gene. ATXN3 is a gene that encodes the enzyme ataxin-3. Ataxin-3 is a member in the ubiquitin-proteasome system which facilitates the destruction of excess or damaged proteins. Spinocerebellar ataxia type 3 is a genetic disorder caused by a trinucleotide repeat expansion within the 3' end of the ATXN3 gene. CACNA1A is a gene that encodes proteins involved in the formation of calcium channels. Spinocerebellar ataxia type 6 is a genetic disorder caused by mutations in the CACNA1A gene. The mutations which cause SCA6 include a trinucleotide repeat expansion in the 3' end of the CACNA1A gene. In some embodiments, the methods provided herein can be used to alter the 3' end of the endogenous ATXN3 gene or CACNA1A gene. In specific embodiments, the target for integration of the transgenes described herein can be intron 9 of the ATXN3 gene or intron 46 of the CACNA1A gene.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and from the claims.

DETAILED DESCRIPTION

Figure 1:
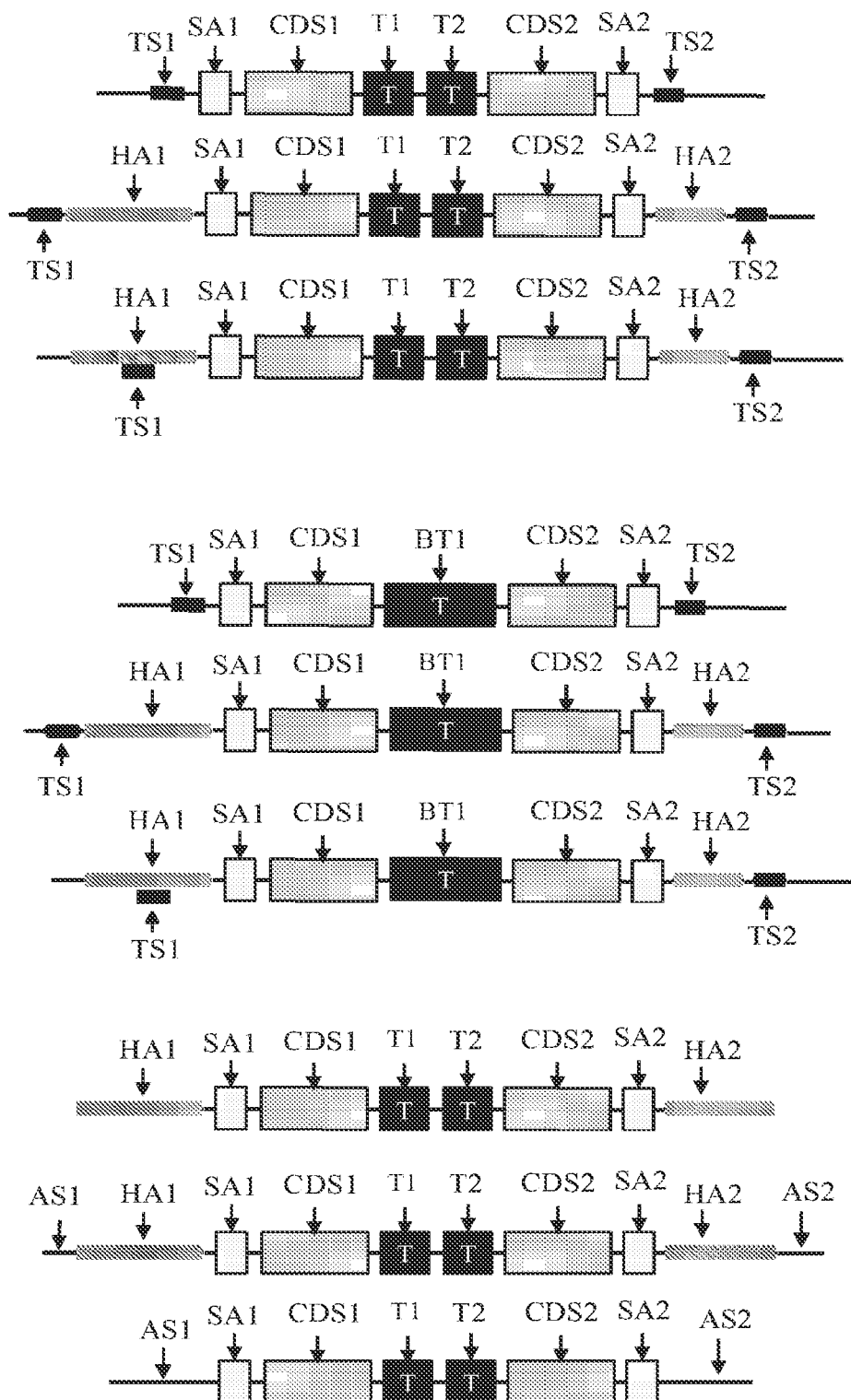
FIG. 1 is an illustration of the transgenes for the targeted insertion into endogenous genes. TS1, target site 1; SA1, splice acceptor site 1, CDS1, coding sequence 1; T1, terminator 1, TS2, target site 2; SA2, splice acceptor site 2, CDS2, coding sequence 2; T2, terminator 2; HA1, homology arm 1; HA2, homology arm 2; BT1, bidirectional terminator 1; AS1, additional sequence 1; AS2, additional sequence 2.

Disclosed herein are methods and compositions for modifying the coding sequence of endogenous genes. In some embodiments, the methods include inserting a transgene into an endogenous gene, wherein the transgene provides a partial coding sequence which substitutes for the endogenous gene's coding sequence.

In one embodiment, this document features a method of integrating a transgene into an endogenous gene, the method including administering a transgene, wherein the transgene comprises a first and second splice acceptor sequence, a first and second partial coding sequence, and one bidirectional terminator or a first and second terminator, and administering one or more rare-cutting endonuclease targeted to a site within the endogenous gene, wherein the transgene is integrated within the endogenous gene. The method can include designing the transgene to have the first splice acceptor operably linked to the first partial coding sequence and the second splice acceptor operably linked to the second partial coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second partial coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. In certain embodiments, the rare-cutting endonuclease can be a CRISPR/Cas12a nuclease or a CRISPR/Cas9 nuclease. The first and second partial coding sequences encode the same amino acids. In an embodiment, the first and second coding sequences can differ in nucleic acid sequence but encode the same amino acids. The transgene can be harbored on a vector, wherein the vector format is selected from double-stranded linear DNA, double-stranded circular DNA, or a viral vector. The viral vector can include an adenovirus vector, an adeno-associated virus vector, or a lentivirus vector. The methods described here can be used with a transgene equal to or less than 4.7 kb. The transgene can comprise a first and second partial coding sequence that encode a partial peptide from a functional protein produced by the target endogenous gene. The target endogenous gene can be aberrant.

In another embodiment, this document provides DNA polynucleotides with a first and second splice acceptor sequence, a first and second partial coding sequence, one bidirectional terminator or a first and second terminator, optionally, a first and second homology arm, and, optionally, a first and second rare-cutting endonuclease target site. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a first and second target site for one or more rare-cutting endonucleases, wherein the target sites flank the first and second splice acceptors. In another embodiment, the DNA polynucleotides can comprise a left and right homology arm which flank the first and second splice acceptors. In this embodiment, the DNA polynucleotide can be harbored within an adeno-associated viral vector. In another embodiment, the DNA polynucleotides can further comprise a first and second target site for one or more rare-cutting endonucleases, wherein the target sites flank the first and second splice acceptors. The first and second target sites can flank the first and second homology arms. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb.

In one embodiment, this document features a method of integrating a transgene into an endogenous gene, the method including administering a transgene, wherein the transgene comprises a left and right transposon end, a first and second splice acceptor sequence, a first and second partial coding sequence, and one bidirectional terminator or a first and second terminator, and administering a transposase targeted to the endogenous gene, where the transgene is integrated in the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second coding sequences, and first and second terminators can be oriented in a tail-to-tail orientation. The transgenes with a tail-to-tail orientation of sequences can further comprise a left and right transposon end flanking the first and second splice acceptors. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. The transposase can be a CRISPR transposase, where the CRISPR transposase comprises the Cas12k or Cas6 protein. The first and second partial coding sequences encode the same amino acids. In an embodiment, the first and second coding sequences can differ in nucleic acid sequence but encode the same amino acids. The transgene can be harbored on a vector, wherein the vector format is selected from double-stranded linear DNA, double-stranded circular DNA, or a viral vector. The viral vector iscan include an adenovirus vector, an adeno-associated virus vector, or a lentivirus vector. The methods described here can be used with a transgene equal to or less than 4.7 kb. The left end can comprise the sequence shown in SEQ ID NO:41, and the right end can comprise the sequence shown in SEQ ID NO:13.

In another embodiment, this document provides DNA polynucleotides with a first and second splice acceptor sequence, a first and second partial coding sequence, one bidirectional terminator or a first and second terminator, and a left and right transposon end. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a left and right transposon end which flank the first and second splice acceptors. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb. The left end can comprise the sequence shown in SEQ ID NO:41, and the right end can comprise the sequence shown in SEQ ID NO:13.

In one embodiment, this document features a method of integrating a transgene into an endogenous gene, the method including administering a transgene, wherein the transgene comprises a first and second splice acceptor sequence, a first and second coding sequence, one bidirectional terminator or a first and second terminator, and a first and second homology arm, wherein the transgene is integrated within the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. The homology arms can flank the first and second splice acceptor sequence, the first and second coding sequence, the one bidirectional terminator or the first and second terminator. The coding sequence can encode a full coding sequence or a partial coding sequence. In an embodiment, transgenes with first and second splice acceptors, first and second coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

As used herein, the terms "nucleic acid" and "polynucleotide," can be used interchangeably. Nucleic acid and polynucleotide can refer to a deoxyribonucleotide or ribonucleotide polymer, in linear or circular conformation, and in either single- or double-stranded form. These terms are not to be construed as limiting with respect to the length of a polymer. The terms can encompass known analogues of natural nucleotides, as well as nucleotides that are modified in the base, sugar and/or phosphate moieties.

The terms "polypeptide," "peptide" and "protein" can be used interchangeably to refer to amino acid residues covalently linked together. The term also applies to proteins in which one or more amino acids are chemical analogues or modified derivatives of corresponding naturally occurring amino acids.

The terms "operatively linked" or "operably linked" are used interchangeably and refer to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence but need not be directly adjacent to it. For example, an enhancer is a transcriptional regulatory sequence that is operatively linked to a coding sequence, even though they are not contiguous. Further, by way of example, a splice acceptor can be operably linked to a partial coding sequence if the splice acceptor enables delineation of an intron's 3' boundary, and if translation of the resulting mature mRNA results in incorporation of the peptide sequence encoded by the partial coding sequence into the final protein product.

As used herein, the term "cleavage" refers to the breakage of the covalent backbone of a nucleic acid molecule. Cleavage can be initiated by a variety of methods including, but not limited to, enzymatic or chemical hydrolysis of a phosphodiester bond. Cleavage can refer to both a single-stranded nick and a double-stranded break. A double-stranded break can occur as a result of two distinct single-stranded nicks. Nucleic acid cleavage can result in the production of either blunt ends or staggered ends. In certain embodiments, rare-cutting endonucleases are used for targeted double-stranded or single-stranded DNA cleavage.

An "exogenous" molecule can refer to a small molecule (e.g., sugars, lipids, amino acids, fatty acids, phenolic compounds, alkaloids), or a macromolecule (e.g., protein, nucleic acid, carbohydrate, lipid, glycoprotein, lipoprotein, polysaccharide), or any modified derivative of the above molecules, or any complex comprising one or more of the above molecules, generated or present outside of a cell, or not normally present in a cell. Exogenous molecules can be introduced into cells. Methods for the introduction or "administering" of exogenous molecules into cells can include lipid-mediated transfer, electroporation, direct injection, cell fusion, particle bombardment, calcium phosphate co-precipitation, DEAE-dextran-mediated transfer and viral vector-mediated transfer. As defined herein, "administering" can refer to the delivery, the providing, or the introduction of exogenous molecules into a cell. If a transgene or a rare-cutting endonuclease is administered to a cell, then the transgene or rare-cutting endonuclease is delivered to, provided, or introduced into the cell. The rare-cutting endonuclease can be administered as purified protein, nucleic acid, or a mixture of purified protein and nucleic acid. The nucleic acid (i.e., RNA or DNA), can encode for the rare-cutting endonuclease, or a part of a rare-cutting endonuclease (e.g., a gRNA). The administering can be achieved though methods such as lipid-mediated transfer, electroporation, direct injection, cell fusion, particle bombardment, calcium phosphate co-precipitation, DEAE-dextran-mediated transfer, viral vector-mediated transfer, or any means suitable of delivering purified protein or nucleic acids, or a mixture of purified protein and nucleic acids, to a cell.

An "endogenous" molecule is a molecule that is present in a particular cell at a particular developmental stage under particular environmental conditions. An endogenous molecule can be a nucleic acid, a chromosome, the genome of a mitochondrion, chloroplast or other organelle, or a naturally occurring episomal nucleic acid. Additional endogenous molecules can include proteins, for example, transcription factors and enzymes.

As used herein, a "gene," refers to a DNA region encoding that encodes a gene product, including all DNA regions which regulate the production of the gene product. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, a "wild type gene" refers to a form of the gene that is present at the highest frequency in a particular population.

An "endogenous gene" refers to a DNA region normally present in a particular cell that encodes a gene product as well as all DNA regions which regulate the production of the gene product.

"Gene expression" refers to the conversion of the information, contained in a gene, into a gene product. A gene product can be the direct transcriptional product of a gene. For example, the gene product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Encoding" refers to the conversion of the information contained in a nucleic acid, into a product, wherein the product can result from the direct transcriptional product of a nucleic acid sequence. For example, the product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

A "target site" or "target sequence" defines a portion of a nucleic acid to which a rare-cutting endonuclease or CRISPR-associated transposase will bind, provided sufficient conditions for binding exist.

As used herein, the term "recombination" refers to a process of exchange of genetic information between two polynucleotides. The term "homologous recombination (HR)" refers to a specialized form of recombination that can take place, for example, during the repair of double-strand breaks. Homologous recombination requires nucleotide sequence homology present on a "donor" molecule. The donor molecule can be used by the cell as a template for repair of a double-strand break. Information within the donor molecule that differs from the genomic sequence at or near the double-strand break can be stably incorporated into the cell's genomic DNA.

The term "integrating" as used herein refers to the process of adding DNA to a target region of DNA. As described herein, integration can be facilitated by several different means, including non-homologous end joining, homologous recombination, or targeted transposition. By way of example, integration of a user-supplied DNA molecule into a target gene can be facilitated by non-homologous end joining. Here, a targeted-double strand break is made within the target gene and a user-supplied DNA molecule is administered. The user-supplied DNA molecule can comprise exposed DNA ends to facilitate capture during repair of the target gene by non-homologous end joining. The exposed ends can be present on the DNA molecule upon administration (i.e., administration of a linear DNA molecule) or created upon administration to the cell (i.e., a rare-cutting endonuclease cleaves the user-supplied DNA molecule within the cell to expose the ends). Additionally, the user-supplied DNA molecule can be harbored on a viral vector, including an adeno-associated virus vector. In another example, integration occurs though homologous recombination. Here, the user-supplied DNA can harbor a left and right homology arm. In another example, integration occurs through transposition. Here, the user-supplied DNA harbors a transposon left and right end.

The term "transgene" as used herein refers to a sequence of nucleic acids that can be transferred to an organism or cell. The transgene may comprise a gene or sequence of nucleic acids not normally present in the target organism or cell. Additionally, the transgene may comprise a copy of a gene or sequence of nucleic acids that is normally present in the target organism or cell. A transgene can be an exogenous DNA sequence introduced into the cytoplasm or nucleus of a target cell. In one embodiment, the transgenes described herein contain partial coding sequences, wherein the partial coding sequences encodes a portion of a protein produced by a gene in the host cell.

As used herein, the term "pathogenic" refers to anything that can cause disease. A pathogenic mutation can refer to a modification in a gene which causes disease. A pathogenic gene refers to a gene comprising a modification which causes disease. By means of example, a pathogenic ATXN3 gene in patients with spinocerebellar ataxia 3 refers to an ATXN3 gene with an expanded CAG trinucleotide repeat, wherein the expanded CAG trinucleotide repeat causes the disease.

As used herein, the term "tail-to-tail" refers to an orientation of two units in opposite and reverse directions. The two units can be two sequences on a single nucleic acid molecule, where the 3' end of each sequence are placed adjacent to each other. For example, a first nucleic acid having the elements, in a 5' to 3' direction, [splice acceptor 1]-[partial coding sequence 1]-[terminator 1] and a second nucleic acid having the elements [splice acceptor 2]-[partial coding sequence 2]-[terminator 2] can be placed in tail-to-tail orientation resulting in [splice acceptor 1]-[partial coding sequence 1]-[terminator 1]-[terminator 2 RC]-[partial coding sequence 2 RC]-[splice acceptor 2 RC], where RC refers to reverse complement.

The term "intron-exon junction" refers to a specific location within a gene. The specific location is between the last nucleotide in an intron and the first nucleotide of the following exon. When integrating a transgene described herein, the transgene can be integrated within the "intron-exon junction." If the transgene comprises cargo, the cargo will be integrated immediately following the last nucleotide in the intron. In some cases, integrating a transgene within the intron-exon junction can result in removal of sequence within the exon (e.g., integration via HR and replacement of sequence within the exon with the cargo within the transgene).

The term "homologous" as used herein refers to a sequence of nucleic acids or amino acids having similarity to a second sequence of nucleic acids or amino acids. In some embodiments, the homologous sequences can have at least 80% sequence identity (e.g., 81%, 85%, 90%, 95%, 96%, 97%, 98%, or 99% sequence identity) to one another.

The term "partial coding sequence" as used herein refers to a sequence of nucleic acids that encodes a partial protein. The partial coding sequence can encode a protein that comprises one or less amino acids as compared to the wild type protein or functional protein. The partial coding sequence can encode a partial protein with homology to the wild type protein or functional protein. The term "partial coding sequence" when referring to ATXN3 refers to a sequence of nucleic acids that encodes a partial ATXN3 protein. The partial ATXN3 protein has one or less amino acids compared to a wild type ATXN3 protein. If modifying the 3' end of the gene, the one or less amino acids can be from the N-terminus end of the protein. If the ATXN3 gene has 11 exons, then the partial coding sequence can comprise sequence encoding the peptide produced by exons 2-11, or 3-11 or 4-11, or 5-11, or 6-11, or 7-11, or 8-11, or 9-11, or 10-11, or 11.

The methods and compositions described in this document can use transgenes having a cargo sequence. The term "cargo" can refer to elements such as the complete or partial coding sequence of a gene, a partial sequence of a gene harboring single-nucleotide polymorphisms relative to the WT or altered target, a splice acceptor, a terminator, a transcriptional regulatory element, purification tags (e.g., glutathione-S-transferase, poly(His), maltose binding protein, Strep-tag, Myc-tag, AviTag, HA-tag, or chitin binding protein) or reporter genes (e.g., GFP, RFP, lacZ, cat, luciferase, puro, neomycin). As defined herein, "cargo" can refer to the sequence within a transgene that is integrated at a target site. For example, "cargo" can refer to the sequence on a transgene between two homology arms, two rare-cutting endonuclease target sites, or a left and right transposon end.

The term "homology sequence" refers to a sequence of nucleic acids that comprises homology to a second nucleic acid. Homology sequence, for example, can be present on a donor molecule as an "arm of homology" or "homology arm." A homology arm can be a sequence of nucleic acids within a donor molecule that facilitates homologous recombination with the second nucleic acid. As defined herein, a homology arm can also be referred to as an "arm". In a donor molecule with two homology arms, the homology arms can be referred to as "arm 1" and "arm 2." In one aspect, a cargo sequence can be flanked with first and second homology arm.

The term "bidirectional terminator" refers to a terminator that can terminate RNA polymerase transcription in either the sense or antisense direction. In contrast to two unidirectional terminators in tail-to-tail orientation, a bidirectional terminator can comprise a non-chimeric sequence of DNA. Examples of bidirectional terminators include the ARO4, TRP1, TRP4, ADH1, CYC 1, GAL1, GALT, and GAL10 terminator.

A 5' or 3' end of a nucleic acid molecule references the directionality and chemical orientation of the nucleic acid. As defined herein, the "5' end of a gene" can comprise the exon with the start codon, but not the exon with the stop codon. As defined herein, the "3' end of a gene" can comprise the exon with the stop codon, but not the exon with the start codon.

The term "ATXN3" gene refers to a gene that encodes the enzyme ataxin-3. A representative sequence of the ATXN3 gene can be found with NCBI Reference Sequence: NG 008198.2 and corresponding SEQ ID NO:42. The exon and intron boundaries can be defined with the sequence provided in SEQ ID NO:42. Specifically, exon 1 includes the sequence from 1 to 54. Exon 2 includes the sequence from 9745 to 9909. Exon 3 includes the sequence from 10446 to 10490. Exon 4 includes the sequence from 12752 to 12837. Exon 5 includes the sequence from 13265 to 13331. Exon 6 includes the sequence from 17766 to 17853. Exon 7 includes the sequence from 23325 to 23457. Exon 8 includes the sequence from 24117 to 24283. Exon 9 includes the sequence from 25522 to 25618. Exon 10 includes the sequence from 35530 to 35648. Exon 11 includes the sequence from 42169 to 48031. Intron 1 includes the sequence from 55 to 9744. Intron 2 includes the sequence from 9910 to 10445. Intron 3 includes the sequence from 10491 to 12751. Intron 4 includes the sequence from 12838 to 13264. Intron 5 includes the sequence from 13332 to 17765. Intron 6 includes the sequence from 17854 to 23324. Intron 7 includes the sequence from 23458 to 24116. Intron 8 includes the sequence from 24284 to 25521. Intron 9 includes the sequence from 25619 to 35529. Intron 10 includes the sequence from 35649 to 42168.

The term "CACNA1A" gene refers to a gene that encodes the calcium voltage-gated channel subunit alphalA protein. A representative sequence of the CACNA1A gene can be found with NCBI Reference Sequence: NG_011569.1 and corresponding SEQ ID NO:43. The exon and intron boundaries can be defined with the sequence provided in SEQ ID NO:43. Specifically, exon 1 includes the sequence from 1 to 529. Exon 2 includes the sequence from 51249 to 51354. Exon 3 includes the sequence from 53446 to 53585. Exon 4 includes the sequence from 134682 to 134773. Exon 5 includes the sequence from 140992 to 141144. Exon 6 includes the sequence from 146662 to 146855. Exon 7 includes the sequence from 170552 to 170655. Exon 8 includes the sequence from 171968 to 172083. Exon 9 includes the sequence from 173536 to 173592. Exon 10 includes the sequence from 176125 to 176217. Exon 11 includes the sequence from 189140 to 189349. Exon 12 includes the sequence from 193680 to 193792. Exon 13 includes the sequence from 197933 to 198045. Exon 14 includes the sequence from 198210 to 198341. Exon 15 includes the sequence from 198607 to 198679. Exon 16 includes the sequence from 202577 to 202694. Exon 17 includes the sequence from 202848 to 202915. Exon 18 includes the sequence from 205805 to 205911. Exon 19 includes the sequence from 207108 to 207917. Exon 20 includes the sequence from 219495 to 219958. Exon 21 includes the sequence from 221255 to 221393. Exon 22 includes the sequence from 223065 to 223194. Exon 23 includes the sequence from 229333 to 229392. Exon 24 includes the sequence from 230505 to 230611. Exon 25 includes the sequence from 243628 to 243727. Exon 26 includes the sequence from 244851 to 245011. Exon 27 includes the sequence from 246760 to 246897. Exon 28 includes the sequence from 248910 to 249111. Exon 29 includes the sequence from 251202 to 251366. Exon 30 includes the sequence from 253360 to 253470. Exon 31 includes the sequence from 261196 to 261279. Exon 32 includes the sequence from 270731 to 270847. Exon 33 includes the sequence from 271187 to 271252. Exon 34 includes the sequence from 271425 to 271540. Exon 35 includes the sequence from 274601 to 274751. Exon 36 includes the sequence from 276252 to 276379. Exon 37 includes the sequence from 277666 to 277762. Exon 38 includes the sequence from 281689 to 281794. Exon 39 includes the sequence from 291853 to 291960. Exon 40 includes the sequence from 292128 to 292228. Exon 41 includes the sequence from 293721 to 293830. Exon 42 includes the sequence from 293939 to 294077. Exon 43 includes the sequence from 294245 to 294358. Exon 44 includes the sequence from 295809 to 295844. Exon 45 includes the sequence from 296963 to 297149. Exon 46 includes the sequence from 297452 to 297705. Exon 47 includes the sequence from 298413 to 300019. Intron 1 includes the sequence from 530 to 51248. Intron 2 includes the sequence from 51355 to 53445. Intron 3 includes the sequence from 53586 to 134681. Intron 4 includes the sequence from 134774 to 140991. Intron 5 includes the sequence from 141145 to 146661. Intron 6 includes the sequence from 146856 to 170551. Intron 7 includes the sequence from 170656 to 171967. Intron 8 includes the sequence from 172084 to 173535. Intron 9 includes the sequence from 173593 to 176124. Intron 10 includes the sequence from 176218 to 189139. Intron 11 includes the sequence from 189350 to 193679. Intron 12 includes the sequence from 193793 to 197932. Intron 13 includes the sequence from 198046 to 198209. Intron 14 includes the sequence from 198342 to 198606. Intron 15 includes the sequence from 198680 to 202576. Intron 16 includes the sequence from 202695 to 202847. Intron 17 includes the sequence from 202916 to 205804. Intron 18 includes the sequence from 205912 to 207107. Intron 19 includes the sequence from 207918 to 219494. Intron 20 includes the sequence from 219959 to 221254. Intron 21 includes the sequence from 221394 to 223064. Intron 22 includes the sequence from 223195 to 229332. Intron 23 includes the sequence from 229393 to 230504. Intron 24 includes the sequence from 230612 to 243627. Intron 25 includes the sequence from 243728 to 244850. Intron 26 includes the sequence from 245012 to 246759. Intron 27 includes the sequence from 246898 to 248909. Intron 28 includes the sequence from 249112 to 251201. Intron 29 includes the sequence from 251367 to 253359. Intron 30 includes the sequence from 253471 to 261195. Intron 31 includes the sequence from 261280 to 270730. Intron 32 includes the sequence from 270848 to 271186. Intron 33 includes the sequence from 271253 to 271424. Intron 34 includes the sequence from 271541 to 274600. Intron 35 includes the sequence from 274752 to 276251. Intron 36 includes the sequence from 276380 to 277665. Intron 37 includes the sequence from 277763 to 281688. Intron 38 includes the sequence from 281795 to 291852. Intron 39 includes the sequence from 291961 to 292127. Intron 40 includes the sequence from 292229 to 293720. Intron 41 includes the sequence from 293831 to 293938. Intron 42 includes the sequence from 294078 to 294244. Intron 43 includes the sequence from 294359 to 295808. Intron 44 includes the sequence from 295845 to 296962. Intron 45 includes the sequence from 297150 to 297451. Intron 46 includes the sequence from 297706 to 298412.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: −i is set to a file containing the first nucleic acid sequence to be compared (e.g., C:\seql.txt); −j is set to a file containing the second nucleic acid sequence to be compared (e.g., C:\seq2.txt); −p is set to blastn; −o is set to any desired file name (e.g., C:\output.txt); −q is set to −1; −r is set to 2; and all other options are left at their default setting. For example, the following command can be used to generate an output file containing a comparison between two sequences: C:\Bl2seq c:\seql.txt −j c:\seq2.txt −p blastn −o c:\output.txt −q −1 −r 2. To compare two amino acid sequences, the options of Bl2seq are set as follows: −i is set to a file containing the first amino acid sequence to be compared (e.g., C:\seql.txt); −j is set to a file containing the second amino acid sequence to be compared (e.g., C:\seq2.txt); −p is set to blastp; −o is set to any desired file name (e.g., C:\output.txt); and all other options are left at their default setting. For example, the following command can be used to generate an output file containing a comparison between two amino acid sequences: C:\Bl2seq c:\seql.txt −j c:\seq2.txt −p blastp −o c:\Aoutput.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. The percent sequence identity value is rounded to the nearest tenth.

In one embodiment, this document features methods for modifying the 3' end of endogenous genes, where endogenous genes have at least one intron between two coding exons. The intron can be any intron which is removed from precursor messenger RNA by normal messenger RNA processing machinery. The intron can be between 20 bp and >500 kb and comprise elements including a splice donor site, branch sequence, and acceptor site. The transgenes disclosed herein for the modification of the 3' end of endogenous genes can comprise multiple functional elements, including target sites for rare-cutting endonucleases, homology arms, splice acceptor sequences, coding sequences, and transcription terminators (FIG. 1).

In one embodiment, the transgene comprises two target sites for one or more rare-cutting endonucleases. The target sites can be a suitable sequence and length for cleavage by a rare-cutting endonuclease. The target site can be amenable to cleavage by CRISPR systems, TAL effector nucleases, zinc-finger nucleases or meganucleases, or a combination of CRISPR systems, TALE nucleases, zinc finger nucleases or meganucleases, or any other site-specific nuclease. The target sites can be positioned such that cleavage by the rare-cutting endonuclease results in liberation of a transgene from a vector. The vector can include viral vectors (e.g., adeno-associated vectors) or non-viral vectors (e.g., plasmids, minicircle vectors). If the transgene comprises two target sites, the target sites can be the same sequence (i.e., targeted by the same rare-cutting endonuclease) or they can be different sequences (i.e., targeted by two or more different rare-cutting endonucleases).

In one embodiment, the transgene comprises a first and second target site for one or more rare-cutting endonucleases along with a first and second homology arm. The first and second homology arms can include sequence that is homologous to a genomic sequence at or near the desired site of integration. The homology arms can be a suitable length for participating in homologous recombination with sequence at or near the desired site of integration. The length of each homology arm can be between 20 nt and 10,000 nt (e.g., 20 nt, 30 nt, 40 nt, 50 nt, 100 nt, 200 nt, 300 nt, 400 nt, 500 nt, 600 nt, 700 nt, 800 nt, 900 nt, 1,000 nt, 2,000 nt, 3,000 nt, 4,000 nt, 5,000 nt, 6,000 nt, 7,000 nt, 8,000 nt, 9,000 nt, 10,000 nt). In one embodiment, a homology arms can comprise functional elements, including a target site for a rare-cutting endonuclease and/or a splice acceptor sequence. In one embodiment, a first homology arm (e.g., a left homology arm) can comprise sequence homologous to the intron being targeted, which includes the splice acceptor site of the intron being targeted. In another embodiment, a second homology arm can comprise sequence homologous to genomic sequence downstream of the intron being targeted (e.g., exon sequence, 3' UTR sequence). However, the second homology arm must not possess splice acceptor functions in the reverse complement direction. To determine if a sequence comprises splice acceptor functions, several steps can be taken, including in silico analysis and experimental tests. To determine if there is potential for splice acceptor functions, the sequence desired for second homology arm can be searched for consensus branch sequences (e.g., YTRAC) and splice acceptor sites (e.g., Y-rich NCAGG). If branch or splice acceptor sequences are present, single nucleotide polymorphisms can be introduced to destroy function, or a different but adjacent sequence not comprising such sequences can be selected. Preferably, the window of sequence that can be used for a second homology arm extends from 1 bp to 10 kb downstream of the intron being targeted for integration. To experimentally determine if the second homology possesses splice acceptor function, a synthetic construct comprising the second homology arm within an intron within a reporter gene can be constructed. The construct can then be administered to an appropriate cell type and monitored for splicing function.

In one embodiment, the transgene comprises two splice acceptor sequences, referred to herein as the first and second splice acceptor sequence. The first and second splice acceptor sequences are positioned within the transgene in opposite directions (i.e., in tail-to-tail orientations) and flanking internal sequences (i.e., coding sequences and terminators). When the transgene is integrated into an intron in forward or reverse directions, the splice acceptor sequences facilitate the removal of the adjacent/upstream intron sequence during mRNA processing. The first and second splice acceptor sequences can be the same sequences or different sequences. One or both splice acceptor sequences can be the splice acceptor sequence of the intron where the transgene is to be integrated. One or both splice acceptor sequences can be a synthetic splice acceptor sequence or a splice acceptor sequence from an intron from a different gene.

In one embodiment, the transgene comprises a first and second coding sequence operably linked to the first and second splice acceptor sequences. The first and second coding sequences are positioned within the transgene in opposite directions (i.e., in tail-to-tail orientations). When the transgene is integrated into an endogenous gene in forward or reverse directions, the first or second coding sequence is transcribed into mRNA by the endogenous gene's promoter. The coding sequences can be designed to correct defective coding sequences, introduce mutations, or introduce novel peptide sequences. The first and second coding sequence can be the same nucleic acid sequence and code for the same protein. Alternatively, the first and second coding sequence can be different nucleic acid sequences and code for the same protein (i.e., using the degeneracy of codons). The coding sequence can encode purification tags (e.g., glutathione-S-transferase, poly(His), maltose binding protein, Strep-tag, Myc-tag, AviTag, HA-tag, or chitin binding protein) or reporter proteins (e.g., GFP, RFP, lacZ, cat, luciferase, puro, neomycin). In one embodiment, the transgene comprises a first and second partial coding sequence operably linked to a first and second splice acceptor sequence, and the transgene does not comprise a promoter.

In one embodiment, the transgene can comprise a bidirectional terminator, or a first and second terminator, operably linked to a first and second coding sequence. The bidirectional terminator, or the first and second terminators are positioned within the transgene in opposite directions (i.e., in tail-to-tail orientations). When the transgene is integrated into an endogenous gene in forward or reverse directions, the bidirectional terminator, or first and second terminators, terminate transcription from the endogenous gene's promoter. The first and second terminators can be the same terminators or different terminators.

Figure 2:
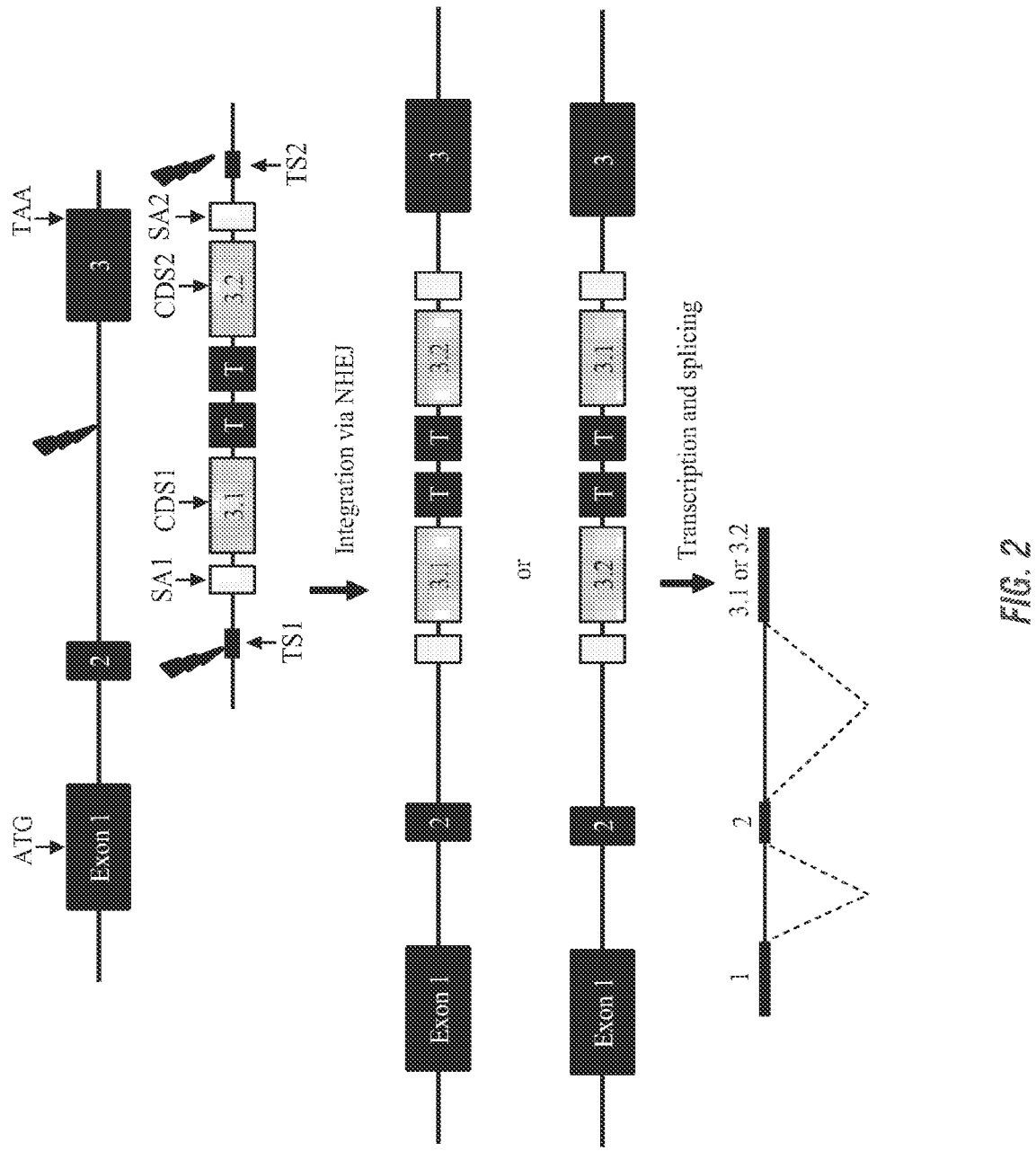
FIG. 2 is an illustration showing integration of a transgene into an exemplary gene. The transgene comprises two target sites for one or more rare-cutting endonucleases, two splice acceptor sequences, two coding sequences (3.1 and 3.2) and two terminators (T). Integration proceeds through non-homologous end joining (NHEJ).

In one embodiment, this document provides a transgene comprising a first and second rare-cutting endonuclease target site, a first and second splice acceptor sequence, a first and second coding sequence, and one bidirectional terminator or a first and second terminator. The transgene can be integrated in endogenous genes via non-homology dependent methods, including non-homologous end joining and alternative non-homologous end joining or by microhomology-mediated end joining. In one aspect, the transgene is integrated into an intron within the endogenous gene (FIG. 2).

Figure 3:
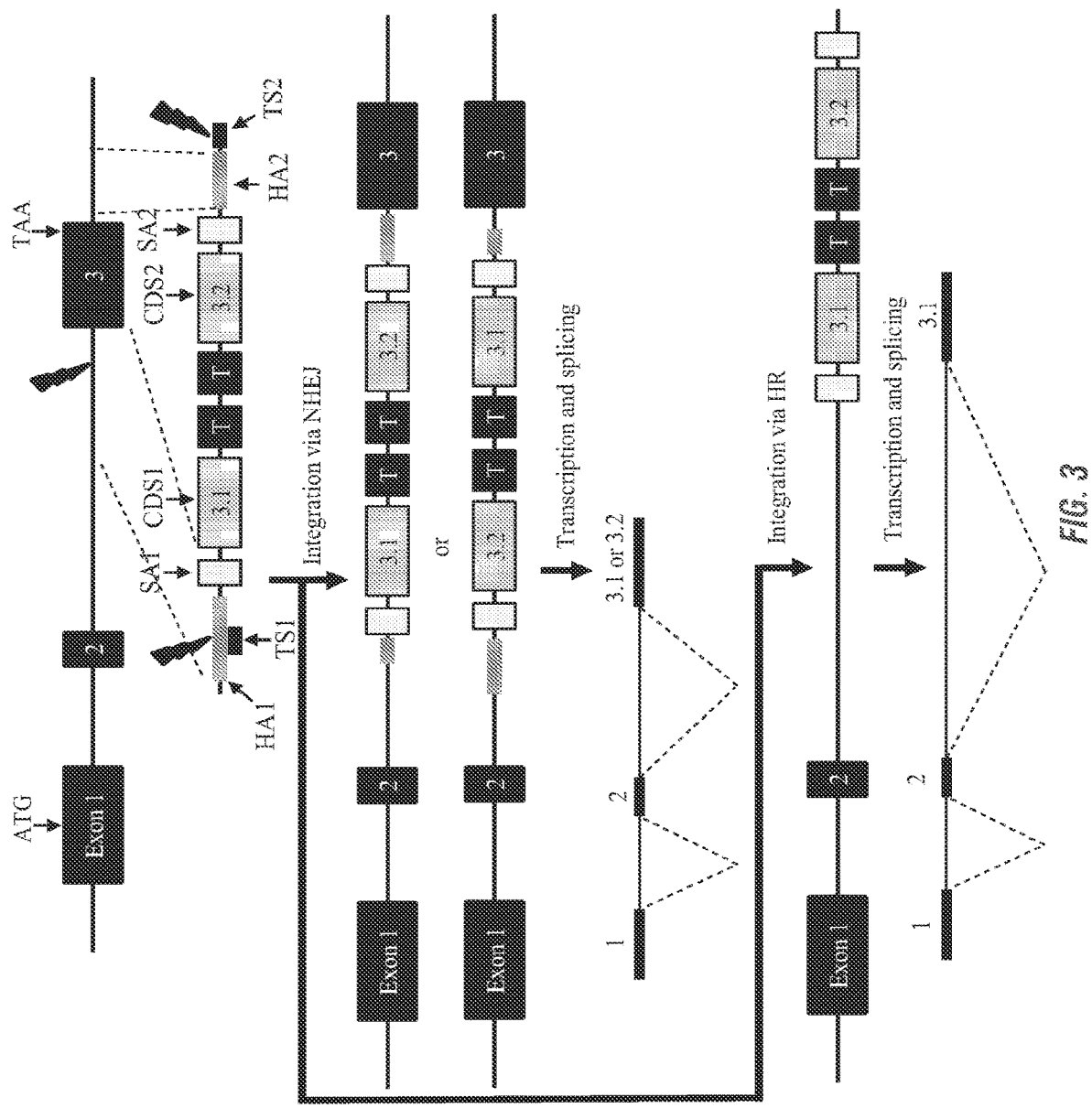
FIG. 3 is an illustration showing integration of a transgene into an exemplary gene. The transgene comprises two homology arms, two target sites for one or more rare-cutting endonucleases, two splice acceptor sequences, two coding sequences (3.1 and 3.2) and two terminators. Integration proceeds through either homologous recombination (HR) or non-homologous end joining (NHEJ).

In another embodiment, this document provides a transgene comprising a first and second homology arm, a first and second rare-cutting endonuclease target site, a first and second splice acceptor sequence, a first and second coding sequence, and one bidirectional terminator or a first and second terminator. The transgene can be integrated in endogenous genes via both homology dependent methods (e.g., synthesis dependent strand annealing and microhomology-mediated end joining) and non-homology dependent methods (e.g., non-homologous end joining and alternative non-homologous end joining). In one aspect, the transgene is integrated into an intron within the endogenous gene (FIG. 3). In another aspect, the transgene is integrated at the end of the intron or the starting of the downstream exon (FIG. 3).

In another embodiment, this document provides a transgene comprising a first and second homology arm, a first and second coding sequence, a first and second splice acceptor sequence, and one bidirectional terminator or a first and second terminator (FIG. 1). In another embodiment, this document provides a transgene comprising, a first and second coding sequence, a first and second splice acceptor sequence, and one bidirectional terminator or a first and second terminator.

In another embodiment, this document provides a transgene comprising a first and second homology arm, a first and second coding sequence, a first and second splice acceptor sequence, one bidirectional terminator or a first and second terminator, and a first and second additional sequence (FIG. 1). In certain embodiments, the additional sequence can be any additional sequence that is present on the transgene at the 5' and 3' ends, however, the additional sequence should not comprise any element that functions as a splice acceptor. The additional sequence can be, for example, inverted terminal repeats of a virus genome. The additional sequence can be present on a transgene having a linear format. The linear format permits integration by NHEJ. For example, a transgene harbored in an adeno-associated virus vector, wherein the additional sequence is the inverted terminal repeats, can be directly integrated by NHEJ at a target site after cleavage by a rare-cutting endonuclease (i.e., no processing of the transgene is required). In another example, the additional sequence is a left and right transposon end.

In another embodiment, this document provides transgenes within viral vectors, including adeno-associated viruses and adenoviruses, where the transgene comprises a first and second splice acceptor sequence, a first and second coding sequence, and one bidirectional terminator or a first and second terminator. Due to the inverted terminal repeats of the viral vectors, the transgenes also comprise a first and second additional sequence.

In another embodiment, this document provides transgenes within viral vectors, including adeno-associated viruses and adenoviruses, where the transgene comprises a first and second homology arm, a first and second splice acceptor sequence, a first and second coding sequence, and one bidirectional terminator or a first and second terminator. Due to the inverted terminal repeats of the viral vectors, the transgenes also comprise a first and second additional sequence.

In some embodiments, the transgenes provided herein can be integrated with transposases. The transposases can include CRISPR transposases (Strecker et al., *Science* 10.1126/science.aax9181, 2019; Klompe et al., *Nature*, 10.1038/s41586-019-1323-z, 2019). The transposases can be used in combination with a transgene comprising, a first and second splice acceptor sequence, a first and second coding sequence, one bidirectional terminator or a first and second terminator (FIG. 1), and a transposon left end and right end. The CRISPR transposases can include the TypeV-U5, C2C5 CRISPR protein, Cas12k, along with proteins tnsB, tnsC, and tniQ. In some embodiments, the Cas12k can be from *Scytonema hofmanni* (SEQ ID NO:30) or *Anabaena cylindrica* (SEQ ID NO:31). In one embodiment, the transgenes described herein comprising a left (SEQ ID NO:32) and right transposon end (SEQ ID NO:33) can be delivered to cells along with ShCas12k, tnsB, tnsC, TniQ and a gRNA (SEQ ID NO:14). Alternatively, the CRISPR transposase can include the Cas6 protein, along with helper proteins including Cas7, Cas8 and TniQ. In one embodiment, the transgenes described herein comprising a left (SEQ ID NO:41) and right transposon end (SEQ ID NO:13) can be delivered to eukaryotic cells along with Cas6 (SEQ ID NO:37), Cas7 (SEQ ID NO:37), Cas8 (SEQ ID NO:37), TniQ (SEQ ID NO:37), TnsA (SEQ ID NO:37), TnsB (SEQ ID NO:37), TnsC (SEQ ID NO:37) and a gRNA (SEQ ID NO:12). The proteins can be administered to cells directly as purified protein or encoded on RNA or DNA. If encoded on RNA or DNA, the sequence can be codon optimized for expression in eukaryotic cells. The gRNA (SEQ ID NO:12) can be placed downstream of an RNA polIII promoter and terminated with a poly(T) terminator.

In some embodiments, the transgenes described herein can have a combination of elements including splice acceptors, partial coding sequences, terminators, homology arms, left and right transposase ends, and sites for cleavage by rare-cutting endonucleases. In one embodiment, the combination can be, from 5' to 3', [splice acceptor 1]-[partial coding sequence 1]-[terminator 1]-[terminator 2 RC]-[partial coding sequence 2 RC]-[splice acceptor 2 RC], where RC stands for reverse complement. This combination can be harbored on a linear DNA molecule or AAV molecule and can be integrated by NHEJ through a targeted break in the target gene. In another embodiment, the combination can be, from 5' to 3', [rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[rare-cutting endonuclease cleavage site 1]. In another embodiment, the combination can be, from 5' to 3', [rare-cutting endonuclease cleavage site 1]-[homology arm 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 2]. In this combination one or more rare-cutting endonucleases can be used to facilitate HR and NHEJ. For example, a single rare-cutting nuclease can cleave the target gene (i.e., a desired intron) and the cleavage sites flanking the homology arms can be designed to be the same target sequence within the intron. In another embodiment, the combination can be, from 5' to 3', [homology arm 1+rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 1]. In this combination, one or more rare-cutting endonucleases can facilitate HR and NHEJ. For example, a single-rare cutting nuclease can cleave within homology arm 1, downstream of homology arm 2, and at the genomic target site (i.e., at the site with homology to the sequence in the homology arm 1). In another embodiment, the combination can be from 5' to 3', [left end for a transposase]-[splice acceptor 1]-[partial coding sequence 1]-[terminator 1]-[terminator 2 RC]-[partial coding sequence 2 RC]-[splice acceptor 2 RC]-[right end for a transposase]. In all embodiments, the splice acceptor 1 and splice acceptor 2 can be the same or different sequences; the partial coding sequence 1 and partial coding sequence 2 can be the same or different sequences; the terminator 1 and terminator 2 can be the same or different sequences.

In embodiments, a transgene comprising the structure [rare-cutting endonuclease cleavage site 1]-[homology arm 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 2] can be integrated into the DNA through delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ.

In other embodiments, a transgene comprising the structure [homology arm 1+rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 1] can be integrated into the DNA thorough delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ. Integration by HR can occur when cleavage is upstream of the site of integration (i.e., within a homology arm).

In embodiments, the location for integration of transgenes can be an intron or an intron-exon junction. When targeting an intron, the partial coding sequence can comprise sequence encoding the peptide produced by the following exons within the endogenous gene. For example, if the transgene is designed to be integrated in intron 9 of an endogenous gene with 11 exons, then the partial coding sequence can comprise sequence encoding the peptide produced by exons 10 and 11 of the endogenous gene. When targeting an intron-exon junction, the transgene can be designed to comprise homology arms with sequence homologous to the 3' of said intron.

In some embodiments, the partial coding sequences can be full coding sequences. The full coding sequence can encode an endogenous gene (e.g., Factor VIII, Factor IX, or INS), or reporter genes (e.g., RFP, GFP, cat, lacZ, luciferase). The full coding sequences can be operably linked to splice acceptors and terminators and placed in a transgene in a tail-to-tail orientation.

The methods and compositions provided herein can be used within to modify endogenous genes within cells. The endogenous genes can include, fibrinogen, prothrombin, tissue factor, Factor V, Factor VII, Factor VIII, Factor IX, Factor X, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, glucocerebrosidase (GBA), α-galactosidase A (GLA), iduronate sulfatase (IDS), iduronidase (IDUA), acid sphingomyelinase (SMPD1), MMAA, MMAB, MMACHC, MMADHC (C2orf25), MTRR, LMBRD1, MTR, propionyl-CoA carboxylase (PCC) (PCCA and/or PCCB subunits), a glucose-6-phosphate transporter (G6PT) protein or glucose-6-phosphatase (G6Pase), an LDL receptor (LDLR), ApoB, LDLRAP-1, a PCSK9, a mitochondrial protein such as NAGS (N-acetyl-glutamate synthetase), CPS1 (carbamoyl phosphate synthetase I), and OTC (ornithine transcarbamylase), ASS (argininosuccinic acid synthetase), ASL (argininosuccinase acid lyase) and/or ARG1 (arginase), and/or a solute carrier family 25 (SLC25A13, an aspartate/glutamate carrier) protein, a UGT1A1 or UDP glucuronsyltransferase polypeptide A, a fumarylacetoacetate hydrolyase (FAH), an alanine-glyoxylate aminotransferase (AGXT) protein, a glyoxylate reductase/hydroxypyruvate reductase (GRHPR) protein, a transthyretin gene (TTR) protein, an ATP7B protein, a phenylalanine hydroxylase (PAH) protein, an USH2A protein, an ATXN protein, and a lipoprotein lyase (LPL) protein.

The transgene may include sequence for modifying the sequence encoding a polypeptide that is lacking or non-functional or having a gain-of-function mutation in the subject having a genetic disease, including but not limited to the following genetic diseases: achondroplasia, achromatopsia, acid maltase deficiency, adenosine deaminase deficiency, adrenoleukodystrophy, aicardi syndrome, alpha-1 antitrypsin deficiency, alpha-thalassemia, androgen insensitivity syndrome, pert syndrome, arrhythmogenic right ventricular dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency, leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome, lysosomal storage diseases (e.g., Gaucher's disease, GM1, Fabry disease and Tay-Sachs disease), mucopolysaccahidosis (e.g. Hunter's disease, Hurler's disease), hemoglobin-opathies (e.g., sickle cell diseases, HbC, α-thalassemia, β-thalassemia) and hemophilias.

Additional diseases that can be treated by targeted integration include von Willebrand disease, usher syndrome, polycystic kidney disease, spinocerebellar ataxia type 3, and spinocerebellar ataxia type 6.

In one embodiment, the genomic modification is the insertion of a transgene in the endogenous CACNA1A genomic sequence. The transgene can include a synthetic and partial coding sequence for the CACNA1A protein. The partial coding sequence can be homologous to coding sequence within a wild type CACNA1A gene, or a functional variant of the wild type CACNA1A gene, or a mutant of the wild type CACNA1A gene. In one embodiment, the transgene encoding the partial CACNA1A protein is inserted into intron 46 or the beginning of exon 47.

In another embodiment, the genomic modification is the insertion of a transgene in the endogenous ATXN3 genomic sequence. The transgene can include a synthetic and partial coding sequence for the ATXN3 protein. The partial coding sequence can be homologous to coding sequence within a wild type ATXN3 gene, or a functional variant of the wild type ATXN3 gene, or a mutant of the wild type ATXN3 gene. In one embodiment, the transgene encoding the partial ATXN3 protein is inserted into intron 9 or the beginning of exon 10.

In one embodiment, the methods and compositions described herein can be used to modify the 3' end of an endogenous gene, thereby resulting in modification of the C-terminus of the protein encoded by the endogenous gene. The modification of the 3' end of the endogenous gene's coding sequence can include the replacement of the final coding exon (i.e., the exon comprising the stop codon), up to an exon that is between the exon with the start coding and the final exon. As defined herein "replacement" refers to the insertion of DNA in a gene, wherein the inserted DNA provides the information for producing the mRNA and protein of 1 or more exons. Replacement can occur by integrating a transgene into the endogenous gene, wherein the transgene comprises one or more coding sequences operably linked to a splice acceptor. The insertion may or may not result in the deletion of sequence within the endogenous gene (e.g., deletion of introns and exons). For example, if a gene comprises 72 exons, and the start codon is within exon 1, the modification can include replacement of exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. In one embodiment, the endogenous gene's exons can be replaced by integrating a transgene into the endogenous gene, wherein the transgene comprises a first and second partial coding sequence, wherein the first and second partial coding sequence encodes a peptide produced by the endogenous genes exons. For example, the transgene's first and second coding sequence can encode a peptide that is produced by the endogenous gene's exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. The transgene can be integrated within the endogenous gene in the upstream intron or at the beginning of the exon corresponding to the first exon within the transgene's partial coding sequence (FIG. 2). The transgene can be designed to be 4.7 kb or less, and incorporated into an AAV vector and particle, and delivered in vivo to target cells.

In an embodiment, the transgene is a sequence of DNA that harbors a first and second partial coding sequence, wherein the partial coding sequences encode a partial protein, wherein the partial protein is homologous to a corresponding region in a functional protein produced from a wild type gene. The host gene or endogenous gene is one in which expression of the protein is aberrant, in other words, is not expressed, is expressed at low levels, or is expressed but the mRNA or protein product or portion thereof is non-functional, has reduced function, or has a gain-of-function, resulting in a disorder in the host.

As described herein, the donor molecule can be in a viral or non-viral vector. The vectors can be in the form of circular or linear double-stranded or single stranded DNA. The donor molecule can be conjugated or associated with a reagent that facilitates stability or cellular update. The reagent can be lipids, calcium phosphate, cationic polymers, DEAE-dextran, dendrimers, polyethylene glycol (PEG) cell penetrating peptides, gas-encapsulated microbubbles or magnetic beads. The donor molecule can be incorporated into a viral particle. The virus can be retroviral, adenoviral, adeno-associated vectors (AAV), herpes simplex, pox virus, hybrid adenoviral vector, epstein-bar virus, lentivirus, or herpes simplex virus.

In certain embodiments, the AAV vectors as described herein can be derived from any AAV. In certain embodiments, the AAV vector is derived from the defective and nonpathogenic parvovirus adeno-associated type 2 virus. All such vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3, 1998; Kearns et al., Gene Ther. 9:748-55, 1996). Other AAV serotypes, including AAV1, AAV2, AAV3, AAV4, AAV5, AAV6, AAV7, AAV8, AAV9 and AAVrh.10 and any novel AAV serotype can also be used in accordance with the present invention. In some embodiments, chimeric AAV is used where the viral origins of the long terminal repeat (LTR) sequences of the viral nucleic acid are heterologous to the viral origin of the capsid sequences. Non-limiting examples include chimeric virus with LTRs derived from AAV2 and capsids derived from AAV5, AAV6, AAV8 or AAV9 (i.e. AAV2/5, AAV2/6, AAV2/8 and AAV2/9, respectively).

The constructs described herein may also be incorporated into an adenoviral vector system. Adenoviral based vectors are capable of very high transduction efficiency in many cell types and do not require cell division. With such vectors, high titer and high levels of expression can been obtained.

The methods and compositions described herein are applicable to any eukaryotic organism in which it is desired to alter the organism through genomic modification. The eukaryotic organisms include plants, algae, animals, fungi and protists. The eukaryotic organisms can also include plant cells, algae cells, animal cells, fungal cells and protist cells.

Exemplary mammalian cells include, but are not limited to, oocytes, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) J. Gen. Virol. 36:59), and myeloma cells like SP2 or NS0 (see, e.g., Galfre and Milstein (1981) Meth. Enzymol. 73(B):3 46). Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, liver stem cells, skin stem cells and neuronal stem cells.

The methods and compositions of the invention can be used in the production of modified organisms. The modified organisms can be small mammals, companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. The methods and compositions of the invention can be used in humans.

Exemplary plants and plant cells which can be modified using the methods described herein include, but are not limited to, monocotyledonous plants (e.g., wheat, maize, rice, millet, barley, sugarcane), dicotyledonous plants (e.g., soybean, potato, tomato, alfalfa), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); vegetative crops for consumption (e.g. soybean and other legumes, squash, peppers, eggplant, celery etc.), flowering plants (e.g., petunia, rose, chrysanthemum), conifers and pine trees (e.g., pine fir, spruce); poplar trees (e.g. *P. tremula×P. alba*); fiber crops (cotton, jute, flax, bamboo) plants used in phytoremediation (e.g., heavy metal accumulating plants); oil crops (e.g., sunflower, rape seed) and plants used for experimental purposes (e.g., Arabidopsis). The methods disclosed herein can be used within the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea*. The term plant cells include isolated plant cells as well as whole plants or portions of whole plants such as seeds, callus, leaves, and roots. The present disclosure also encompasses seeds of the plants described above wherein the seed has the has been modified using the compositions and/or methods described herein. The present disclosure further encompasses the progeny, clones, cell lines or cells of the transgenic plants described above wherein said progeny, clone, cell line or cell has the transgene or gene construct. Exemplary algae species include microalgae, diatoms, *Botryococcus braunii, Chlorella, Dunaliella tertiolecta, Gracileria, Pleurochrysis carterae, Sorgassum* and *Ulva*.

The methods described in this document can include the use of rare-cutting endonucleases for stimulating homologous recombination or non-homologous integration of a transgene molecule into an endogenous gene. The rare-cutting endonuclease can include CRISPR, TALENs, or zinc-finger nucleases (ZFNs). The CRISPR system can include CRISPR/Cas9 or CRISPR/Cas12a (Cpf1). The CRISPR system can include variants which display broad PAM capability (Hu et al., *Nature* 556, 57-63, 2018; Nishimasu et al., *Science* DOI: 10.1126, 2018) or higher on-target binding or cleavage activity (Kleinstiver et al., *Nature* 529:490-495, 2016). The gene editing reagent can be in the format of a nuclease (Mali et al., *Science* 339:823-826, 2013; Christian et al., *Genetics* 186:757-761, 2010), nickase (Cong et al., *Science* 339:819-823, 2013; Wu et al., *Biochemical and Biophysical Research Communications* 1:261-266, 2014), CRISPR-FokI dimers (Tsai et al., *Nature Biotechnology* 32:569-576, 2014), or paired CRISPR nickases (Ran et al., *Cell* 154:1380-1389, 2013).

The methods and compositions described in this document can be used in a circumstance where it is desired to modify the 3' end of the coding sequence of an endogenous gene. For example, patients with SCA3 or SCA6 have expanded CAG repeats in exons 10 (second to last exon) and exon 47 (last exon), respectively. Patients with SCA3 or SCA6 may benefit from replacement of exons 10-11 and exon 47, respectively. In other examples, patients with genetic disorders due to loss of function mutations within the 3' end of an endogenous gene could benefit from replacement of the final exons of said gene.

The invention will be further described in the following examples, which do not limit the scope of the invention described in the claims.

EXAMPLES

Example 1: Targeted Integration of DNA in the ATXN3 Gene

Three plasmids were constructed with transgenes designed to integrate into the ATXN3 gene in human cells. All transgenes were designed to be inserted within intron 9 or the junction of intron 9 and exon 10 of the ATXN3 gene and all transgenes were designed to insert at least one splice acceptor and at least one functional coding sequence for exons 10 and 11 of the ATXN3 gene. The first plasmid, designated pBA1135, comprised a left and right homology arm with sequence homologous to the 3' end of intron 9 and 5' end of intron 10 (i.e., successful gene targeting would result in removal of exon 10 and replacement with the cargo sequence within pBA1135). Between the homology arms, from 5' to 3', was a splice acceptor (splice acceptor from ATXN3 intron 9), coding sequence for exons 10 and 11 of ATXN3, SV40 terminator, reverse BGH terminator, reverse coding sequence for exons 10 and 11 (codon adjusted), and reverse splice acceptor. The sequence for the pBA1135 transgene is shown in SEQ ID NO:17. A corresponding Cas9 nuclease was designed to cleave i) within intron 9 of the ATXN3 gene, ii) within the left homology arm of pBA1135, and iii) at the 3' end of the right homology arm of pBA1135. Successful cleavage of the plasmid was expected to liberate the transgene, thereby enabling the sequence to be used as a template for HR or for integration via NHEJ. The Cas9 gRNA target site is shown in SEQ ID NO:18. The individual elements within pBA1135 are shown in SEQ ID NOS:44-51. SEQ ID NO:44 comprises the left homology arm, nuclease target site, and splice acceptor. SEQ ID NO:45 comprises the partial coding sequence (exon 10 and 11) of a non-pathogenic ATXN3 gene. SEQ ID NO:46 comprises the SV40 p(A) terminator sequence. SEQ ID NO:47 comprises the BGH terminator in reverse complement. SEQ ID NO:48 comprises the reverse complement, codon adjusted partial coding sequence (exon 10 and 11) of a non-pathogenic ATXN3 gene. SEQ ID NO:49 comprises the sequence for the splice acceptor. SEQ ID NO:50 comprises the sequence for the right homology arm. SEQ ID NO:51 comprises the target site sequence for the nuclease. The second plasmid, designated pBA1136, comprised the same cargo as pBA1135, however, the homology arms were removed. Nuclease target sites were kept to facilitate liberation of the transgene from the plasmid. Successful cleavage of the plasmid was expected to liberate the transgene, thereby enabling the sequence to be used for integration by NHEJ into the ATXN3 gene. The sequence of pBA1136 is shown in SEQ ID NO:19. The third plasmid, designated pBA1137, comprised the same sequence as pBA1135, except for the reverse sequences and nuclease target site (i.e., reverse terminator, reverse coding sequence and reverse splice acceptor). Plasmid pBA1137 was used as a control for conventional HR based methods. The sequence of pBA1137 is shown in SEQ ID NO:20.

Transfection was performed using HEK293T cells. HEK293T cells were maintained at 37° C. and 5% CO2 in DMEM high supplemented with 10% fetal bovine serum (FBS). HEK293T cells were transfected with 2 ug of donor, 2 ug of guide RNA (RNA format) and 2 ug of Cas9 (RNA format). Transfections were performed using electroporation. Genomic DNA was isolated 72 hours post transfection and assessed for integration events. A list of primers used to detect integration or genomic DNA is shown in Table 1.

TABLE 1

Primers for detecting integration of transgenes in ATXN3.

| Primer Name | Sequence (5' to 3') | SEQ ID NO: |
|---|---|---|
| oNJB043 | CAAAGGTGCCCTTGAGGTT | 21 |
| oNJB044 | AGGAGAAGTCTGCCGTTACT | 22 |
| oNJB113 | GGACAAACCACAACTAGAATGC | 23 |
| oNJB114 | TAGGAAAGGACAGTGGGAGT | 24 |
| oNJB116 | CCATTATGTCTCAGTTGTTCAGTG | 25 |
| oNJB156 | CCAGACCATCTCAGACACC | 26 |
| oNJB162 | GGCTGGGCTTCCACTTAC | 27 |
| oNJB167 | GTGGTTTGTCCAAACTCATCAA | 28 |
| oNJB170 | AGTAACTCTGCACTTCCCATTG | 29 |

Figure 8:
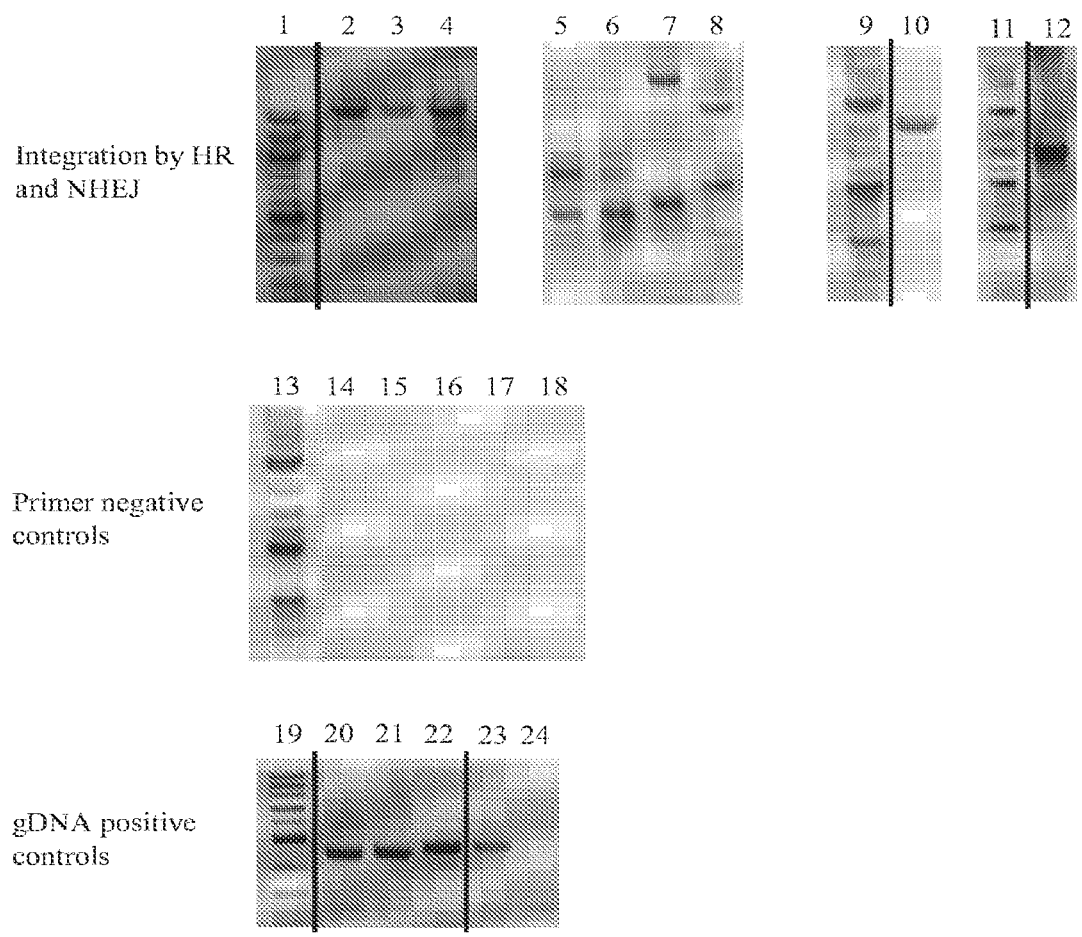
FIG. 8 are images of gels detecting integration of transgenes into the ATXN3 gene. 1, 100 bp ladder with top band running at 1,517 bp; 2, pBA1135 5' junction; 3, pBA1136 5' junction; 4, pBA1137 5' junction; 5, pBA1135 3' junction; 6, pBA1136 3' junction; 7, pBA1137 3' junction; 8, 1kb ladder with darker bands running at 500 bp, 1,000 bp and 3,000 bp; 9, 1 kb ladder with darker bands running at 500 bp, 1,000 bp and 3,000 bp; 10, pBA1135 inverted 5' junction; 11, 1 kb ladder with darker bands running at 500 bp, 1,000 bp and 3,000 bp; 12, pBA1136 inverted 5' junction; 13, 1 kb ladder with darker bands running at 500 bp, 1,000 bp and 3,000 bp; 14; primer pair oNJB156+oNJB113; 15, primer pair 114+162; 16, primer pair oNJB116+oNJB113; 17, primer pair oNJB114+oNJB170; 18, primer pair oNJB167+oNJB170; 19, 100 bp ladder with the dark band running at 500 bp; 20, genomic DNA from transfection with pBA1135 and nuclease; 21, genomic DNA from transfection with pBA1136 and nuclease; 22, genomic DNA from transfection with pBA1137 and nuclease; 23, genomic DNA from transfection with water; 24, no DNA control.

To detect the integration of pBA1135, pBA1136 and pBA1137, PCRs were performed on the genomic DNA. Regarding pBA1137, the transgene was designed to be integrated precisely by HR. Accordingly, bands were detected in the 5' and 3' junction PCRs, which indicate precise insertion into exon 10 (FIG. 8 lanes 4 and 7). Expected band sizes were 1,520 bp for the 5' junction and 786 bp for the 3' junction. Primers oNJB113 and oNJB116 were used for the 5' junction PCR. Primers oNJB167 and oNJB170 were used for the 3' junction PCR. Regarding pBA1136, as no homology arms were present, the transgene was predicted to insert via NHEJ insertion. Appropriate band bands were observed for the transgene integrating in the forward and reverse directions. Integration in the forward direction can be seen in FIG. 8 lanes 3 (expected size approximately 1,520 bp) and 6 (expected size approximately 1,519 bp). Integrating in the reverse direction can be seen in FIG. 8 lane 12 (expected size approximately 1,520 bp). Primers oNJB113 and oNJB116 were used for the 5' junction PCR. Primers oNJB114 and oNJB170 were used for the 3' junction PCR. Primers oNJB116 and oNJB114 were used for the inverse 5' junction PCR. Regarding ppBA1135, both homology arms and nuclease cleavage sites were present on the transgene. Integration by HR was observed by detecting bands in the 5' and 3' junction PCRs (FIG. 8 lane 2 and 5). Further, integration by NHEJ was observed by detecting bands in an inverse 5' junction PCR (FIG. 8 lane 10). Expected size for the 5' junction PCR was 1,520 bp. Expected size for the 3' junction PCR was 1,157 bp. Expected size for the inverse 5' junction PCR was approximately 1,520 bp. Primers oNJB113 and oNJB116 were used for the 5' junction PCR. Primers oNJB114 and oNJB170 were used for the 3' junction PCR. Primers oNJB116 and oNJB114 were used for the inverse 5' junction PCR.

The results show that the described transgenes comprising bidirectional partial coding sequences can be integrated into genomic DNA through multiple different repair pathways.

Example 2: Targeted Integration of DNA in the CACNA1A Gene

Figure 4:
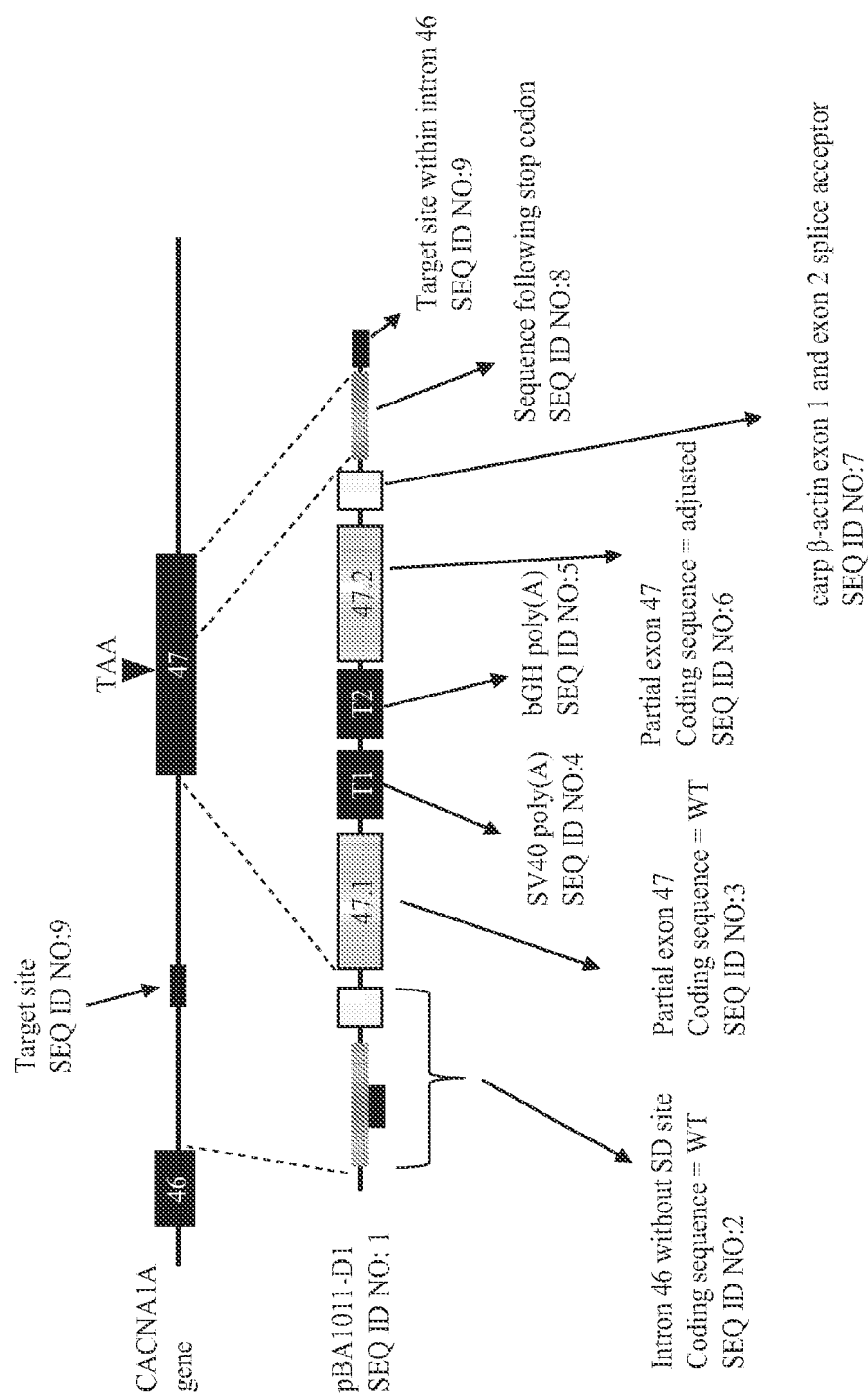
FIG. 4 is an illustration of exon 46, intron 46 and intron 47 of the CACNA1A gene. Also shown is the pB1011-D1 transgene for integration in the CACNA1A gene.

A CACNA1A-targeting transgene is designed to replace the 3' end of the CACNA1A coding sequence. A plasmid is constructed with a transgene designed to integrate WT coding sequence into intron 46 or the start of exon 47 (FIG. 4). The transgene comprises a first homology arm which is homologous to sequence immediately following the splice donor site in intron 46. The first homology arm also comprises the target site for a nuclease (SEQ ID NO:9) and a splice acceptor sequence. The first homology arm is followed by a first coding sequence comprising the CACNA1A exon 47 and a non-expanded CAG repeat sequence (SEQ ID NO:3). Following the first coding sequence is a SV40 poly(A) termination sequence (SEQ ID NO:4). In a tail-to-tail orientation, a second set of functional elements is present. The beginning of the second set of elements comprises a target site for the nuclease (SEQ ID NO:9) followed by a second homology arm. The second homology arm harbors 446 bp which is homologous to sequence immediately following the stop coding (SEQ ID NO:8). This sequence was determined to be free of consensus branch or splice acceptor sequences via in silico analysis. Following the second homology arm is a second splice acceptor from carp beta-actin intron 1 (SEQ ID NO:7). Following the splice acceptor is a codon optimized version of the CACNA1A exon 47 (SEQ ID NO:6) and a bGH poly(A) terminator (SEQ ID NO:5).

A corresponding Cas12a nuclease is designed to create three double-strand breaks following transfection of the plasmid: i) within intron 46 of the endogenous CACNA1A gene, 2) within the first homology arm in the pBA1011-D1 transgene, and 3) following the second homology arm in the pBA1011-D1 transgene. The target sequence for the Cas12a nuclease is shown in SEQ ID NO:9.

Figure 5:
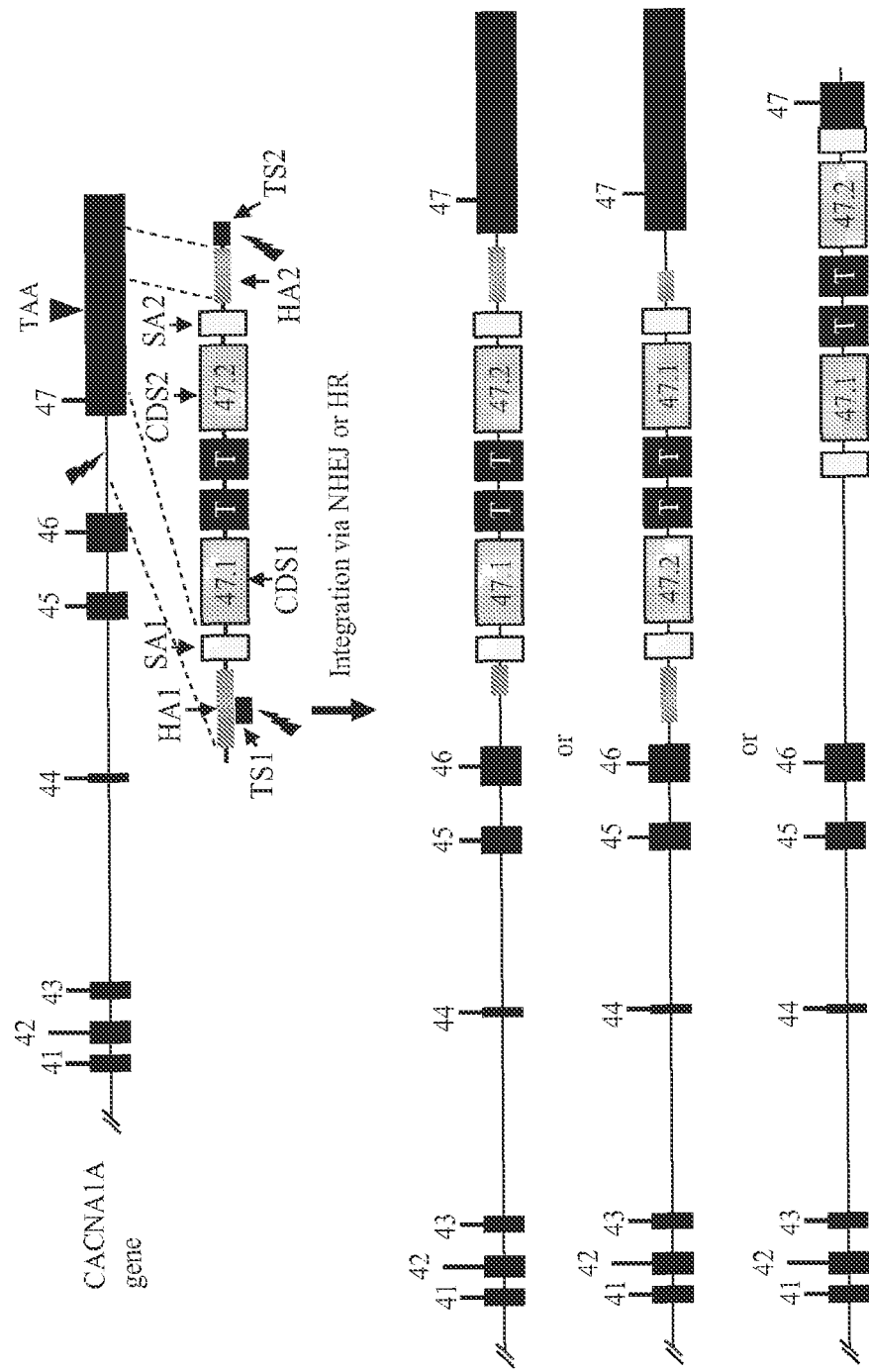
FIG. 5 is an illustration of the integration outcomes for the pB1011-D1 transgene within the CACNA1A gene.
Figure 6:
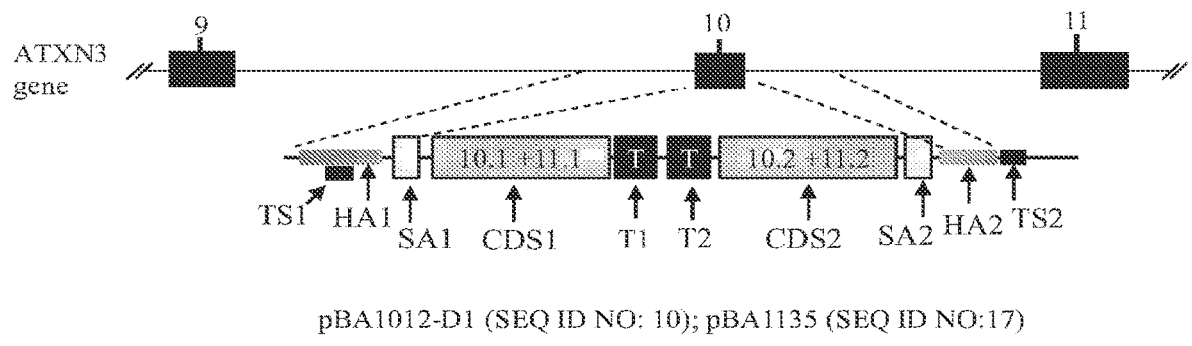
FIG. 6 is an illustration of exon 9, intron 9, exon 10, intron 10 and exon 11 of the ATXN3 gene. Also shown is the pB1012-D1 transgene for integration in the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100X. HEK293 cells are transfected with each of the plasmid constructs and combinations thereof using Lipofectamine 3000. Two days post transfection, DNA is extracted and assessed for mutations and targeted insertions within the CACNA1A gene. Nuclease activity is analyzed using the Cel-I assay or by deep sequencing of amplicons comprising the CRISPR/Cas12a target sequence. Successful integration of the transgene is analyzed using PCR (FIG. 5).

Example 3: Targeted Integration of DNA in the ATXN3 Gene

An ATXN3-targeting transgene is designed to replace the 3' end of the ATXN coding sequence (exons 10 and 11). A plasmid is constructed with a transgene designed to integrate WT coding sequence into intron 9 or the start of exon 10 (FIG. 5). The transgene comprises a first homology arm which is homologous to sequence intron 9 (SEQ ID NO:10). The first homology arm also comprises the target site for a Cas12a nuclease and a splice acceptor sequence. The first homology arm is followed by a first coding sequence comprising the ATXN3 exon 10 and 11 and a non-expanded CAG repeat sequence. Following the first coding sequence is a SV40 poly(A) termination sequence. In a tail-to-tail orientation, a second set of functional elements is present. The beginning of the second set of elements comprises a target site for the Cas12a nuclease followed by a second homology arm. The second homology arm harbors 379 bp which is homologous to sequence immediately following the end of exon 10 (i.e., the start of intron 10). This sequence was determined via in silico analysis to have a limited number of potential branch or splice acceptor sequences. Following the second homology arm is a second splice acceptor from carp beta-actin intron 1. Following the splice acceptor is a codon optimized version of the ATXN3 exons 10 and 11 and a bGH poly(A) terminator.

A corresponding Cas12a nuclease is designed to create three double-strand breaks following transfection of the plasmid: i) within intron 9 of the endogenous ATXN3 gene, 2) within the first homology arm in the pBA1012-D1 transgene, and 3) following the second homology arm in the pBA1012-D1 transgene. The target sequence for the Cas12a nuclease is shown in SEQ ID NO:11.

Figure 7:
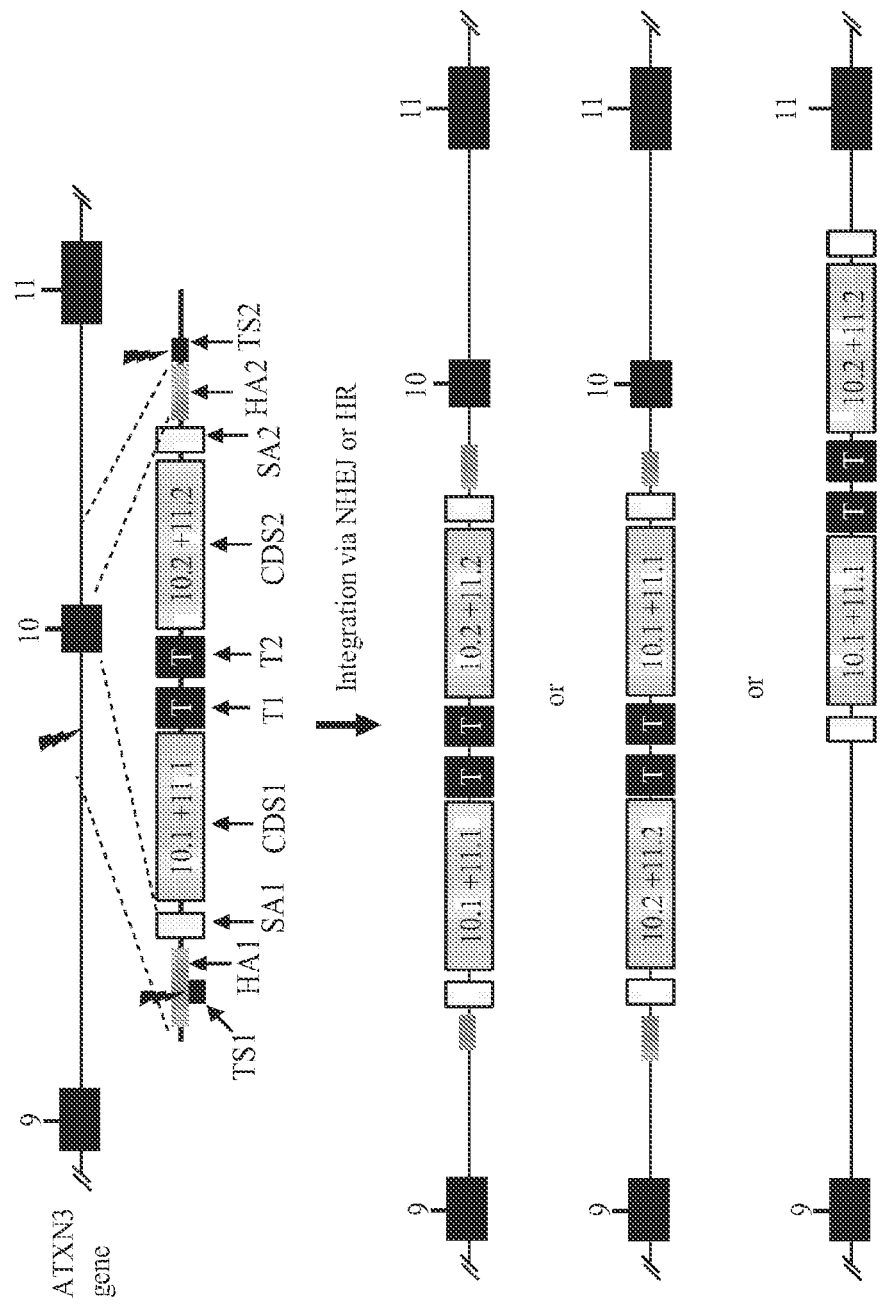
FIG. 7 is an illustration of the integration outcomes for the pB1012-D1 transgene within the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100X. HEK293 cells are transfected with each of the plasmid constructs and combinations thereof using Lipofectamine 3000. Two days post transfection, DNA is extracted and assessed for mutations and targeted insertions within the ATXN3 gene. Nuclease activity is analyzed using the Cel-I assay or by deep sequencing of amplicons comprising the CRISPR/Cas12a target sequence. Successful integration of the transgene is analyzed using PCR (FIG. 7).

Example 4: Targeted Integration of DNA in the ATXN3 Gene Using Cas12k Transposases An ATXN3-targeting transgene is designed to replace the 3' end of the ATXN coding sequence (exons 10 and 11). A plasmid is constructed with a transgene designed to integrate WT coding sequence into intron 9 or the start of exon 10. The transgene comprises a transposon right end and left end, a first and second splice acceptor, a first and second coding sequence (encoding amino acids from exons 10 and 11), and a first and second terminator. The sequence between the transposon right and left ends is shown in SEQ ID NO: 17.

Plasmids are engineered to express the *Scytonema hofmanni* tnsB, tnsC, tniQ and Cas12k (SEQ ID NO:30) using eukaryotic promoters. A second plasmid is engineered to express the corresponding Cas12k guide RNA (SEQ ID NO:14). The guide RNA targeted sequence CCGCCCGACCTTTCACTTTC (SEQ ID NO:15). The Cas12k transposon plasmids is cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100X. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Example 5: Targeted Integration of DNA in the CACNA1A Gene

A CACNA1A-targeting transgene is designed to replace the 3' end of the CACNA1A coding sequence. A plasmid is constructed with a transgene designed to integrate WT coding sequence into intron 46 or the start of exon 47. The transgene comprises a transposon right end and left end, a first and second splice acceptor, a first and second coding sequence (encoding amino acids from exon 47), and a first and second terminator.

Plasmids are engineered to express the Scytonema hofmanni tnsB, tnsC, tniQ and Cas12k (SEQ ID NO:30) using eukaryotic promoters. A second plasmid is engineered to express the corresponding Cas12k guide RNA (SEQ ID NO:14). The guide RNA is designed to target sequence CCCGGATCCCGGCTGTGACC (SEQ ID NO: 16). The Cas12k transposon plasmids are cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100X. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgene comprising from 5' to 3' orientation: a first splice acceptor, a first coding sequence, a first terminator, a second terminator reverse complement, a second coding sequence reverse complement, and a second splice acceptor reverse complement, wherein the first coding sequence is operably linked to the first splice acceptor and first terminator, and the second coding sequence is operably linked to the second splice acceptor and second terminator, wherein the first terminator is selected from an SV40 poly(A) or BGH poly(A), wherein the first and second coding sequences differ in nucleic acid sequence but encode the same amino acids, wherein said amino acids encoded by the first and second coding sequences correspond to amino acids encoded by an endogenous Factor IX gene, and wherein the transgene is equal to or less than 4.7 kb.

2. The transgene of claim 1, wherein the second terminator is selected from an SV40 poly(A) or BGH poly(A).

3. The transgene of claim 2, wherein the amino acids encoded by the first and second coding sequences have at least 80% sequence identity to the amino acids encoded by the endogenous Factor IX gene, wherein the percent sequence identity is calculated by matching amino acids encoded by the first and second coding sequence with amino acids encoded by an endogenous Factor IX gene and dividing the number of matches by the length of the amino acids encoded by the first and second coding sequence, followed by multiplying the resulting value by 100.

4. The transgene of claim 3, wherein the amino acids encoded by the first and second coding sequences have about 98% sequence identity to the amino acids encoded by an endogenous Factor IX gene.

5. The transgene of claim 3, wherein the amino acids encoded by the first and second coding sequences have about 99% sequence identity to the amino acids encoded by an endogenous Factor IX gene.

6. The transgene of claim 3, wherein the transgene is harbored on a viral vector.

7. The transgene of claim 6, wherein the viral vector is selected from the group consisting of an adenovirus vector, an adeno-associated virus vector, and a lentivirus vector.

8. The method of claim 7, wherein the viral vector is an adeno-associated viral vector.

9. The transgene of claim 8, wherein the viral vector is incorporated into a viral particle.

10. The transgene of claim 9, wherein the transgene does not comprise homology arms.

11. The transgene of claim 10, wherein the first splice acceptor comprises a splice acceptor sequence from an intron of the endogenous Factor IX gene.

12. An adeno-associated viral vector comprising:
(i) a transgene comprising from 5' to 3' orientation a first splice acceptor, a first coding sequence, a first terminator, a second terminator reverse complement, a second coding sequence reverse complement, and a second splice acceptor reverse complement, wherein the first coding sequence is operably linked to the first splice acceptor and first terminator, and the second coding sequence is operably linked to the second splice acceptor and second terminator, wherein the first and second coding sequences differ in nucleic acid sequence but encode the same amino acids, wherein said amino acids encoded by the first and second coding sequences correspond to amino acids encoded by an endogenous gene, and
wherein the transgene is equal to or less than 4.7 kb; and
(ii) adeno-associated virus inverted terminal repeats flanking the transgene.

13. The adeno-associated viral vector of claim 12, wherein the endogenous gene is Factor IX.

14. The adeno-associated viral vector of claim 13, wherein the first and second coding sequences encode amino acids having at least 80% sequence identity to the amino acids encoded by the endogenous Factor IX gene, wherein the percent sequence identity is calculated by matching amino acids encoded by the first and second coding sequence with amino acids encoded by an endogenous Factor IX gene and dividing the number of matches by the length of the amino acids encoded by the first and second coding sequence, followed by multiplying the resulting value by 100.

15. The adeno-associated viral vector of claim 14, wherein the amino acids encoded by the first and second coding sequences have about 98% sequence identity to the amino acids encoded by an endogenous Factor IX gene.

16. The adeno-associated viral vector of claim 14, wherein the amino acids encoded by the first and second coding sequences have about 99% sequence identity to the amino acids encoded by an endogenous Factor IX gene.

17. The adeno-associated viral vector of claim 13, wherein the first terminator is selected from an SV40 poly(A) or BGH poly(A).

18. The adeno-associated viral vector of claim 17, wherein the second terminator is selected from an SV40 poly(A) or BGH poly(A).

19. The adeno-associated viral vector of claim 18, wherein the viral vector is incorporated into a viral particle.

20. The adeno-associated viral vector of claim 18, wherein the transgene does not comprise homology arms.

21. The adeno-associated viral vector of claim 20, wherein the first splice acceptor comprises splice acceptor sequence from an intron of the endogenous Factor IX gene.

22. The adeno-associated viral vector of claim 20, wherein the first terminator is SV40 poly(A) and the second terminator is BGH poly(A).

* * * * *